United States Patent
Kawamoto et al.

Patent Number: 6,090,802
Date of Patent: Jul. 18, 2000

[54] 1-METHYLCARBAPENEM DERIVATIVES

[75] Inventors: Isao Kawamoto; Yasuo Shimoji; Katsuya Ishikawa, all of Tokyo; Katsuhiko Kojima, Yono; Hiroshi Yasuda, Yokohama; Satoshi Ohya, Tokyo; Yukio Utsui, Tokorozawa, all of Japan

[73] Assignee: Sankyo Company, Limited, Tokyo, Japan

[21] Appl. No.: 09/095,925

[22] Filed: Jun. 12, 1998

Related U.S. Application Data

[63] Continuation-in-part of application No. PCT/JP96/03726, Dec. 20, 1996, abandoned.

[30] Foreign Application Priority Data

Dec. 21, 1995 [JP] Japan ................................. 7-333135
Nov. 20, 1996 [JP] Japan ................................. 8-308940

[51] Int. Cl.$^7$ ...................... A61K 31/409; C07D 477/20
[52] U.S. Cl. ............................................. 514/210; 540/350
[58] Field of Search ............................. 514/210; 540/350

[56] References Cited

U.S. PATENT DOCUMENTS

| | | | |
|---|---|---|---|
| 5,122,604 | 6/1992 | Sunagawa et al. | 514/210 |
| 5,712,267 | 1/1998 | Kawamoto | 540/350 |
| 5,977,097 | 11/1999 | Kawamoto | 540/350 |

FOREIGN PATENT DOCUMENTS

| | | |
|---|---|---|
| 0 126 587 | 11/1984 | European Pat. Off. |
| 0 449 191 | 10/1991 | European Pat. Off. |
| 0 518 558 | 12/1992 | European Pat. Off. |
| 0 560 613 | 9/1993 | European Pat. Off. |
| 0 641 795 | 3/1995 | European Pat. Off. |
| 5-310740 | 11/1993 | Japan . |
| 5-339269 | 12/1993 | Japan . |
| 6-172356 | 6/1994 | Japan . |
| 6-199860 | 7/1994 | Japan . |
| 2 279 073 | 12/1994 | United Kingdom . |
| WO 95/10520 | 4/1995 | WIPO . |

OTHER PUBLICATIONS

Abstract for JP 11–71277 & translation thereof, Mar. 1999.
Hackh's Chemical Dictionary, 4th Edition (Grant, Ed) p. 35, 1969.

*Primary Examiner*—Mark L. Berch
*Attorney, Agent, or Firm*—Frishauf, Holtz, Goodman, Langer & Chick, P.C.

[57] ABSTRACT

A 1-methylcarbapenem compound represented by the following formula (I):

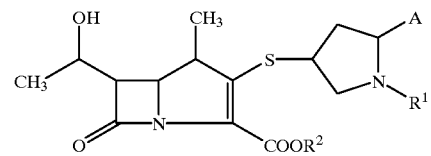

wherein $R^1$ represents hydrogen or $C_1$–$C_4$ alkyl; $R^2$ represents hydrogen or an ester residue; and A represents a group of the formula (A1)

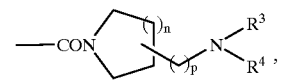

(A1)

wherein n is 0, 1 or 2, P is 0, 1 or 2, $R^3$ is hydrogen or $C_1$–$C_4$ alkyl and $R^4$ is a group (Q2)

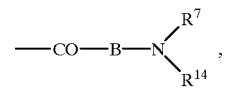

(Q2)

wherein B is phenylene, phenylene($C_1$–$C_3$)alkyl, cyclohexylene, cyclohexylene($C_1$–$C_3$)alkyl or $C_1$–$C_5$ alkylene, $R^7$ is hydrogen or $C_1$–$C_4$ alkyl, and $R^{14}$ is a group —C(=NH)$R^8$, wherein $R^8$ is hydrogen or $C_1$–$C_4$ alkyl or a group —N$R^9 R^{10}$, wherein $R^9$ and $R^{10}$ are the same or different and are hydrogen or $C_1$–$C_4$ alkyl; or a pharmacologically acceptable salt thereof.

14 Claims, No Drawings

1-METHYLCARBAPENEM DERIVATIVES

This application is a continuation-in-part application of international application PCT/JP96/03726 filed Dec. 20, 1996, now abandoned.

TECHNICAL FIELD

The present invention relates to 1-methylcarbapenem derivatives having excellent antibacterial activity, compositions for the prevention or treatment of infectious diseases which comprise any one of said derivatives as an effective ingredient, use of said derivatives for the preparation of a medicament used for the prevention or treatment of infectious diseases, and a prevention or treatment method which comprises administering a pharmacologically effective amount of any one of said derivatives to warm-blooded animals.

BACKGROUND ART

It is reported (in H. Kropp et al., Antimicrob. Agents, Chemother., 22, 62 (1982); S. R. Norrby et al., ibid., 23, 300 (1983)) that thienamycin derivatives have excellent antibacterial activity, but that they lose their activity, due to decomposition by dehydropeptidase I, which is an inactivating enzyme of thienamycin dervatives present in the human body and exhibit low urinary recovery rates.

In addition, it is known that imipenem, which is one of the thienamycin derivatives, exhibits nephrotoxicity. Compounds which can overcome these defects and exhibit excellent antibacterial activity are now being searched for. Carbapenem derivatives having a methyl group at the 1-position of the catbapenem skeleton and a 2-substituted pyrrolidin-4-ylthio group at the 2-position have been disclosed, for example, U.S. Pat. No. 5,122,604, Japanese Patent Application Kokai No. Hei 5-339269, Japanese Patent Application Kokai No. Hei 6-172356 and Japanese Patent Application Kokai No. Hei 6-199860.

DISCLOSURE OF THE INVENTION

With a view toward overcoming the above-described defects of thienamycin derivatives and obtaining a compound which exhibits stronger antibacterial activity, the present inventors carried out investigations. The present invention provides a new group of 1-methylcarbapenem derivatives (I) which possess superior antibacterial activity and metabolic stability (improved urinary recovery rates and more stable against dehydropeptidase I and β-lactamase) as well as low nephrotoxicity. The compounds (I) are effective as a preventive or remedy for infectious diseases.

The present invention provides a new group of 1-methylcarbapenem derivatives, a composition for the prevention or treatment of infectious diseases which comprises said derivatives as an effective ingredient, use of the derivatives for the preparation of a pharmaceutical for the prevention or treatment of infectious diseases, a method for the prevention or treatment of infectious diseases which comprises administering a pharmacologically effective amount of the derivatives to warm-blooded animals, and a synthetic process for preparation of the derivatives.

SUMMARY OF THE INVENTION

The 1-methylcarbapenem derivative of the present invention is represented by the following formula:

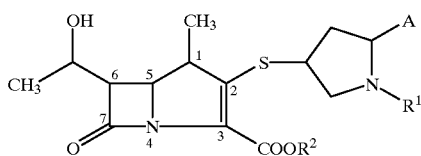

(I)

wherein:
$R^1$ represents a hydrogen atom or a $C_{1-4}$ alkyl group,
$R^2$ represents a hydrogen atom or an ester residue which can be hydrolyzed in vivo, and
A is a group represented by the formula (A1), (A2), (A3) or (A4);

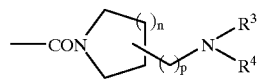

(A1)

(A2)

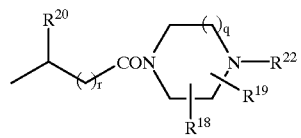

(A3)

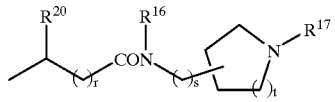

(A4)

wherein, in the formula (A1):
n stands for 0, 1 or 2,
p stands for 0, 1 or 2,
$R^3$ represents a hydrogen atom or a $C_{1-4}$ alkyl group, and
$R^4$ is a group represented by the formula (Q1) or (Q2);

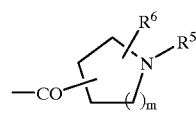

(Q1)

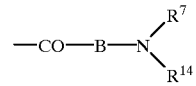

(Q2)

wherein, in the formula (Q1):
m stands for 0, 1 or 2,
$R^5$ represents a hydrogen atom, a $C_{1-4}$ alkyl group which may have one substituent (said substituent is an amino, hydroxyl, carbamoyl, carbamoyloxy, cyano, sulfamoyl or carboxy group), or a group represented by the formula —C(=NH)$R^8$ [in which $R^8$ is a hydrogen atom, a $C_{1-4}$ alkyl group or a group represented by the formula —NR$^9$R$^{10}$ (in which $R^9$ and $R^{10}$ are the same as or different from each other and each represents a hydrogen atom or a $C_{1-4}$ alkyl group)], and $R^6$ represents a hydrogen atom, a hydroxyl group, a halogen atom or a group represented by the formula —$NR^{11}R^{12}$ [wherein $R^{11}$ and $R^{12}$ are the same as or different from each other and each represents a hydrogen atom or a $C_{1-4}$ alkyl group], and in the formula (Q2):

B represents a phenylene, phenylenealkyl (the alkyl part of said phenylenealkyl group is a $C_{1-3}$ alkyl), cyclohexylene, cyclohexylenealkyl (the alkyl part of said cyclohexylenealkyl group is a $C_{1-3}$ alkyl) or a $C_{1-5}$ alkylene group which may have one to three substituents [said substituents independently represent an amino, hydroxyl, cyclohexylalkyl (the alkyl part of said cyclohexylalkyl is a $C_{1-3}$ alkyl), $C_{1-4}$ alkyl, phenyl or benzyl group], $R^7$ represents a hydrogen atom or a $C_{1-4}$ alkyl group, and $R^{14}$ is a hydrogen atom, a $C_{1-4}$ alkyl group or a group represented by the formula —C(=NH)$R^8$ [wherein $R^8$ represents a hydrogen atom, a $C_{1-4}$ alkyl group or a group represented by the formula —$NR^9R^{10}$ (in which $R^9$ and $R^{10}$ are the same as or different each other and each represents a hydrogen atom or a $C_{1-4}$ alkyl group)];

in the formula (A2):

r stands for 0, 1 or 2, n stands for 0, 1 or 2, p stands for 0, 1 or 2, $R^{20}$ represents a hydrogen atom or a hydroxyl group, $R^{13}$ represents a hydrogen atom or a $C_{1-4}$ alkyl group which may have one substituent (said substituent is an amino, hydroxyl, carbamoyl, carbamoyloxy, cyano, sulfamoyl or carboxy group), and $R^{21}$ represents a hydrogen atom, a $C_{1-4}$ alkyl group which may have one substituent (said substituent is an amino, hydroxyl, carbamoyl, carbamoyloxy, cyano, sulfamoyl or carboxy group) or a group represented by the formula —C(=NH)$R^8$ [wherein $R^8$ represents a hydrogen atom, a $C_{1-4}$ alkyl group or a group represented by the formula —$NR^9R^{10}$ (in which $R^9$ and $R^{10}$ are the same as or different from each other and each represents a hydrogen atom or a $C_{1-4}$ alkyl group)];

in the formula (A3):

r stands for 0, 1 or 2, q stands for 0, 1 or 2, $R^{18}$ and $R^{19}$ are the same as or different from each other and each represents a hydrogen atom or a $C_{1-4}$ alkyl group, $R^{20}$ represents a hydrogen atom or a hydroxyl group, and $R^{22}$ represents a hydrogen atom, a $C_{1-4}$ alkyl group which may have one substituent (said substituent is an amino, hydroxyl, carbamoyl, carbamoyloxy, cyano, sulfamoyl or carboxy group) or a group represented by the formula —C(=NH)$R^8$ (wherein $R^8$ represents a hydrogen atom, a $C_{1-4}$ alkyl group or a group represented by the formula —$NR^9R^{10}$ (in which $R^9$ and $R^{10}$ are the same as or different from each other and represents a hydrogen atom or a $C_{1-4}$ alkyl group)]; and in the formula (A4):

r stands for 0, 1 or 2, s stands for 0 or 1, t stands for 0, 1 or 2, $R^{16}$ represents a hydrogen atom or a $C_{1-4}$ alkyl group, $R^{17}$ represents a hydrogen atom, a $C_{1-4}$ alkyl group or a group represented by the formula —C(=NH)$R^8$ [wherein $R^8$ represents a hydrogen atom, a $C_{1-4}$ alkyl group or a group represented by the formula —$NR^9R^{10}$ (in which $R^9$ and $R^{10}$ each are the same as or different from each other and represents a hydrogen atom or a $C_{1-4}$ alkyl group)], and $R^{20}$ represents a hydrogen atom or a hydroxyl group.

DETAILED DESCRIPTION OF THE INVENTION

In the above formula, examples of "$C_{1-4}$ alkyl group" in the definition of $R^1$, $R^3$, $R^5$, $R^7$, $R^8$, $R^9$, $R^{10}$, $R^{11}$, $R^{12}$, $R^{13}$, $R^{14}$, $R^{16}$, $R^{17}$, $R^{18}$, $R^{19}$, $R^{21}$ and $R^{22}$ include the methyl, ethyl, propyl, isopropyl, butyl, isobutyl, sec-butyl and t-butyl group, of which the methyl and ethyl groups are preferred, the methyl group being most preferred.

$R^1$, $R^3$, $R^7$, $R^9$, $R^{10}$, $R^{11}$, $R^{12}$, $R^{16}$, $R^{18}$ and $R^{19}$ preferably represent the hydrogen atom, the methyl and ethyl group, of which the hydrogen atom and the methyl group are preferred, the hydrogen atom being most preferred.

The "substituent" of "a $C_{1-4}$ alkyl group which may have one substituent" in the definition of $R^5$, $R^{13}$, $R^{21}$ or $R^{22}$ preferably represent the amino, hydroxyl, carbamoyl, cyano and carboxy groups.

Examples of the "$C_{1-4}$ alkyl group which may have one substituent" may include the methyl, ethyl, propyl, butyl, aminoethyl, aminopropyl, hydroxyethyl, hydroxypropyl, carbamoylmethyl, carbamoylethyl, carbamoyloxyethyl, cyanomethyl, cyanoethyl, sulfamoylmethyl, sulfamoylethyl, carboxyethyl, carboxymethyl and carboxypropyl groups, of which the methyl, ethyl, 2-aminoethyl, 2-hydroxyethyl, carbamoylmethyl, cyanomethyl and carboxymethyl groups are preferred.

Examples of $R^{13}$ include the hydrogen atom and methyl, ethyl, 2-hydroxyethyl, 2-aminoethyl, carbamoylethyl, cyanomethyl and carboxymethyl groups, of which the hydrogen atom and the methyl group are preferred, the hydrogen atom being most preferred.

Examples of "a group represented by the formula —$NR^9R^{10}$" in the definition of $R^8$ may include the amino, methylamino, dimethylamino, ethylamino and diethylamino groups, of which the amino group is preferred.

Examples of $R^8$ include the hydrogen atom and methyl, ethyl, amino, methylamino, dimethylamino, ethylamino and diethylamino groups, of which the hydrogen atom, the methyl and amino groups are preferred, the amino group being most preferred.

Examples of the "group represented by the formula —C(=NH)$R^8$" in the definition of $R^5$, $R^{14}$, $R^{17}$, $R^{21}$ and $R^{22}$ include the formimidoyl, acetimidoyl and amidino groups, of which the armidino group is preferred.

Examples of $R^5$ include the hydrogen atom and the methyl, ethyl, 2-hydroxyethyl, 2-aminoethyl, carbamoylmethyl, cyanomethyl, carboxymethyl, formimidoyl, acetimidoyl and amidino groups, of which the hydrogen atom and the methyl, formimidoyl, acetimidoyl and amidino groups are preferred, the hydrogen atom, the methyl and amidino groups being more preferred; and the hydrogen atom is most preferred.

Examples of $R^{14}$ include the hydrogen atom and the methyl, ethyl, formimidoyl, acetimidoyl and amidino groups, of which the hydrogen atom, the methyl and amidino groups are preferred, the hydrogen atom and the amidino group being more preferred; and the amidino group is most preferred.

Examples of $R^{17}$ include the hydrogen atom and the methyl, ethyl, formimidoyl, acetimidoyl and amidino groups, of which the hydrogen atom, the acetimidoyl and amidino groups are preferred, the hydrogen atom and the amidino group being most preferred.

Examples of $R^{21}$ include the hydrogen atom and the methyl, ethyl, 2-hydroxyethyl, 2-aminoethyl, carbamoylmethyl, cyanomethyl, carboxymethyl, formimidoyl, acetimidoyl and amidino groups, of which the hydrogen atom and the methyl, formimidoyl, acetimidoyl and amidino groups are preferred, the hydrogen atom and the methyl and amidino groups being more preferred; and the hydrogen atom and the methyl group are most preferred.

Examples of $R^{22}$ include the hydrogen atom and the methyl, ethyl, 2-hydroxyethyl, 2-aminoethyl, carbamoylmethyl, cyanomethyl, carboxymethyl, formimidoyl, acetimidoyl and amidino groups, of which the hydrogen atom and the methyl, formimidoyl, acetimidoyl and amidino groups are preferred, the hydrogen atom and the amidino group being more preferred; and the amidino group is most preferred.

Examples of the "halogen atom" in the definition of $R^6$ include fluorine, chlorine and bromine atoms, of which the chlorine atom is preferred.

Examples of the "group represented by the formula —$NR^{11}R^{12}$" in the definition of $R^6$ include the amino, methylamino, dimethylamino, ethylamino and diethylamino groups, of which the amino group is preferred.

Examples of $R^6$ include the hydrogen atom and the hydroxyl and amino groups, of which the hydrogen atom and the hydroxyl group are preferred, the hydrogen atom being most preferred.

Examples of the "phenylene group" in the definition or B may include the 1,2-phenylene, 1,3-phenylene and 1,4-phenylene groups, of which the 1,4-phenylene group is preferred.

Examples of the "cyclohexylene group" in the definition of B may include the 1,2-cyclohexylene, 1,3-cyclohexylene and 1,4-cyclohexylene groups, of which the 1,4-cyclohexylene group is preferred.

In the definition of B, the "alkyl" part of the "phenylene alkyl group" or "cyclohexylene alkyl group" represents a linear or branched $C_{1-3}$ alkyl group. Examples may include the methyl, ethyl and propyl groups, of which the methyl and ethyl groups are preferred, the methyl group being most preferred.

Examples of the above-described "phenylenealkyl group" may include the 1,4-pheylenemethyl, 1,4-phenyleneethyl, 1,4-phenylenepropyl, 1,3-phenylenemethyl, 1,3-phenyleneethyl, 1,2-phenylenemethyl and 1,2-phenyleneethyl groups, of which the 1,4-phenylenemethyl group is preferred.

Examples of the above-described "cyclohexylenealkyl group" may include the 1,4-cyclohexylenemethyl, 1,4-cyclohexyleneethyl, 1,4-cyclohexylenepropyl, 1,3-cyclohexylenemethyl, 1,3-cyclohexyleneethyl, 1,2-cyclohexylenemethyl and 1,2-cyclohexyleneethyl groups, of which the 1,4-cyclohexylenemethyl group is preferred.

The "alkylene" part of the "alkylene group which may have one to three substituents" in the definition of B means a linear $C_{1-5}$ alkylene group. Examples may include the methylene, ethylene, trimethylene, tetramethylene and pentamethylene groups, of which the methylene, ethylene, timethylene and tetramethylene groups are preferred, the methylene, ethylene and trimethylene groups being more preferred; and the methylene group is most preferred.

The "alkyl" part of the "cyclohexylalkyl group" of the "substituents" of the above-described alkylene group is a linear $C_{1-3}$ alkyl group. Examples include the methyl, ethyl and propyl groups, of which the methyl group is preferred.

Examples of the above-described "cyclohexylalkyl group" may include the cyclohexylmethyl, cyclohexylethyl and cyclohexylpropyl groups, of which the cyclohexylmethyl group is preferred.

The "alkyl group" of the "substituents" of the above-described alkylene group is a linear or branched $C_{1-4}$ alkyl group. Examples may include the methyl, ethyl, propyl, isopropyl, butyl, isobutyl, sec-butyl and t-butyl groups, of which the methyl, ethyl, isopropyl and isobutyl groups are preferred, the methyl and isobutyl groups being more preferred; and the methyl group is most preferred.

Examples of B include the 1,4-phenylene, 1,4-cyclohexylenemethyl, methylene, methylmethylene (—CH(CH$_3$)—), ethylene, trimethylene and 2-hydroxypropylene groups, of which the methylene, methylmethylene (—CH(CH$_3$)—), ethylene, trimethylene and 2-hydroxypropylene groups are preferred, the methylene, methylmethylene (—CH(CH$_3$)—) and ethylene groups being more preferred; and the methylene group is most preferred.

A is preferably represented by the formula (A1), (A2) or (A3).

$R^4$ is preferably represented by the formula (Q2).

$R^{20}$ preferably represents a hydroxyl group.

The term "an ester residue which can be hydrolyzed in vivo" in the definition of $R^2$ means a group which can be hydrolysed by a chemical or biological method such as hydrolysis in the living body to afford a free acid or salt thereof. Whether the derivative has such a property or not can be determined by administering it to an animal such as a rat or mouse through intravenous injection and studying the body fluid of the animal after administration whether the original derivative or pharmacologically acceptable salt thereof can be detected or not. Examples of such ester residues include acyloxyalkyl, alkoxycarbonyloxyalkyl, phthalidyl groups and (2-oxo-1,3-dioxolen-4-yl)alkyl groups which may have an alkyl or aryl group at its 5-position.

The "acyl" part of the "acyloxyalkyl group" represents a linear or branched $C_{1-6}$ alkanoyl group which may be substituted by a $C_{3-6}$ cycloalkyl group, while the alkyl part represents a linear or branched $C_{1-4}$ alkyl group. Examples of the acyloxyalkyl group, may include the pivaloyloxymethyl, isobutyryloxymethyl, 1-(isobutyryloxy)ethyl, acetoxymethyl, 1-(acetoxy)ethyl, 1-methylcyclohexylcarbonyloxymethyl, 1-methylcyclopentylcarbonyloxymethyl, 2-ethylbutyryloxymethyl and hexanoyloxymethyl groups, of which the pivaloyloxymethyl, acetoxymethyl and 1-methylcyclohexylcarbonyloxymethyl groups are preferred.

The "alkoxy" part of the "alkoxycarbonyloxyalkyl group" represents a linear or branched $C_{1-8}$ alkoxy or cycloalkyloxy group, while the alkyl part represents a linear or branched $C_{1-4}$ alkyl group. Examples of the alkoxycarbonyloxyalkyl group may include the t-butoxycarbonyloxymethyl, 1-(methoxycarbonyloxy)ethyl, 1-(ethoxycarbonyloxy)ethyl, 1-(isopropoxycarbonyloxy)ethyl, 1-(t-butoxycarbonyloxy)ethyl, 1-(cyclohexylcarbonyloxy)ethyl and 1-(cyclopentylcarbonyloxy)ethyl groups, of which the 1-(isopropoxycarbonyloxy)ethyl and 1-(cyclohexylcarbonyloxy)ethyl groups are preferred.

Examples of the 1-(2-oxo-1,3-dioxolen-4-yl)alkyl group which may have an alkyl or aryl group at its 5-position may include the 2-oxo-1,3-dioxolen-4-ylmethyl, 1-(2-oxo-1,3-dioxolen-4-yl)ethyl, 5-methyl-2-oxo-1,3-dioxolen-4-ylmethyl, 1-(5-methyl-2-oxo-1,3-dioxolen-4-yl)ethyl, 5-ethyl-2-oxo-1,3-dioxolen-4-ylmethyl, 5-propyl-2-oxo-1,3-dioxolen-4-ylmethyl and 5-phenyl-2-oxo-1,3-dioxolen-4-ylmethyl groups, of which the 5-methyl-2-oxo-1,3-dioxolen-4-ylmethyl group is preferred.

$R^2$ preferably represents a hydrogen atom or an ester residue which can be hydrolyzed in vivo. Preferred examples of the ester residue include the 5-methyl-2-oxo-1,3-dioxolen-4-ylmethyl, acetoxymethyl, pivaloyloxymethyl, 1-methylcyclohexylcarbonyloxymethyl, 1-(isopropoxycarbonyloxy)ethyl and 1-(cyclohexyloxycarbonyloxy)ethyl groups, of which the hydrogen atom is most preferred.

n preferably stands for 0 or 1, of which 1 is most preferred.

p preferably stands for 0 or 1, of which 0 is most preferred.

m preferably stands for 1.

r preferably stands for 0 or 1, of which 1 is most preferred.

q preferably stands for 1 or 2, of which 1 is most preferred.

s preferably stands for 0.

t preferably stands for 0 or 1, of which 1 is most preferred.

In the group represented by the formula (A1) or (A2), there is no particular limitation of the substituent position of a group represented by the formula —$(CH_2)_p$—$NR^3R^4$ or —$(CH_2)_p$—$NR^{13}R^{21}$. When n stands for 0, the 3-position of the nitrogen-containing ring (azetidine) is preferred. When n stands for 1, the 3-position of the nitrogen-containing ring (pyrrolidine) is preferred. When n stands for 2, the 3- or 4-position of the nitrogen-containing ring (piperidine) is preferred.

There is no particular limitation of the substituent position of $R^{18}$ or $R^{19}$ in the group represented by the formula (A3).

There is no particular limitation of the substituent position of the nitrogen-containing ring in the group represented by the formula (A-4). When t stands for 0, the 3-position of said nitrogen-containing ring (azetidine) is preferred. When t stands for 1, the 3-position of said nitrogen-containing ring (pyrrolidine) is preferred. When t stands for 2, the 3- or 4-position of said nitrogen-containing ring (piperidine) is preferred.

There is no particular limitation of the substituent position of the —CO— part in the group represented by the formula (Q1), however, the 2-position of the nitrogen-containing ring is preferred in any case where m stands for 0, 1 and 2.

There is no particular limitation of the substituent position of $R^6$, but the 4-position of the pyrrolidine ring is preferred when m stands for 1.

The compound (I) can be converted into its pharmacologically acceptable salt if necessary.

Examples of the pharmacologically acceptable salt include salts of a mineral acid such as hydrochloride, hydrobromide, hydroiodide, phosphate, sulfate and nitrate; sulfonates such as methanesulfonate, ethanesulfonate, benzenesulfonate and p-toluenesulfonate; acid addition salts, for example, organic acid salts such as oxalate, tartrate, citrate, maleate, succinate, acetate, benzoate, mandelate, ascorbate, lactate, gluconate and malate; amino acid salts such as glycine salt, lysine salt, arginine salt, ornithine salt, glutamate and aspartate; inorganic salts such as lithium salt, sodium salt, potassium salt, calcium salt and magnesium salt; and salts with an organic base such as ammonium salt, triethylamine salt, diisopropylamine salt and cyclohexylamine salt. Of which the hydrochloride, hydrobromide, phosphate, sulfate, methanesulfonate, p-toluenesulfonate, oxalate, tartrate, citrate, acetate, lactate, glutamate, aspartate, sodium salt, potassium salt, ammonium salt and triethylamine salt are preferred, the hydrochloride, sulfate, methanesulfonate, citrate, acetate and lactate being more preferred; and the hydrochloride and sulfonate are most preferred.

The salt of compound (I) happens to form a hydrate or a product absorbing water when it is left alone in the air, it is prepared by the lyophilization of its aqueous solution, or recrystallization. Such salts are also included in the present invention.

The compound (I) of the present invention includes an isomer and a mixture of isomers thereof. A preferred example of the isomer is a compound which has an R configuration at the 1-position, a (5S,6S) configuration at the 5- and 6-positions similarly to thienamycin, and an R configuration at the α-position having a hydroxyl group at the substituent of the 6-position. The (2S,4S) configuration easily introduced from (2S,4R)-4-hydroxyproline is preferred as the 2- and 4- positions of the pyrrolidine part of the substituent at the 2-position of carbapenem derivatives.

Following compounds having formula (I) are preferred:

(1) compounds wherein $R^1$ represents the hydrogen atom or the methyl group;

(2) compounds wherein $R^1$ represents the hydrogen atom;

(3) compounds wherein $R^2$ represents the hydrogen atom;

(4) compounds wherein A is the group represented by the formula (A1), $R^4$ is the group represented by the formula (Q1) and
   (4-1) n stands for 0 or 1,
   (4-2) p stands for 0 or 1,
   (4-3) p stands for 0,
   (4-4) $R^3$ represents the hydrogen atom, the methyl or ethyl group,
   (4-5) $R^3$ represents the hydrogen atom or the methyl group,
   (4-6) $R^3$ represents the hydrogen atom,
   (4-7) m stands for 1,
   (4-8) $R^5$ represents the hydrogen atom or the methyl, ethyl, 2-amninoethyl, 2-hydroxyethyl, carbamoylmethyl, cyanomethyl, carboxymethyl, formimidoyl, acetimidoyl or amidino group,
   (4-9) $R^5$ represents the hydrogen atom or the methyl, formimidoyl, acetimidoyl or amidino group,
   (4-10) $R^5$ represents the hydrogen atom or the methyl or amidino group,
   (4-11) $R^5$ represents the hydrogen atom,
   (4-12) $R^6$ represents the hydrogen atom or the hydroxyl, amino, methylamino or dimethylamino group,
   (4-13) $R^6$ represents the hydrogen atom or the hydroxyl group, and
   (4-14) $R^6$ represents the hydrogen atom;

(5) compounds wherein A is the group represented by the formula (A-1), $R^4$ is the group represented by the formula (Q2) and
   (5-1) n stands for 0 or 1,
   (5-2) p stands for 0 or 1,
   (5-3) p stands for 0,
   (5-4) $R^3$ represents the hydrogen atom, the methyl or ethyl group,
   (5-5) $R^3$ represents the hydrogen atom or the methyl group, (5-6) $R^3$ represents the hydrogen atom,
(5-7) $R^7$ represents the hydrogen atom, the methyl or ethyl group,
(5-8) $R^7$ represents the hydrogen atom or the methyl group,
(5-9) $R^7$ represents the hydrogen atom,
(5-10) $R^{14}$ represents the hydrogen atom or the methyl, ethyl, formimidoyl, acetimidoyl or amidino group,
(5-11) $R^{14}$ represents the hydrogen atom, the methyl or amidino group,
(5-12) $R^{14}$ represents the hydrogen atom or the amidino group,
(5-13) $R^{14}$ represents the amidino group,
(5-14) B represents the 1,4-phenylene, 1,4-cyclohexylenemethyl, methylene, methylmethylene (—CH(CH$_3$)—), ethylene, trimethylene or 2-hydroxypropylene group,
(5-15) B represents the methylene, methylmethylene (—CH(CH$_3$)—), ethylene, trimethylene or 2-hydroxypropylene group,
(5-16) B represents the methylene, methylmethylene (—CH(CH$_3$)—) or ethylene group, and
(5-17) B represents the methylene group, respectively;
(6) compounds wherein A is the group represented by the formula (A2) and
(6-1) r stands for 0 or 1,
(6-2) r stands for 1,
(6-3) n stands for 0 or 1,
(6-4) p stands for 0 or 1,
(6-5) p stands for 0,
(6-6) $R^{13}$ represents the hydrogen atom or the methyl, ethyl, 2-aminoethyl, 2-hydroxyethyl, carbamoylmethyl, cyanomethyl or carboxymethyl group,
(6-7) $R^{13}$ represents the hydrogen atom or the methyl group,
(6-8) $R^{13}$ represents the hydrogen atom,
(6-9) $R^{20}$ represents the hydrogen atom or the hydroxyl group,
(6-10) $R^{20}$ represents the hydroxyl group,
(6-11) $R^{21}$ represents the hydrogen atom or the methyl, ethyl, 2-aminoethyl, 2-hydroxyethyl, carbamoylmethyl, cyanomethyl, carboxymethyl, formimidoyl, acetimidoyl or amidino group,
(6-12) $R^{21}$ represents the hydrogen atom or the methyl, formimidoyl, acetimidoyl or amidino group,
(6-13) $R^{21}$ represents the hydrogen atom, the methyl group or then amidino group, and
(6-14) $R^{21}$ represents the hydrogen atom or the methyl group;
(7) compounds wherein A is the group represented by the formula (A-3) and
(7-1) r stands for 0 or 1,
(7-2) r stands for 1,
(7-3) q stands for 1 or 2,
(7-4) q stands for 1,
(7-5) $R^{20}$ represents the hydrogen atom or the hydroxyl group,
(7-6) $R^{20}$ represents the hydroxyl group,
(7-7) $R^{18}$ and $R^{19}$ are the same as or different from each other and each represents the hydrogen atom or the methyl group,
(7-8) $R^{18}$ and $R^{19}$ each represents the hydrogen atom,
(7-9) $R^{22}$ represents the hydrogen atom or the methyl, ethyl, 2-aminoethyl, 2-hydroxyethyl, carbamoylmethyl, cyanomethyl, carboxymethyl, formimidoyl, acetimidoyl or amidino group,
(7-10) $R^{22}$ represents the hydrogen atom or the methyl, formimidoyl, acetimidoyl or amidino group,
(7-11) $R^{22}$ represents the hydrogen atom or the amidino group, and
(7-12) $R^{22}$ represents the amidino group;
(8) compounds wherein A is the group represented by the formula (A4) and
(8-1) r stands for 0 or 1,
(8-2) r stands for 1,
(8-3) s stands for 0,
(8-4) t stands for 0, 1 or 2,
(8-5) t stands for 1,
(8-6) $R^{16}$ represents the hydrogen atom, the methyl group or an ethyl group,
(8-7) $R^{16}$ represents the hydrogen atom or the methyl group,
(8-8) $R^{16}$ represents the hydrogen atom,
(8-9) $R^{17}$ represents the hydrogen atom or the methyl, ethyl, formimidoyl, acetimidoyl or amidino group,
(8-10) $R^{17}$ represents the hydrogen atom, the acetimidoyl or amidino group,
(8-11) $R^{17}$ represents the hydrogen atom or the amidino group,
(8-12) $R^{20}$ represents the hydrogen atom or the hydroxyl group, and
(8-13) $R^{20}$ represents the hydroxyl group, respectively; and
(9) the compound wherein A is the group represented by the formula (A1), (A2) or (A3).

In addition, compounds obtained by any combination from (1) to (9) are also preferred. Examples are:
(1) the compounds exemplified by the combination selected freely from the group consisting of (1)–(2), (3), (4-1), (4-2)–(4-3), (4-4)–(4-6), (4-7), (4-8)–(4-11) and (4-12)–(4-14),
(2) the compounds exemplified by the combination selected freely from the group consisting of (1)–(2), (3), (5-1), (5-2)–(5-3), (5-4)–(5-6), (5-7)–(5-9), (5-10)–(5-13) and (5-14)–(5-17),
(3) the compounds exemplified by the combination selected freely from the group consisting of (1)–(2), (3), (6-1)–(6-2), (6-3), (6-4)–(6-5), (6-6)–(6-8), (6-9)–(6-10) and (6-11)–(6-14),
(4) the compounds exemplified by the combination selected freely from the group consisting of (1)–(2), (3), (7-1)–(7-2), (7-3)–(7-4), (7-5)–(7-6), (7-7)–(7-8) and (7-9)–(7-12), or
(5) the compounds exemplified by the combination selected freely from the group consisting of (1)–(2), (3), (8-1)–(8-2), (8-3), (8-4)–(8-5), (8-6)–(8-8), (8-9)–(8-11) and (8-12)–(8-13).

Examples are Shown Below
(1)-1: Compounds Wherein
$R^1$ represents the hydrogen atom or the methyl group,
$R^2$ represents the hydrogen atom,
A is the group represented by the formula (A1), $R^4$ is the group represented by the formula (Q1),
n stands for 0 or 1,
p stands for 0 or 1,
$R^3$ represents the hydrogen atom, the methyl group or the ethyl group,
m stands for 0, 1 or 2,
$R^5$ represents the hydrogen atom or the methyl, ethyl, 2-aminoethyl, 2-hydroxyethyl, carbamoylmethyl, cyanomethyl, carboxymethyl, formimidoyl, acetimidoyl or amidino group, and $R^6$ represents the hydrogen atom or the hydroxyl group.

(1)-2: Compounds Wherein
$R^1$ represents the hydrogen atom,
$R^2$ represents the hydrogen atom,
A is the group represented by the formula (A1) and $R^4$ is the group represented by the formula (Q1),
n stands for 0 or 1,
p stands for 0,
$R^3$ represents the hydrogen atom or the methyl group,
m stands for 1,
$R^5$ represents the hydrogen atom or the methyl, formimidoyl, acetimidoyl or amidino group, and
$R^6$ represents the hydrogen atom or the hydroxyl group.

(1)-3: Compounds Wherein
$R^1$ represents the hydrogen atom,
$R^2$ represents the hydrogen atom,
A is the group represented by the formula (A1), $R^4$ represents the group represented by the formula (Q1),
n stands for 0 or 1,
p stands for 0
$R^3$ represents the hydrogen atom,
m stands for 1,
$R^5$ represents the hydrogen atom, the methyl or amidino group, and
$R^6$ represents the hydrogen atom.

(2)-1: Compounds Wherein
$R^1$ represents the hydrogen atom or the methyl group,
$R^2$ represents the hydrogen atom,
A is the group represented by the formula (A1), $R^4$ represents the group represented by the formula (Q2),
n stands for 0 or 1,
p stands for 0 or 1,
$R^3$ represents the hydrogen atom, the methyl or ethyl group,
$R^7$ represents the hydrogen atom, the methyl or ethyl group,
$R^{14}$ represents the hydrogen atom or the methyl, ethyl, formimidoyl, acetimidoyl or amidino group, and
B represents the 1,4-phenylene, 1,4-cyclohexylenemethyl, methylene, methylmethylene (—CH(CH$_3$)—), ethylene, trimethylene or 2-hydroxypropylene group.

(2)-2: Compounds Wherein
$R^1$ represents the hydrogen atom,
$R^2$ represents the hydrogen atom,
A is the group represented by the formula (A1), $R^4$ is the group represented by the formula (Q2),
n stands for 0 or 1,
p stands for 0,
$R^3$ represents the hydrogen atom or the methyl group,
$R^7$ represents the hydrogen atom or the methyl group,
$R^{14}$ represents the hydrogen atom, the methyl or amidino group, and
B represents the methylene, methylmethylene (—CH(CH$_3$)—), ethylene, trimethylene or 2-hydroxypropylene group.

(2)-3: Compounds Wherein
$R^1$ represents the hydrogen atom,
$R^2$ represents the hydrogen atom,
A is the group represented by the formula (A1), $R^4$ is the group represented by the formula (Q2),
n stands for 0 or 1,
p stands for 0,
$R^3$ represents the hydrogen atom,
$R^7$ represents the hydrogen atom,
$R^{14}$ represents the hydrogen atom or the amidino group, and
B represents the methylene, methylmethylene (—CH(CH$_3$)—) or ethylene group.

(3)-1: Compounds Wherein
$R^1$ represents the hydrogen atom or the methyl group,
$R^2$ represents the hydrogen atom,
A is the group represented by the formula (A2),
r stands for 0 or 1,
n stands for 0 or 1,
p stands for 0 or 1,
$R^{13}$ represents the hydrogen atom or the methyl, ethyl, 2-hydroxyethyl, 2-aminoethyl, carbamoylmethyl, cyanomethyl or carboxymethyl group,
$R^{20}$ represents the hydrogen atom or the hydroxyl group, and
$R^{21}$ represents the hydrogen atom or the methyl, ethyl, 2-aminoethyl, 2-hydroxyethyl, carbamoylmethyl, cyanomethyl, carboxymethyl, formimidoyl, acetimidoyl or amidino group.

(3)-2: Compounds Wherein
$R^1$ represents the hydrogen atom,
$R^2$ represents the hydrogen atom,
A is the group represented by the formula (A2),
r stands for 1,
n stands for 1,
p stands for 0 or 1,
$R^{13}$ represents the hydrogen atom or the methyl group,
$R^{20}$ represents the hydroxyl group, and
$R^{21}$ represents the hydrogen atom or the methyl, formimidoyl, acetimidoyl or amidino group.

(3)-3: Compounds Wherein
$R^1$ represents the hydrogen atom,
$R^2$ represents the hydrogen atom,
A is the group represented by the formula (A2),
r stands for 1,
n stands for 1,
p stands for 0 or 1,
$R^{13}$ represents the hydrogen atom,
$R^{20}$ represents a hydroxyl group, and
$R^{21}$ represents the hydrogen atom or the methyl or amidino group.

(4)-1: Compounds Wherein
$R^1$ represents the hydrogen atom or the methyl group,
$R^2$ represents the hydrogen atom,
A is the group represented by the formula (A3),
r stands for 0 or 1,
q stands for 1 or 2,
$R^{18}$ and $R^{19}$ are the same as or different from each other and each represents the hydrogen atom or the methyl group,
$R^{20}$ represents the hydrogen atom or the hydroxyl group, and $R^{22}$ represents the hydrogen atom or the methyl, ethyl, 2-aminoethyl, 2-hydroxyethyl, carbamoylmethyl, cyanomethyl, carboxymethyl, formimidoyl, acetimidoyl or amidino group.

(4)-2: Compounds Wherein
$R^1$ represents the hydrogen atom,
$R^2$ represents the hydrogen atom,
A is the group represented by the formula (A3),
r stands for 1,
q stands for 1,
$R^{18}$ and $R^{19}$ represent the hydrogen atom,
$R^{20}$ represents the hydroxyl group, and
$R^{22}$ represents the hydrogen atom or the methyl, formimidoyl, acetimidoyl or amidino group.

(4)-3: Compounds Wherein
$R^1$ represents the hydrogen atom,
$R^2$ represents a hydrogen atom,
A is the group represented by the formula (A3),
r stands for 1,
q stands for 1,
$R^{18}$ and $R^{19}$ represent the hydrogen atom,
$R^{20}$ represents the hydroxyl group, and
$R^{22}$ represents the hydrogen atom or the amidino group.

(5)-1: Compounds Wherein
$R^1$ represents the hydrogen atom or the methyl group,
$R^2$ represents the hydrogen atom,
A is the group represented by the formula (A4),
r stands for 0 or 1,
s stands for 0,
t stands for 1,
$R^{16}$ represents the hydrogen atom or the methyl group,
$R^{17}$ represents the hydrogen atom or the methyl, ethyl, formimidoyl, acetimidoyl or amidino group, and
$R^{20}$ represents the hydrogen atom or the hydroxyl group.

(5)-2: Compounds Wherein
$R^1$ represents the hydrogen atom,
$R^2$ represents the hydrogen atom,
A is the group represented by the formula (A4),
r stands for 1,
s stands for 0,
t stands for 1,
$R^{16}$ represents the hydrogen atom or the methyl group,
$R^{17}$ represents the hydrogen atom or the acetimidoyl or amidino group, and
$R^{20}$ represents the hydroxyl group.

Preferable compounds represented by the formula (I) can be exemplified in Tables 1 to 4. It should however be borne in mind that compounds (I) of the present invention are not limited to such exemplified compounds.

TABLE 1

Compound A1

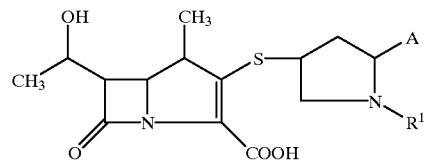

| Cpd. No. | $R^1$ | A |
|---|---|---|
| 1-1 | H | 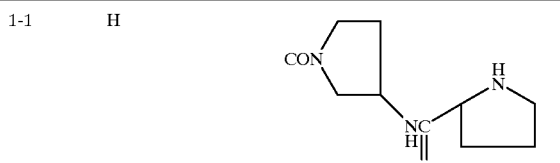 |
| 2 | H | 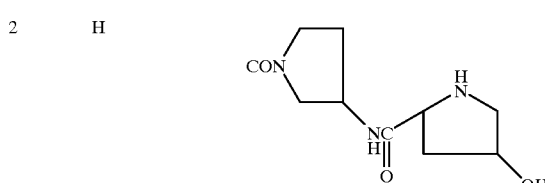 |
| 3 | H | 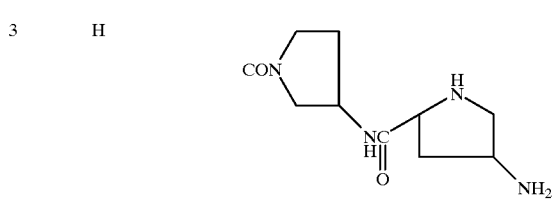 |

TABLE 1-continued
Compound A1
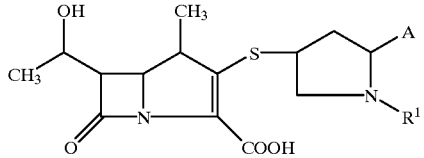
| Cpd. No. | R¹ | A |
|---|---|---|
| 4 | H | 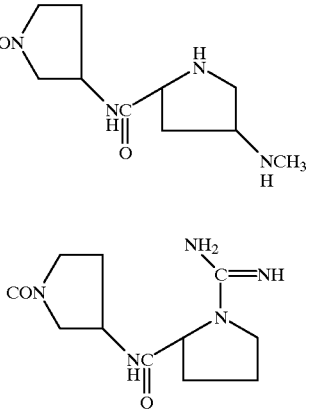 |
| 5 | H | 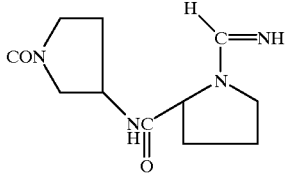 |
| 6 | H | 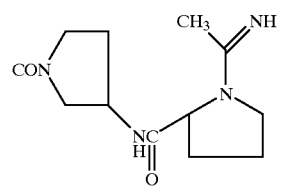 |
| 7 | H | 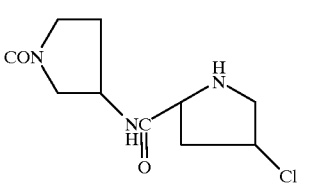 |
| 8 | H | 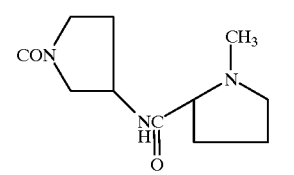 |
| 9 | H |  |

TABLE 1-continued
Compound A1
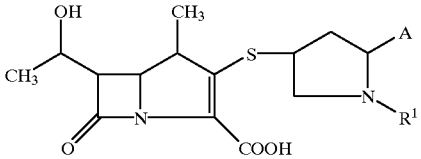
| Cpd. No. | R¹ | A |
|---|---|---|
| 10 | CH₃ | 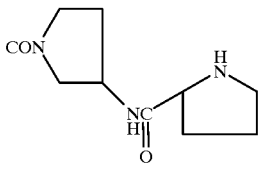 |
| 11 | H | 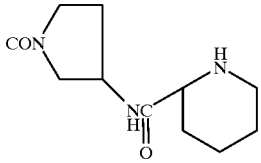 |
| 12 | H | 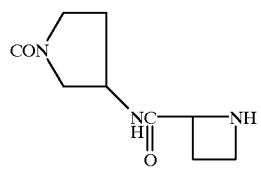 |
| 13 | H | 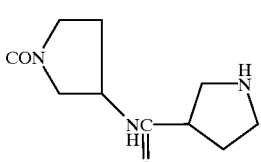 |
| 14 | H | 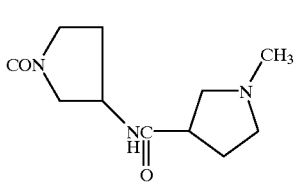 |
| 15 | H | 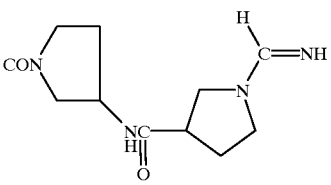 |
| 16 | H | 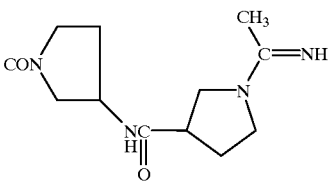 |

TABLE 1-continued

Compound A1

| Cpd. No. | R¹ | A |
|---|---|---|
| 17 | H | (3-pyrrolidinyl with N-C(=NH)NH₂ substituent, connected via NHC(=O) to azetidine-CON) |
| 18 | CH₃ | (pyrrolidin-3-yl connected via NHC(=O) to pyrrolidine-CON) |
| 19 | CH₃ | (3-pyrrolidinyl with N-C(=NH)NH₂ substituent, connected via NHC(=O) to pyrrolidine-CON) |
| 20 | H | (pyrrolidin-2-yl connected via NHC(=O) to azetidine-CON) |
| 21 | H | (N-methyl-pyrrolidin-2-yl connected via NHC(=O) to azetidine-CON) |
| 22 | H | (pyrrolidin-2-yl with N-CH=NH substituent, connected via NHC(=O) to azetidine-CON) |
| 23 | CH₃ | (pyrrolidin-2-yl with N-C(CH₃)=NH substituent, connected via NHC(=O) to azetidine-CON) |

TABLE 1-continued
Compound A1
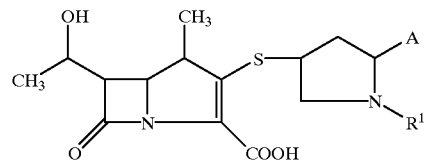
| Cpd. No. | R¹ | A |
|---|---|---|
| 24 | H | 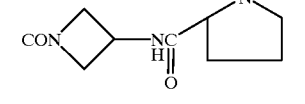 |
| 25 | H | 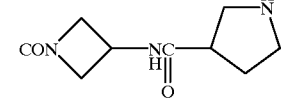 |
| 26 | H |  |
| 27 | H | 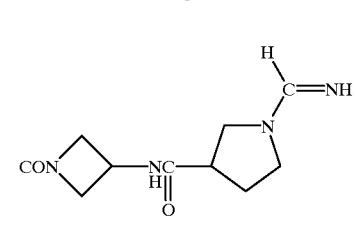 |
| 28 | H | 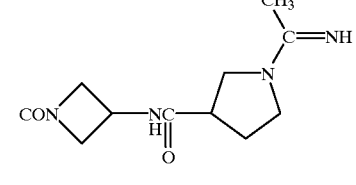 |
| 29 | H | 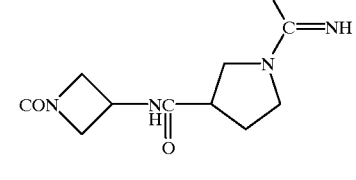 |
| 30 | CH₃ | 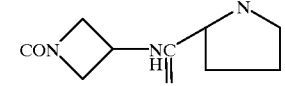 |

TABLE 1-continued
Compound A1
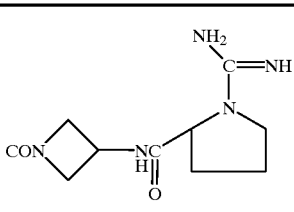
| Cpd. No. | R¹ | A |
|---|---|---|
| 31 | CH₃ | 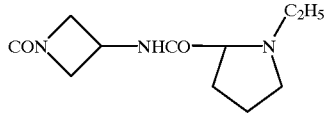 |
| 32 | H | 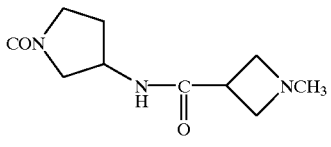 |
| 33 | H | 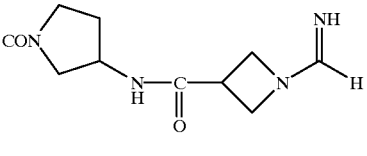 |
| 34 | H | 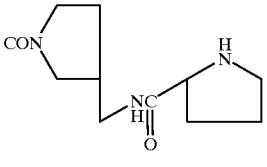 |
| 35 | H | 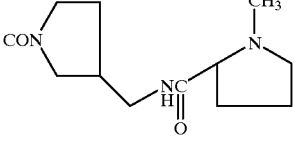 |
| 36 | H | 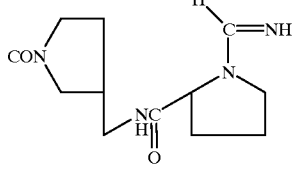 |
| 37 | H | |

TABLE 1-continued
Compound A1
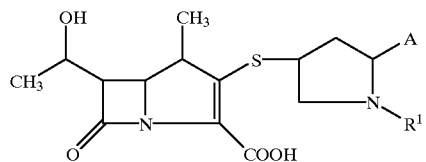
| Cpd. No. | R¹ | A |
|---|---|---|
| 38 | H | (structure) |
| 39 | H | (structure) |
| 40 | CH₃ | (structure) |
| 41 | H | (structure) |
| 42 | H | (structure) |
| 43 | H | (structure) |
| 44 | H | (structure) |

TABLE 1-continued

Compound A1

| Cpd. No. | R¹ | A |
|---|---|---|
| 45 | H | (structure) |
| 46 | H | (structure) |
| 47 | H | (structure) |
| 48 | H | (structure) |
| 49 | H | (structure) |
| 50 | H | (structure) |
| 51 | H | (structure) |

TABLE 1-continued

Compound A1

[Structure: carbapenem core with OH-CH(CH3)- group, CH3 substituent, S-linked pyrrolidine bearing N-R¹ and substituent A, with COOH and β-lactam C=O]

| Cpd. No. | R¹ | A |
|---|---|---|
| 52 | H | [pyrrolidine-CO-N, 3-position: NH-C(=O)-CH2-NH-C(=NH)-CH3] |
| 53 | H | [pyrrolidine-CO-N, 3-position: NH-C(=O)-CH2CH2-NH-C(=NH)-NH2] |
| 54 | H | [pyrrolidine-CO-N, 3-position: NH-C(=O)-CH2CH2-NH-CH=NH] |
| 55 | H | [pyrrolidine-CO-N, 3-position: NH-C(=O)-CH2CH2-NH-C(=NH)-CH3] |
| 56 | H | [pyrrolidine-CO-N, 3-position: NH-C(=O)-CH2-N(CH3)-C(=NH)-NH2] |
| 57 | CH3 | [pyrrolidine-CO-N, 3-position: NH-C(=O)-CH2-N(CH3)-C(=NH)-NH2] |
| 58 | H | [pyrrolidine-CO-N, 3-position: NH-C(=O)-CH(CH(CH3)2)-NH-C(=NH)-NH2] |

TABLE 1-continued

Compound A1

| Cpd. No. | R¹ | A |
|---|---|---|
| 59 | H | (pyrrolidine-CO-N)-NH-C(=O)-NH-CH(CH₃)-NH-C(=NH)-NH₂ |
| 60 | H | (pyrrolidine-CO-N)-NH-C(=O)-NH-CH(CH₃)-NH-CH=NH |
| 61 | H | (pyrrolidine-CO-N)-NH-C(=O)-NH-CH(CH₃)-NH-C(=NH)-CH₃ |
| 62 | H | (azetidine-CO-N)-NH-C(=O)-NH-CH₂-NH-C(=NH)-NH₂ |
| 63 | H | (azetidine-CO-N)-NH-C(=O)-NH-CH₂-NH-CH=NH |
| 64 | H | (azetidine-CO-N)-NH-C(=O)-NH-CH₂-NH-C(=NH)-CH₃ |
| 65 | H | (azetidine-CO-N)-NH-C(=O)-NH-CH₂CH₂-NH-C(=NH)-NH₂ |
| 66 | H | (azetidine-CO-N)-NH-C(=O)-NH-CH₂CH₂-NH-CH=NH |

TABLE 1-continued
Compound A1
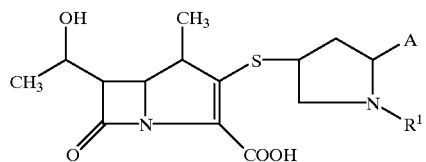
| Cpd. No. | R¹ | A |
|---|---|---|
| 67 | H | 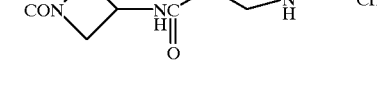 |
| 68 | H | 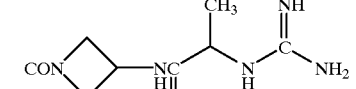 |
| 69 | H | 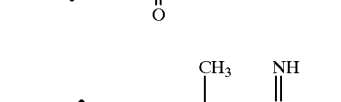 |
| 70 | H | 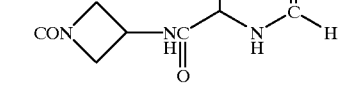 |
| 71 | H | 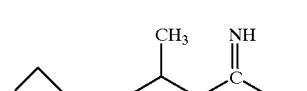 |
| 72 | H | 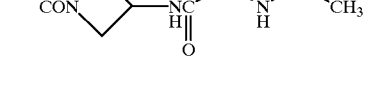 |
| 73 | H |  |
| 74 | H | 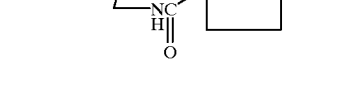 |

TABLE 1-continued

Compound A1

| Cpd. No. | R¹ | A |
|---|---|---|
| 75 | H | pyrrolidin-3-ylmethyl-NHC(=O)-NH-CH₂-NH-C(=NH)NH₂ |
| 76 | H | pyrrolidin-3-ylmethyl-NHC(=O)-NH-CH₂-NH-C(=NH)H |
| 77 | H | pyrrolidin-3-ylmethyl-NHC(=O)-NH-CH₂-NH-C(=NH)CH₃ |
| 78 | H | pyrrolidin-3-ylmethyl-NHC(=O)-NH-CH₂CH₂-NH-C(=NH)NH₂ |
| 79 | H | pyrrolidin-3-ylmethyl-NHC(=O)-NH-CH₂CH₂-NH-C(=NH)H |
| 80 | H | pyrrolidin-3-ylmethyl-NHC(=O)-NH-CH₂CH₂-NH-C(=NH)CH₃ |
| 81 | H | pyrrolidin-3-ylmethyl-NHC(=O)-NH-CH(CH₃)-NH-C(=NH)NH₂ |
| 82 | H | pyrrolidin-3-ylmethyl-NHC(=O)-NH-CH(CH₃)-NH-C(=NH)H |

TABLE 1-continued

Compound A1

| Cpd. No. | R¹ | A |
|---|---|---|
| 83 | H | pyrrolidine-CON, N(H)C(=O)-CH(CH₃)-NH-C(=NH)CH₃ |
| 84 | CH₃ | pyrrolidine-CON, N(H)C(=O)-CH₂-NH-C(=NH)NH₂ |
| 85 | CH₃ | pyrrolidine-CON, N(H)C(=O)-CH₂CH₂-NH-C(=NH)NH₂ |
| 86 | CH₃ | pyrrolidine-CON, N(H)C(=O)-CH(CH₃)-NH-C(=NH)NH₂ |
| 87 | CH₃ | pyrrolidine-CON, N(H)C(=O)-CH₂-NH-C(=NH)H |
| 88 | CH₃ | pyrrolidine-CON, N(H)C(=O)-CH₂-NH-C(=NH)CH₃ |
| 89 | CH₃ | pyrrolidine-CON, N(H)C(=O)-CH₂CH₂-NH-C(=NH)H |
| 90 | CH₃ | pyrrolidine-CON, N(H)C(=O)-CH₂CH₂-NH-C(=NH)CH₃ |

TABLE 1-continued

Compound A1

| Cpd. No. | R¹ | A |
|---|---|---|
| 91 | $CH_3$ | (3-pyrrolidinyl with N-CO-)-NH-CH($CH_3$)-NH-CH=NH |
| 92 | $CH_3$ | (3-pyrrolidinyl with N-CO-)-NH-CH($CH_3$)-NH-C(=NH)-$CH_3$ |
| 93 | H | (3-pyrrolidinyl with N-CO-)-NH-C(=O)-$CH_2$-NH-C(=NH)-N($CH_3$)$_2$ |
| 94 | H | (3-pyrrolidinyl with N-CO-)-NH-C(=O)-CH($NH_2$)-$CH_2CH_2CH_2$-NH-C(=NH)-$NH_2$ |
| 95 | $CH_3$ | (3-azetidinyl with N-CO-)-NH-C(=O)-$CH_2$-NH-C(=NH)-$NH_2$ |
| 96 | $CH_3$ | (4-piperidinyl with N-CO-)-NH-C(=O)-$CH_2$-NH-C(=NH)-$NH_2$ |
| 97 | H | (3-pyrrolidinyl with N-CO-)-NH-C(=O)-CH(OH)-$CH_2CH_2CH_2$-NH-C(=NH)-$NH_2$ |
| 98 | H | (3-piperidinyl with N-CO-)-NH-C(=O)-$CH_2$-NH-CH=NH |

TABLE 1-continued
Compound A1
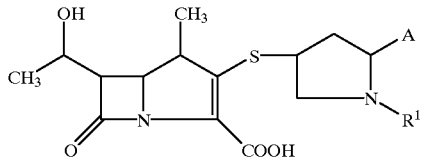
| Cpd. No. | R¹ | A |
|---|---|---|
| 99 | H | 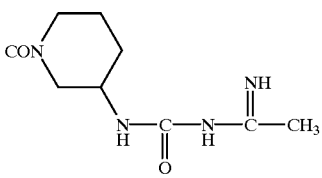 |
| 100 | H | 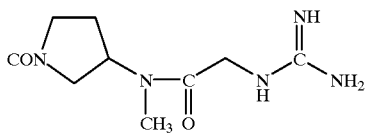 |
| 101 | H | 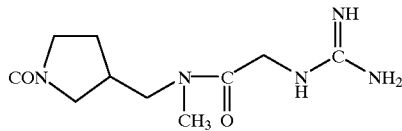 |
| 102 | H | 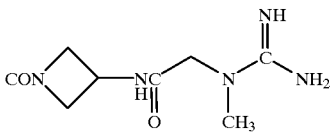 |
| 103 | CH₃ | 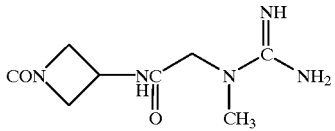 |
| 104 | CH₃ | 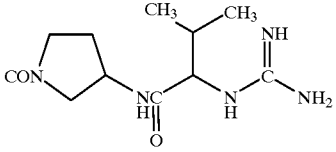 |
| 105 | H | 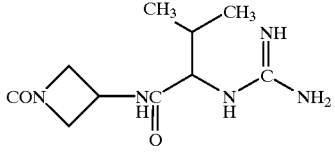 |
| 106 | CH₃ | 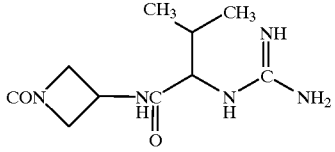 |

TABLE 1-continued
Compound A1
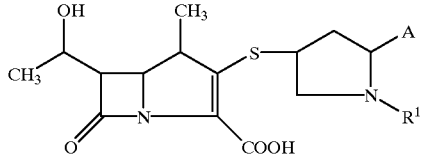
| Cpd. No. | R¹ | A |
|---|---|---|
| 107 | H | 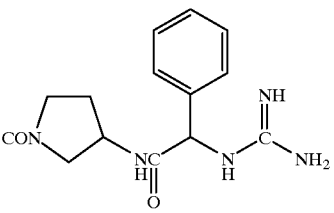 |
| 108 | CH₃ | 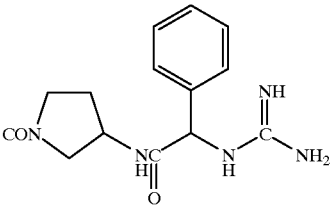 |
| 109 | H | 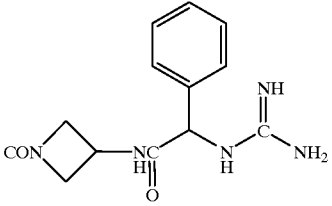 |
| 110 | CH₃ | 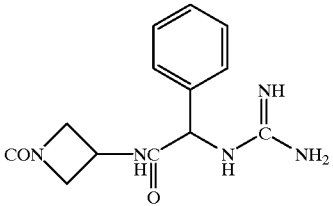 |
| 111 | H | 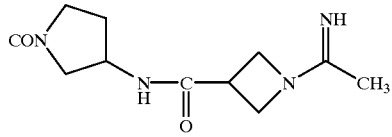 |
| 112 | H | 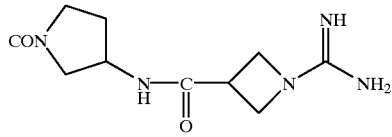 |

TABLE 1-continued
Compound A1
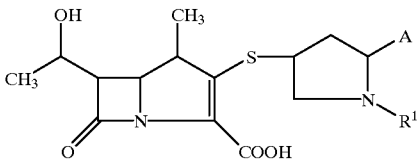
| Cpd. No. | R¹ | A |
|---|---|---|
| 113 | H | 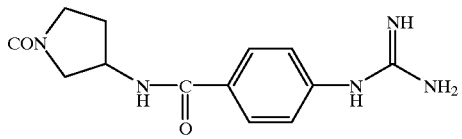 |
| 114 | H | 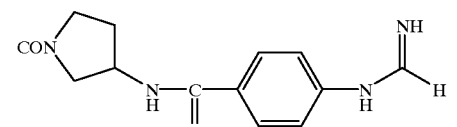 |
| 115 | H | 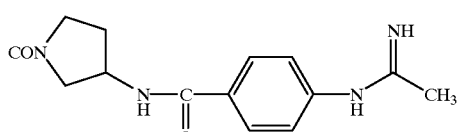 |
| 116 | H | 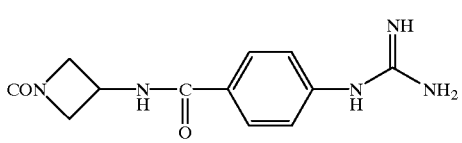 |
| 117 | H | 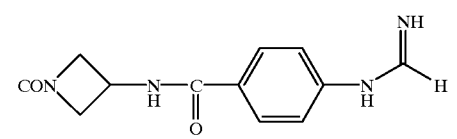 |
| 118 | H | 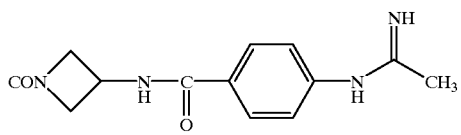 |
| 119 | H | 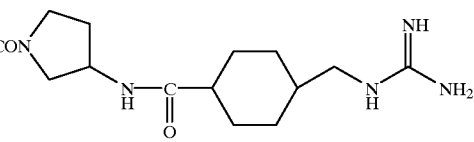 |
| 120 | H | 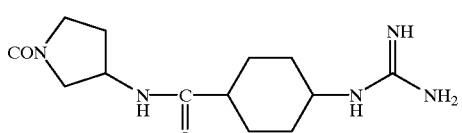 |

TABLE 1-continued
Compound A1
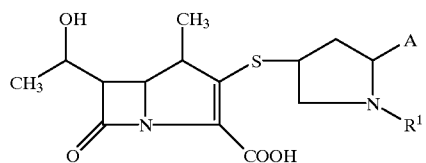
| Cpd. No. | R[1] | A |
|---|---|---|
| 121 | H |  |
| 122 | H |  |
| 123 | H |  |
| 124 | H |  |
| 125 | H | 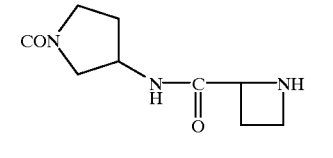 |
| 126 | H | 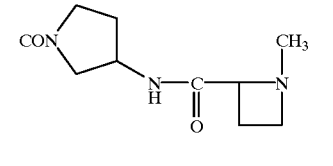 |
| 127 | H | 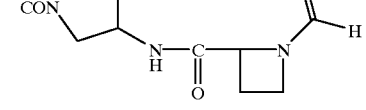 |
| 128 | H | 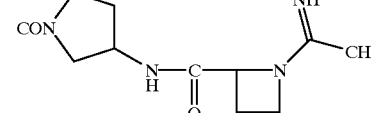 |

TABLE 1-continued
Compound A1
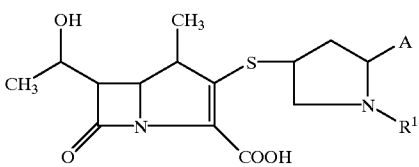
| Cpd. No. | R¹ | A |
|---|---|---|
| 129 | H | 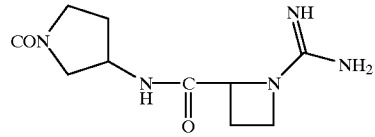 |
| 130 | H | 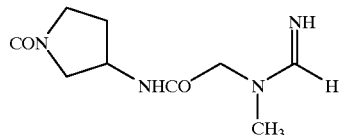 |
| 131 | H | 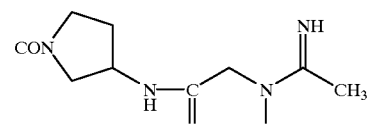 |
| 132 | H | 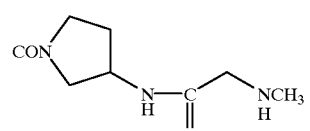 |
| 133 | H | 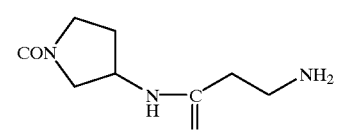 |
| 134 | H | 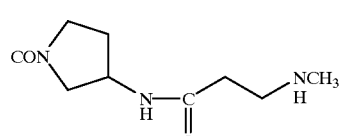 |
| 135 | H | 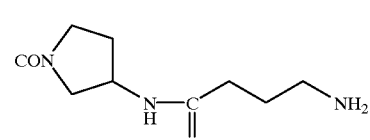 |
| 136 | H | 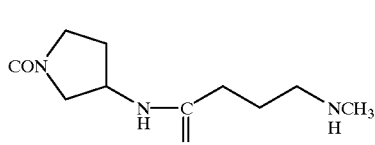 |

TABLE 1-continued
Compound A1
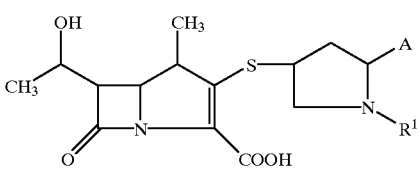
| Cpd. No. | R¹ | A |
|---|---|---|
| 137 | H | 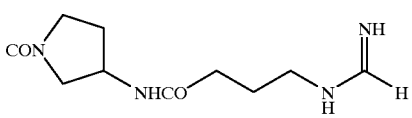 |
| 138 | H | 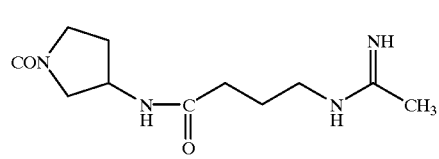 |
| 139 | H | 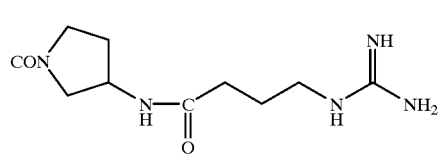 |
| 140 | H | 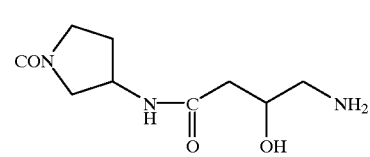 |
| 141 | H | 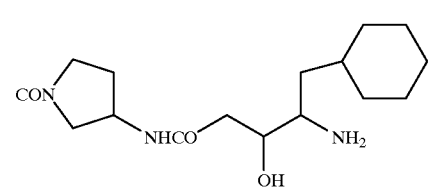 |
| 142 | H | 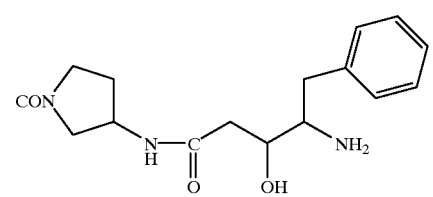 |
| 143 | H | 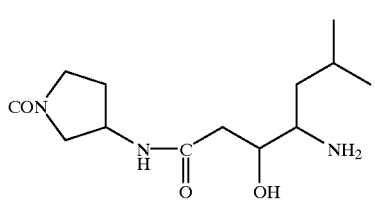 |
| 144 | H | 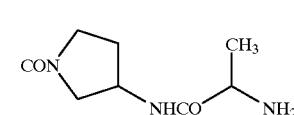 |

TABLE 1-continued
Compound A1
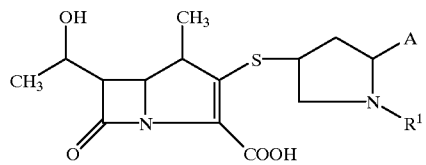
| Cpd. No. | R[1] | A |
|---|---|---|
| 145 | H | 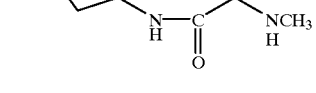 |
| 146 | H | 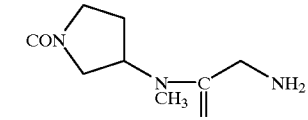 |
| 147 | H | 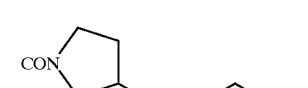 |
| 148 | H | 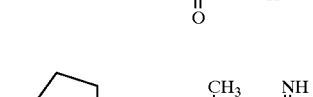 |
| 149 | H | 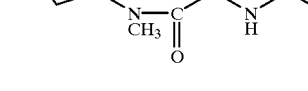 |
| 150 | H | 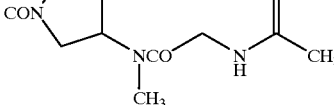 |
| 151 | H | 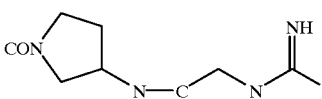 |
| 152 | H | 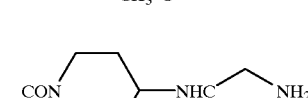 |

TABLE 1-continued
Compound A1
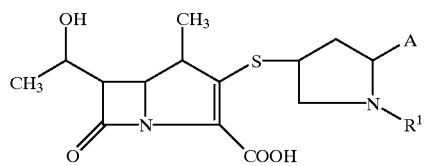
| Cpd. No. | R[1] | A |
|---|---|---|
| 153 | H | |
| 154 | H | |
| 155 | H | |
| 156 | H | |
| 157 | H | |
| 158 | H | |
| 159 | CH$_3$ | |
| 160 | CH$_3$ | |
| 161 | H | |

TABLE 1-continued

Compound A1

| Cpd. No. | R¹ | A |
|---|---|---|
| 162 | H | (pyrrolidin-3-ylmethyl)-NH-C(=O)-NH-CH₂-NHCH₃ substituent |
| 163 | H | (pyrrolidin-3-ylmethyl)-NH-C(=O)-N(CH₃)-CH₂-C(=NH)NH₂ |
| 164 | H | (pyrrolidin-3-ylmethyl)-N(CH₃)-C(=O)-CH₂-NH₂ |
| 165 | H | (pyrrolidin-3-ylmethyl)-N(CH₃)-C(=O)-CH₂-NHCH₃ |
| 167 | H | (pyrrolidin-3-ylmethyl)-N(CH₃)-C(=O)-CH₂-NH-CH=NH |
| 168 | H | (pyrrolidin-3-ylmethyl)-N(CH₃)-C(=O)-CH₂-NH-C(=NH)CH₃ |
| 169 | H | (pyrrolidin-3-yl)-N(CH₃)-C(=O)-CH₂-NH-C(=NH)NH₂ |
| 170 | H | (pyrrolidin-3-yl)-N(CH₃)-C(=O)-CH₂-N(CH₃)-C(=NH)NH₂ |

TABLE 1-continued
Compound A1
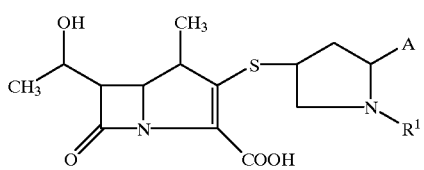
| Cpd. No. | R¹ | A |
|---|---|---|
| 171 | H | 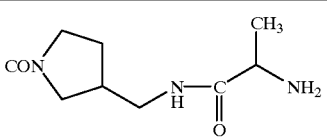 |
| 172 | H | 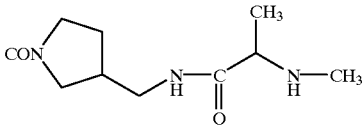 |
| 173 | H | 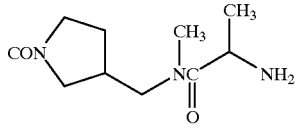 |
| 174 | H | 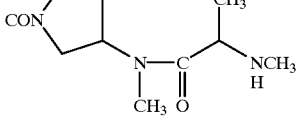 |
| 175 | H | 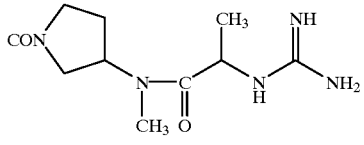 |
| 176 | H | 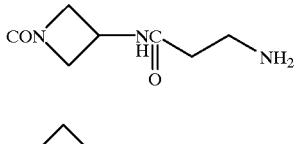 |
| 177 | H | 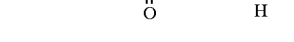 |
| 178 | H | 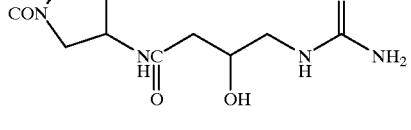 |
| 179 | H | 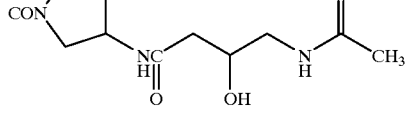 |

TABLE 1-continued
Compound A1
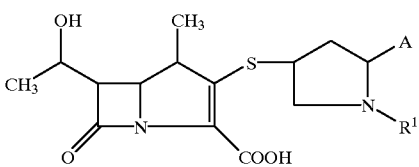
| Cpd. No. | R¹ | A |
|---|---|---|
| 180 | H | 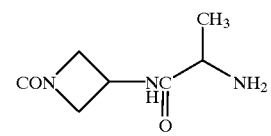 |
| 181 | H | 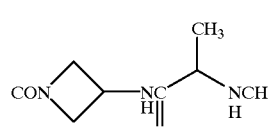 |
| 183 | H | 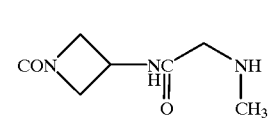 |
| 184 | H | 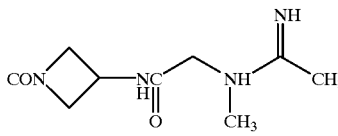 |
| 185 | H | 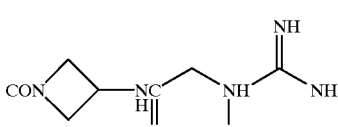 |
| 186 | H | 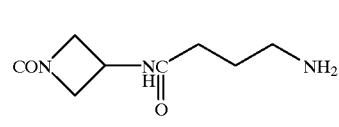 |
| 187 | H | 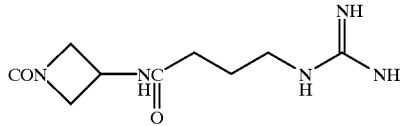 |
| 188 | H | 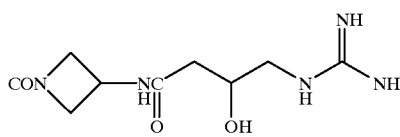 |
| 189 | H | 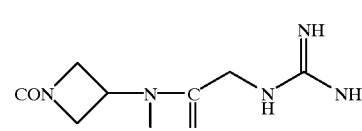 |

TABLE 2

Compound A2

[Structure: carbapenem core with OH-CH(CH3)- substituent, methyl group, and S-linked pyrrolidine bearing substituent A and N-R¹, with COOH group]

| Cpd. No. | R¹ | A |
|---|---|---|
| 2-1 | H | pyrrolidine with 2-hydroxypropanoyl on N and 3-NH₂ |
| 2 | H | pyrrolidine with 2-hydroxypropanoyl on N and 3-CH₂NH₂ |
| 3 | H | pyrrolidine with 2-hydroxypropanoyl on N and 3-NH-C(=NH)-NH₂ |
| 4 | H | pyrrolidine with 2-hydroxypropanoyl on N and 3-NH-CH=NH |
| 5 | H | pyrrolidine with 2-hydroxypropanoyl on N and 3-NH-C(CH₃)=NH |
| 6 | H | pyrrolidine with 2-hydroxypropanoyl on N and 3-NH-C(=NH)-N(CH₃)₂ |
| 7 | H | pyrrolidine with 2-hydroxypropanoyl on N and 3-NHCH₃ |
| 8 | H | pyrrolidine with 2-hydroxypropanoyl on N and 3-N(CH₃)₂ |
| 9 | H | pyrrolidine with 2-hydroxypropanoyl on N and 3-CH₂NHCH₃ |
| 10 | H | pyrrolidine with 2-hydroxypropanoyl on N and 3-CH₂N(CH₃)₂ |
| 11 | H | pyrrolidine with 2-hydroxypropanoyl on N and 3-CH₂-NH-C(=NH)-NH₂ |
| 12 | H | pyrrolidine with 2-hydroxypropanoyl on N and 3-CH₂-NH-CH=NH |
| 13 | H | pyrrolidine with 2-hydroxypropanoyl on N and 3-CH₂-NH-C(CH₃)=NH |
| 14 | H | pyrrolidine with 2-hydroxypropanoyl on N and 3-N(CH₃)-CH=NH |

TABLE 2-continued
Compound A2
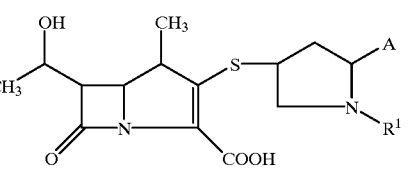
| Cpd. No. | R¹ | A |
|---|---|---|
| 15 | H | 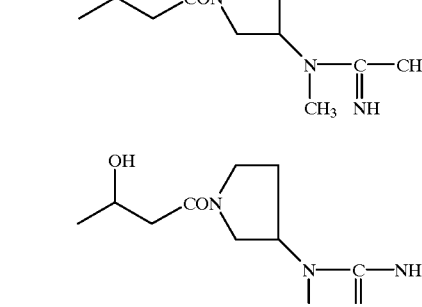 |
| 16 | H | 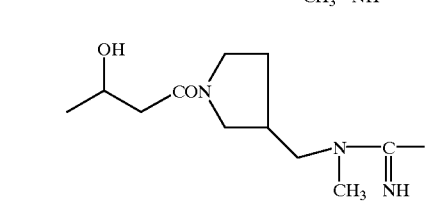 |
| 17 | H | 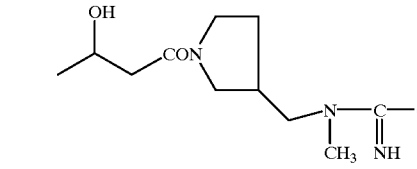 |
| 18 | H | 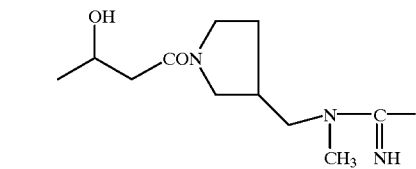 |
| 19 | H | 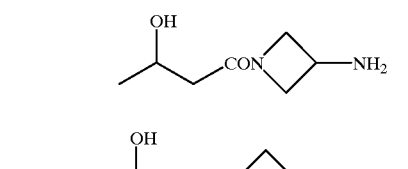 |
| 20 | H | 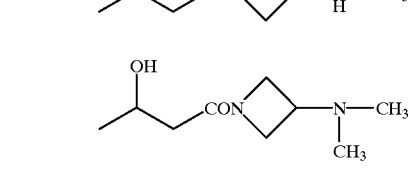 |
| 21 | H |  |
| 22 | H | 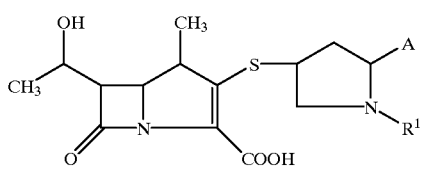 |
| 23 | H | 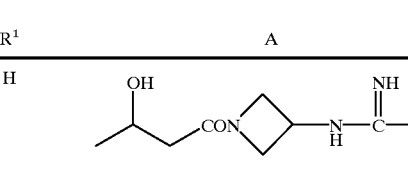 |
| 24 | H | 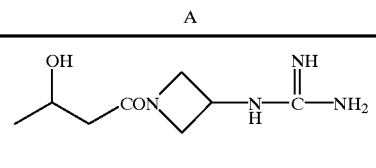 |
| 25 | H | 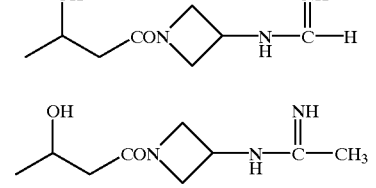 |
| 26 | H | 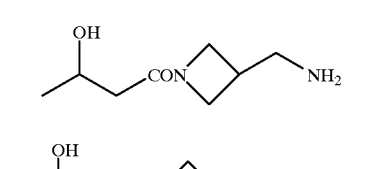 |
| 27 | H | 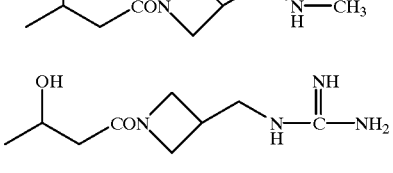 |
| 28 | H | 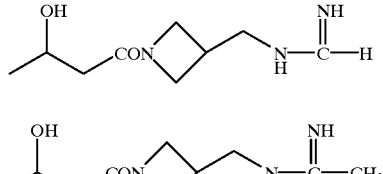 |
| 29 | H | 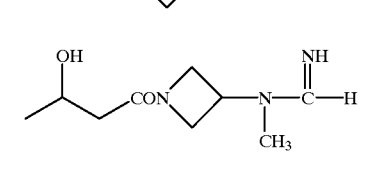 |
| 30 | H | 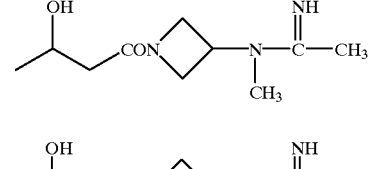 |
| 31 | H | 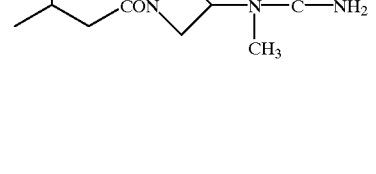 |
| 32 | H |  |
| 33 | H |  |

TABLE 2-continued

Compound A2

| Cpd. No. | R¹ | A |
|---|---|---|
| 34 | H | (3-hydroxypropanoyl-azetidin-3-yl)methyl-N-methyl-formamidine |
| 35 | H | (3-hydroxypropanoyl-azetidin-3-yl)methyl-N-methyl-acetamidine |
| 36 | H | (3-hydroxypropanoyl-azetidin-3-yl)methyl-N-methyl-guanidine |
| 37 | H | 1-(3-hydroxypropanoyl)-3-aminopiperidine |
| 38 | H | 1-(3-hydroxypropanoyl)-3-guanidinopiperidine |
| 39 | H | 1-(3-hydroxypropanoyl)-3-formamidinoaminopiperidine |
| 40 | H | 1-(3-hydroxypropanoyl)-3-acetamidinoaminopiperidine |
| 41 | H | 1-(3-hydroxypropanoyl)-3-methylaminopiperidine |
| 42 | H | 1-(3-hydroxypropanoyl)-3-(N-methylacetamidinomethyl)piperidine |
| 43 | H | 1-(3-hydroxypropanoyl)-3-(guanidinomethyl)piperidine |
| 44 | H | 1-(3-hydroxypropanoyl)-3-(formamidinoaminomethyl)piperidine |
| 45 | H | 1-(3-hydroxypropanoyl)-3-(acetamidinoaminomethyl)piperidine |
| 46 | H | 1-(3-hydroxypropanoyl)-3-(methylaminomethyl)piperidine |
| 47 | H | 1-(3-hydroxypropanoyl)-4-(aminomethyl)piperidine |
| 48 | H | 1-(3-hydroxypropanoyl)-4-(methylaminomethyl)piperidine |
| 49 | H | 1-(3-hydroxypropanoyl)-4-(guanidinomethyl)piperidine |

TABLE 2-continued
Compound A2
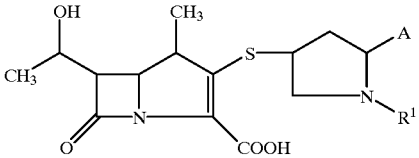
| Cpd. No. | R¹ | A |
|---|---|---|
| 50 | H | 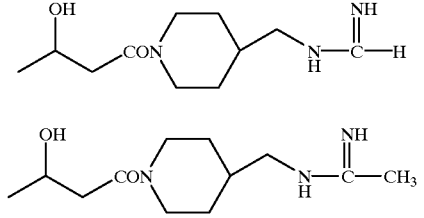 |
| 51 | H | 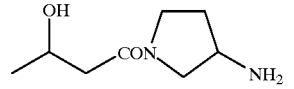 |
| 52 | CH₃ | 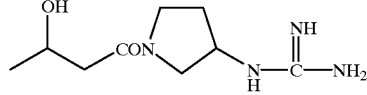 |
| 53 | CH₃ | 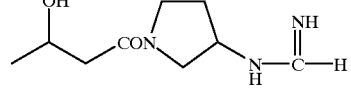 |
| 54 | CH₃ | 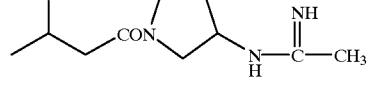 |
| 55 | CH₃ | 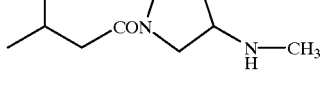 |
| 56 | CH₃ | 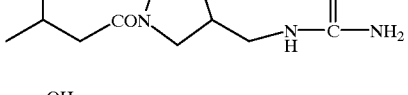 |
| 57 | CH₃ | 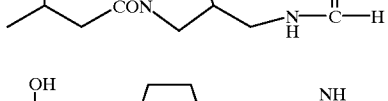 |
| 58 | CH₃ | 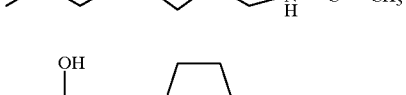 |
| 59 | CH₃ |  |
| 60 | CH₃ | 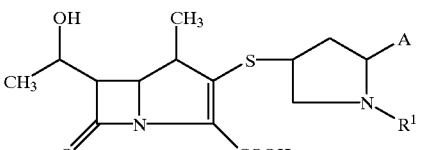 |
TABLE 2-continued
Compound A2
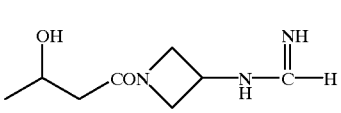
| Cpd. No. | R¹ | A |
|---|---|---|
| 61 | CH₃ | 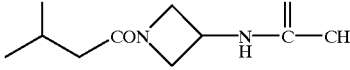 |
| 62 | CH₃ | 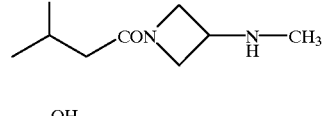 |
| 63 | CH₃ | 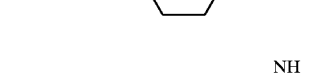 |
| 64 | CH₃ | 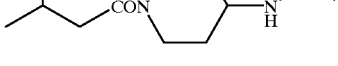 |
| 65 | H | 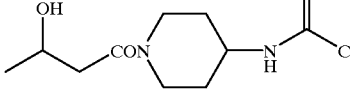 |
| 66 | H |  |
| 67 | H |  |
| 68 | H | 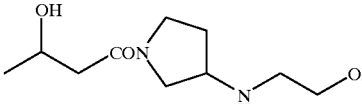 |
| 69 | H | |
| 70 | H | |

TABLE 2-continued

Compound A2

| Cpd. No. | R¹ | A |
|---|---|---|
| 71 | H | (1-propanoyl-pyrrolidin-3-yl), 3-NH₂ |
| 72 | H | (1-propanoyl-pyrrolidin-3-yl)-NH-C(=NH)-NH₂ |
| 73 | H | (1-propanoyl-pyrrolidin-3-yl)-NH-CH=NH |
| 74 | H | (1-propanoyl-pyrrolidin-3-yl)-NH-C(=NH)-CH₃ |
| 75 | H | (1-propanoyl-pyrrolidin-3-yl)-NHCH₃ |
| 76 | H | 1-(3-hydroxybutanoyl)-pyrrolidin-3-yl-NH-CH₂CH₂-NH₂ |
| 77 | H | (1-propanoyl-pyrrolidin-3-yl)-N(CH₃)₂ |
| 78 | H | (1-propanoyl-azetidin-3-yl), NH₂ |
| 79 | H | (1-propanoyl-azetidin-3-yl)-NH-C(=NH)-NH₂ |
| 80 | H | (1-propanoyl-azetidin-3-yl)-NH-CH=NH |
| 81 | H | (1-propanoyl-azetidin-3-yl)-NH-C(=NH)-CH₃ |
| 82 | H | (1-propanoyl-azetidin-3-yl)-N(CH₃)₂ |
| 83 | H | (1-propanoyl-piperidin-4-yl), NH₂ |
| 84 | H | (1-propanoyl-piperidin-4-yl)-NH-C(=NH)-NH₂ |
| 85 | H | (1-propanoyl-piperidin-4-yl)-NH-CH=NH |
| 86 | H | (1-propanoyl-piperidin-4-yl)-NH-C(=NH)-CH₃ |
| 87 | H | (1-propanoyl-piperidin-4-yl)-NHCH₃ |
| 88 | H | (1-propanoyl-piperidin-4-yl)-N(CH₃)₂ |
| 89 | H | (1-propanoyl-piperidin-3-yl)-NHCH₃ |

TABLE 2-continued

Compound A2

(structure: carbapenem core with OH-CH(CH3)- substituent, CH3, S-linked pyrrolidine bearing A and N-R¹, carbonyl, COOH)

| Cpd. No. | R¹ | A |
|---|---|---|
| 90 | H | N-propanoyl-piperidine-3-amine (CON-piperidine with NH₂) |
| 91 | H | N-propanoyl-piperidine with guanidino group (NH-C(=NH)-NH₂) |
| 92 | H | N-propanoyl-piperidine with formamidino (NH-CH=NH) |
| 93 | H | N-propanoyl-piperidine with acetamidino (NH-C(=NH)-CH₃) |
| 94 | H | N-propanoyl-piperidine-3-methyl-amine (CH₂NH₂) |
| 95 | H | N-propanoyl-piperidine-CH₂-NH-C(=NH)-NH₂ |
| 96 | H | N-propanoyl-piperidine-CH₂-NH-CH=NH |
| 97 | H | N-propanoyl-piperidine-CH₂-NH-C(=NH)-CH₃ |
| 98 | CH₃ | N-propanoyl-pyrrolidine-NH₂ |
| 99 | CH₃ | N-propanoyl-pyrrolidine with guanidino (NH-C(=NH)-NH₂) |
| 100 | CH₃ | N-propanoyl-azetidine-NH₂ |
| 101 | CH₃ | N-propanoyl-azetidine with guanidino (NH-C(=NH)-NH₂) |
| 102 | CH₃ | N-propanoyl-piperidine-NH₂ |
| 103 | CH₃ | N-propanoyl-piperidine with guanidino (NH-C(=NH)-NH₂) |
| 104 | H | N-propanoyl-pyrrolidine-NH₂ |
| 105 | H | N-propanoyl-pyrrolidine with guanidino (NH-C(=NH)-NH₂) |
| 106 | H | N-propanoyl-pyrrolidine with formamidino (NH-CH=NH) |

TABLE 2-continued
Compound A2
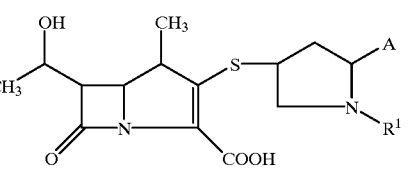
| Cpd. No. | R[1] | A |
|---|---|---|
| 107 | H | 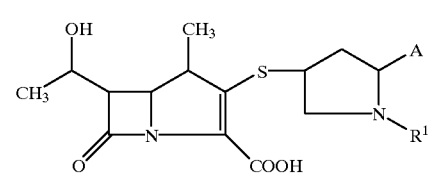 |
| 108 | H | 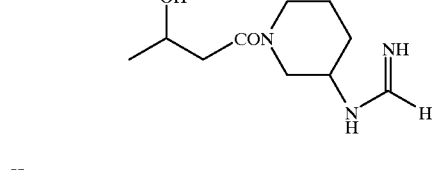 |
| 109 | H | 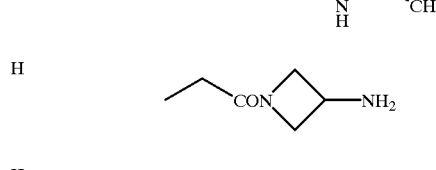 |
| 110 | H | 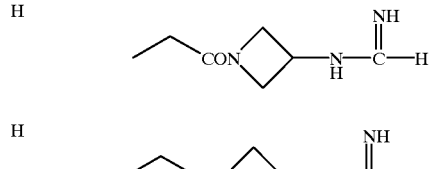 |
| 111 | H | 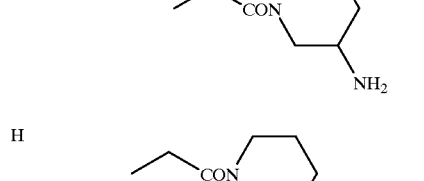 |
| 112 | H | 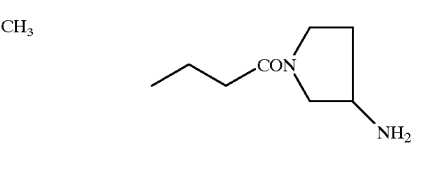 |
| 113 | H | 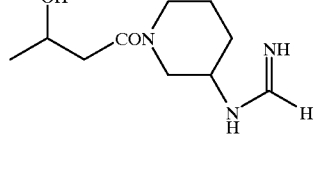 |
| 114 | H | 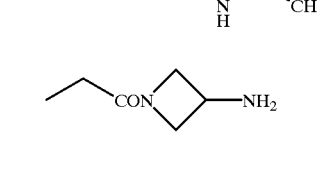 |
| 115 | H | 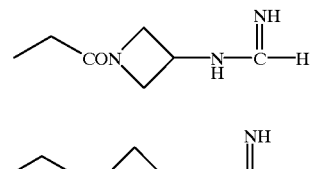 |
TABLE 2-continued
Compound A2
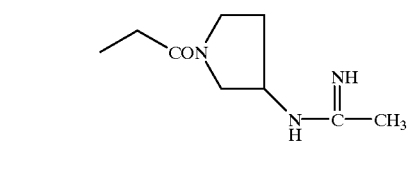
| Cpd. No. | R[1] | A |
|---|---|---|
| 116 | H | 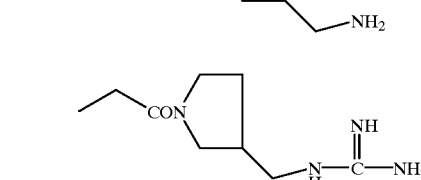 |
| 117 | H | 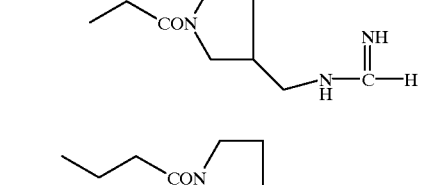 |
| 118 | H | 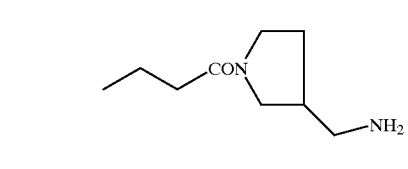 |
| 119 | H | 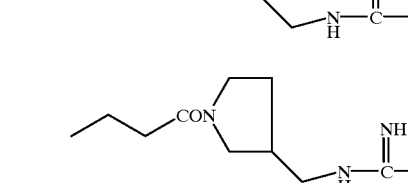 |
| 120 | H | 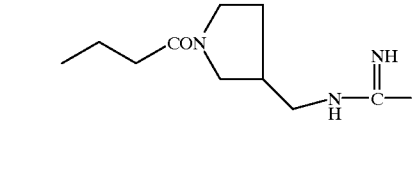 |
| 121 | H |  |
| 122 | H | 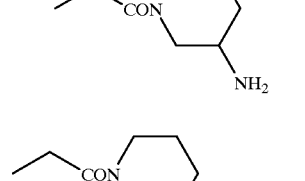 |
| 123 | H | 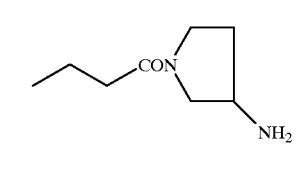 |
| 124 | CH$_3$ |  |

TABLE 2-continued

Compound A2

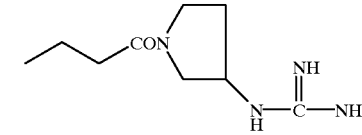

| Cpd. No. | R¹ | A |
|---|---|---|
| 125 | CH₃ | 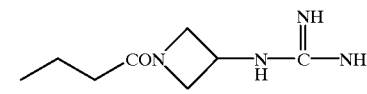 |
| 126 | CH₃ | 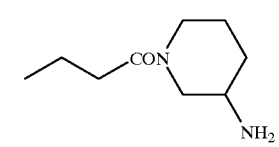 |
| 127 | CH₃ | 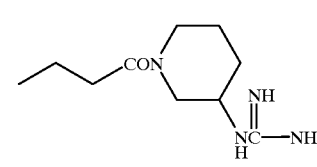 |
| 128 | CH₃ | 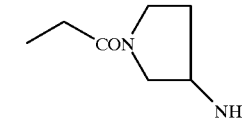 |
| 129 | CH₃ | 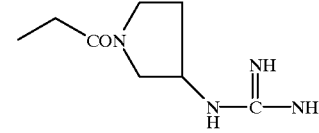 |
| 130 | CH₃ |  |
| 131 | CH₃ | 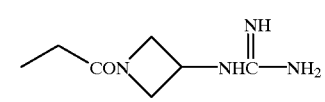 |
| 132 | CH₃ | 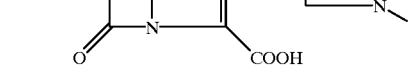 |
| 133 | CH₃ | 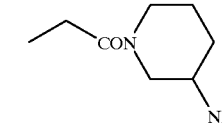 |

TABLE 2-continued

Compound A2

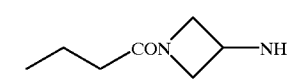

| Cpd. No. | R¹ | A |
|---|---|---|
| 134 | CH₃ | (ethyl-CON-piperidine-NH₂) |
| 135 | CH₃ | (ethyl-CON-piperidine-NHC(=NH)NH₂) |

TABLE 3

Compound A3

| Cpd. No. | R¹ | A |
|---|---|---|
| 3-1 | H | (OH-CH(CH₃)-CH₂-CO-piperazine-N-C(=NH)NH₂) |
| 2 | H | (OH-CH(CH₃)-CH₂-CO-piperazine-N-C(=NH)H) |
| 3 | H | (OH-CH(CH₃)-CH₂-CO-piperazine-N-C(=NH)CH₃) |
| 4 | H | (OH-CH(CH₃)-CH₂-CO-piperazine-NH) |
| 5 | H | (OH-CH(CH₃)-CH₂-CO-piperazine-N-CH₃) |

TABLE 3-continued

Compound A3

(structure: carbapenem with hydroxyethyl, methyl, and thio-pyrrolidine substituents bearing A and R¹ groups; COOH)

| Cpd. No. | R¹ | A |
|---|---|---|
| 6 | H | -CO-N(piperazine)N-CH₂CH(OH)- ... -CH₂CH₂OH |
| 7 | H | -CH(OH)CH₂-CO-N(piperazine)N-CH₂CONH₂ |
| 8 | H | -CH(OH)CH₂-CO-N(piperazine)N-CH₂COOH |
| 9 | H | -CH(OH)CH₂-CO-N(piperazine)N-CH₂CH₂NH₂ |
| 10 | H | -CH(OH)CH₂-CO-N(piperazine)NH |
| 11 | H | -CH(OH)CH₂-CO-N(piperazine)N-C(=NH)NH₂ |
| 12 | H | -CH(OH)CH₂-CO-N(piperazine)N-CH=NH |
| 13 | H | -CH(OH)CH₂-CO-N(piperazine)N-C(=NH)CH₃ |
| 14 | H | -CH(OH)CH₂-CO-N(piperazine)N-CH₂COOH |
| 15 | H | -CH₂CH₂-CO-N(piperazine)N-C(=NH)NH₂ |
| 16 | H | -CH₂CH₂CH₂-CO-N(piperazine)N-CH=NH |

TABLE 3-continued

Compound A3

| Cpd. No. | R¹ | A |
|---|---|---|
| 17 | H | -CH₂CH₂CH₂-CO-N(piperazine)N-C(=NH)CH₃ |
| 18 | H | -CH₂CH₂CH₂-CO-N(piperazine)NH |
| 19 | CH₃ | -CH(OH)CH₂-CO-N(piperazine)N-C(=NH)NH₂ |
| 20 | CH₃ | -CH(OH)CH₂-CO-N(piperazine)N-CH=NH |
| 21 | CH₃ | -CH(OH)CH₂-CO-N(piperazine)N-C(=NH)CH₃ |
| 22 | H | -CH₂CH₂-CO-N(piperazine)N-C(=NH)NH₂ |
| 23 | H | -CH₂CH₂-CO-N(piperazine)N-CH=NH |
| 24 | H | -CH₂CH₂-CO-N(piperazine)N-C(=NH)CH₃ |
| 25 | CH₃ | -CH(OH)CH₂-CO-N(piperazine)N-C(=NH)NH₂ |
| 26 | CH₃ | -CH(OH)CH₂-CO-N(piperazine)N-CH=NH |
| 27 | CH₃ | -CH(OH)CH₂-CO-N(piperazine)N-C(=NH)CH₃ |

TABLE 3-continued

Compound A3

Structure: carbapenem core with 1-hydroxyethyl, methyl, and thio-pyrrolidine substituents, with A on pyrrolidine and R¹ on pyrrolidine N.

| Cpd. No. | R¹ | A |
|---|---|---|
| 28 | H | -CON(piperazine)-C(=NH)-NH₂ (propyl-CO-) |
| 29 | H | -CON(piperazine)-CH=NH (propyl-CO-) |
| 30 | H | -CON(piperazine)-C(=NH)-CH₃ (propyl-CO-) |
| 31 | H | -CON(piperazine)-C(=NH)-NH₂ (ethyl-CO-) |
| 32 | H | -CON(piperazine)-CH=NH (ethyl-CO-) |
| 33 | H | -CON(piperazine)-C(=NH)-CH₃ (ethyl-CO-) |
| 34 | H | 3-hydroxybutanoyl-piperazinyl-CH₂CH₂-OH |
| 35 | H | 3-hydroxybutanoyl-piperazinyl-CH₂-CONH₂ |
| 36 | H | 3-hydroxybutanoyl-piperazinyl-CH₂CH₂-NH₂ |

TABLE 4

Compound A4

Structure: carbapenem core with 1-hydroxyethyl, methyl, and thio-pyrrolidine substituents, with A on pyrrolidine and R¹ on pyrrolidine N.

| Cpd. No. | R¹ | A |
|---|---|---|
| 4-1 | H | 3-hydroxybutanoylamino-pyrrolidine (NH) |
| 2 | H | 3-hydroxybutanoylamino-pyrrolidine, N-CH=NH |
| 3 | H | 3-hydroxybutanoylamino-pyrrolidine, N-C(=NH)CH₃ |
| 4 | H | 3-hydroxybutanoylamino-pyrrolidine, N-C(=NH)NH₂ |
| 5 | H | 3-hydroxybutanoyl-N(CH₃)-pyrrolidine (NH) |
| 6 | H | 3-hydroxybutanoyl-N(CH₃)-pyrrolidine, N-CH=NH |

TABLE 4-continued

Compound A4

[Structure: carbapenem core with OH, CH₃, S-pyrrolidine-A, N-R¹, COOH substituents]

| Cpd. No. | R¹ | A |
|---|---|---|
| 7 | H | [3-hydroxybutyryl-N(CH₃)-pyrrolidine with N-C(=NH)CH₃] |
| 8 | H | [3-hydroxybutyryl-N(CH₃)-pyrrolidine with N-C(=NH)NH₂] |
| 9 | H | [3-hydroxybutyryl-NH-pyrrolidine with N-CH₃] |
| 10 | H | [3-hydroxybutyryl-NH-CH₂-pyrrolidine (NH)] |
| 11 | H | [3-hydroxybutyryl-NH-piperidine with N-CH₃] |
| 12 | H | [3-hydroxybutyryl-NH-piperidine (NH)] |
| 13 | H | [3-hydroxybutyryl-NH-piperidine with N-CH=NH] |
| 14 | H | [3-hydroxybutyryl-NH-piperidine with N-C(=NH)CH₃] |
| 15 | H | [3-hydroxybutyryl-NH-piperidine with N-C(=NH)NH₂] |
| 16 | H | [3-hydroxybutyryl-NH-azetidine (NH)] |
| 17 | H | [3-hydroxybutyryl-NH-azetidine with N-CH₃] |
| 18 | H | [3-hydroxybutyryl-NH-azetidine with N-CH=NH] |
| 19 | H | [3-hydroxybutyryl-NH-azetidine with N-C(=NH)CH₃] |
| 20 | H | [3-hydroxybutyryl-NH-azetidine with N-C(=NH)NH₂] |

Among the compounds exemplified in the above Tables, following compounds are preferred: Compound Number No. 1-1, 1-2, 1-5, 1-6, 1-7, 1-9, 1-11, 1-12, 1-13, 1-14, 1-15, 1-16, 1-17, 1-20, 1-21, 1-22, 1-24, 1-25, 1-26, 1-27, 1-28, 1-29, 1-33, 1-34, 1-35, 1-36, 1-37, 1-38, 1-39, 1-41, 1-42, 1-43, 1-44, 1-45, 1-50, 1-51, 1-53, 1-54, 1-55, 1-56, 1-59, 1-60, 1-61, 1-62, 1-63, 1-64, 1-65, 1-66, 1-67, 1-68, 1-69, 1-70, 1-71, 1-75, 1-76, 1-77, 1-78, 1-79, 1-80, 1-81, 1-82, 1-83, 1-100, 1-101, 1-102, 1-111, 1-112, 1-125, 1-126, 1-127, 1-128, 1-129, 1-130, 1-131, 1-132, 1-133, 1-134, 1-135, 1-136, 1-137, 1-138, 1-139, 1-140, 1-144, 1-145, 1-146, 1-147, 1-148, 1-149, 1-150, 1-161, 1-162, 1-163, 1-164, 1-165, 1-167, 1-168, 1-169, 1-170, 1-171, 1-172, 1-173, 1-174, 1-175, 1-176, 1-177, 1-178, 1-179, 1-180, 1-181, 1-183, 1-184, 1-185, 1-186, 1-187, 1-188, 1-189, 2-1, 2-2, 2-3, 2-4, 2-5, 2-7, 2-8, 2-9, 2-10, 2-11, 2-12, 2-13, 2-14, 2-15, 2-16, 2-17, 2-18, 2-19, 2-20, 2-21, 2-22, 2-23, 2-24, 2-25, 2-26, 2-27, 2-28, 2-29, 2-30, 2-31, 2-32, 2-33, 2-34, 2-35, 2-36, 3-1, 3-2, 3-3, 3-4, 3-5, 3-10, 3-11, 3-12, 3-13, 4-1, 4-2, 4-3, 4-4, 4-5, 4-6, 4-7 or 4-8 or a pharmacologically acceptable salt thereof.

of which following compounds are more preferred:

2-{2-[3-(prolylamino)pyrrolidin-1-ylcarbonyl]pyrrolidin-4-ylthio}-6-(1-hydroxyethyl)-1-methyl-1-carbapen-2-em-3-carboxylic acid (Exemplified Compound 1-1), 2-{2-[3-(2-guanidinoacetylamino)pyrrolidin-1-ylcarbonyl]pyrrolidin-4-ylthio}-6-(1-hydroxyethyl)-1-methyl-1-carbapen-2-em-3-carboxylic acid (Exemplified Compound 1-50), 2-{2-{3-[2-(1-methylguanidino)acetylamino]pyrrolidin-1-ylcarbonyl}pyrrolidin-4-ylthio}-6-(1-hydroxyethyl)-1-methyl-1-carbapen-2-em-3-carboxylic acid (Exemplified Compound 1-56), 2-{2-{3-[2-guanidino-2-methylacetylamino]pyrrolidin-1-ylcarbonyl}pyrrolidin-4-ylthio}-6-(1-hydroxyethyl)-1-methyl-1-carbapen-2-em-3-carboxylic acid (Exemplified Compound 1-59), 2-{2-[3-(3-guanidinopropanoylamimo)azetidin-1-ylcarbonyl]pyrrolidin-4-ylthio}-6-(1-hydroxyethyl)-1-methyl-1carbapen-2-em-3-carboxylic acid (Exemplified Compound 1-65), 2-{2-[3-(2-guanidino-2-methylacetylamino)azetidin-1-ylcarbonyl]pyrrolidin-4-ylthio}-6-(1-hydroxyethyl)-1-methyl-1-carbapen-2-em-3-carboxylic acid (Exemplified Compound 1-68), 2-{2-{3-[N-(2-guanidinoacetyl)-N-methylamino]pyrrolidin-1-ylcarbonyl}-pyrrolidin-4-ylthio}-6-(1-hydroxyethyl)-1-methyl-1-carbapen-2-em-3-carboxylic acid (Exemplified Compound 1-150), 2-{2-[3-(4-guanidino-3-hydroxybutanoylamino)azetidin-1-ylcarbonyl]pyrrolidin-4-ylthio}-6-(1-hydroxyethyl)-1-methyl-1-carbapen-2-em-3-carboxylic acid (Exemplified Compound 1-188), 2-{2-[2-(3-aminopyrrolidin-1-ylcarbonyl)-1-hydroxyethyl]pyrrolidin-4-ylthio}-6-(1-hydroxyethyl)-1-methyl-1-carbapen-2-em-3-carboxylic acid (Exemplified Compound 2-1), 2-{2-[2-(3-aminomethylpyrrolidin-1-ylcarbonyl)-1-hydroxyethyl]pyrrolidin-4-ylthio}-6-(1-hydroxyethyl)-1-methyl-1-carbapen-2-em-3-carboxylic acid (Exemplified Compound 2-2), 2-{2-[2-(3-guanidinopyrrolidin-1-ylcarbonyl)-1-hydroxyethyl]pyrrolidin-4-ylthio}-6-(1-hydroxyethyl)-1-methyl-1-carbapen-2-em-3-carboxylic acid (Exemplified Compound 2-3), 2-{2-[2-(3-acetimidoylaminopyrrolidin-1-ylaminocarbonyl)-1-hydroxyethyl]pyrrolidin-4-ylthio}-6-(1-hydroxyethyl)-1-methyl-1carbapen-2-em-3-carboxylic acid (Exemplified Compound 2-5), 2-{2-[1-hydroxy-2-(3-methylaminopyrrolidin-1-ylcarbonyl)ethyl]pyrrolidin-4-ylthio}-6-(1-hydroxyethyl)-1-methyl-1-carbapen-2-em-3-carboxylic acid (Exemplified Compound 2-7), 2-{2-[1-hydroxy-2-(3-methylaminomethylpyrrolidin-1-ylcarbonyl)ethyl]pyrrolidin-4-ylthio}-6-(1-hydroxyethyl)-1-methyl-1-carbapen-2-em-3-carboxylic acid Exemplified Compound 2-9), 2-{2-[2-(4-guanylpiperazin-1-ylcarbonyl)-1-hydroxyethyl]pyrrolidin-4-ylthio}-6(1-hydroxyethyl)-1-methyl-1-carbapen-2-em-3-carboxylic acid (Exemplified Compound 3-1), 2-{2-[1-hydroxy-2-(piperazin-1-ylcarbonyl)ethyl]pyrrolidin-4-ylthio}-6-(1-hydroxyethyl)-1-methyl-1-carbapen-2-em-3-carboxylic acid (Exemplified Compound 3-4), 2-{2-[1-hydroxy-2-(pyrrolidin-3-ylaminocarbonyl)ethyl]pyrrolidin-4-ylthio}-6-(1-hydroxyethyl)-1-methyl-1-carbapen-2-em-3-carboxylic acid (Exemplified Compound 4-1) or 2-{2-[1-hydroxy-2-(N-methyl-N-pyrrolidin-3-ylaminocarbonyl)ethyl]pyrrolidin-4-ylthio}-6-(1-hydroxyethyl)-1-methyl-1-carbapen-2-em-3-carboxylic acid (Exemplified Compound 4-5), or a pharmacologically acceptable salt thereof.

The 1-methylcarbapenem derivative of the present invention represented by the formula (I) can be prepared by reacting a carbapenem compound represented by the following formula:

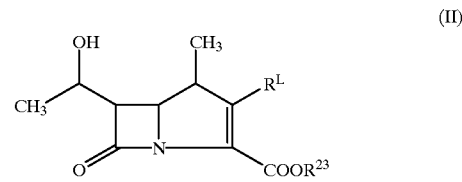

(II)

wherein $R^L$ represents a leaving group and $R^{23}$ represents a protecting group of a carboxyl group with a mercaptopyrrolidine derivative represented by the following formula:

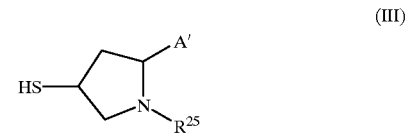

(III)

wherein $R^{25}$ represents a protecting group of an amino group or a $C_{1-4}$ alkyl group and A' has the same meaning as A except that the amino group, hydroxyl group, imino group and carboxyl group contained in the group represented by A are protected; and then removing the protecting group, if necessary. Furthermore, it can be converted into its pharmacologically acceptable salt or ester which is hydrolyzable in vivo if necessary.

Described specifically, the compound (I) of the present invention can be prepared by either one of the processes which will be illustrated below (Process A and Process B).

[Process A]

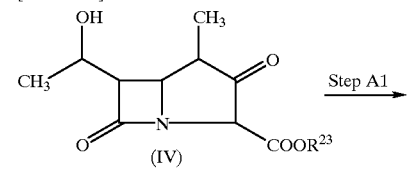

(IV)

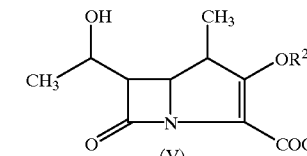

(V)

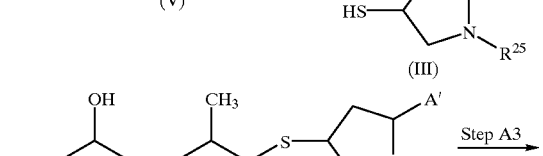

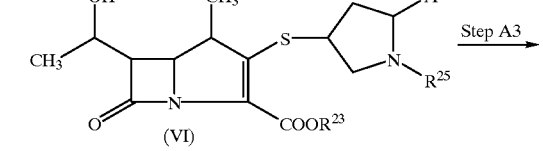

(VI)

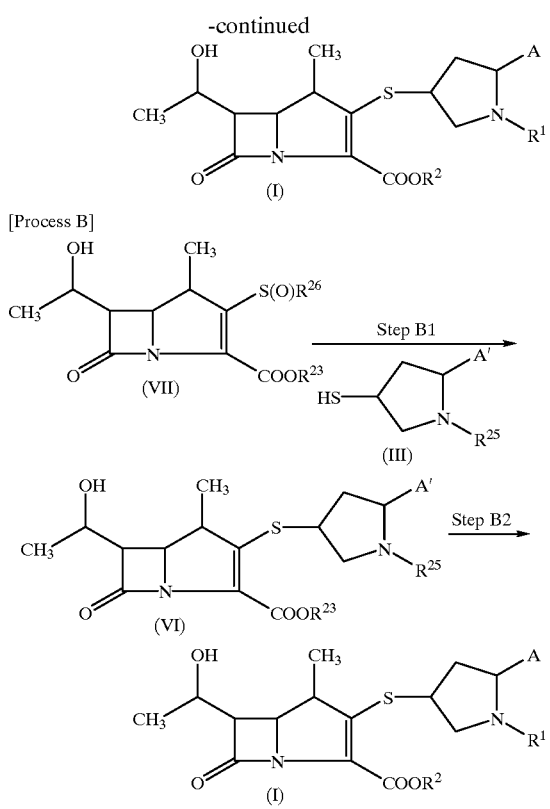

[Process B]

wherein $R^1$, $R^2$, A, $R^{23}$, $R^{25}$ and A' have the same meanings as described above.

$R^{24}$ represents a $C_{1-4}$ alkanesulfonyl group such as methanesulfonyl, trifluoromethanesulfonyl, ethanesulfonyl, propanesulfonyl, isopropanesulfonyl or butanesulfonyl; a $C_{6-10}$ arylsulfonyl group such as phenylsulfonyl, tolylsulfonyl or naphthylsulfonyl; a di-($C_{1-6}$ alkyl)phosphoryl group such as dimethylphosphoryl, diethylphosphoryl, dipropylphosphoryl, diisopropylphosphoryl, dibutylphosphoryl, dipentylphosphoryl or dihexylphosphoryl; or a di($C_{6-10}$ aryl)phosphoryl group such as diphenylphosphoryl or ditolylphosphoryl, of which the diphenylphosphoryl group is preferred.

$R^{26}$ represents a $C_{1-4}$ alkyl group such as methyl, ethyl, propyl or isopropyl; a halogeno-($C_{1-4}$ alkyl) group such as fluoromethyl, chloromethyl, fluoroethyl, chloroethyl, fluoropropyl, difluoromethyl, difluoroethyl, dichloroethyl, trifluoromethyl or trifluoroethyl; a 2-acetylaminoethyl group; a 2-acetylaminovinyl group; a $C_{6-10}$ aryl group, such as phenyl or naphthyl (said aryl group may have one to three, same or different substituents as described below. Examples of the substituent include halogen atoms such as fluorine, chlorine and bromine; $C_{1-4}$ alkyl groups such as methyl, ethyl, propyl and isopropyl; $C_{1-4}$ alkoxy groups such as methoxy, ethoxy, propoxy and isopropoxy; $C_{1-4}$ alkoxycarbonyl groups such as methoxycarbonyl, ethoxycarbonyl and t-butoxycarbonyl; a carbamoyl group and mono- or di-($C_{1-4}$ alkyl)carbamoyl groups; a nitro group; a hydroxyl group; and a cyano group); or a heteroaryl group which have one or two nitrogen atoms, such as pyridyl or pyrimidinyl (said heteroaryl group may have one to three, same or different substituents as described below. Examples of the substituent include halogen atoms and $C_{1-4}$ alkyl groups which have been exemplified above as the substituent of the aryl group).

Incidentally, the "leaving group" of $R^L$ is a group, for example, represented by the formula $R^{24}O$ or $R^{26}S(O)$.

Examples of the "protecting group of the carboxy group" of $R^{23}$ may include $C_{1-4}$ alkyl groups such as methyl, ethyl and t-butyl; $C_{7-13}$ aralkyl groups such as benzyl, diphenylmethyl, 4-methoxybenzyl, 4-nitrobenzyl and 2-nitrobenzyl which may have a substituent; alkenyl groups such as allyl, 2-chloroallyl and 2-methylallyl; haloalkyl groups such as 2,2,2-trichloroethyl, 2,2-dibromoethyl and 2,2,2-tribromoethyl, and 2-trimethylsilylethyl group. The 4-nitrobenzyl and benzyl groups are preferred.

The protecting group for the hydroxyl, amino, imino or carboxy group contained in A' or $R^{25}$ is a protecting group ordinarily used in the field of organic synthetic hemistry, of which the 4-nitrobenzyloxycarbonyl, benzyloxycarbonyl, 4-nitrobenzyl or benzyl group are preferred.

Process A is a process for the preparation of Compound (I).

Step A1 is a step for preparing a compound represented by the formula (V) by reacting a compound represented by the formula (IV), with a sulfonylating or phosphorylating agent in an inactive solvent in the presence of a base.

Examples of the sulfonylating agent may include $C_{1-4}$ alkanesulfonic anhydrides such as methanesulfonic anhydride, trifluoromethanesulfonic anhydride and ethanesulfonic anhydride; $C_{6-10}$ arylsulfonic anhydrides such as benzenesulfonic anhydride and p-toluenesulfonic anhydride, of which the p-toluenesulfonic anhydride is preferred.

Examples of the phosphorylating agent may include di($C_{1-4}$ alkyl)phosphoryl halides such as dimethylphosphoryl chloride and diethylphosphoryl chloride; and di($C_{6-10}$ aryl)phosphoryl halides such as diphenylphosphoryl chloride and diphenylphosphoryl bromide, of which the diphenylphosphoryl chloride is preferred.

There is no particular limitation on the nature of the solvent to be employed, provided that it has no adverse effect on the reaction. Examples include halogenated hydrocarbons such as methylene chloride, 1,2-dichloroethane and chloroform; nitriles such as acetonitrile; amides such as N,N-dimethylformamide and N-dimethylacetamide; esters such as ethyl acetate and methyl acetate; and ethers such as diethyl ether, tetrahydrofuran and dioxane, of which the acetonitrile, N,N-dimethylformamide and tetrahydrofuran are preferred, the acetonitrile being most preferred.

There is no particular limitation on the nature of the base to be employed, provided that it does not affect the other part of the molecule, particularly, the β-lactam ring. Preferred examples of the base include organic amines such as triethylamine, diisopropylethylamine, pyridine and 4-dimethylaminopyridine, of which diisopropylethylamine is most preferred.

Although no particular limitation is imposed on the reaction temperature, the reaction at a relatively low temperature is desired in order to suppress the side reaction. The reaction is usually carried out at temperature from −20° C. to 40° C. (preferably from −10° C. to 20° C.). The reaction time depends mainly on the reaction temperature or nature of the reaction reagent, however, a period from 10 minutes to 5 hours will usually suffice (preferably from 15 minutes to 1 hour).

After the completion of the reaction, the resulting compound (V) of the present step is obtained from the reaction mixture by a known method per se. For example, to the reaction mixture or the residue obtained by distilling off the solvent from the reaction mixture, an organic solvent which is not miscible with water is added, followed by washing with water and distilling off the organic solvent. The resulting compound so obtained can be purified, if necessary by a known method per se in the art, for example, recrystallization, reprecipitation or chromatography. It is also possible to subject the resulting compound (V) to the subsequent step without isolation, if desired.

Step A2 is a step for preparing the compound represented by the formula (VI) and it is accomplished by reacting Compound (V) with a mercaptopyrrolidine derivative represented by the formula (III) in an inactive solvent in the presence of a base.

There is no particular limitation on the nature of the solvent to be employed, provided that it has no adverse effect on the reaction. Examples include halogenated hydrocarbons such as methylene chloride, 1,2-dichloroethane and chloroform; nitriles such as acetonitrile; amides such as N,N-dimethylformamide and N,N-dimethylacetamide; esters such as ethyl acetate and methyl acetate; and ethers such as diethyl ether, tetrahydrofuran and dioxane, of which the acetonitrile, N,N-dimethylformamide and tetrahydrofuran are preferred, the acetonitrile being most preferred.

Although there is no particular limitation on the nature of the base to be employed. preferred examples may include organic amines such as triethylamine and diisopropylethylamine and inorganic bases such as potassium carbonate and sodium carbonate, of which dilsopropylethylamine is most preferred.

Although no particular limitation is imposed on the reaction temperature, the reaction is usually carried out at temperature from −20° C. to 40° C. (preferably from −10° C. to 20° C.). The reaction time ranges from 30 minutes to 108 hours (preferably from 1 hour to 18 hours).

After the completion of the reaction, the resulting compound (VI) of the present step is obtained from the reaction mixture by a known method per se. For example, to the reaction mixture or the residue obtained by distilling off the solvent from the reaction mixture, an organic solvent which is not miscible with water is added, followed by washing with water and distilling off the organic solvent. The resulting compound can be purified further, if necessary, by a known method per set, for example, recrystallization, reprecipitation or chromatography. It is also possible to subject the resulting compound (VI) to the subsequent step without isolation, if necessary.

Step A3 is a step to covert Compound (VI) to Compound (I) and it is accomplished by removing the protecting group from the compound (VI).

Although the method for removing the protecting group $R^{23}$ depends on the protecting group employed, it is generally removed by the method ordinarily employed in the field of synthetic organic chemistry. Described specifically, if the protecting group $R^{23}$ is removed by reduction, for example if it is haloalkyl, aralkyl or benzhydryl group, it may be removed by contact with reducing agent.

When the protecting group for the carboxyl group is, for example, a haloalkyl group such as 2,2-dibromoethyl or 2,2,2-trichloroethyl, a combination of zinc with acetic acid is preferred as a reducing agent.

Although there is no particular limitation on the nature of the solvent to be employed, alcohols such as methanol and ethanol, ethers such as tetrahydrofuran and dioxane, fatty acids such as acetic acid, and mixed solvents of such an organic solvent and water are preferred.

The reaction temperature usually ranges from 0° C. to 40° C. (preferably from 10° C. to 30° C). The reaction time depends on the nature of the protecting group employed or reducing agent, however, it generally ranges from 5 minutes to 12 hours (preferably from 30 minutes to 4 hours).

If the protecting group is an aralkyl group such as benzyl or 4-nitrobenzyl or a benzhydryl group, examples of the reducing agent may include catalytic hydrogenation agents such as a combination of hydrogen with palladium-carbon and alkali metal sulfides such as sodium sulfide and potassium sulfide, of which the combination of hydrogen with palladium-carbon catalyst is preferred.

Although there is no particular limitation on the nature of the solvent to be employed, provided that it has no adverse effect on the reaction, alcohols such as methanol and ethanol, ethers such as tetrahydrofuran and dioxane and mixed solvents of such an organic solvent and water are preferred.

The reaction temperature usually ranges from 0° C. to 50° C. (preferably from 10° C. to 40° C.). The reaction time depends on the protecting group employed or reducing agent, however, it usually ranges from 5 minutes to 12 hours (preferably from 30 minutes to 4 hours).

After the completion of the reaction, the resulting compound in the removing reaction of the protective group is obtained from the reaction mixture by a known method per se. For example, the resulting compound can be obtained by filtering off an insoluble matter from the reaction mixture and then distilling off the solvent.

The resulting compound (I) can be purified, if necessary, by a known method per se, for example, recrystallization, preparative thin-layer chromatography or column chromatography. It can be converted by a known method per se into an ester which can be hydrolyzed in vivo, if necessary or it can be purified as a pharmacologically acceptable salt by a known method per se.

When a protecting group of the hydroxyl, imino, amino or carboxy group (for example, in the case of a 4-nitrobenzyloxycarbonyl group or 4-nitrobenzyl group) is contained in A' or $R^{25}$, the protective group can be removed simultaneously with the above-described protective group for the carboxy group.

On the other hand, Process B is another process for the preparation of Compound (I). The raw material compound represented by the formula (VII) used in this synthetic process is prepared by the process disclosed in Japanese Patent Application Kokai No. Sho 62-30781.

Step B1 is a step for preparing the compound represented by the formula (VI). This step is accomplished by reacting Compound (VII) with a mercaptopyrrolidine derivative (III) in an inactive solvent in the presence of a base.

There is no particular limitation on the nature of the solvent to be employed, provided that it has no adverse effect on the reaction. Examples may include tetrahydrofuran, acetonitrile, dimethylformamide, dimethyl sulfoxide and water, and mixture thereof, of which the acetonitrile is preferred.

There is no particular limitation on the nature of the base to be employed, provided that it does not affect the other part of the molecule, particularly, the β-lactam ring. Examples may include organic amines such as diisopropylethylamine, triethylamine, N-methylpiperidine and 4-dimethylaminopyridine; and inorganic bases such as potassium carbonate and sodium bicarbonate, of which diisopropylethylamine is preferred.

Although no particular limitation is imposed on the reaction temperature, it is preferred to carry out the reaction at a relatively low temperature in order to suppress the side reaction. The reaction temperature usually ranges from −20° C. to 40° C. (preferably from −10° C. to 20° C.).

The reaction time mainly depends on the reaction temperature or the nature of the reagent, however, usually ranges from 15 minutes to 75 hours (preferably from 30 minutes to 18 hours).

After the completion of the reaction, the resulting compound (VI) of this step is obtained from the reaction mixture by a known method per se. To the reaction mixture or a residue available by distilling off the solvent from the reaction mixture, an organic solvent which is not miscible with water is added, followed by washing with water and distilling off the organic solvent. The resulting compound can be purified further, if necessary, by a known method per se, for example, recrystallization, reprecipitation or chromatography. It is also possible to subject the resulting compound (VI) to the subsequent step without isolation, if necessary.

When A' or $R^{25}$ contains a protecting group, the compound represented by the formula (I) can be obtained in a similar manner to the process as described in Process A, more specifically, by removing the protective group from A' or $R^{25}$ and the protective group of the carboxy group and then converting it to an ester which can be hydrolyzed in vivo, if necessary.

The compound represented by the formula (I) thus obtained by Process A or B can be converted into its pharmacologically acceptable salt by the process and technique known in the field of β-lactam antibiotics.

Incidentally, mercaptan (IV) to be used as a raw material can be prepared by the known process, for example, any one of the processes disclosed in I. Kawamoto et al., Synlett, 575 (1995), Japanese Patent Application Kokai No. Hei 2-28180, Japanese Patent Application Kokai No. Hei 2-3687, Japanese Patent Application Kokai No. Hei 4-211083 and Japanese Patent Application Kokai No. Hei 5-339269.

ADVANTAGE OF THE INVENTION

The compound represented by the above formula (I) and pharmacologically acceptable salt thereof exhibit excellent antibacterial action over a broad spectrum and has β-lactamase inhibitory activity. In addition, thienamycin compounds are apt to decompose by dehydropeptidase I in vivo of mammals, while the Compound (I) of the present invention exhibits excellent stability against dehydropeptidase I which is known as an enzyme serving as a catalyst for the inactivation of thienamycin. The Compound (I) has a high urinary recovery rate, and has weak nephrotoxicity. The Compound (I) of the present invention exhibited strong activity against a wide range of bacteria including Gram positive bacteria such as *Staphylococcus aureus* and *Bacillus subtilis*, Gram negative bacteria such as *Escherichia coli*, *Shigella* species, *Klebsiella pneumoniae*, *Proteus* species, *Serratia* species, *Enterobacter* species and *Pseudomonas aeruginosa*, and anaerobe such as *Bacteroides fragilis*. Accordingly, the Compound (I) of the present invention is useful as a preventive or remedy (preferably remedy) for microbial infections caused by the above-exemplified bacteria.

CAPABILITY OF UTILITY IN INDUSTRY

When Compound (I) or pharmacologically acceptable salt thereof is used as an antibacterial agent, it can be administered orally in the form of tablets, capsules, granules, powders or syrups by using it as is or mixing it with a necessary pharmacologically acceptable additive such as excipient or diluent; or administered parenterally in the form of injections.

The above formulations can be prepared in a known manner by using additives, examples of additive: an excipient (ex. sugar derivatives such as lactose, sucrose, glucose, mannitol or sorbitol; starch derivatives such as corn starch, potato starch, α-starch, dextrin or carboxymethyl starch; cellulose derivatives such as crystalline cellulose, low-substituted hydroxypropylcellulose, hydroxypropylmethylcellulose, carboxymethylcellulose, carboxymethylcellulose calcium or internally-cross-linked carboxymethylcellulose sodium; acacia; dextran; pullulan; silicate derivatives such as light anhydrous silicic acid, synthetic aluminum silicate or magnesium aluminometasilicate; phosphate derivatives such as calcium phosphate; carbonate derivatives such as calcium carbonate; or sulfate derivatives such as calcium sulfate), a binder (ex. the above-exemplified excipient; gelatin; polyvinylpyrrolidone; Macrogol), disintegrator (ex. the above-exemplified excipient or chemically modified starch cellulose derivative such as crosscarmellose sodium, carboxymethyl starch sodium or cross-linked polyvinylpyrrolidone), lubricant (ex. talc; stearic acid; metal salts of stearic acid such as calcium stearate or magnesium stearate; colloidal silica; veegum; wax such as spermaceti; boric acid; glycol; carboxylic acids such as fumaric acid or adipic acid; sodium carboxylate such as sodium benzoate; sulfate such as sodium sulfate; leucine; lauryl sulfate such as sodium lauryl sulfate or magnesium lauryl sulfate; silicic acid such as silicic anhydride or silicic hydrate; starch derivatives exemplified above in the excipient), stabilizer (ex. parahydroxybenzoates such as methyl p-hydroxybenzoate or propyl p-hydroxybenzoate; alcohols such as chlorobutanol, benzyl alcohol or phenylethyl alcohol; benzalkonium chloride; phenol derivatives such as phenol or cresol; thimerosal; acetic anhydride; or sorbic acid), corrigent (ex. ordinarily-employed sweeteners, souring agents or flavors), suspending agent (ex. Polysorbate 80, carboxymethylcellulose sodium), diluent or solvent for formulation (ex. water, ethanol or glycerin).

The dose of the compound of the present invention will vary, depending upon the age and condition of the patient. Orally, it is administered in an amount of 1 mg in a single dose as a lower limit (preferably 5 mg) and 2000 mg in a single dose as an upper limit (preferably 1000 mg), while intravenously, it is administered in an amount of 1 mg in a single dose as a lower limit (preferably 5 mg) and 2000 mg in a single dose as an upper limit (preferably 1000 mg). It is desired to administer the above dosage to an adult in one to six portions per day depending upon the condition of the patient.

BEST MODES FOR CARRYING OUT THE INVENTION

The present invention will hereinafter be described more specifically by examples, referential examples, tests and formulation examples. It should however be borne in mind that the present invention is not limited to or by these examples. Incidentally, in the nuclear magnetic resonance spectrum in the examples and referential examples, sodium trimethylsilylpropionate-$d_4$ was used as an internal standard for the measurement in heavy water, while tetramethylsilane was used as an internal standard in the other solvents, unless otherwise specifically indicated.

EXAMPLE 1

(1R,5S,6S)-6-(1R)-[1-Hydroxyethyl]-1-methyl-2-[(2S,4S)-2-[(3S)-3-(L-prolylamino)pyrrolidin-1-ylcarbonyl]pyrrolidin-4-ylthio]-1-carbapen-2-em-3-carboxylic acid (Exemplified Compound 1-1)

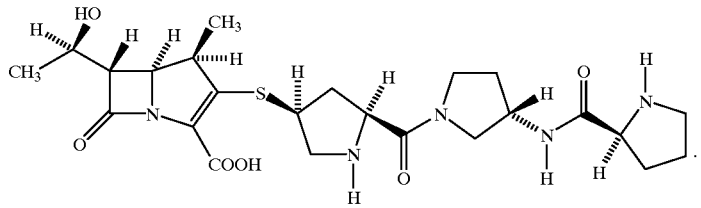

(1) To a suspension of 4-nitrobenzyl (1R,5R,6S)-6-[(1R)-1-hydroxyethyl]-1-methyl-2-(diphenylphosphoryloxy)-1-carbapen-2-em-3-carboxylate (868 mg) in anhydrous acetonitrile (13 ml), N,N-diisopropylethylamine (254 μl) and a solution of (2S,4S)-4-mercapto-1-(4-nitrobenzyloxycarboyl)-2-[(3S)-3-[1-(4-niitrobenzyloxycarbonyl)-L-prolylamino]pyrrolidin-1-ylcarbonyl]pyrrolidine (945 mg) in anhydrous acetonitrile (12 ml) were added under ice cooling while stirring. The resulting mixture was stirred overnight at 0° C. The reaction mixture was concentrated by evaporation under reduced pressure. To the residue, ethyl acetate was added. The resulting mixture was washed with water and saturated saline, dried over anhydrous magnesium sulfate and then concentrated by evaporation under reduced pressure. The residue was subjected to chromatography on a silica gel column and eluted successively with ethyl acetate-dichloromethane (1:1), methanol-ethyl acetate-dichioromethane (7:46.5:46.5) and then methanol-ethyl acetate-dichioromethane (10:45:45). Fractions containing the desired compound were combined, followed by distilling off under reduced pressure, whereby 4-nitrobenzyl (1R,5S,6S)-6-[(1R)-1-hydroxyethyl]-1-methyl- 2-[(2S,4S)-1-(4-nitrobenzyloxycarbonyl)-2-[(3S)-3-[1-(4-nitrobenzyloxycarbonyl)-L-prolylamino]pyrrolidin-1-ylcarbonyl]pyrrolidin-4-ylthio]-carbapen-2-em-3-carboxylate (1.08 g) was obtained as a powder.

Infrared absorption spectrum (KBr) νmax cm$^{-1}$:1775, 1709, 1660, 1607, 1522, 1440, 1404, 1346.

Nuclear magnetic resonance spectrum (400 MHz, CDCl$_3$) δ ppm: 1.27 (3H, dd, J=14.3, 7.5 Hz), 1.37 (3H, d, J=6.3 Hz), 1.62–2.76 (8H, m), 3.17–3.80 (9H, m), 3.85–4.57 (6H, m), 5.05–5.38 (6H, m), 5.50 (1H, dd, J=13.9,2.6 Hz), 7.40–7.53 (4H, m), 7.65 (2H, J=8.5 Hz), 8.13–8.30 (6H, m).

(2) To a solution of the compound (1.06 g), which had been obtained in (1), in tetrahydrofuran (18 ml) and water (9 ml), a 7.5% palladium-carbon catalyst (2.1 g) was added. The resulting mixture was subjected to hydrogenation reaction at an external temperature of 30° C. for 2 hours. After the completion of the reaction, the catalyst was filtered off and the filtrate was washed with diethyl ether and concentrated by evaporation under reduced pressure. The residue was subjected to reversed-phase column chromatography ["Cosmosil 75C$_{18}$-PREP" (NACALAI TESQUE, INC.)] and eluted with acetonitrile-water (5:95). Fractions containing the desired compound were combined, concentrated by evaporation under reduced pressure and then lyophilized, whereby the title compound (133.3 mg) was obtained as a powder.

Infrared absorption spectrum (KBr) νmax cm$^{-1}$: 3402, 1775, 1637, 1599, 1455, 1386, 1284, 1260.

Nuclear magnetic resonance spectrum (400 MHz, D$_2$O) δ ppm: 1.22 (3H, dd, J=7.2,2.6 Hz), 1.30 (3H, d, J=6.4 Hz), 1.55–1.74 (1H, m), 1.91–2.13 (4H, m), 2.20–2.49 (2H, m), 2.71–2.83 (1H, m), 3.06–3.15 (1H, m), 3.19–3.29 (1H, m), 3.31–3.90 (9H, m), 4.04 (1H, dt, J=22.3, 8.1 Hz), 4.19–4.35 (3H, m), 4.41–4.53 (1H, m).

EXAMPLE 2

(1R,5S,6S)-6-[(1R)-1-Hydroxyethyl]-[2-[(2S,4S)-2-[(3S)-3-(L-hydroxprolylamino)pyrrolidin-1-ylcarbonyl]pyrrolidin-4-ylthio]-1-methyl-1-carbapen-2-em-3-carboxylic acid (Exemplified Compound 1-2)

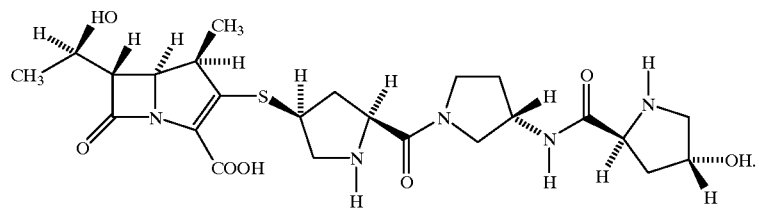

(1) By using 4-nitrobenzyl (1R,5R,6S)-6-[(1R)-1-hydroxyethyl]-1-methyl-2-(diphenylphosphoryloxy)-1-carbapen-2-em-3-carboxylate (885 mg) and (2S,4S)-4-mercapto-2-[(3S)-3-[(2S,4R)-1-(4-nitrobenzyloxycarbonyl)-4-(4-nitrobenzyloxycarbonyloxy)-L-prolylamino]pyrrolidin-1-ylcarbonyl]pyrrolidine (1.29 g), reaction and purification were carried out in a similar manner to that described in Example 1-(1), whereby 4-nitrobenzyl (1R,5R,6S)-6-[(1R)-1-hydroxyethyl]-1-methyl-2-[(2S,4S)-1-(4-nitrobenzyloxycarbonyl)-2-[(3S)-3-[1-(4-nitrobenzyloxycarbonyl)-3-(4-nitrobenzyloxycarbonyloxyl)-L-hydroxyprolylamino]pyrrolidin-1-ylcarbonyl]pyrrolidin-4-ylthio]-1-carbapen-2-em-3-carboxylate (1.19 g) was obtained as a pale yellow amorphous substance.

Infrared absorption spectrum (KBr) vmax cm$^{-1}$: 3392, 1754, 1710, 1660, 1608, 1523, 1438, 1404, 1346, 1264.

Nuclear magnetic resonance spectrum (400 MHz, CDCl$_3$) δ ppm: 1.23–1.43 (6H, m), 1.90–2.76 (6H, m), 3.18–4.57 (16H, m), 5.03–5.35 (8H, m), 5.45–5.55 (1H, m), 7.36–7.70 (8H, m), 8.08–8.28 (8H, m).

(2) In a similar manner to that described in Example 1-(2), the compound (1.16 g) obtained in (1) was subjected to hydrogenation reaction and purification, whereby the title compound (118 mg) was obtained as a powder.

Infrared absorption spectrum (KBr) vmax cm$^{-1}$: 3365, 1754, 1638, 1596, 1452, 1387, 1287, 1263.

Nuclear magnetic resonance spectrum (400 MHz, D$_2$O) δ ppm: 1.22 (3H, d, J=6.8 Hz), 1.30 (3H, d, J=6.4 Hz), 1.64–1.81 (1H, m), 1.96–2.16 (2H, m), 2.20–2.44 (2H, m), 2.76–2.92 (1H, m), 3.15–3.95 (11H, m), 4.13–5.43 (5H, m), 4.64 (1H, bs).

EXAMPLE 3

(1R,5S,6S)-6-[(1R)-1-Hydroxyethyl]-1-methyl-2-[(2S,4S)-2-[(3S)-3-(1-methyl-L-prolylamino)pyrrolidin-1-ylcarbonyl]pyrrolidin-4-ylthio]-1-carbapen-2-em-3-carboxylic acid (Exemplified Compound 1-9)

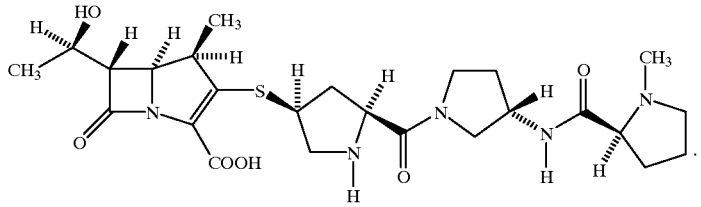

(1) By using 4-nitrobenzyl (1R,5R,6S)-6-[(1R)-1-hydroxyethyl]-1-methyl-2-(diphenylphosphoryloxy)-1-carbapen-2-em-3-carboxylate (1.14 g) and (2S,4S)-4-mercapto-2-[(3S)-3-(1-methyl-L-prolylamino]pyrrolidin-1-ylcarbonyl)-1-(4-nitrobenzyloxycarbonyl)pyrrolidine (1.03 g), reaction and purification were carried out in a similar manner to that described in Example 1-(1), whereby 4-nitrobenzyl (1R,5S,6S)-6-[(1R)-1-hydroxyethyl]-1-methyl-2-[(2S,4)-1-(4-nitrobenzyloxycarbonyl)-2-[(3S)-3-(1-methyl-L-prolylamino)pyrrolidin-1-ylcarbonyl]pyrrolidin-4-ylthio]-1-carbapen-2-em-3-carboxylate (803 mg) was obtained.

Infrared absorption spectrum (KBr) vmax cm$^{-1}$: 3352, 1774, 1711, 1656, 1607, 1522, 1445, 1404, 1346.

Nuclear magnetic resonance spectrum (400 MHz, CDCl$_3$) δ ppm: 1.18–1.30 (3H, m), 1.37 (2H, d, J=6.3 Hz), 1.50–2.45 (12H, m), 2.60–2.75 (1H, m), 2.88 (1H, bs), 3.00–4.60 (12H, m), 5.05–5.53 (5H, m), 7.40–7.55 (2H, m), 7.65 (2H, d, J=8.6 Hz), 8.17–8.28 (4H, m).

(2) In a similar manner to that described in Example 1-(2), the compound (400 mg) obtained in (1) was subjected to hydrogenation reaction and purification, whereby the title compound (114.3 mg) was obtained as a powder.

Infrared absorption spectrum (KBr) vmax cm$^{-1}$: 3409, 1758, 1651, 1604, 1558, 1455, 1383, 1284, 1257.

Nuclear magnetic resonance spectrum (400 MHz, D$_2$O) δ ppm: 1.22 (3H, dd, J=7.1, 3.3 Hz), 1.30 (3H, d, J=6.4 Hz), 1.58–1.76 (1H, m), 1.93–2.55 (6H, m), 2.74–2.88 (1H, m), 2.79 (3H, d, J=5.2 Hz), 2.98–3.20 (2H, m), 3.25–3.94 (10H, m), 4.06–4.32 (3H, m), 4.43–4.53 (1H, m).

EXAMPLE 4

(1R,5S,6S)-6-[(1R)-1-Hydroxyethyl]-1-methyl-2-[(2S,4S)-2-[(3S)-3-(piperidin-2-ylcarbonylamino)pyrrolidin-1-ylcarbonyl]pyrrolidin-4-ylthio]-1-carbapen-2-em-3-carboxylic acid (Exemplified Compound 1-11)

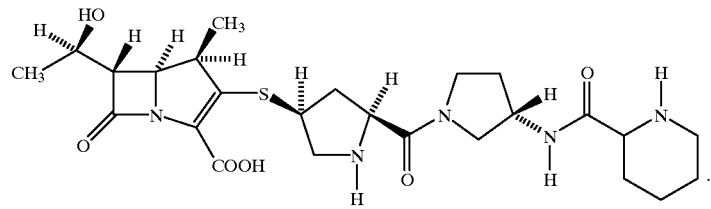

(1) By using 4-nitrobenzyl (1R,5R,6S)-6-[(1R)-1-hydroxyethyl]-1-methyl-2-(diphenylphosphoryloxy)-1-carbapen-2-em-3-carboxylate (885 mg) and (2S,4S)-4-mercapto-1-(4-nitrobenzyloxycarbonyl)-2-[(3S)-3-[1-(4-nitrobenzyloxycarbonyl)-piperidin-2-ylcarbonylamino]pyrrolidin-1-ylcarbonyl]pyrrolidine (1.03 g), reaction and purification were carried out in a similar manner to that described in Example 1-(1), whereby 4-nitrobenzyl (1R,5S, 6S)-6-[(1R)-1-hydroxyethyl]-1-methyl-2-[(2S,4S)-1-(4-nitrobenzyloxycarbonyl)-2-[(3S)-3-[1-(4-nitrobenzyloxycarbonyl)piperidin-2-ylcarbonylamnino]pyrrolidin-1-ylcarbonyl]pyrrolidin-4-ylthio]-1-carbapen-2-em-3-carboxylate (1.18 g) was obtained as a pale yellow amorphous substance.

Infrared absorption spectrum (KBr) vmax cm$^{-1}$: 338, 1775, 1707, 1607, 1522, 1439, 1346.

Nuclear magnetic resonance spectrum (400 MHz, CDCl₃) δ ppm: 1.18–2.40 (10H, bm), 1.23–1.33 (3H, m), 1.37 (3H, d, J=6.2 Hz), 2.52–2.75 (1H, m), 3.23–3.92 (7H, m), 3.94–4.33 (4H, m), 4.40–4.65 (2H, m), 4.72 (1H, bs), 5.00–5.40 (6H, m), 5.55 (1H, d, J=13.7 Hz), 7.38–7.58 (4H, m), 7.65 (2H, d, J=8.6 Hz), 8.12–8.32 (6H, m).

(2) The compound (1.16 g) obtained in (1) was subjected to hydrogenation reaction and purification in a similar manner to that described in Example 1-(2). An isomer (R- or S-form) (66.2 mg) at the 2-position of piperidine having a high polarity was obtained from the fraction eluted firstly in the reversed-phase chromatography.

Infrared absorption spectrum (KBr) νmax cm⁻¹: 3407, 3276, 1756, 1637, 1597, 1453, 1386, 1285.

Nuclear magnetic resonance spectrum (400 MHz, D₂O) δ ppm: 1.22 (3H, dd, J=7.1,2.1 Hz), 1.30 (3H, d, J=6.4 Hz), 1.53–1.76 (4H, m), 1.83–2.17 (4H, m), 2.19–2.38 (1H, m), 2.70–2.82 (1H, m), 2.97–3.13 (2H, m), 3.17–3.26 (1H, m), 3.36–3.52 (4H, m), 3.52–3.88 (5H, m), 4.02 (1H, dt, J=23.4, 8.2 Hz), 4.19–4.31 (2H, m), 4.39–4.50 (1H, m).

From the fraction eluted secondly, an isomer (R- or S-form) (78.2 mg) at the 2-position of the piperidine having a low polarity was obtained.

Infrared absorption spectrum (KBr) νmax cm⁻¹:3280, 1757,1634,1596, 1453, 1386, 1285, 1182, 1147.

Nuclear magnetic resonance spectrum (400 MHz, D₂O) δ ppm: 1.22 (3H, t, J=6.7 Hz), 1.30 (3H, dd, J=6.2, 2.1 Hz), 1.52–1.77 (4H, m), 1.83–2.36 (5H, m), 2.65–2.80 (1H, m), 2.95–3.14 (2H, m), 3.16–3.25 (1H, m), 3.29–3.89 (9H, m), 3.95–4.08 (1H, m), 4.19–4.32 (2H, m), 4.39–4.48 (1H, m).

EXAMPLE 5

(1R,5S,6S)-2-[(2S,4S)-2-[(3S)-3-[(2S)-Azetidin-2-ylcarbonylamino]pyrrolidin-1-ylcarbonyl]pyrrolidin-4-ylthio]-6-[(1R)-1-hydroxyethyl]-1-methyl-1-carbapen-2-em-3-carboxylic acid (Exemplified Compound 1-12)

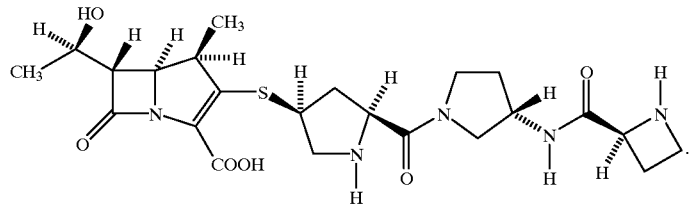

(1) By using 4-nitrobenzyl (1R,5R,6S)-6-[(1R)-1-hydroxyethyl]-1-methyl-2-(diphenylphosphoryloxy)-1-carbapen-2-em-3-carboxylate (960 mg) and (2S,4S)-4-mercapto-1-(4-nitrobenzyloxycarbonyl)-2-[(3S)-3-[(2S)-1-(4-nitrobenzyloxycarbonyl)azetidin-2-ylcarbonylamino]pyrrolidin-1-ylcarbonyl]pyrrolidine (1.06 g), reaction and purification were carried out in a similar manner to that described in Example 1-(1), whereby 4-nitrobenzyl (1R,5S,6S)-6-[(1R)-1-hydroxyethyl]-1-methyl-2-[(2S,4S)-1-(4-nitrobenzyloxycarbonyl)-2-[(3S)-3-[(2S)-1-(4-nitrobenzyloxycarbonyl)azetidin-2-ylcarbonylamino]pyrrolidin-1-ylcarbonyl]pyrrolidin-4-ylthio]-1-carbapen-2-em-3-carboxylate (1.14 g) was obtained as a powder.

Infrared absorption spectrum (KBr) νmax cm⁻¹: 3378, 1774, 1712, 1659, 1607, 1522, 1440, 1403, 1346.

Nuclear magnetic resonance spectrum (400 MHz, CDCl₃) δ ppm: 1.20–1.34 (3H, m), 1.36 (3H, d, J=6.1 Hz), 1.55–2.80 (6H, m), 3.20–3.33 (1H, m), 3.33–4.20 (9H, m), 4.2–4.33 (2H, m), 4.37–4.60 (2H, m), 4.60–4.80 (1H, m), 5.00–5.35 (6H, m), 5.45–5.55 (1H, m), 7.38–7.70 (6H, m), 8.12–8.30 (6H, m).

(2) The compound (1.12 g) obtained in (1) was subjected to hydrogenation reaction and purification in a similar manner to that described in Example 1-(2), whereby the target compound (84.7 mg) was obtained as a powder.

Infrared absorption spectrum (KBr) νmax cm⁻¹: 3415, 1756, 1641, 1605, 1453, 1385, 1283.

Nuclear magnetic resonance spectrum (400 MHz, CDCl₃) δ ppm: 1.22 (3H, dd, J=7.2,3.5 Hz), 1.30 (3H, d, J=6.3 Hz), 1.62–1.78 (1H, m), 1.93–2.13 (1H, m), 2.17–2.40 (1H, m), 2.47–2.65 (1H, m), 2.75–2.93 (2H, m), 3.10–3.20 (1H, m), 3.25–3.80 (7H, m), 3.82–4.00 (2H, m), 4.08–4.35 (4H, m), 4.43–4.57 (1H, m), 5.04 (1H, dd, J=9.3, 7.6 Hz).

EXAMPLE 6

(1R,5S,6S)-6-[(1R)-1-Hydroxyethyl]-1-methyl-2-[(2S,4S)-2-[3-(L-prolylamino)-azetidin-1-ylcarbonyl]pyrrolidin-4-ylthio]-1-carbapen-2-3-carboxylic acid (Exemplified Compound 1-20)

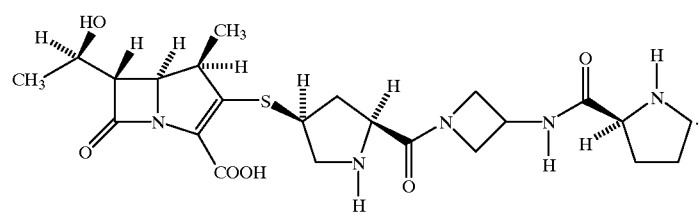

(1) To a solution of 4-nitrobenzyl (1R,5R,6S)-6-[(1R)-1-hydroxyethyl]-1-methyl-2-(diphenylphosphoryloxy)-1-carbapen-2-em-3-carboxylate (701 mg) in anhydrous N,N-dimethylformamide (DMF) (10 ml), N,N-diisopropylethylamine (206 μl) and a solution of (2S,4S)-4-mercapto-1-(4-nitrobenzyloxycarbonyl)-2-[3-[1-(4-nitrobenzyloxycarbonyl)-L-prolylamino)azetidin-1-ylcarbonyl]pyrrolindine (770 mg) in anhydrous DMF (35 ml) were added while stirring at −20° C. The resulting mixture was stirred overnight at −20° C. To the reaction mixture, ethyl acetate was added. The resulting mixture was washed with water and saturated saline, dried over anhydrous magnesium sulfate and then concentrated by evaporation under reduced pressure. The residue was subjected to chromatography on a silica gel column in a similar manner to that described in Example 1-(1), whereby 4-nitrobenzyl (1R,5S,6S)-6-[(1R)-1-hydroxyethyl]-1-methyl-2-[(2S,4S)-1-(4-nitrobenzyloxycarbonyl)-2-[3-[1-(4-nitrobenzyloxycarbonyl)-L-prolylamino)azetidin-1-ylcarbonyl]pyrrolidin-4-ylthio]-1-carbapen-2-em-3-carboxylate (816 mg) was obtained.

Infrared absorption spectrum (KBr) νmax cm$^{-1}$: 1775, 1709, 1664, 1608, 1522, 1346.

Nuclear magnetic resonance spectrum (270 MHz, DMSO-d$_6$) δ ppm: 1.08–1.27 (6H, m), 1.60–1.95 (4H, bm), 2.00–2.30 (1H, b), 2.60–2.85 (1H, b), 3.00–4.55 (16H, m), 5.00–5.35 (4H, m), 5.30, 5.46 (each 1H, d, J=13.9), 7.37–7.80 (6H, m), 8.10–8.32 (6H, m), 8.53–8.80 (1H, b).

(2) The compound (790 mg) obtained in (1) was subjected to hydrogenation reaction and purification in a similar to that described in Example 1-(2), whereby the title compound (99.8 mg) was obtained as a powder.

Infrared absorption spectrum (KBr) νmax cm$^{-1}$: 3416, 1754, 1645, 1597, 1461, 1386, 1287, 1263, 1182, 1150.

Nuclear magnetic resonance spectrum (400 MHz, D$_2$O) δ ppm: 1.22 (3H, d, J=7.2 Hz), 1.33 (3H, d, J=6.2 Hz), 1.64–1.75 (1H, m), 1.97–2.12 (3H, m), 2.38–2.46 (1H, m), 2.60–2.74 (1H, m), 3.00–3.10 (1H, m), 3.17–3.29 (1H, m), 3.32–3.49 (4H, m), 3.74–3.93 (2H, m), 3.95–4.05 (1H, m), 4.14–4.30 (3H, m), 4.32–4.48 (2H, m), 4.57–4.75 (2H, m).

EXAMPLE 7

(1R,5S,6S)-6-[(1R)-1-Hydroxyethyl]-1-methyl-2-[(2S,4S)-2-[(3S)-3-(D-prolylamino)pyrrolidin-1-ylcarbonyl]pyrrolidin-4-ylthio]-1-carbapen-2-em-3-carboxylic acid (Exemplified Compound 1-1)

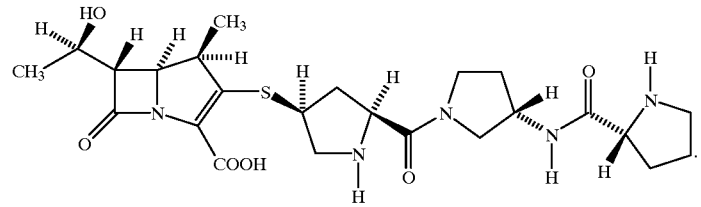

The title compound can be obtained in a similar manner to that described in Example 1-(1) and (2) by using 4-nitrobenzyl (1R,5R,6S)-6-[(1R)-1-hydroxyethyl]-1-methyl-2-(diphenylphosphoryloxy)-1-carbapen-2-em-3-carboxylate and (2S,4S)-4-mercapto-1-(4-nitrobenzyloxycarbonyl)-2-[(3S)-3-[1-(4-nitrobenzyloxycarbonyl)-D-prolylamino]pyrrolidin-1-ylcarbonyl]pyrrolidine.

EXAMPLE 8

(1R,5S,6S)-2-[(2S,4S)-2-[(3S)-3-(Guanidinoacetylamino)pyrrolidin-1-ylcarbonyl]-pyrrolidin-4-ylthio]-6-(1R)-1-hydroxyethyl]-1-methyl-1-carbapen-2-em-3-carboxylic acid (Exemplified Compound 1-50)

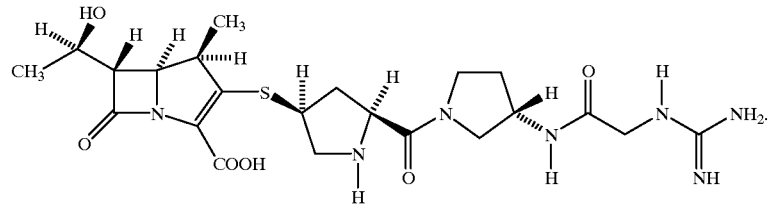

(1) By using 4-nitrobenzyl (1R,5R,6S)-6-[(1R)-1-hydroxyethyl]-1-methyl-2-(diphenylphosphoryloxy)-1-carbapen-2-em-3-carboxylate (697 mg) and (2S,4S)-4-mercapto-1-(4-nitrobenzyloxycarbonyl)-2-[(3S)-3-[(4-nitrobenzyloxycarbonyl)guanidinoacetylamino]pyrrolidin-1-ylcarbonyl]pyrrolidine (751 mg), reaction and purification were carried out in a similar manner to that described in Example 1-(1), whereby 4-nitrobenzyl (1R,5S,6S)-2-[(2S,4S)-1-(4-nitrobenzyloxycarbonyl)-2-[(3S)-3-[(4-nitrobenzyloxycarbonyl)guanidinoacetylamino]pyrrolidin-1-ylcarbonyl]pyrrolidin-4-ylthio]-6-[(1R)-1-hydroxyethyl]-1-methyl-1-carbapen-2-em-3-carboxylate (563 mg) was obtained as a powder.

Infared absorption spectrum (KBr) νmax cm$^{-1}$: 3389, 1771, 1706, 1652, 1608, 1522, 1444, 1405, 1383, 1347.

Nuclear magnetic resonance spectrum (400 MHz, DMSO-d$_6$) δ ppm: 1.10–1.25 (6H, m), 1.62–2.18 (3H, m), 2.70–2.90 (1H, m), 3.10–4.37 (14H, m), 4.43–4.68 (1H, m), 5.03–5.27 (4H, m), 5.30, 5.46 (each 1H, d, J=14.1 Hz), 7.46–7.77 (6H, m), 8.15–8.33 (6H, m).

(2) The compound (542 mg) obtained in (1) was subjected to hydrogenation reaction and purification in a similar manner to that described in Example 1-(2), whereby the title compound (90.8 mg) was obtained as a powder.

Infrared absorption spectrum (KBr) νmax cm$^{-1}$: 3340, 1754, 1665, 1634, 1452, 1390.

Nuclear magnetic resonance spectrum (400 MHz, D$_2$O) δ ppm: 1.01 (3H, dd, J=7.3, 3.4 Hz), 1.10 (3H, d, J=6.4 Hz), 1.33–1.52 (1H, m), 1.73–1.90 (1H, m), 1.97–2.15 (1H, m), 2.47–2.58 (1H, m), 2.81–2.92 (1H, m), 2.94–3.03 (1H, m), 3.13–3.31 (3H, m), 3.31–3.67 (4H, m), 3.73–3.87 (3H, m), 3.97–4.09 (2H, m), 4.20–4.30 (1H, m).

EXAMPLE 9

(1R,5S,6S)-2-[(2S,4S)-2-[(3S)-3-(L-Arginylamino)pyrrolidin-1-ylcarbonyl]pyrrolidin-4-ylthio]-6-[(1R)-1-hydroxyethyl]-1-methyl-1-carbapen-2-em-3-carboxylic acid (Exemplified Compound 1-94)

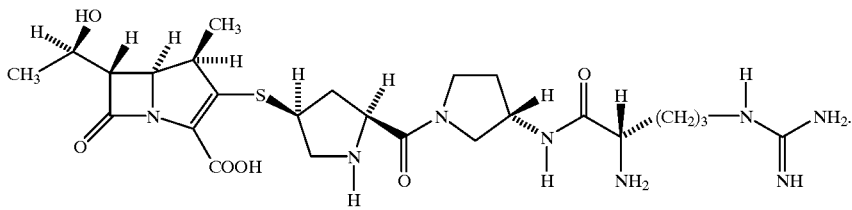

(1) To a suspension of 4-nitrobenzyl (1R,5R,6S)-6-[(1R)-1-hydroxyethyl]-1-methyl-2-(diphenylphosphoryloxy)-1-carbapen-2-em-3-carboxylate (624 mg) in anhydrous acetonitrile (10 ml), N,N-diisopropylethylamine (183 μl) and a solution of (2S,4S)-4-mercapto-1-(4-nitrobenzyloxycarbonyl)-2-[(3S)-3-[α,ω-di(4-nitrobenzyloxycarbonyl)-L-arginylamino]pyrrolidin-1-ylcarbonyl]pyrrolidine (953 mg) in anhydrous acetonitrile (10 ml) was added while stirring under ice cooling. The resulting mixture was stirred overnight at 0° C. The reaction mixture was concentrated by evaporation under reduced pressure. Ethyl acetate was then added to the residue. The resulting mixture was washed with water and saturated saline, dried over anhydrous magnesium sulfate and then concentrated by evaporation under reduced pressure. The residue was subjected to chromatography on a silica gel column and eluted successively with benzene-acetonitrile (1:1), and then methanol-benzene-acetonitrile of ratio from (3:48.5:48.5), (4:48:48) to (5:47.5:47.5). Fractions containing the desired compound were combined, followed by distilling off under reduced pressure, whereby 4-nitrobenzyl (1R,5R,6S)-6-[(1R)-1-hydroxyethyl]-1-methyl-2-[(2S,4S)-1-(4-nitrobenzyloxycarbonyl)-2-[(3S)-3-[α,ω-di(4-nitrobenzyloxycarbonyl)-L-arginylamino]pyrrolidin-1-ylcarbonyl]pyrrolidin-4-ylthio]-1-2-em-3-carboxylate (645 mg) was obtained as a powder.

Infrared absorption spectrum (KBr) νmax cm$^{-1}$: 3385, 1773, 1712, 1652, 1607, 1521, 1441, 1403, 1381, 1346.

Nuclear magnetic resonance spectrum (400 MHz, DMSO-d$_6$) δ ppm: 1.00–1.25 (6H, m), 1.30–2.20 (7H, m), 2.70–2.90 (1H, m), 2.95–4.35 (15H, m), 4.42–4.70 (1H, m), 5.00–5.50 (8H, m), 7.47–7.79 (8H, m), 8.12–8.32 (8H, m).

(2) The compound (603 mg) obtained in (1) was subjected to hydrogenation reaction and purification in a similar manner to that described in Example 1-(2), whereby the title compound (97.4 mg) was obtained as a powder.

Infrared absorption spectrum (KBr) νmax cm$^{-1}$: 3352, 1753, 1634, 1454, 1390, 1286, 1263, 1183.

Nuclear magnetic resonance spectrum (400 MHz, D$_2$O) δ ppm: 1.21 (3H, t, J=7.8 Hz), 1.30 (3H, d, J=6.3 Hz), 1.40–1.74 (5H, m), 1.45–2.12 (1H, m), 2.17–2.38 (1H, m), 2.65–2.81 (1H, m), 3.00–3.10 (1H, m), 3.12–3.31 (3H, m), 3.35–4.08 (9H, m), 4.15–4.30 (2H, m), 4.33–4.47 (1H, m).

EXAMPLE 10

(1R,5S,6S)-6-[(1R)-1-Hydroxyethyl]-1-methyl-2-[(2S,4S)-2-[(3R)-3-(L-prolylamino)pyrrolidin-1-ylcarbonyl]pyrrolidin-4-ylthio]-1-carbapen-2-em-3-carboxylic acid (Exemplified Compound 1-1)

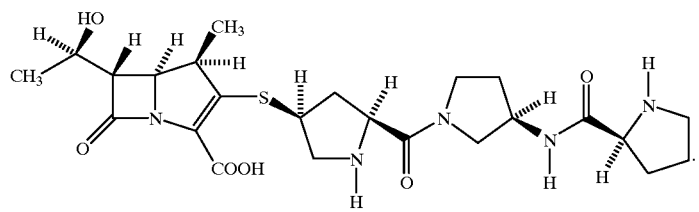

The title compound can be obtained in a similar manner to that described in Example 1-(1) and (2) by using 4-nitrobenzyl (1R,5R,6S)-6-[(1R)-1-hydroxyethyl)-1-methyl- 2-(diphenylphosphoryloxy)-1-carbapen-2-em-3-carboxylate and (2S,4S)-4-mercapto-1-(4-nitrobenzyloxycarbonyl)-2-[(3R)-3-[1-(4-nitrobenzyloxycarbonyl)-L-prolylamino]pyrrolidin-1-ylcarbonyl]pyrrolidine.

EXAMPLE 11

(1R,5S,6S)-2-[(3S)-3-Aminopyrrolidin-1ylcarbonylmethyl]pyrrolidin-4-ylthio]-6-[(1R)-1-hydroxyethyl]-1-methyl-1-carbapen-2-em-3-carboxylic acid (Exemplified Compound 2-104)

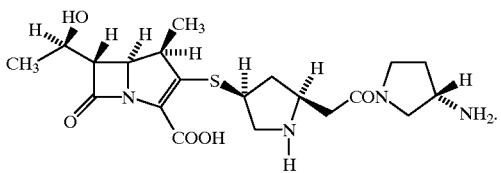

(1) To a solution of 4-nitrobenzyl (1R,5R,6S)-2-(diphenylphosphoryloxy)-6-[(1R)-1-hydroxyethyl]-1-methyl-1-carbapen-2-em-3-carboxylate (478 mg) in anhydrous acetonitrile (5.5 ml), a solution of (2R,4S)-4-mercapto-1-(4-nitrobenzyloxycarbonyl)-2-[(3S)-3-(4-nitrobenzyloxycarbonylamino)pyrrolidin-1-ylcarbonylmethyl]pyrrolidine (450 mg) in anhydrous acetonitrile (5.5 ml) and diisopropylethylamine (0.140 ml) were added under ice cooling. The resulting mixture was allowed to stand for one day at the same temperature. The reaction mixture was concentrated by evaporation under reduced pressure. The residue was extracted with ethyl acetate. The extract was washed with water and saline, dried over anhydrous sodium sulfate. The solvent was distilled off and the residue was subjected to chromatography on a silica gel column. From the fraction eluted with ethyl acetate-methanol (20:1), 4-nitrobenzyl (1R,5R,6S)-2-[(2R,4S)-1-(4-nitrobenzyloxycarbonyl)-2-[(3S)-3-(4-nitrobenzyloxycarbonylamino)pyrrolidin-1-ylcarbonylmethyl]pyrrolidin-4-ylthio]-6-[(1R)-1-hydroxyethyl]-1-methyl-1-carbapen-2-em-3-carboxylate (675 mg) was obtained as a powder.

Infrared absorption spectrum (KBr) vmax cm$^{-1}$: 1773, 1706, 1633, 1608, 1522, 1447, 1402, 1347.

Nuclear magnetic resonance spectrum (400 MHz, CDCl$_3$) δ ppm: 1.28 (3H, d, J=7.3 Hz), 1.37 (3H, d, J=6.3 Hz), 1.88–2.27 (3H, m), 2.40–2.63 (1H, m), 2.75–2.93 (2H, m), 3.18–3.72 (9H, m), 3.93–4.15 (1H, m), 4.25–4.44 (4H, m), 5.09–5.52 (6H, m), 7.48–7.66 (6H, m), 8.19–8.23 (6H, m).

(2) The compound (675 mg) obtained in (1) was dissolved in tetrahydrofuran (32 ml)—water (23 ml). To the resulting solution, a 10% palladium-carbon catalyst (1.37 g) was added, followed by hydrogenation at room temperature for 90 minutes. The catalyst was filtered off and the filtrate was concentrated by evaporation under reduced pressure to remove the tetrahydrofuran. The residue was washed with diethyl ether. The water layer was concentrated by evaporation under reduced pressure. The residue was subjected to reversed-phase chromatography ("Cosmosil 75C$_{18}$-PREP" produced by NACALAI TESQUE, INC.) and eluted with acetonitrile-water (8:92). The fraction containing the desired compound was concentrated by evaporation under reduced pressure and lyophilized, whereby the title compound (98 mg) was obtained as a powder.

Infrared absorption spectrum (KBr) vmax cm$^{-1}$: 1754, 1625, 1606, 1455, 1388.

Nuclear magnetic resonance spectrum (400 MHz, D$_2$O) δ ppm: 1.23 (3H, d, J=7.3 Hz), 1.30 (3H, d, J=6.4 Hz), 1.57–1.64 (1H, m), 1.90–2.07 (1H, m), 2.20–2.38 (1H, m), 2.65–2.73 (1H, m), 2.86–2.90 (2H, m), 3.20 (1H, dd, J=12.3, 3.8 Hz), 3.35–3.95 (10H, m), 4.21–4.29 (2H, m).

EXAMPLE 12

(1R,5S,6S)-2-[(2S,4S)-2-[1-Hydroxy-2-[(3S)-3-aminopyrrolidin-1-ylcarbonyl]ethyl]-pyrrolidin-4-ylthio]-6-[(1R)-1-hydroxyethyl]-1-methyl-1-carbapen-2-em-3-carboxylic acid (Exemplified Compound 2-1)

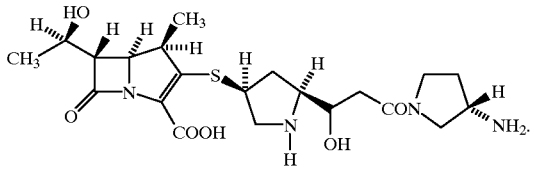

(1) To a solution of 4-nitrobenzyl (1R,5R,6S)-2-(diphenylphosphoryloxy)-6-[(1R)-1-hydroxyethyl]-1-methyl-1-carbapen-2-em-3-carboxylate (562 mg) in anhydrous acetonitrile (5 ml), a solution of (2S,4S)-2-[1-hydroxy-2-[(3S)-(4-nitrobenzyloxycarbonylamino) pyrrolidin-1-ylcarbonyl]ethyl]-4-mercapto-1-(4-nitrobenzyloxycarbonyl)pyrrolidine (555 mg) in anhydrous acetonitrile (5 ml) and diisopropylethylamine (0.145 ml) were added under ice cooling. The resulting mixture was allowed to stand at the same temperature for one day. The reaction mixture was concentrated by evaporation under reduced pressure and the residue was extracted with ethyl acetate. The extract was washed successively with water and saline and then dried over anhydrous sodium sulfate. The solvent was distilled off. The residue was subjected to chromatography on a silica gel column. From the fractions eluted with ethyl acetate-methanol (20:1), 4-nitrobenzyl (1R,5S,6S)-2-[(2S,4S)-2-[1-hydroxy-2-[(3S)-3-(4-nitrobenzyloxycarbonylamino)pyrrolidin-1-ylcarbonyl) ethyl]-1-(4-nitrobenzyloxycarbonyl)pyrrolidin-4-ylthio]-6-[(1R)-1-hydroxyethyl]-1-methyl-1-carbapen-2-em-3-carboxylate (482 mg) was obtained as a powder.

Infrared absorption spectrum (KBr) vmax cm$^{-1}$: 3405, 1772, 1706, 1624, 1608, 1522, 1449, 1404, 1375, 1347.

Nuclear magnetic resonance spectrum (270 MHz, CDCl$_3$) δ ppm: 1.27 (3H, d, J=7.2 Hz), 1.37 (3H, d, J=6.2 Hz), 1.80–2.65 (6H, m), 3.20–3.79 (9H, m), 4.00–442 (5H, m), 5.11–5.52 (6H, m), 7.51 (4H, d, J=8.3 Hz), 7.65 (2H, d, J=8.3 Hz), 8.22 (6H, d, J=8.3 Hz).

(2) The compound (482 mg) obtained in (1) was dissolved in tetrahydrofuran (22.8 ml)—water (16.3 ml). To the resulting solution, a 10% palladium-carbon catalyst (0.97 g) was added, followed by hydrogenation at room temperature for 90 minutes. The catalyst was then filtered off and the filtrate was concentrated by evaporation under reduced pressure to remove the tetrahydrofuran. The residue was washed with diethyl ether. The water layer was concentrated by evaporation under reduced pressure. The residue was subjected to reversed-phase chromatography ("Cosmosil 75C$_{18}$-PREP" produced by NACALAI TESQUE, INC.). From the fractions eluted with acetonitrile-water (8:92), the title compound (94 mg) was obtained in the powdery form.

Infrared absorption spectrum (KBr) vmax cm$^{-1}$: 3417, 1754, 1610, 1455, 1389.

Nuclear magnetic resonance spectrum (270 MHz, CDCl$_3$) δ ppm: 1.23 (3H, d, J=7.2 Hz), 1.30 (3H, d, J=6.4 Hz), 1.52–2.70 (6H, m), 3.03–3.98 (11H, m), 4.21–4.29 (3H, m).

EXAMPLE 13

(1R,5S,6S)-2-[(2R,4S)-2-[2-[(3S)-3-Aminopyrrolidin-1-ylcarbonyl]ethyl]pyrrolidin-4-ylthio]-6-(1R)-1-hydroxyethyl]-1-methyl-1-carbapen-2-em-3-carboxylic acid (Exemplified Compound 2-71)

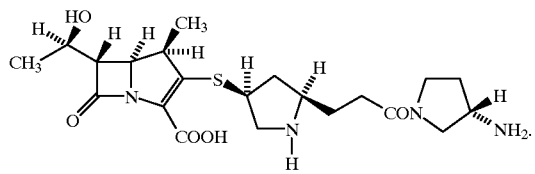

(1) To a solution of 4-nitrobenzyl (1R,5R,6S)-2-(diphenylphosphoryloxy)-6-[(1R)-1-hydroxyethyl]-1-methyl-1-carbapen-2-em-3-carboxylate (1.01 g) in anhydrous acetonitrile (10 ml), a solution of (2R,4S)-4-mercapto-1-(4-nitrobenzyloxycarbonyl)-2-[(3S)-3-(4-nitrobenzyloxycarbonylamino)pyrrolidin-1-ylcarbonyl-(E)-ethenyl]-pyrrolidine (972 mg) in anhydrous acetonitrile (10 ml) and diisopropylethylamine (0.296 ml) were added under ice cooling. The resulting mixture was allowed to stand at the same temperature for one day. The reaction mixture was concentrated by evaporation under reduced pressure and the residue was extracted with ethyl acetate. The extract was washed successively with water and saline and then dried over anhydrous sodium sulfate. The solvent was distilled off. The residue was subjected to chromatography on a silica gel column and eluted with methylene chloride-acetone of ratio from (6:1) to (1:1). Desired fractions were combined, followed by distilling off, whereby 4-nitrobenzyl (1R,5S,6S)-2-[(2R,4S)-1-(4-nitrobenzyloxycarbonyl)-2-[(3S)-3-(4-nitrobenzyloxycarbonylamino)pyrrolidin-1-ylcarbonyl-(E)-ethenyl]pyrrolidin-4-ylthio]-6-[(1R)-1-hydroxyethyl]-1-methyl-1-carbapen-2-em-3-carboxylate (1.079 g) was obtained as a powder.

Infrared absorption spectrum (KBr) vmax cm$^{-1}$: 1777, 1712, 1667, 1607, 1521, 1447, 1428, 1402, 1382, 1346, 1321.

Nuclear magnetic resonance spectrum (270 MHz, CDCl$_3$) δ ppm: 1.27 (3H, m), 1.36 (3H, m), 1.74–2.26 (3H, m), 2.58–2.70 (1H, m), 3.26–4.27 (13H, m), 4.50–4.61 (1H, m), 5.06–5.50 (7H, m), 5.97–6.21 (1H, m), 6.76–6.91 (1H, m), 7.27–7.64 (6H, m), 8.18–8.22 (6H, m).

(2) The compound (731 mg) obtained in (1) was dissolved in tetrahydrofuran (30 ml)—water (25 ml). To the resulting solution, a 10% palladium-carbon catalyst (2.06 g) was added, followed by hydrogenation at room temperature for 90 minutes. The catalyst was then filtered off and the filtrate was concentrated by evaporation under reduced pressure to remove the tetrahydrofuran. The residue was washed with diethyl ether. The water layer was concentrated by evaporation under reduced pressure. The residue was subjected to reversed-phase chromatography ("Cosmosil 75C$_{18}$-PREP" produced by NACALAI TESQUE, INC.). Among the fractions eluted with acetonitrile-water (8:92), fractions containing the desired compound were concentrated by evaporation under reduced pressure and lyophilized, whereby the title compound (73 mg) was obtained as a powder.

Nuclear magnetic resonance spectrum (270 MHz, D$_2$O) δ ppm: 1.23 (3H, d, J=7.2 Hz), 1.30 (3H, d, J=6.5 Hz), 1.51–1.68 (1H, m), 1.82–2.18 (3H, m), 2.19–2.38 (1H, m), 2.46–2.58 (2H, m), 2.62–2.76 (1H, m), 3.20–4.00 (11H, m), 4.18–4.30 (2H, m).

EXAMPLE 14

(1R,5S,6S)-2-[(2R,4S)-2-[2-(3R)-3-Aminopyrrolidin-1-ylcarbonyl]ethyl]pyrrolidin-4-ylthio]-6-[(1R)-1-hydroxyethyl]-1-methyl-1-carbapen-2-em-3-carboxylic acid (Exemplified Compound 2-71)

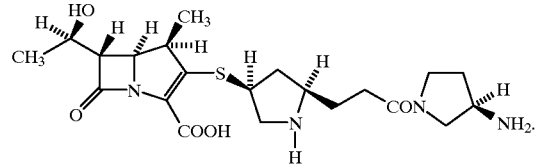

The title compound can be obtained in a similar manner to that described in Example 13-(1) and (2) by using 4-nitrobenzyl (1R,5R,6S)-2-(diphenylphosphoryloxy)-6-[(1R)-1-hydroxyethyl]-1-methyl-1-carbapen-2-em-3-carboxylate and (2R,4S)-4-mercapto-1-(4-nitrobenzyloxycarbonyl)-2-[(3R)-3-[(4-nitrobenzyloxycarbonylamino)pyrrolidin-1-ylcarbonyl-(E)-ethenyl]pyrrolidine.

EXAMPLE 15

(1R,5S,6S)-2-[(2S,4S)-2-[(3S)-3-(3-Guanidinopropanoylamino)pyrrolodin-1-ylcarbonyl]pyrrolidin-4-ylthio]-6-[(1R)-1-hydroxyethyl]-1-methyl-1-carbapen-2-em-3-carboxylic acid (Exemplified Compound 1-53)

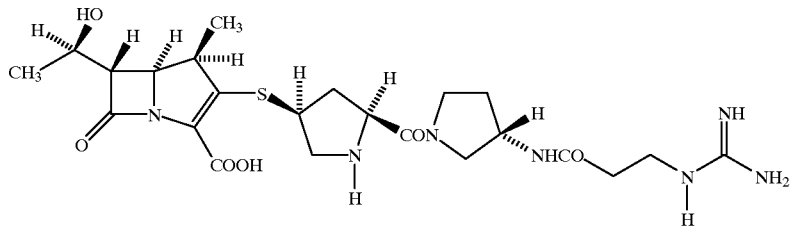

(1) By using 4-nitrobenzyl (1R,5R,6S)-6-[(1R)-1-hydroxyethyl]-1-methyl-2-(diphenylphosphoryloxy)-1-carbapen-2-em-3-carboxylate (1.02 g) and (2S,4S)-4-mercapto-1-(4-nitrobenzyloxycarbonyl)-2-[(3S)-3-[3-(4-nitrobenzyloxycarbonyl)guanidinopropanoylamino]pyrrolidin-1-ylcarbonyl]pyrrolidine (1.18 g), reaction and purification were carried out in a similar manner to that described in Example 1-(1), whereby 4-nitrobenzyl (1R,5S,6S)-6-[(1R)-1-hydroxyethyl]-1-methyl-2-[(2S,4S)-1-(4-nitrobenzyloxycarbonyl)-2-[[(3S)-3-[3-(4-nitrobenzyloxycarbonyl)guanidinopropanoylamino]pyrrolidin-1-ylcarbonyl]pyrrolidin-4-ylthio]-1-carbapen-2-em-3-carboxylate (1.11 g) was obtained as a powder.

Infrared absorption spectrum (KBr) vmax cm$^{-1}$: 3385, 1773, 1709, 1652, 1607, 1522, 1441, 1404, 1382.

Nuclear magnetic resonance spectrum (400 MHz, DMSO-d$_6$) δ ppm: 1.05–1.22 (6H, m), 1.62–2.40 (5H, m), 2.72–2.09 (1H, m), 3.07–4.37 (14H, m), 4.44–4.68 (1H, m), 5.03–5.27 (4H, m), 5.30, 5.46 (each 1H, d, J=14.1 Hz), 7.47–7.76 (6H, m), 8.13–8.27 (6H, m).

(2) To a solution of the compound (1.09 g), which had been obtained in (1), in tetrahydrofuran (25 ml)-water (15 ml), a 7.5% palladium-carbon catalyst (0.8 g) was added, followed by hydrogenation at 30° C. for 2 hours. The reaction mixture was treated in a similar manner to that described in Example 1(2), whereby the title compound (314.3 mg) was obtained as a colorless powder.

Infrared absorption spectrum (KBr) vmax cm$^{-1}$: 3333, 1756, 1645, 1455, 1388, 1286, 1257, 1182.

Nuclear magnetic resonance spectrum (400 MHz, D$_2$O) δ ppm: 1.22 (3H, dd, J=7.2,3.8 Hz), 1.30 (3H, d, J=6.4 Hz), 1.57–1.70 (1H, m), 1.91–2.09 (1H, m), 2.15–2.35 (1H, m), 2.49–2.62 (2H, m), 2.66–2.79 (1H, m), 3.01–3.11 (1H, m), 3.13–3.23 (1H, m), 3.35–3.87 (9H, m), 3.91–4.07 (1H, m), 4.18–4.30 (2H, m), 4.35–4.47 (1H, m).

EXAMPLE 16

(1R,5S,6S)-2-[(2S,4S)-2-[3-(Guanidinoacetylamino)azetidine-1-ylcarbonyl]pyrrolidin-4-ylthio]-6-[(1R)-1-hydroxyethyl]-1-methyl-1-carbapen-2-em-3-carboxylic acid (Exemplified Compound 1-62)

(1) By using 4-nitrobenzyl (1R,5S,6S)-6-[(1R)-1-hydroxyethyl]-1-methyl-2-diphenylphosphoryl-1-carbapen-2-em-3-carboxylate (2.14 g) and (2S,4S)-4-mercapto-1-(4-nitrobenzyloxycarbonyl)-2-[3-[[2,3-di(4-nitrobenzyloxycarbonyl)guanidino)acetylamino]azetidin-1-ylcarbonyl]pyrrolidine (1.59 g), reaction and purification were carried out in a similar manner to that described in Example 1-(1), whereby 4-nitrobenzyl (1R,5S,6S)-6-[(1R)-1-hydroxyethyl]-1-methyl-2-[(2S,4S)-1-(4-nitrobenzyloxycarbonyl)-2-[3-[[2,3-di(4-nitrobenzyloxycarbonyl)guanidino]acetylamino]-azetidin-1-ylcarbonyl]pyrrolidin-4-ylthio]-1-carbapenem-3-carboxylate (1.80 g) was obtained as a powder.

Infrared absorption spectrum (KBr) vmax cm$^{-1}$: 3335, 1775, 1735, 1709, 1645, 1626, 1608, 1522, 1496, 1439, 1405, 1377, 1347, 1322, 1290, 1269.

Nuclear magnetic resonance spectrum (400 MHz, CDCl$_3$) δ ppm: 1.33–1.41 (6H, m), 2.02–2.27 (2H, m), 2.52–2.82 (1H, m), 3.26–4.54 (15H, m), 4.63–4.80 (1H, m), 5.07–5.36 (6H, m), 5.43–5.60 (1H, m), 7.38–7.70 (8H, m), 8.10–8.25 (8H, m), 8.93 (1H, s), 11.65 (1H, s).

FAB-MS m/z: 1182 [M+H]$^+$.

(2) To a solution of the compound (1.78 g), which had been obtained in (1), in tetrahydrofuran (50 ml) and water (30 ml), a 7.5% palladium-carbon catalyst (1.3 g) was added, followed by hydrogenation at 30° C. for 2 hours. The reaction mixture was treated in a similar manner to that described in Example 1-(2), whereby the title compound (450.6 mg) was obtained as a powder.

Infrared absorption spectrum (KBr) vmax cm$^{-1}$: 3331, 1755, 1652, 1593, 1462, 1388, 1282, 1259, 1182, 1149, 1107, 1074, 1017.

Nuclear magnetic resonance spectrum (400 MHz, D$_2$O) δ ppm: 1.22 (3H, d, J=7.1 Hz), 1.30 (3H, d, J=6.3 Hz), 1.60–1.73 (1H, m), 2.57–2.70 (1H, m), 2.97–3.06 (1H, m), 3.15–3.24 (1H, m), 3.35–3.49 (2H, m), 3.73–3.88 (2H, m), 3.91–4.02 (1H, m), 4.05 (2H, s), 4.14–4.30 (3H, m), 4.33–4.46 (1H, m), 4.57–4.74 (2H, m).

FAB-MS m/z: 510 [M+H]$^+$.

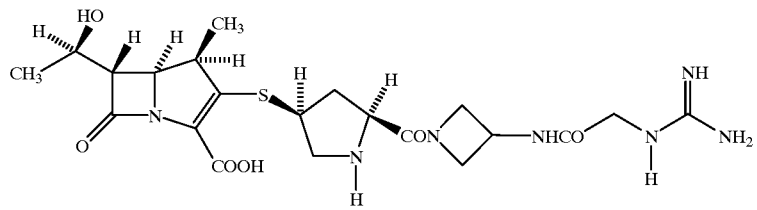

EXAMPLE 17

(1R,5S,6S)-2-[(2S,4S)-2-[3-(3-Guanidinopropanoylamino)azetidin-1-ylcarbonyl]-pyrrolidin-4-ylthio]-6-[(1R)-1-hydroxyethyl]-1-methyl-1-carbapen-2-em-3-carboxylic acid
(Exemplified Compound 1-65)

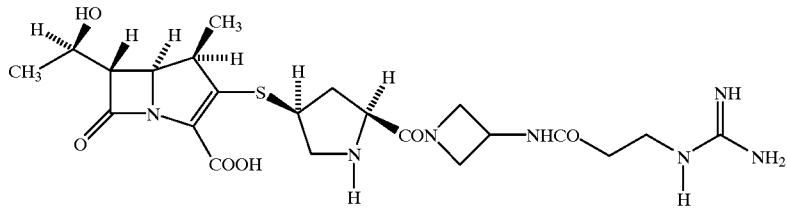

(1) By using 4-nitrobenzyl (1R,5S,6S)-6-[(1R)-1-hydroxyethyl]-1-methyl-2-diphenylphosphoryl-1-carbapenem-3-carboxylate (1.08 g) and (2S,4S)-4-mercapto-1-(4-nitrobenzyloxycarbonyl)-2-[3-[3-[2,3-di(4-nitrobenzyloxycarbonyl)guanidino]-propanolylamino]azetidin-1-ylcarbonyl]pyrrolidine (1.48 g), reaction and purification were carried out in a similar manner to that described in Example 1-(1), whereby 4-nitrobenzyl (1R,5S,6S)-6-[(1R)-1-hydroxyethyl]-1-methyl-2-[(2S,4S)-1-(4-nitrobenzyloxycarbonyl)-2-[3-[3-[2,3-di(4-nitrobenzyloxycarbonyl)guanidino]-propanoylamino]azetidin-1-ylcarbonyl]pyrrolidin-4-ylthio]-1-carbapene-3-carboxylate (0.688 g) was obtained as a powder.

Infrared absorption spectrum (KBr) vmax cm$^{-1}$: 3339, 1775, 1711, 1644, 1608, 1566, 1522, 1440, 1406, 1379, 1347, 1322, 1261, 1208.

Nuclear magnetic resonance spectrum (400 MHz, CDCl$_3$) δ ppm: 1.18–1.40 (6H, m), 1.90–2.22 (2H, m), 2.40–2.80 (3H, m), 3.25–3.55 (3H, m), 3.60–4.56 (10H, m), 4.65–4.85 (1H, m), 5.07–5.40 (8H, m), 5.45–5.55 (1H, m), 7.42–7.70 (8H, m), 8.13–8.30 (8H, m), 8.82–8.98 (1H, m), 11.72 (1H, s).

FAB-MS m/z: 1196 [M+H]$^+$.

(2) To a solution of the compound (1.14 g), which had been obtained in (1), in tetrahydrofuran (25 ml) and water (15 ml), a 7.5% palladium-carbon catalyst (0.8 g) was added, followed by hydrogenation at 30° C. for 2 hours. The reaction mixture was treated in a similar manner to that described in Example 1-(2), whereby the title compound (293.6 mg) was obtained as a powder.

Infrared absorption spectrum (KBr) vmax cm$^{-1}$: 3331, 1755, 1649, 1596, 1463, 1387, 1286, 1257, 1225, 1182, 1149, 1108.

Nuclear magnetic resonance spectrum (400 MHz D$_2$O) δ ppm: 1.22 (3H, d, J=7.2 Hz), 1.30 (3H, d, J=6.5 Hz), 1.60–1.72 (1H, m), 2.53–2.71 (3H, m), 2.93–3.07 (1H, m), 3.15–3.24 (1H, m), 3.36–3.46 (2H, m), 3.50 (2H, t, J=6.3 Hz), 3.73–3.88 (2H, m), 3.90–3.98 (1H, m), 4.10–4.30 (3H, m), 4.33–445 (1H, m), 4.51–4.69 (2H, m).

FAB-MS m/z: 524 [M+H]$^+$.

EXAMPLE 18

(1R,5S,6S)-2-[(2S,4S)-2-[(3S)-3-(4-Amino-3-hydroxybutanoylamino)pyrrolidin-1-ylcarbonyl]pyrrolidin-4-ylthio]-6-[(1R)-1-hydroxyethyl]-1-methyl-1-carbapen-2-em-3-carboxylic acid
(Exemplified Compound 1-140)

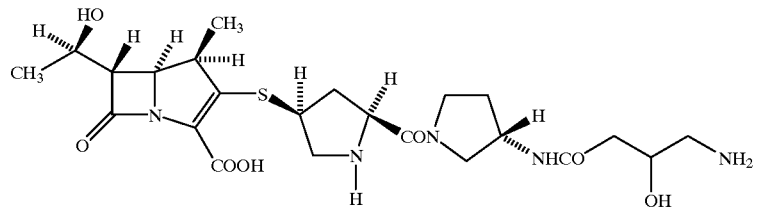

(1) By using 4-nitrobenzyl (1R,5R,6S)-6-[(1R)-1-hydroxyethyl]-1-methyl-2-diphenylphosphoryl-1-carbapen-2-em-3-carboxylate (1.78 g) and (2S,4S)-2-[(3S)-3-[3-hydroxy-4-(4-nitrobenzyloxycarbonyl)aminobutanoylamino]pyrrolidin-1-ylcarbonyl]-4-mercapto-1-(4-nitrobenzyloxycarbonyl)pyrrolidine (2.0 g), reaction and purification were carried out in a similar manner to that described in Example 1-(1), whereby 4-nitrobenzyl (1R,5S,6S)-6-[(1R)-1-hydroxyethyl]-2-[(2S,4S)-2-[(3S)-3-[3-hydroxy-4-(4-nitrobenzyloxycarbonyl)aminobutanoylamino]pyrrolidin-1-ylcarbonyl]-1-(4-nitrobenzyloxycarbonyl)pyrrolidin-4-ylthio]-1-methyl-1-carbapen-2-em-3-carboxylate (2.52 g) was obtained as an amorphous substance.

Infrared absorption spectrum (KBr) vmax cm$^{-1}$: 3353, 1773, 1710, 1648,1607, 1522, 1443, 1347.

Nuclear magnetic resonance spectrum (400 MHz, DMSO-d$_6$) δ ppm: 1.10–1.23 (6H, m), 1.65–1.86 (6H, m), 2.06–2.23 (2H, m), 2.73–3.45 (4H, m), 3.47–3.73 (6H, m), 3.77–4.31 (6H, m), 4.48–4.89 (2H, m), 5.07–5.48 (6H, m), 7.31–7.73 (6H, m), 8.02–8.25 (6H, m).

(2) To a solution of the compound (2.50 g), which had been obtained in (1), in tetrahydrofuran (50 ml) and water (50 ml), a 7.5% palladium-carbon catalyst (2.5 g) was added. Hydrogen was allowed to be absorbed into the resulting solution for 2 hours while stirring at an external temperature of 30° C. The reaction mixture was treated in a similar manner to that described in Example 1-(2), whereby the title compound (430 mg) was obtained as a powder.

Infrared absorption spectrum (KBr) vmax cm$^{-1}$: 3375, 1755, 1641, 1595, 1555, 1454, 1388.

Nuclear magnetic resonance spectrum (400 MHz, D$_2$O) δ ppm: 1.22 (3H, dd, J=7.1,2.0 Hz), 1.30 (3H, d, J=6.4 Hz), 1.58–1.71 (1H, m), 1.92–2.09 (1H, m), 2.18–2.34 (1H, m), 2.42–2.56 (2H, m), 2.72–2.79 (1H, m), 2.94–3.01 (1H, m), 3.06–3.27 (3H, m), 3.36–3.87 (7H, m), 4.00–4.10 (1H, m), 4.21–4.28 (3H, m), 4.39–4.47 (1H, m).

EXAMPLE 19

(1R,5S,5S)-2-[(2S,4S)-2-[(3S)-3-(4-Guanidino-3-hydroxybutanoylamino)pyrrolidin-1-ylcarbonyl]pyrrolidin-4-ylthio]-6-[(1R)-1-hydroxyethyl]-1-methyl-1-carbapen-2-em-3-carboxylic acid
(Exemplified Compound 1-178)

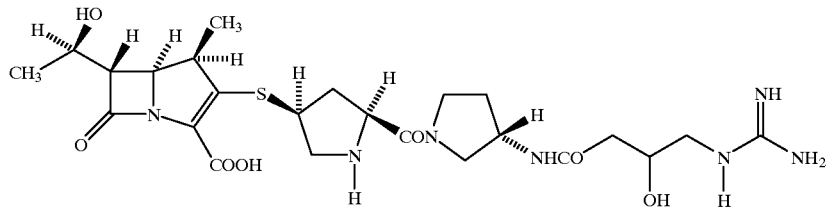

(1) By using 4-nitrobenzyl (1R,5R,6S)-6-[(1R)-1-hydroxyethyl]-1-methyl-2-diphenylphosphoryl-1-carbapen-2-em-3-carboxylate (1.55 g) and (2S,4S)-2-[(3S)-3-[4-[2,3-di(4-nitrobenzyloxycarbonyl)guanidino]-3-hydroxybutanoylamino]pyrrolidin-1-ylcarbonyl]-4-mercapto-1-(4-nitrobenzyloxycarbonyl)pyrrolidine (2.34 g), reaction and purification were carried out in a similar manner to that described as in Example 1-(1), whereby 4-nitrobenzyl (1R,5S,6S)-6-[(1R)-1-hydroxyethyl]-2-[(2S,4S)-2-[(3S)-3-[4-[2,3-di(4-nitrobenzyloxycarbonyl)guanidino]-2-hydroxybutanoylamino]pyrrolidin-1-ylcarbonyl]-1-(4-nitrobenzyloxycarbonyl)pyrrolidin-4-ylthio]-1-methyl-1-carbapen-2-em-3-carboxylate (2.08 g) was obtained as an amorphous substance.

Infrared absorption spectrum (KBr) vmax cm$^{-1}$: 3340, 1774, 1732, 1712, 1645, 1608, 1522, 1440, 1347.

Nuclear magnetic resonance spectrum (400 MHz, CDCl$_3$) δ ppm: 1.21–1.37 (6H, m), 1.85–2.38 (6H, m), 2.59–2.66 (1H, m), 3.27–3.90 (1H, m), 3.98–4.29 (5H, m), 4.46–4.54 (2H, m), 5.05–5.51 (8H, m), 7.41–7.66 (8H, m), 8.16–8.25 (8H, m), 8.69–8.71 (1H, m), 11.71–11.73 (1H, m).

(2) To a solution of the compound (2.00 g), which had been obtained in (1), in tetrahydrofuran (60 ml) and water (40 ml), a 7.5% palladium-carbon catalyst (2.00 g) was added, Hydrogen was allowed to be absorbed into the resulting solution for 2 hours while stirring at an external temperature of 30° C. The reaction mixture was treated in a similar manner to that described in Example 1-(2), whereby 410 mg of the title compound was obtained as a powder.

Infrared absorption spectrum (KBr) vmax cm$^{-1}$: 3340, 2968, 1754, 1642, 1453, 1390.

Nuclear magnetic resonance spectrum (400 MHz, D$_2$O) δ ppm: 1.22 (3H, dd, J=6.7,3.7 Hz), 1.30 (3H, d, J=6.4 Hz), 1.53–1.69 (1H, m), 1.92–2.09 (1H, m), 2.17–2.34 (1H, m), 2.40–2.52 (2H, m), 2.70–2.78 (1H, m), 3.04–3.10 (1H, m), 3.17–3.27 (2H, m), 3.33–3.50 (4H, m), 3.54–3.85 (4H, m), 3.96–4.05 (1H, m), 4.16–4.28 (3H, m), 4.38–4.43 (1H, m).

EXAMPLE 20

(1R,5S,6S)-2-[(2S,4S)-2-[(3S)-3-[(3S,4S)-4-Amino-3-hydroxy-6-methylheptanoyl-amino]pyrrolidin-1-ylcarbonyl]pyrrolidin-4-ylthio]-6-[(1R)-1-hydroxyethyl]-1-methyl-1-carbapen-2-em-3-carboxylic acid (Exemplified Compound 1-143)

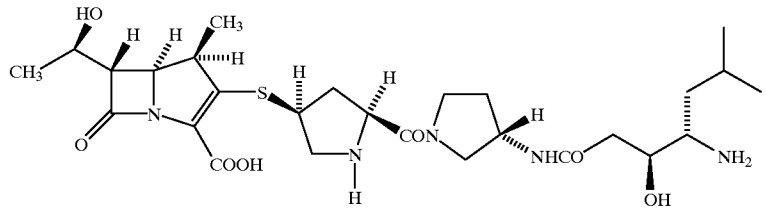

(1) By using 4-nitrobenzyl (1R,5R,6S)-6-[(1R)-1-hydroxyethyl]-1-methyl-2-diphenylphosphoryl-1-carbapen-2-em-3-carboxylate (2.16 g) and (2S,4S)-2-[(3S)-3-[(3S,4S)-3-hydroxy-6-methyl-4-(4-nitrobenzyloxycarbonyl)aminoheptanoylamino]-pyrrolidin-1-ylcarbonyl]-4-mercapto-1-(4-nitrobenzyloxycarbonyl)pyrrolidine (2.66 g), reaction and purification were carried out in a similar manner to that described in Example 1-(1), whereby 4-nitrobenzyl (1R,5S,6S)-6-[(1R)-1-hydroxyethyl]-2-(2S,4S)-2-[(3S)-3-[(3S,4S)-3-hydroxy-6-methyl-4-(4-nitrobenzyloxycarbonyl)-aminoheptanoylamino]pyrrolidin-1-ylcarbonyl]-1-(4-nitrobenzyloxycarbonyl)-pyrrolidin-4-ylthio]-1-methyl-1-carbapen-2-em-3-carboxylate (3.44 g) was obtained as an amorphous substance.

Infrared absorption spectrum (KBr) νmax cm⁻¹: 3400, 1773, 1712, 1652, 1607, 1522, 1442, 1347.

Nuclear magnetic resonance spectrum (400 MHz, CDCl₃) δ ppm: 0.89–0.92 (6H, m), 1.30–1.39 (6H, m), 1.59–1.68 (2H, m), 1.98–2.61 (6H, m), 3.21–4.10 (12H, m), 4.26–4.52 (5H, m), 4.87–5.00 (2H, m), 5.09–5.53 (6H, m), 6.89–6.91 (1H, m), 7.41–7.67 (6H, m), 8.10–8.23 (6H, m).

(2) The compound (3.30 g) obtained in (1) was subjected to hydrogenation reaction in a similar manner to that described in Example 1-(2), whereby the title compound (580 mg) was obtained as a powder.

Infrared absorption spectrum (KBr) νmax cm⁻¹: 3370, 1756, 1641, 1595, 1467, 1388.

Nuclear magnetic resonance spectrum (400 MHz, D₂O) δ ppm: 0.93–0.96 (6H, m), 1.22 (3H, dd, J=7.2,1.9 Hz), 1.30 (3H, d, J=6.4 Hz), 1.50–1.75 (4H, m), 1.98–2.08 (1H, m), 2.20–2.32 (1H, m), 2.45–2.53 (1H, m), 2.59–2.64 (1H, m), 2.71–2.79 (1H, m), 3.05–3.11 (1H, m), 3.17–3.31 (2H, m), 3.39–3.86 (7H, m), 3.98–4.10 (2H, m), 4.20–4.28 (2H, m), 4.40–4.47 (1H, m).

Infrared absorption spectrum (KBr) νmax cm⁻¹: 3390, 1775, 1713, 1654, 1607, 1523, 1448, 1346.

Nuclear magnetic resonance spectrum (400 MHz, CDCl₃) δ ppm: 0.79–0.99 (2H, m), 1.08–1.44 (11H, m), 1.52–1.88 (8H, m), 1.97–2.69 (6H, m), 3.18–4.06 (11H, m), 4.23–4.34 (2H, m), 4.48–4.53 (3H, m), 4.82–5.53 (6H, m), 6.83–6.87 (1H, m), 7.43–7.67 (6H, m), 8.12–8.24 (6H, m).

(2) The compound (2.00 g) obtained in (1) was subjected to hydrogenation reaction in a similar manner to that described in Example 1-(2), whereby the title compound (227 mg) was obtained as a powder.

Infrared absorption spectrum (KBr) νmax cm⁻¹: 3377, 1755, 1638, 1603, 1450, 1387.

Nuclear magnetic resonance spectrum (400 MHz, D₂O) δ ppm: 0.85–1.08 (2H, m), 1.14–1.92 (12H, m), 1.22 (3H, dd, J=7.1,1.1 Hz), 1.30 (3H, d, J=6.3 Hz), 1.95–2.09 (1H, m), 2.18–2.34 (1H, m), 2.45–2.78 (3H, m), 3.04–3.85 (10H, m), 3.96–4.10 (2H, m), 4.20–4.28 (2H, m), 4.39–4.46 (1H, m).

EXAMPLE 21

(1R,5S,6S)-2-[(2S,4S)-2-(3S)-3-[(3S,4S)-4-Amino-5-cyclohexyl-3-hydroxypentanoylamino]pyrrolidin-1-ylcarbonyl]pyrrolidin-4-ylthiol-6-[(1R)-1-hydroxyethyl]-1-methyl-1-carbapen-2-em-3-carboxylic acid (Exemplified Compound 1-141)

EXAMPLE 22

(1R,5S,6S)-2-[(2S,4S)-2-[(3S)-3-[(3R,4S)-4-Amino-3-hydroxy-5-phenylpentanoylamino]pyrrolidin-1-ylcarbonyl]pyrrolidin-4-ylthio]-6-[(1R)-1-hydroxyethyl]-1-methyl-1-carbapen-2-em-3-carboxylic acid (Exemplified Compound 1-142)

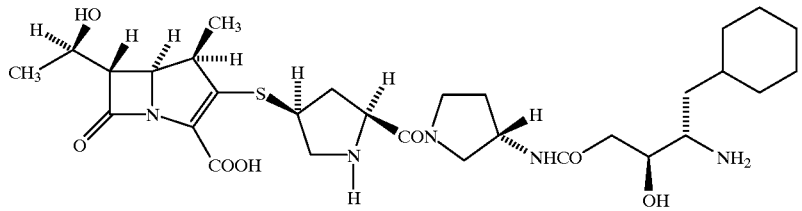

(1) By using 4-nitrobenzyl (1R,5R,6S)-6-[(1R)-1-hydroxyethyl]-1-methyl-2-diphenylphosphoryloxy-1-carbapen-2-em-3-carboxylate (1.53 g) and (2S,4S)-2-[(3S)-3-[(3S,4S)-5-cyclohexyl-3-hydroxy-4-(4-nitrobenzyloxycarbonyl)aminopentanoylamino]pyrrolidin-

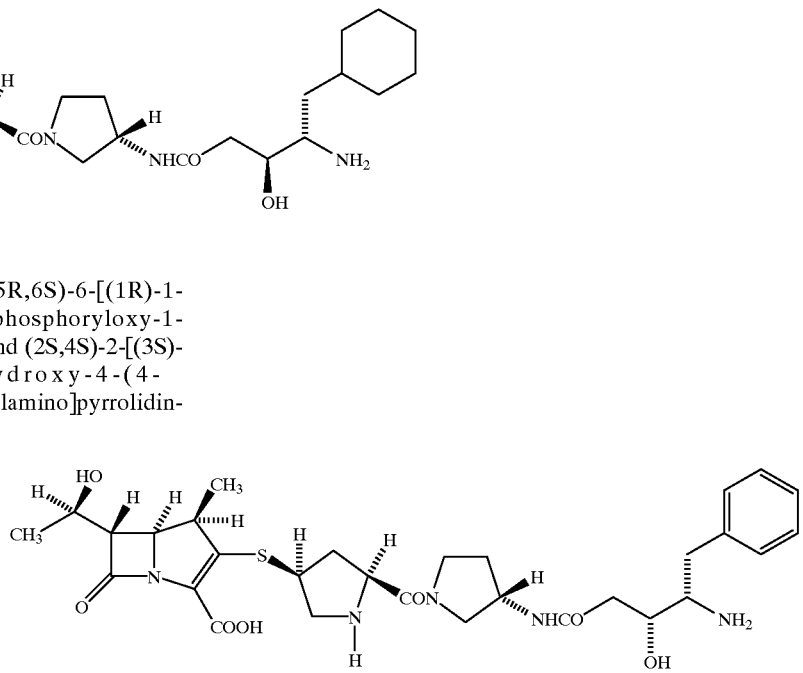

1-ylcarbonyl]-4-mercapto-1-(4-nitrobenzyloxycarbonyl)pyrrolidine (2.00 g), reaction and purification were carried out in a similar manner to that described in Example 1-(1), whereby 4-nitrobenzyl (1R,5S,6S)-6-[(1R)-1-hydroxyethyl]-2-[(2S,4S)-2-[(3S)-3-[(3S,4S)-5-cyclohexyl-3-hydroxy-4-(4-nitrobenzyloxycarbonyl)aminopentanoylamino]pyrrolidin-1-ylcarbonyl]-1-(4-nitrobenzyloxycarbonyl)pyrrolidin-4-ylthio]-1-methyl-1-carbapen-2-em-3-carboxylate (2.10 g) was obtained as an amorphous substance.

(1) By using 4-nitrobenzyl (1R,5R,6S)-6-[(1R)-1-hydroxyethyl]-1-methyl-2-diphenylphosphoryloxy-1-carbapen-2-em-3-carboxylate (1.40 g) and (2S,4S)-2-[(3S)-3-[(3R,4S)-3-hydroxy-4-(4-nitrobenzyloxycarbonyl)amino-5-phenylpentanoylamino]-pyrrolidin-1-ylcarbonyl]-4-mercapto-1-(4-nitrobenzyloxycarbonyl)pyrrolidine (1.80 g), reaction and purification were carried out in a similar manner to that described in Example 1-(1), whereby 4-nitrobenzyl (1R,5S,6S)-6-[(1R)-1-hydroxyethyl]-2-[(2S,4S)-2-[(3S)-3-[(3R,4S)-3-hydroxy-4-(4- nitrobenzyloxycarbonyl)amino-5-phenylpentanoylamino]pyrrolidin-1-ylcarbonyl]-1-(4-nitrobenzyloxycarbonyl)-pyrrolidin-4-ylthio]-1-methyl-1-carbapen-2-em-3-carboxylate (2.13 g) was obtained as an amorphous substance.

Infrared absorption spectrum (KBr) νmax cm$^{-1}$: 3350, 1773, 1710, 1648, 1607, 1522, 1443, 1346.

Nuclear magnetic resonance spectrum (400 MHz, DMSO-d$_6$) δ ppm: 1.17–1.19 (6H, m), 165–1.99 (3H, m), 2.06–2.56 (4H, m), 2.76–2.83 (1H, m), 2.99–3.66 (12H, m), 3.76–4.46 (6H, m), 4.48–4.65 (1H, m), 4.96–5.48 (6H, m), 7.16–7.73 (11H, m), 8.07–8.25 (6H, m).

(2) The compound (2.10 g) obtained in (1) was subjected to hydrogenation reaction in a similar manner to that described in Example 1-(2), whereby 300 mg of the title compound was obtained as a powder.

Infrared absorption spectrum (KBr) νmax cm$^{-1}$: 3281, 1757, 1641, 1595, 1455, 1387.

Nuclear magnetic resonance spectrum (400 MHz, D$_2$O) δ ppm: 1.21 (3H, t, J=6.6 Hz), 1.30 (3H, dd, J=6.3, 2.5 Hz), 1.59–1.72 (1H, m), 1.92–2.08 (1H, m), 2.18–2.34 (1H, m), 2.51–2.63 (2H, m), 2.72–2.85 (2H, m), 3.07–3.16 (2H, m), 3.22–3.28 (1H, m), 3.34–3.50 (3H, m), 3.54–3.74 (4H, m), 3.76–3.87 (1H, m), 3.22–3.28 (1H, m), 3.34–3.50 (3H, m), 3.54–3.74 (4H, m), 3.76–3.87 (1H, m), 4.02–4.11 (1H, m), 4.19–4.46 (4H, m), 7.34–7.46 (5H, m).

EXAMPLE 23

(1R,5S,6S)-2-[(2S,4S)-2-[(3S)-3-[(4-Guanidinomethylcyclohexyl)carbonylamino]-pyrrolidin-1-ylcarbonyl]pyrrolidin-4-ylthio]-6-[(1R)-1-hydroxyethyl]-1-methyl-1-carbapen-2-em-3-carboxylic acid (Exemplified Compound 1-119)

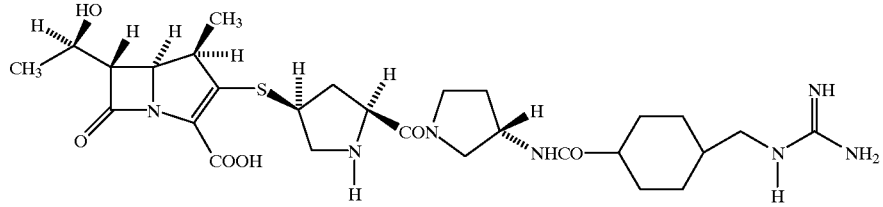

(1) By using 4-nitrobenzyl (1R,5R,6S)-6-[(1R)-1-hydroxyethyl]-1-methyl-2-diphenylphosphoryloxy-1-carbapen-2-em-3-carboxylate (1.13 g) and (2S,4S)-4-mercapto-1-(4-nitrobenzyloxycarbonyl)-2-[(3S)-3-[[4-di(4-nitrobenzyloxycarbonyl)-guanidinomethylcyclohexyl]carbonylamino]pyrrolidin-1-ylcarbonyl]pyrrolidine (1.85 g), reaction and purification were carried out in a similar manner to that described in Example 1-(1), whereby 4-nitrobenzyl (1R,5S,6S)-6-[(1R)-1-hydroxyethyl]-2-[(2S,4S)-1-(4-nitrobenzyloxycarbonyl)-2-[(3S)-3-[[4-di(4-nitrobenzyloxycarbonyl)guanidinomethylcyclohexyl]carbonylamino]pyrrolidin-1-ylcarbonyl]pyrrolidin-4-ylthio]-1-methyl-1-carbapen-2-em-3-carboxylate (1.89 g) was obtained as an amorphous substance.

Infrared absorption spectrum (KBr) νmax cm$^{-1}$: 3393, 2933, 1773, 1717, 1657, 1608, 1522, 1442, 1347.

Nuclear magnetic resonance spectrum (400 MHz, DMSO-d$_6$) δ ppm: 0.84–0.99 (2H, m), 1.24–1.44 (6H, m), 1.64–2.25 (10H, m), 2.58–2.68 (1H, m), 2.88 (1H, s), 2.96 (1H, s), 3.27–4.57 (16H, m), 4.91–5.61 (8H, m), 7.37–7.67 (8H, m), 8.11–8.28 (8H, m), 9.30–9.50 (2H, m).

(2) The compound (1.80 g) obtained in (1) was subjected to hydrogenation reaction in a similar manner to that described in Example 1-(2), whereby the title compound (354 mg) was obtained as a powder.

Infrared absorption spectrum (KBr) νmax cm$^{-1}$: 3337, 2931, 1755, 1642, 1546, 1451, 1387.

Nuclear magnetic resonance spectrum (400 MHz, D$_2$O) δ ppm: 0.98–1.07 (2H, m), 1.22 (3H, dd, J=7.1, 4.7 Hz), 1.30(3H, d, J=6.3 Hz), 1.36–1.67 (4H, m), 1.78–1.92 (2H, m), 1.95–2.06 (1H, m), 2.18–2.32 (2H, m), 2.69–2.79 (1H, m), 2.99–3.15 (3H, m), 3.17–3.22 (1H, m), 3.38–3.84 (7H, m), 3.93–4.03 (1H, m), 4.19–4.28 (2H, m), 4.33–4.41 (1H, m).

EXAMPLE 24

(1R,5S,6S)-2-[(2S,4S)-2-[(3S)-3-[(4-guanidinobenzoyl)amino]pyrrolidin-1-ylcarbonyl]pyrrolidin-4-ylthio]-6-[(1R)-1-hydroxyethyl]-1-methyl-1-carbapen-2-em-3-carboxylic acid (Exemplified Compound 1-113)

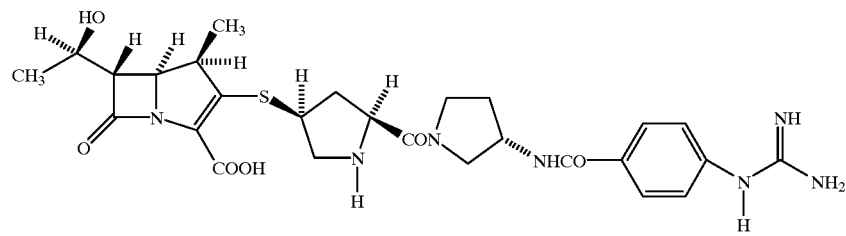

(1) By using 4-nitrobenzyl (1R,5R,6S)-6-[(1R)-1-hydroxyethyl]-1-methyl-2-diphenylphosphoryloxy-1-carbapen-2-em-3-carboxylate (0.59 g) and (2S,4S)-4-mercapto-1-(4-nitrobenzyloxycarbonyl)-2-[(3S)-3-[[4-di(4-nitrobenzyloxycarbonyl)guanidinobenzoyl]amino]pyrrolidin-1-ylcarbonyl]pyrrolidine (0.91 g), reaction and purification were carried out in a similar manner to that described in Example 1-(1), whereby 4-nitrobenzyl (1R,5S,6S)-6-[(1R)-1-hydroxyethyl]-2-[(2S,4S)-1-(4-nitrobenzyloxycarbonyl)-2-[(3S)-3-[[4-di(4-nitrobenzyloxycarbonyl)guanidinobenzoyl]-amino]pyrrolidin-1-ylcarbonyl]pyrrolidin-4-ylthio]-1-methyl-1-carbapen-2-em-3-carboxylate (0.89 g) was obtained as an amorphous substance.

Infrared absorption spectrum (KBr) νmax cm$^{-1}$: 3397, 1773, 1727, 1717, 1655, 1609, 1522, 1347.

Nuclear magnetic resonance spectrum (400 MHz, CD$_3$CN) δ ppm: 1.12–1.26 (6H, m), 1.67–2.30 (4H, m), 2.69–2.84 (1H, m), 3.18–3.98 (9H, m), 4.05–4.28 (3H, m), 4.39–4.64 (2H, m), 4.93–5.48 (8H, m), 6.97–7.38 (8H, m), 7.46–7.85 (5H, m), 8.05–8.23 (7H, m), 9.10–9.38 (2H, m).

(2) The compound (0.87 g) obtained in (1) was subjected to hydrogenation reaction in a similar manner to that described in Example 1-(2), whereby the title compound (130 mg) was obtained as a powder.

Infrared absorption spectrum (KBr) νmax cm$^{-1}$: 3328, 1754, 1638, 1606, 1571, 1507, 1457, 1388.

Nuclear magnetic resonance spectrum (400 MHz, D$_2$O) δ ppm: 1.15 (3H, dd, J=45.3, 7.1 Hz), 1.28–1.31 (3H, m), 1.49–1.70 (1H, m), 2.09–2.21 (1H, m), 2.28–2.43 (1H, m), 2.69–2.78 (1H, m), 3.02–3.07 (1H, m), 3.18–3.23 (1H, m), 3.32–3.44 (2H, m), 3.54–3.89 (5H, m), 4.00–4.07 (1H, m), 4.15–4.26 (2H, m), 4.57–4.63 (1H, m), 7.42 (2H, dd, J=6.8, 1.8 Hz), 7.83 (2H, dd, J=6.8, 1.8 Hz).

EXAMPLE 25

(1R,5S,6S)-2-[(2S,4S)-2-[(3S)-3-[(2S)-2-Guanidino-2-methylacetylamino]pyrrolidin-1-ylcarbonyl]pyrrolidin-4-ylthio]-6-[(1R)-1-hydroxyethyl]-1-methyl-1-carbapen-2-em-3-carboxylic acid
(Exemplified Compound 1-59)

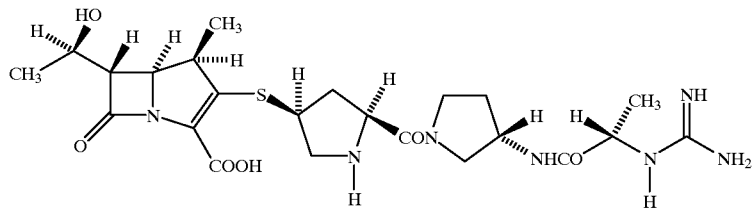

(1) By using 4-nitrobenzyl (1R,5R,6S)-6-[(1R)-1-hydroxyethyl]-1-methyl-2-diphenylphosphoryloxy-1-carbapen-2-em-3-carboxylate (1.21 g) and (2S,4S)-2-[(3S)-3-[(2S)-2-[2,3-di(4-nitrobenzyloxycarbonyl)guanidino]-2-methylacetylamino]-pyrrolidin-1-ylcarbonyl]-4-mercapto-1-(4-nitrobenzyloxycarbonyl)pyrrolidine (1.68 g), reaction and purification were carried out in a similar manner to that described in Example 1-(1), whereby 4-nitrobenzyl (1R,5S,6S)-2-[(2S,4S)-2-[(3S)-3-[(2S)-2-[2,3-di(4-nitrobenzyloxycarbonyl)guanidino]-2-methylacetylamino]pyrrolidin-1-ylcarbonyl]-1-(4-nitrobenzyloxycarbonyl)pyrrolidin-4-ylthio]-6-[(1R)-1-hydroxyethyl]-1-methyl-1-carbapen-2-em-3-carboxylate (1.92 g) was obtained as an amorphous substance.

Infrared absorption spectrum (KBr) νmax cm$^{-1}$: 3331, 1775, 1734, 1710, 1645, 1623, 1609, 1522.

Nuclear magnetic resonance spectrum (400 MHz, CDCl$_3$) δ ppm: 1.23–1.50 (9H, m), 1.65–2.25 (3H, m), 2.50–2.70 (1H, m), 3.23–3.90 (8H, m), 3.94–4.06 (1H, m), 4.22–4.62 (5H, m), 5.04–5.55 (8H, m), 7.00–7.10 (1H, m), 7.38–7.69 (8H, m), 8.09–8.29 (8H, m), 8.94 (1H, d, J=6.8 Hz), 11.62 (1H, s).

(2) The compound (1.88 g) obtained in (1) was subjected to hydrogenation reaction and purification in a similar manner to that described in Example 1-(2), whereby the title compound (361 mg) was obtained as a powder.

Infrared absorption spectrum (KBr) νmax cm$^{-1}$: 3333, 1756, 1633, 1454, 1389, 1344, 1312.

Nuclear magnetic resonance spectrum (400 MHz, D$_2$O) δ ppm: 1.22 (3H, dd, J=7.2, 3.0 Hz), 1.30 (3H, d, J=6.3 Hz), 1.45 (3H, d, J=7.1 Hz), 1.50–1.59 (1H, m), 1.60–1.70 (1H, m), 1.95–2.12 (1H, m), 2.19–2.37 (1H, m), 2.67–2.80 (1H, m), 3.20–3.11 (1H, m), 3.13–3.23 (1H, m), 3.36–3.52 (3H, m), 3.54–3.88 (4H, m), 3.92–4.06 (1H, m), 4.16–4.31 (3H, m), 4.39–4.51 (1H, m).

EXAMPLE 26

(1R,5S,6S)-2-[(2S,4S)-2-[3-(2S)-2-Guanidino-2-methylacetalamino]azetidin-1-ylcarbonyl]pyrrolidin-4-ylthio]-6-[(1R)-1-hydroxyethyl]-1-methyl-1-carbapen-2-em-3-carboxylic acid (Exemplified Compound 1-68)

EXAMPLE 27

(1R,5S,6S)-2-[(2S,4S)-2-[(3S)-3-[(2R)-2-Guanidino-2-methylacetylamino]pyrrolidin-1-ylcarbonyl]pyrrolidin-4-ylthio]-6-[(1R)-1-hydroxyethyl]-1-methyl-1-carbapen-2-em-3-carboxylic acid (Exemplified Compound 1-59)

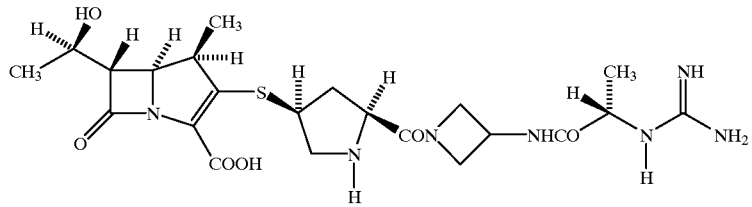

(1) By using 4-nitrobenzyl (1R,5R,6S)-6-[(1R)-1-hydroxyethyl]-1-methyl-2-diphenylphosphoryloxy-1-carbapen-2-em-3-carboxylate (969 mg) and (2S,4S)-2-[3-[(2S)-2-[2,3-di(4-nitrobenzyloxycarbonyl)guanidinol-2-methylacetylamino]azetidin-1-ylcarbonyl]-4-mercapto-1-(4-nitrobenzyloxycarbonyl]pyrrolidine (1.32 g), reaction and purification were carried out in a similar manner to that described in Example 1-(1), whereby 4-nitrobenzyl (1R,5S,6S)-2-[(2S,4S)-2-[3-[(2S)-2-[2,3-di(4-nitrobenzyloxycarbonyl)guanidino]-2-methylacetylamino]azetidin-1-ylcarbonyl]-1-(4-nitrobenzyloxycarbonyl)pyrolidin-4-ylthio]-6-[(1R)-1-hydroxyethyl]-1-methyl-1-carbapen-2-em-3-carboxylate (1.36 g) was obtained as an amorphous substance.

Infrared absorption spectrum (KBr) vmax cm$^{-1}$: 3328, 1775, 1734, 1710, 1645, 1623, 1609, 1522.

Nuclear magnetic resonance spectrum (400 MHz, CDCl$_3$) δ ppm: 1.28–1.50 (9H, m), 1.90–2.28 (1H, m), 2.48–2.80 (1H, m), 3.25–3.57 (3H, m), 3.63–4.80 (11H, m), 4.97–5.60 (8H, m), 7.39 (1H, d, J=7.9 Hz), 7.43–7.70 (8H, m), 8.10–8.30 (8H, m), 8.78 (1H, d, J=6.7 Hz), 11.64 (1H, s).

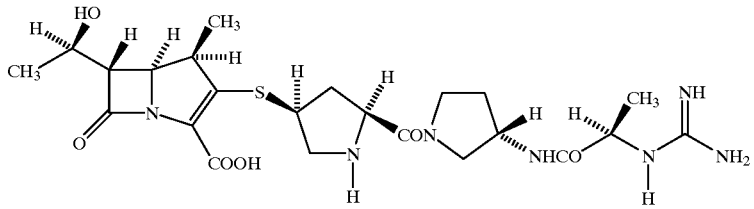

(2) The compound (1.34 g) obtained in (1) was subjected to hydrogenation reaction and purification in a similar manner to that described in Example 1-(2), hereby the title compound (321 mg) was obtained as a powder.

Infrared absorption spectrum (KBr) vmax cm$^{-1}$: 3335, 1754, 1649, 1594, 1462, 1389, 1312, 1287, 1256.

Nuclear magnetic resonance spectrum (400 MHz, D$_2$O) δ ppm: 1.22 (3H, d, J=7.2 Hz), 1.30 (3H, d, J=6.4 Hz), 1.48 (3H, d, J=7.0 Hz), 1.62–1.75 (1H, m), 2.58–2.72 (1H, m), 2.98–3.07 (1H, m), 3.16–3.25 (1H, m), 3.33–3.51 (2H, m), 3.75–3.90 (2H, m), 3.94–4.03 (1H, m), 4.14–4.31 (4H, m), 4.34–4.45 (1H, m), 4.58–4.73 (2H, m).

(1) By using 4-nitrobenzyl (1R,5R,6S)-6-[(1R)-1-hydroxyethyl]-1-methyl-2-diphenylphosphoryloxy-1-carbapen-2-em-3-carboxylate (826 mg) and (2S,4S)-4-mercapto-1-(4-nitrobenzyloxycarbonyl)-2-[(3S)-3-[(2R)-2-[2,3-di(4-nitrobenzyloxycarbonyl)guanidino]-2-methylacetylamino]pyrrolidin-1-ylcarbonyl]pyrrolidine (1.204 g), the reaction and purification were carried out in a similar manner to that described in Example 1-(1), whereby 4-nitrobenzyl (1R,5S,6S)-2-[(2S,4S)-2-[[(3S)-3-[(2R)-2-[2,3-di(4-nitrobenzyloxycarbonyl)guanidino]-2-methylacetylamino]pyrrolidin-1-ylcarbonyl]-1-(4-nitrobenzyloxycarbonyl)pyrrolidin-4-ylthio]-6-[(1R)-1-hydroxyethyl]-1-methyl-1-carbapen-2-em-3-carboxylate (1.653 g) was obtained as an amorphous substance.

Infrared absorption spectrum (KBr) vmax cm$^{-1}$: 3331, 1774, 1733, 1711, 1645, 1623, 1609, 1523.

Nuclear magnetic resonance spectrum (270 MHz, CDCl$_3$) δ ppm: 1.20–1.50 (9H, m), 1.70–1.93 (1H, b), 2.10–2.30

(2H, m), 2.50–2.70 (1H, m), 3.24–4.63 (14H, m), 4.97–5.56 (8H, m), 7.40–7.70 (8H, m), 8.10–8.28 (8H, m).

(2) The compound (1.637 g) obtained in (1) was subjected to hydrogenation reaction and purification in a similar manner to that described in Example 1-(2), whereby the title compound (260 mg) was obtained as a powder.

Infrared absorption spectrum (KBr) vmax cm$^{-1}$: 3335, 1755, 1648, 1453, 1389.

Nuclear magnetic resonance spectrum (400 MHz, D$_2$O) δ ppm: 1.22 (3H, dd, J=7.2,4.6 Hz), 1.30 (3H, d, J=6.4 Hz), 1.46 (3H, d, J=7.1 Hz), 1.43–1.72 (1H, m), 1.97–2.11 (1H, m), 2.17–2.37 (1H, m), 2.65–2.78 (1H, m), 3.02–3.11 (1H, m), 3.13–3.28 (1H, m), 3.35–3.87 (7H, m), 3.92–4.06 (1H, m), 4.16–4.30 (3H, m), 4.37–4.47 (1H, m).

EXAMPLE 28

(1R,5S,6S)-2-[(2S,4S)-2-[3-[(2R)-2-Guanidino-2-methylacelylamnino]azetidin-1-ylcarbonyl]pyrrolidin-4-ylthio]-6-[(1R)-1-hydroxyethyl]-1-methyl-1-carbapen-2-em-3-carboxylic acid (Exemplified Compound 1-68)

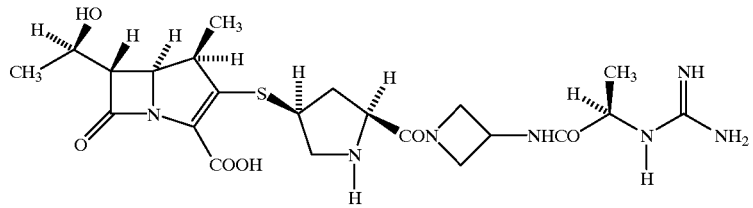

(1) By using 4-nitrobenzyl (1R,5R,6S)-6-[(1R)-1-hydroxyethyl]-1-methyl-2-diphenylphosphoryloxy-1-carbapen-2-em-3-carboxylate (612 mg) and (2S,4S)-4-mercapto-1-(4-nitrobenzyloxycarbonyl)-2-[3-[(2R)-2-[2,3-di(4-nitobenzyloxycarbonyl)guanidino]-2methylacetylamino]azetidin-1-ylcarbonyl]pyrrolidine (894 mg), reaction and purification were carried out in a similar manner to that described in Example 1-(1), whereby 4-nitrobenzyl (1R,5S,6S)-2-[(2S,4S)-2-[3-[(2R)-2-[2,3-di(4-nitrobenzyloxycarbonyl)guanidino]-2-methylacetylamino]azetidin-1-ylcarbonyl]-1-(4-nitrobenzyloxycarbonyl)pyrrolidin-4-ylthio]-6-[(1R)-1-hydroxyethyl]-1-methyl-1-carbapen-2-em-3-carboxylate (1.08 g) was obtained as an amorphous substance.

Infrared absorption spectrum (KBr) vmax cm$^{-1}$: 3420, 1773, 1736, 1709, 1645, 1623, 1609, 1523.

Nuclear magnetic resonance spectrum (270 MHz, CDCl$_3$) δ ppm: 1.29 (3H, d, J=7.1 Hz), 1.37 (3H, d, J=6.2 Hz), 1.45 (3H, d, J=6.9 Hz), 1.90–2.22 (1H, m), 2.43–2.66 (1H, m), 3.24–4.80 (14H, m), 5.03–5.58 (8H, m), 7.40–7.70 (8H, m), 7.75 (1H, d, J=7.5 Hz), 8.13–8.28 (8H, m), 8.74 (1H, t, J=7.1 Hz), 11.65 (1H, s).

(2) The compound (1.034 g) obtained in (1) was subjected to hydrogenation reaction and purification in a similar manner to that described in Example 1-(2), whereby the title compound (179 mg) was obtained as a powder.

Infrared absorption spectrum (KBr) vmax cm$^{-1}$: 3333, 1756, 1649, 1462, 1387, 1313, 1286, 1255.

Nuclear magnetic resonance spectrum (400 MHz, D$_2$O) δ ppm: 1.22 (3H, d, J=7.2 Hz), 1.30 (3H, d, J=6.4 Hz), 1.48 (3H, d, J=7.0 Hz), 1.61–1.74 (1H, m), 2.58–2.78 (1H, m), 2.98–3.08 (1H, m), 3.17–3.27 (1H, m), 3.33–3.49 (2H, m), 3.73–3.90 (2H, m), 3.93–4.03 (1H, m), 4.15–4.30 (4H, m), 4.33–4.47 (1H, m), 4.55–4.74 (2H, m).

EXAMPLE 29

(1R,5S,6S)-2-[(2S,4S)-2-[(3S)-3-[2-(1-Methylguanidino)acetylamino]pyrrolidin-1-ylcarbonyl]pyrrolidin-4-ylthio]-6-[(1R)-1-hydroxyethyl]-1-methyl-1-carbapen-2-em-3-carboxylic acid (Exemplified Compound 1-56)

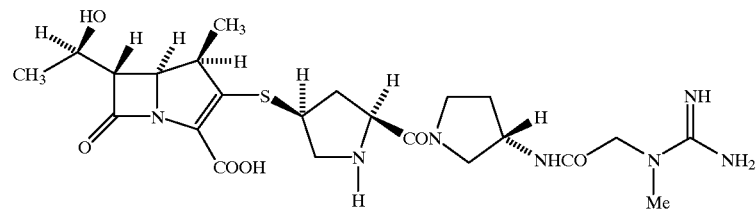

(1) By using 4-nitrobenzyl (1R,5R,6S)-6-[(1R)-1-hydroxyethyl]-1-methyl-2-diphenylphosphoryloxy-1-carbapen-2-em-3-carboxylate (936 mg) and (2S,4S)-2-[(3S)-3-[2-[1-methyl-2,3-di(4-nitrobenzyloxycarbonyl)guanidino]acetylamino]pyrrolidin-1-ylcarbonyl]-4-mercapto-1-(4-nitrobenzyloxycarbonyl)pyrrolidine (1.30 g), reaction and purification were carried out in a similar manner to that described in Example 1-(1), whereby 4-nitrobenzyl (1R,5S,6S)-6-[(1R)-1-hydroxyethyl]-2-[(2S,4S)-2-[(3S)-3-[2-[1-methyl-2,3-di(4-nitrobenzyloxycarbonyl)guanidino]acetylamino]pyrrolidin-1-ylcarbonyl]-1-(4-nitrobenzyloxycarbonyl)pyrrolidin-4-ylthio]-1-methyl-1-carbapen-2-em-3-carboxylate (972 mg) was obtained as an amorphous substance.

Infrared absorption spectrum (KBr) vmax cm$^{-1}$: 3343, 1768, 1709, 1656, 1608, 1522, 1445, 1404.

Nuclear magnetic resonance spectrum (400 MHz, CDCl₃) δ ppm: 1.20–1.43 (6H, m), 1.75–2.26 (3H, m), 2.55–2.72 (1H, m), 3.04–3.14 (3H, m), 3.23–4.53 (15H, m), 4.92–5.03 (6H, m), 7.38 (1H, d, J=8.6 Hz), 7.43–7.68 (8H, m), 8.08–8.32 (8H, m), 10.32 (1H, s).

(2) The compound (956 mg) obtained in (1) was subjected to hydrogenation reaction and purification in a similar manner to that described in Example 1-(2), whereby the title compound (192 mg) was obtained as a powder.

Infrared absorption spectrum (KBr) νmax cm⁻¹: 3353, 1753, 1664, 1622, 1452, 1390, 1285, 1262.

Nuclear magnetic resonance spectrum (400 MHz, D₂O) δ ppm: 1.22 (3H, dd, J=7.2, 2.6 Hz), 1.30 (3H, d, J=6.4 Hz), 1.54–1.71 (1H, m), 1.95–2.12 (1H, m), 2.18–2.37 (1H, m), 2.67–2.79 (1H, m), 3.00–3.12 (4H, m), 3.15–3.24 (1H, m), 3.35–3.89 (7H, m), 3.93–4.07 (1H, m), 4.10–4.30 (4H, m), 4.41–4.52 (1H, m).

EXAMPLE 30

(1R,5S,6S)-6-[(1R)-1-Hydroxyethyl]-1-methyl-2-[(2S,4S)-2-[3-[2-(1-methyl-guanidino)acetylamino]azetidin-1-ylcarbonyl]pyrrolidin-4-ylthio]-1-carbapen-2-em-3-carboxylic acid (Exemplified Compound 1-102)

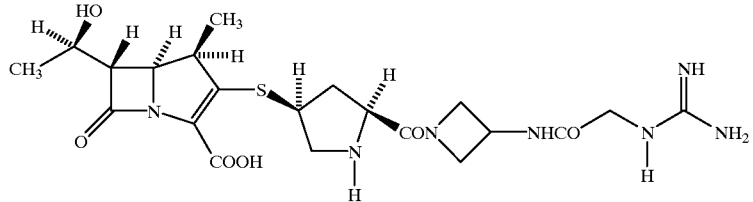

(1) By using 4-nitrobenzyl (1R,5R,6S)-6-[(1R)-1-hydroxyethyl]-1-methyl-2-diphenylphosphoryloxy-1-carbapen-2-em-3-carboxylate (926 mg) and (2S,4S)-2-[3-[2-[2,3-di(4-nitrobenzyloxycarbonyl)-1-methylguanidino]acetylamino]azetidin-1-ylcarbonyl]-4-mercapto-1-(4-nitrobenzyloxycarbonyl)pyrrolidine (1.26 g), reaction and purification were carried out in a similar manner to that described in Example 1-(1), whereby 4-nitrobenzyl (1R,5S,6S)-2-[(2S,4S)-2-[3-[2-[2,3-di(4-nitrobenzyloxycarbonyl)-1-methylguanidino]acetylamino]azetidin-1-ylcarbonyl]-1-(4-nitrobenzyloxycarbonyl)pyrrolidin-4-ylthio]-6-[(1R)-1-hydroxyethyl]-1-methyl-1-cabapen-2-em-3-carboxylate (958 mg) was obtained as an amorphous substance.

Infrared absorption spectrum (KBr) νmax cm⁻¹: 3392, 1767, 1707, 1671, 1608, 1522, 1451, 1403.

Nuclear magnetic resonance spectrum (400 MHz, CDCl₃) δ ppm: 1.23–1.42 (6H, m), 1.91–2.15 (1H, m), 2.50–2.75 (1H, m), 3.05–4.50 (17H, m), 4.57–4.78 (1H, m), 5.03–5.55 (8H, m), 7.35–7.69 (8H, m), 8.08–8.32 (8H, m).

(2) The compound (931 mg) obtained in (1) was subjected to hydrogenation reaction and purification in a similar manner to that described in Example 1-(2), whereby the target compound (185 mg) was obtained as a powder.

Infrared absorption spectrum (KBr) νmax cm⁻¹: 3339, 3241, 1754, 1656, 1614, 1462, 1387, 1315, 1280.

Nuclear magnetic resonance spectrum (400 MHz, D₂O) δ ppm: 1.22 (3H, d, J=7.2 Hz), 1.30 (3H, d, J=6.5 Hz), 1.61–1.74 (1H, m), 2.58–2.72 (1H, m), 2.98–3.12 (4H, m), 3.15–3.26 (1H, m), 3.31–3.49 (2H, m), 3.74–3.90 (2H, m), 3.96–4.05 (1H, m), 4.13–4.32 (5H, m), 4.34–4.46 (1H, m), 4.52–4.75 (2H, m).

EXAMPLE 31

(1R,5S,6S)-2-[(2S,4S)-2-[(3S)-3-[L-(N-Amidino)prolyl]amino]pyrrolidin-1-ylcarbonyl]pyrrolidin-4-ylthio]-6-[(1R)-1-hydroxyethyl]-1-methyl-1-carbapen-2em-3-carboxylic acid (Exemplified Compound 1-5)

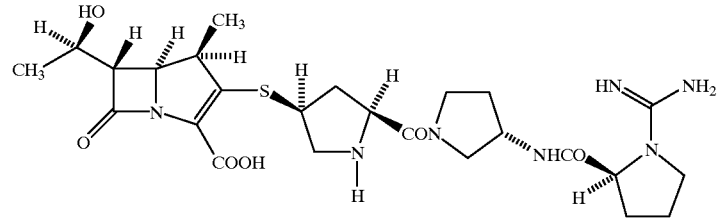

(1) By using 4-nitrobenzyl (1R,5R,6S)-6-[(1R)-1-hydroxyethyl]-1-methyl-2-diphenylphosphoryloxy-1-carbapen-2-em-3-carboxylate (1.18 g) and (2S,4S)-2-[(3S)-3-[L-[N-[2,3-di(4-nitrobenzyloxycarbonyl)amidino]prolyl]amino]pyrrolidin-1-ylcarbonyl]-4-mercapto-1-(4-nitrobenzyloxycarbonyl)pyrrolidine (1.69 g), reaction and purification were carried out in a similar to that described in Example 1-(1), whereby 4-nitrobenzyl (1R,5S,6S)-2-[(2S,4S)-2-[[(3S)-3-[L-[N-[2,3-di(4-nitrobenzyloxycarbonyl)amidino]prolyl]amino]pyrrolidin-1-ylcarbonyl]-1-(4-nitrobenzyloxycarbonyl)-pyrrolidin-4-ylthio]-6-[(1R)-1-hydroxyethyl]-1-methyl-1-carbapen-2-em-3-carboxylate (1.46 g) was obtained as an amorphous substance.

Infrared absorption spectrum (KBr) vmax cm$^{-1}$: 3351, 1768, 1709, 1656, 1608, 1522, 1496, 1442.

Nuclear magnetic resonance spectrum (400 MHz, CDCl$_3$) δ ppm: 1.17–1.44 (6H, m), 1.73–2.30 (8H, m), 2.50–2.69 (1H, m), 3.19–3.80 (10H, m), 3.87–5.54 (13H, m), 7.32–7.70 (8H, m), 8.10–8.33 (8H, m).

(2) The compound (1.46 g) obtained in (1) was subjected to hydrogenation reaction and purification in a similar manner to that described in Example 1-(2), whereby the title compound (277 mg) was obtained in a powdery form.

Infrared absorption spectrum (KBr) vmax cm$^{-1}$: 3339, 1754, 1652, 1609, 1454, 1386, 1286.

Nuclear magnetic resonance spectrum (400 MHz, D$_2$O) δ ppm: 1.22 (3H, dd, J=7.2, 1.1 Hz), 1.30 (3H, d, J=6.5 Hz), 1.50–1.70 (1H, m), 1.90–2.17 (4H, m), 2.19–2.48 (2H, m), 2.68–2.80 (1H, m), 3.02–3.11 (1H, m), 3.13–3.23 (1H, m), 3.36–3.88 (9H, m), 3.91 4.07 (1H, m), 4.18–4.29 (2H, m), 4.40–4.55 (2H, m).

EXAMPLE 32

(1R,5S,6S)-2-[(2S,4S)-2-[(3S)-3-(4-guanidinobutanoylamino)pyrrolidin-1-ylcarbonyl]-pyrrolidin-4-ylthio]-6-[(1-R)-1-hydroxyethyl]-1-methyl-1-carbapen-2-em-3-carboxylic acid
(Exemplified Compound 1-139)

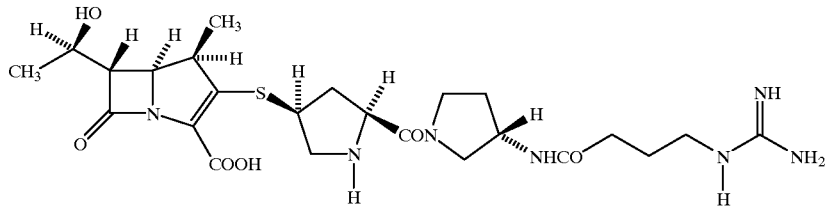

(1) By using 4-nitrobenzyl (1R,5R,6S)-6-[(1R)-1-hydroxyethyl]-1-methyl-2-diphenylphosphoryloxy-1-carbapen-2-em-3-carboxylate (1.48 g) and (2S,4S)-2-[(3S)-3-[4-[2,3-di(4-nitrobenzyloxycarbonyl)guanidino]butanoylamino]pyrrolidin-1-ylcarbonyl]-4-mercapto-1-(4-nitrobenzyloxycarbonyl)pyrrolidine (2.20 g), reaction and purification were carried out in a similar manner to that described in Example 1-(1), whereby 4-nitrobenzyl (1R,5S,6S)-2-[(2S,4S)-2-[(3S)-3-[4-[2,3-di(4-nitrobenzyloxycarbonyl)guanidino]butanoylamino]pyrrolidin-1-ylcarbonyl]-1-(4-nitrobenzyloxycarbonyl)pyrrolidin-4-ylthio]-6-[(1R)-1-hydroxyethyl]-1-methyl-1-carbapen-2-em-3-carboxylate (2.82 g) was obtained as an amorphous substance.

Infrared absorption spectrum (KBr) vmax cm$^{-1}$: 3341, 1773, 1732, 1712, 1644, 1608, 1522, 1437, 1347.

Nuclear magnetic resonance spectrum (400 MHz, CDCl$_3$) δ ppm: 1.21–1.32 (3H, m), 1.36 (3H, d, J=6.4 Hz), 1.79–2.05 (6H, m), 2.09–2.28 (3H, m), 2.60–2.66 (1H, m), 3.27–4.10 (10H, m), 4.22–4.29 (2H, m), 4.45–4.56 (2H, m), 5.05–5.51 (8H, m), 6.44–6.83 (1H, m), 7.421–7.66 (8H, m), 8.15–8.25 (8H, m), 8.42–8.49 (1H, m), 11.79 (1H, d, J=12.3 Hz).

(2) The compound (2.80 g) obtained in (1) was subjected to hydrogenation reaction and purification in a similar manner to that described in Example 1-(2), whereby the title compound (540 mg) was obtained as a powder.

Infrared absorption spectrum (KBr) vmax cm$^{-1}$: 3333, 2967, 1754, 1645, 1552, 1453, 1388.

Nuclear magnetic resonance spectrum (400 MHz, D$_2$O) δ ppm: 1.22 (3H, dd, J=7.1, 4.9 Hz), 1.30 (3H, d, J=6.4 Hz), 1.49–1.69 (1H, m), 1.84–2.05 (3H, m), 2.19–2.35 (3H, m), 2.69–2.77 (1H, m), 3.03–3.09 (1H, m), 3.16–3.23 (3H, m), 3.38–3.50 (3H, m), 3.57–3.83 (4H, m), 3.94–4.04 (1H, m), 4.20–4.28 (2H, m), 4.37–4.42 (1H, m).

EXAMPLE 33

(1R,5S,6S)-2-[(2S,4S)-2-[3-(4-Guanidinobutanoylamino)azetidin-1-ylcarbonyl]pyrrolidin-4-ylthio]-6-[(1R)-1-hydroxyethyl]-1-methyl-1-carbapen-2-em-3-carboxylic acid
(Exemplified Compound 1-187)

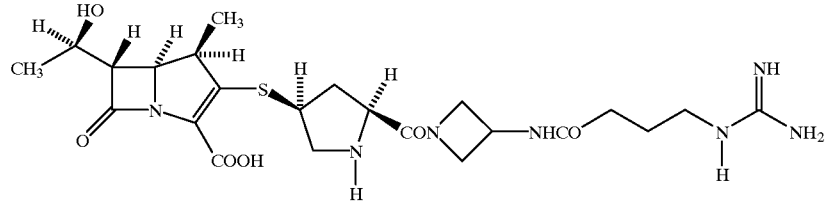

(1) By using 4-nitrobenzyl (1R,5R,6S)-6-[(1R)-1-hydroxyethyl]-1-methyl-2-diphenylphosphoryloxy-1-carbapen-2-em-3-carboxylate (1.30 g) and (2S,4S)-2-[3-[4-[2,3-di(4-nitrobenzyloxycarbonyl)guanidino]butanoylamino]azetidin-1-ylcarbonyl]-4-mercapto-1-(4-nitrobenzyloxycarbonyl)pyrrolidine (1.90 g), reaction and purification were carried out in a similar manner to that described in Example 1-(1), whereby 4-nitrobenzyl (1R,5S, 6S)-2-[(2S,4S)-2-[3-[4-[2,3-di(4-nitobenzyloxycarbonyl)guanidino]butanoylamino]azetidin-1-ylcarbonyl]-1-(nitrobenzyloxycarbonyl)-pyrrolidin-4-ylthio]-6-[(1R)-1- hydroxyethyl]-1-methyl-1-carbapen-2-em-3-carboxylate (2.05 g) was obtained as an amorphous substance.

Infrared absorption spectrum (KBr) νmax cm$^{-1}$: 3340, 1773, 1711, 1645, 1608, 1522, 1438, 1347.

Nuclear magnetic resonance spectrum (400 MHz, CDCl$_3$) δ ppm: 1.20–1.29 (3H, m), 1.35 (3H, d, J=6.3 Hz), 1.88–2.28 (6H, m), 2.50–2.62 (1H, m), 3.27–3.52 (5H, m), 3.64–3.76 (1H, m), 3.89–4.44 (8H, m), 4.67–4.79 (1H, m), 5.09–5.52 (8H, m), 7.39–7.67 (9H, m), 8.17–8.25 (8H, m), 8.46–8.53 (1H, m), 11.80 (1H, s).

(2) The compound (2.00 g) obtained in (1) was subjected to hydrogenation reaction and purification in a similar manner to that described in Example 1-(2), whereby the title compound (410 mg) was obtained as a powder.

Infrared absorption spectrum (KBr) νmax cm$^{-1}$: 3333, 2967, 1754, 1649, 1551, 1466, 1387.

Nuclear magnetic resonance spectrum (400 MHz, D$_2$O) δ ppm: 1.22 (3H, d, J=7.1 Hz), 1.30 (3H, d, J=6.1 Hz), 1.62–1.71 (1H, m), 1.86–1.93(2H, m), 2.35–2.39(2H, m), 2.60–2.71(1H, m), 2.99–3.05(1H, m), 3.17–3.25(3H, m), 3.36–3.48(2H, m), 3.76–3.97(3H, m), 4.12–4.28(3H, m), 4.34–4.41(1H, m), 4.57–4.67(2H, m).

EXAMPLE 34

(1R,5S,6S)-2-[(2S,4S)-2-[3-(4-Guanidino-3-hydroxybutanoylamino)azetidin-1-ylcarbonyl]pyrrolidin-4-ylthio]-6-[(1R)-1-hydroxyethyl]-1-methyl-1-carbapen-2-em-3-carboxylic acid
(Exemplified Compound 1-188)

hydroxyethyl]-1-methyl-1-carbapen-2-em-3-carboxylate (1.73 g) was obtained as an amorphous substance.

Infrared absorption spectrum (KBr) νmax cm$^{-1}$: 3343, 1773, 1710, 1645, 1608, 1522, 1442, 1347.

Nuclear magnetic resonance spectrum (400 MHz, CDCl$_3$) δ ppm: 1.24–1.29 (3H, m), 1.35 (3H, d, J=6.2 Hz), 2.01–2.27 (2H, m), 2.36–2.40 (2H, m), 2.55–2.62 (1H, m), 3.27–3.53 (4H, m), 3.59–3.76 (2H, m), 3.85–4.01 (2H, m), 4.06–4.44 (7H, m), 4.46–4.73 (1H, m), 4.93–5.51 (9H, m), 7.00–7.27 (1H, m), 7.46–7.66 (8H, m), 8.17–8.25 (8H, m), 8.69–8.73 (1H, m), 11.72 (1H, s).

(2) The compound (1.70 g) obtained in (1) was subjected to hydrogenation reaction and purification in a similar manner to that described in Example 1-(2), whereby the title target compound (210 mg) was obtained in the powdery form.

Infrared absorption spectrum (KBr) νmax cm$^{-1}$: 3337, 2967, 1755, 1649, 1595, 1462, 1387.

Nuclear magnetic resonance spectrum (400 MHz, D$_2$O) δ ppm: 1.22 (3H, d, J=7.2 Hz), 1.30 (3H, d, J=6.3 Hz), 1.63–1.71 (1H, m), 2.44–2.56 (2H, m), 2.60–2.70 (1H, m), 2.99–3.05 (1H, m), 3.17–3.29 (2H, m), 3.35–3.44 (3H, m), 3.75–3.88 (2H, m), 3.94–3.99 (1H, m), 4.15–4.28 (4H, m), 4.34–4.43 (1H, m), 4.57–4.68 (2H, m).

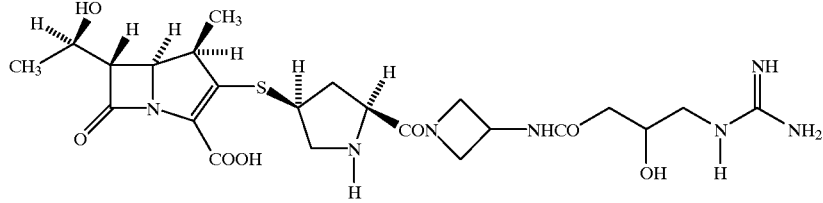

(1) By using 4-nitrobenzyl (1R,5R,6S)-6-[(1R)-1-hydroxyethyl]-1-methyl-2-diphenylphosphoryloxy-1-carbapen-2-em-3-carboxylate (1.19 g) and (2S,4S)-2-[[3-[4-[2,3-di(4-nitrobenzyloxycarbonyl)guanidino]-3-hydroxybutanoylamino]azetidin-1-yl]carbonyl]-4-mercapto-1-(4-nitrobenzyloxycarbonyl)pyrrolidine (1.76 g), reaction and purification were carried out in a similar manner to that described in Example 1-(1), whereby 4-nitrobenzyl (1R,5S,6S)-2-[(2S,4S)-2-[[3-[4-[2,3-di(4-nitrobenzyloxycarbonyl)guanidino]-3-hydroxybutanoylamino[azetidin-1--yl]carbonyl]-1-(4-nitrobenzyloxycarbonyl)pyrrolidin-4-ylthio]-6-[(1R)-1-

EXAMPLE 35

(1R,5S,6S)-2-[(2S,4S)-2-[(3S)-3-(2-Guanidinoacetylamino)pyrrolidin-1-ylcarbonyl]-pyrrolidin-4-ylthio]-6-[(1R)-1-hydroxyethyl]-1-methyl-1-carbapen-2-em-3-carboxylic acid
(Exemplified Compound 1-59)

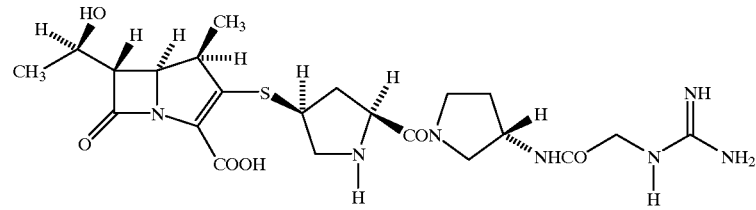

(1) By using 4-nitrobenzyl (1R,5R,6S)-6-[(1R)-1-hydroxyethyl]-1-methyl-2-diphenylphosphoryloxy-1-carbapen-2-em-3-carboxylate (6.35 g) and (2S,4S)-2-[(3S)-3-[2-[2,3-di(4-nitrobenzyloxycarbonyl)guanidino]acetylamino]pyrrolidin-1-ylcarbonyl]-4-mercapto-1-(4-nitrobenzyloxycarbonyl)pyrrolidine (8.44 g), reaction and purification were carried out in a similar manner to that described in Example 1-(1), whereby 4-nitrobenzyl (1R,5S,6S)-2-[(2S,4S)-2-[(3S)-3-[2-[2,3-di(4-nitrobenzyloxycarbonyl)-guanidino]acetylamino]pyrrolidin- 4-ylthio]-6-[(1R)-1-hydroxyethyl]-1-methyl-1-carbapen-2-em-3-carboxylate (9.64 g) was obtained as an amorphous substance.

Infrared absorption spectrum (KBr) vmax cm$^{-1}$: 3334, 1773, 1738, 1709, 1645, 1608, 1549, 1522.

Nuclear magnetic resonance spectrum (400 MHz, DMSO-d$_6$) δ ppm: 1.10–1.25 (6H, m), 1.58–2.20 (3H, m), 2.70–2.90 (1H, m), 3.10–4.70 (15H, m), 4.95–5.50 (8H, m), 7.45–7.78 (8H, m), 8.13–8.41 (8H, m).

(2) The compound (4.00 g) obtained in (1) was subjected to hydrogenation reaction and purification in a similar manner to that described in Example 1-(2), whereby the title compound (663 mg) was obtained as a powder.

Ultraviolet absorption spectrum $\lambda_{max}$ (H$_2$O) nm: 299.

Infrared absorption spectrum (KBr) vmax cm$^{-1}$: 3340, 1754, 1665, 1634, 1452, 1390.

Nuclear magnetic resonance spectrum (400 MHz, D$_2$O) δ ppm: 1.01 (3H, dd, J=7.3, 3.4 Hz), 1.10 (3H, d, J=6.4 Hz), 1.33–1.52 (1H, m), 1.73–1.90 (1H, m), 1.97–2.15 (1H, m), 2.47–2.58 (1H, m), 2.81–2.92 (1H, m), 2.94–3.03 (1H, m), 3.13–3.31 (3H, m), 3.31–3.67 (4H, m), 3.73–3.87 (3H, m), 3.97–4.09 (2H, m), 4.20–4.30 (1H, m).

EXAMPLE 36
(1R,5S,6S)-2-[(2S,4S)-2-[(3S)-3-[N-(2-Guanidinoacetyl)-N-methylamino]pyrrolidin-1-ylcarbonyl]pyrrolidin-4-ylthio]-6-[(1R)-1-hydroxyethyl]-1-methyl-1-carbapen-2-em-3-carboxylic acid (Exemplified Compound 1-100)

In a similar manner to that described in Example 1-(1) and (2), the title compound can be obtained.

EXAMPLE 37
(1R,5S,6S)-2-[(2S,4S)-2-[(3S)-3-[N-[2-(1-Methylguanidino)acetyl]-N-methylamino]pyrrolidin-1-ylcarbonyl]pyrrolidin-4-ylthio]-6-[(1R)-1-hydroxyethyl]-1-methyl-1-carbapen-2-em-3-carboxylic acid (Exemplified Compound 1-170)

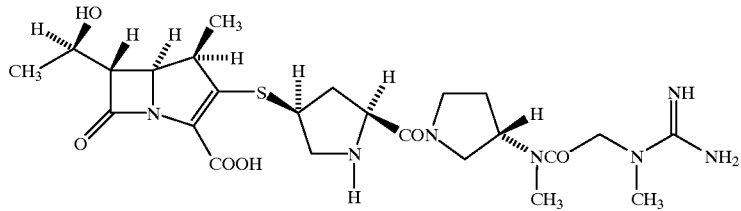

In a similar manner to that described in Example 1-(1) and (2), the title compound can be obtained.

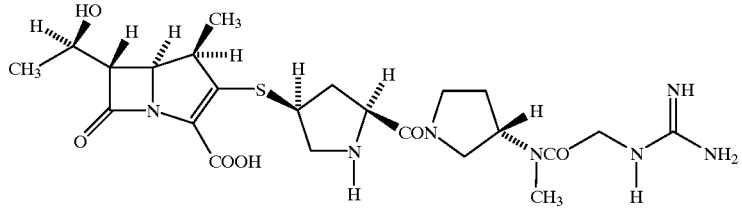

EXAMPLE 38

(1R,5S,6S)-2-[(2S,4S)-2-[3-[N-(2-Guanidinoacetyl)-N-methylamino]azetidin-1-ylcarbonyl]pyrrolidin-4-ylthio]-6-[(1R)-1-hydroxyethyl]-1-methyl-1-carbapen-2-em-3-carboxylic acid (Exemplified Compound 1-189)

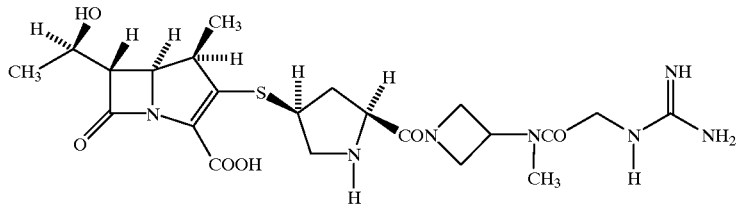

In a similar manner to that described in Example 1-(1) and (2), the title compound can be obtained.

EXAMPLE 39

(1R,5S,6S)-2-[(2S,4S)-2-[4-(2-Guanidinoacetylamino)piperidin-1-ylcarbonyl]pyrrolidin-4-ylthio]-6-[(1R)-1-hydroxyethyl]-1-methyl-1-carbapen-2-em-3-carboxylic acid (Exemplified Compound 1-72)

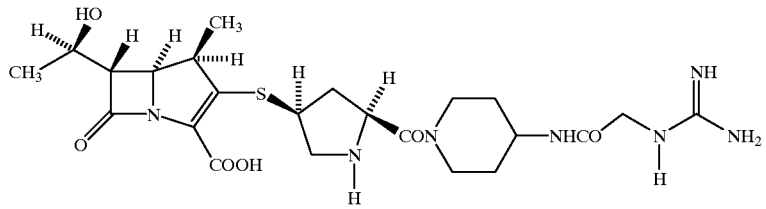

In a similar manner to that described in Example 1-(1) and (2), the title compound can be obtained.

EXAMPLE 40

(1R,5S,6S)-2-[(2S,4S)-2-[1-Hydroxy-2-[(3S)-3-methylaminopyrrolidin-1-ylcarbonyl]ethyl]pyrrolidin-4-ylthio]-6-[(1R)-1-hydroxyethyl]-1-methyl-1-carbapen-2-em-3-carboxylic acid (Exemplified Compound 2-7)

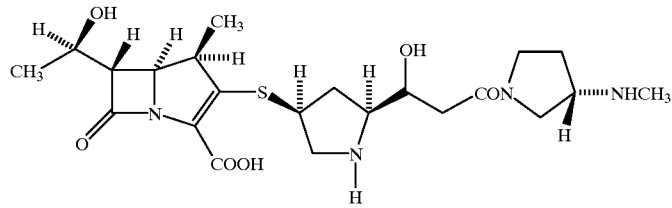

(1) To a suspension of 4-nitrobenzyl (1R,5R,6S)-6-[(1R)-1-hydroxyethyl]-1-methyl-2-(diphenylphosphoryloxy)-1-carbapen-2-em-3-carboxylate (864 mg) in anhydrous acetonitrile (9 ml), N,N-diisopropylethylamine (0.253 ml) and a solution of (2S,4S)-2-[1-hydroxy-2-[(3S)-3-[N-methyl-N-(4-nitrobenzyloxycarbonyl)amino]pyrrolidin-1-ylcarbonyl]ethyl]-4-mercapto-1-(4-nitrobenzyloxycarbonyl)pyrrolidine (875 mg) in anhydrous acetonitrile (9 ml) was added while stirring under ice cooling. The resulting mixture was stirred overnight at 0° C. The reaction mixture was concentrated by evaporation under reduced pressure. Ethyl acetate was then added to the residue. The resulting mixture was washed with water and saturated saline, dried over anhydrous magnesium sulfate and then concentrated by evaporation under reduced pressure. The residue was subjected to chromatography on a silica gel column and eluted successively with ethyl acetate and methanol-ethyl acetate (1:15). Desired fractions were combined, followed by distilling off under reduced pressure, whereby 4-nitrobenzyl (1R,5S,6S)-6-[(1R)-1-hydroxyethyl]-2-(2S,4S)-2-[1-hydroxy-2-[(3S)-3-[N-methyl-N-(4-nitrobenzyloxycarbonyl)amino]pyrrolidin-1-ylcarbonyl]ethyl]-1-(4-nitrobenzyloxycarbonyl)pyrrolidin-1-ylcarbonyl]pyrrolidin-4-ylthio]-1-methyl-1-carbapen-2-em-3-carboxylate (1.099 g) was obtained as a powder.

Infrared absorption spectrum (KBr) vmax cm$^{-1}$: 3437, 1774, 1704, 1625, 1608, 1522, 1447, 1406, 1376, 1346.

Nuclear magnetic resonance spectrum (400 MHz, CDCl$_3$) δ ppm: 1.27 (3H, d, J=7.0 Hz), 1.37 (3H, d, J=6.2 Hz), 1.92–2.65 (6H, m), 2.90 (3H, d, J=9.0 Hz), 3.12–3.80 (9H, m), 3.99–4.86 (5H, m), 5.13–5.52 (6H, m), 7.52 (4H, d, J=8.4 Hz), 7.65 (2H, d, J=8.4 Hz), 8.20–8.25 (6H, m).

(2) To a solution of the compound (731 mg), which had been obtained in (1), in tetrahydrofuran (35 ml) and water (25 ml), a 10% palladium-carbon catalyst (1.482 g) was added. Hydrogen was then allowed to absorb to the resulting mixture for 2 hours while stirring at an external temperature of 30° C. The catalyst was then filtered off. The filtrate was washed with diethyl ether and then concentrated by evaporation under reduced pressure. The residue was subjected to reversed-phase chromatography ["Cosmosil 75C$_{18}$-PREP" (NACALAI TESQUE, INC.)] and eluted with acetonitrile-water (6:94). Desired fractions were combined, followed by distilling off under reduced pressure and lyophilization, whereby the title compound (152.7 mg) was obtained as a powder.

Infrared absorption spectrum (KBr) vmax cm$^{-1}$: 3391, 1756, 1615, 1453, 1388.

Nuclear magnetic resonance spectrum (400 MHz, D$_2$O) δ ppm: 1.23 (3H, d, J=7.1 Hz), 1.30 (3H, d, J=6.4 Hz), 1.52–1.69 (1H, m), 2.00–2.19 (1H, m), 2.28–2.45 (1H, m), 2.45–2.71 (6H, m), 3.03–3.20 (1H, m), 3.31–3.98 (10H, m), 4.19–4.30 (3H, m).

EXAMPLE 41

(1R,5S,6S)-2-[(2S,4S)-2-[2-[(3S)-3-guanidinopyrrolidin-1-ylcarbonyl]-1-hydroxyethyl]-pyrrolidin-4-ylthio]-6-[(1R)-1-hydroxyethyl]-1-methyl-1-carbapen-2-em-3-carboxylic acid
(Exemplified Compound 2-3)

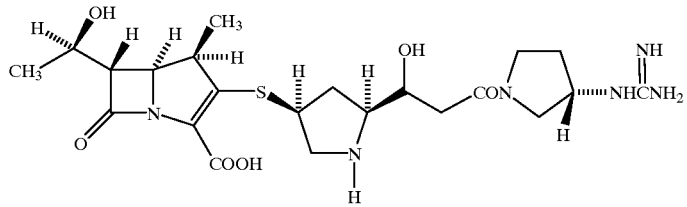

(1) By using 4-nitrobenzyl (1R,5R,6S)-6-[(1R)-1-hydroxyethyl]-1-methyl-2-(diphenylphosphoryloxy)-1-carbapen-2-em-3-carboxylate (645 mg) and (2S,4S)-2-[1-hydroxy-2-[(3S)-3-[3-(4-nitrobenzyloxycarbonyl) guanidino]pyrrolidin-1-ylcarbonyl]ethyl]4-mercapto-1-(4-nitrobenzyloxycarbonyl)pyrrolidine (682 mg), reaction and purification were carried out in a similar manner to that described in Example 40-(1), whereby 4-nitrobenzyl (1R, 5S,6S)-6-[(1R)-1-hydroxyethyl]-2-[(2S,4S)-2-[1-hydroxy-2-[(3S)-3-[3-(4-nitrobenzyloxycarbonyl)guanidino] pyrrolidin-1-ylcarbonyl]ethyl-1-(4-nitrobenzyloxycarbonyl) pyrrolidin-4-ylthio]-1-methyl-1-carbapen-2-em-3-carboxylate (664 mg) was obtained.

Infrared absorption spectrum (KBr) vmax cm$^{-1}$: 3387, 1773, 1703, 1618, 1608, 1521, 1445, 1404, 1377, 1347, 1284.

Nuclear magnetic resonance spectrum (400 MHz, CDCl$_3$) δ ppm: 1.12–1.21 (6H, m), 1.64–2.42 (6H, m), 2.88–4.51 (12H, m), 4.95–5.50 (8H, m), 7.51–7.77 (6H, m), 8.14–8.30 (6H, m).

(2) To a solution of the compound (664 mg), which had been obtained in (1), in tetrahydrofuran (31.4 ml) and water (22.4 ml), a 10% palladium-carbon catalyst (1.35 g) was added. Hydrogen was then allowed to absorb to the resulting mixture for 2 hours, while stirring at an external temperature of 30° C. The reaction mixture was treated in a similar manner to that described in Example 40-(2), whereby the title compound (153.7 mg) was obtained as a powder.

Infrared absorption spectrum (KBr) vmax cm$^{-1}$: 3344, 1755, 1675, 1615, 1456, 1389.

Nuclear magnetic resonance spectrum (400 MHz, D$_2$O) δ ppm: 1.23 (3H, d, J=7.2 Hz), 1.30 (3H, d, J=6.4 Hz), 1.39–1.60 (1H, m), 2.02–2.21 (1H, m), 2.21–2.30 (1H, m), 2.30–2.52 (1H, m), 2.52–2.76 (2H, m), 2.92–3.06 (1H, m), 3.16–3.97 (9H, m), 4.01–4.39 (4H, m).

EXAMPLE 42

(1R,5S,6S)-2-[(2S,4S)-2-[2-[(3R)-3-Aminopyrrolidin-1-ylcarbonyl]-1-hydroxyethyl]-pyrrolidin-4-ylthio]-6-[(1R)-1-hydroxyethyl]-1-methyl-1-carbapen-2-em-3-carboxylic acid
(Exemplified Compound 2-1)

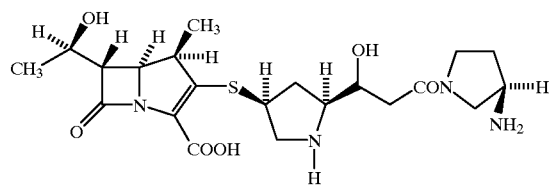

(1) By using 4-nitrobenzyl (1R,5R,6S)-6-[(1R)-1-hydroxyethyl]-1-methyl-2-(diphenylphosphoryloxy)-1-carbapen-2-em-3-carboxylate (1.47 g) and (2S,4S)-2-[1-hydroxy-2-[(3R)-3-(4-nitrobenzyloxycarbonylamino) pyrrolidin-1-ylcarbonyl]ethyl]-4-mercapto-1-(4-nitrobenzyloxycarbonyl)pyrrolidine (1.454 g), reaction and purification were carried out in a similar manner to that described in Example 40-(1), whereby 4-nitrobenzyl (1R, 5S,6S)-6-[(1R)-1-hydroxyethyl]-2-[(2S,4S)-2-[1-hydroxy-2-[(3R)-3-(4-nitrobenzyloxycarbonylamino)pyrrolidin-1-ylcarbonyl]ethyl]-1-(4-nitrobenzyloxycarbonyl)pyrrolidin-4-ylthio]-1-methyl-1-carbapen-2-em-3-carboxylate (2.207 g) was obtained.

Infrared absorption spectrum (KBr) vmax cm$^{-1}$: 3400, 1773, 1706, 1624, 1608, 1522, 1448, 1404, 1376, 1347.

Nuclear magnetic resonance spectrum (400 MHz, CDCl$_3$) δ ppm: 1.26 (3H, d, J=7.4 Hz), 1.35 (3H, d, J=6.2 Hz), 1.84–2.65 (6H, m), 3.14–3.78 (9H, m), 4.06–4.38 (5H, m), 5.11–5.54 (6H, m), 7.44–7.59 (4H, m), 7.60–7.69 (2H, m), 8.20 (6H, d, J=8.6 Hz).

(2) To a solution of the compound (886 mg), which had been obtained in (1), in tetrahydrofuran (41.9 ml) and water (29.9 ml), a 10% palladium-carbon catalyst (1.796 g) was added. Hydrogen was allowed to be absorbed into the resulting mixture for 2 hours, while stirring at an external temperature of 30° C. The reaction mixture was treated in a similar manner to that described in Example 40-(2), whereby the title compound (189.6 mg) was obtained as a powder.

Infrared absorption spectrum (KBr) vmax cm$^{-1}$: 3406, 1755, 1610, 1453, 1389.

Nuclear magnetic resonance spectrum (400 MHz, D$_2$O) δ ppm: 1.23 (3H, d, J=6.9 Hz), 1.30 (3H, d, J=6.3 Hz), 1.53–1.80 (1H, m), 1.92–2.17 (1H, m), 2.21–2.74 (4H, m), 3.09–3.25 (1H, m), 3.34–4.01 (10H, m), 4.10–4.38 (3H, m).

EXAMPLE 43

(1R,5S,6S)-6-[(1R)-1-Hydroxyethyl]-2-[(2S,4S)-2-[1-hydroxy-2-[(3R)-3-methylaminopyrrolidin-1-ylcarbonyl]ethyl]pyrrolidin-4-ylthio]-1-methyl-1-carbapen-2-em-3-carboxylic acid (Exemplified Compound 2-7)

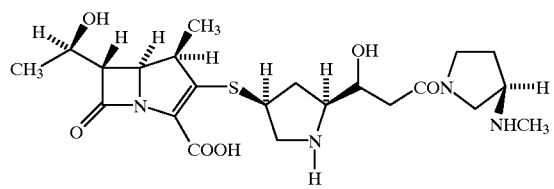

Infrared absorption spectrum (KBr) vmax cm$^{-1}$: 3365, 1756, 1614, 1453, 1387.

Nuclear magnetic resonance spectrum (400 MHz, D$_2$O) δ ppm: 1.23 (3H, d, J=6.9 Hz), 1.30 (3H, d, J=6.3 Hz), 1.54–1.71 (1H, m), 2.00–2.21 (1H, m), 2.29–2.75 (7H, m), 3.03–3.21 (1H, m), 3.31–3.99 (10H, m), 4.15–4.30 (3H, m).

EXAMPLE 44

(1R,5S,6S)-6-[(1R)-1-Hydroxyethyl]-2-[(2S,4S)-2-[1-hydroxy-2-[(3R)-3-methylaminomethylpyrrolidin-1-ylcarbonyl]ethyl]pyrrolidin-4-ylthio]-1-methyl-1-carbapen-2-em-3-carboxylic acid (Exemplified Compound 2-9)

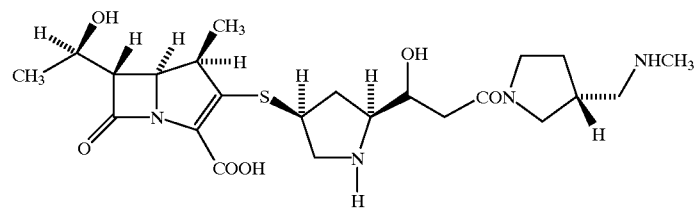

(1) By using 4-nitrobenzyl (1R,5R,6S)-6-[(1R)-1-hydroxyethyl]-1-methyl-2-(diphenylphosphoryloxy)-1-carbapen-2-em-3-carboxylate (819 mg) and (2S,4S)-2-[1-hydroxy-2-[(3R)-3-(N-methyl-N-4-nitrobenzyloxycarbonylamino)pyrrolidin-1-ylcarbonyl]ethyl]-4-mercapto-1-(4-nitrobenzyloxycarbonyl)pyrrolidine (830 mg), reaction and purification were carried out in a similar manner to that described in Example 40-(1), whereby 4-nitrobenzyl (1R,5S,6S)-6-[(1R)-1-hydroxyethyl]-2-[(2S,4S)-2-[1-hydroxy-2-[(3S)-3-(N-methyl-N-4-nitrobenzyloxycarbonylamino)pyrrolidin-1-ylcarbonyl]ethyl]-1-(4-nitrobenzyloxycarbonyl)pyrrolidin-4-ylthio]-1-methyl-1-carbapen-2-em-3-carboxylate (919 mg) was obtained.

Infrared absorption spectrum (KBr) vmax cm$^{-1}$: 3439, 1773, 1703, 1625, 1608, 1522, 1447, 1406, 1378.

Nuclear magnetic resonance spectrum (400 MHz, CDCl$_3$) δ ppm: 1.27 (3H, d, J=7.3 Hz), 1.37 (3H, d, J=6.3 Hz), 1.91–2.65 (6H, m), 2.90 (3H, d, J=8.1 Hz), 3.19–3.80 (9H, m), 3.97–4.55 (5H, m), 5.13–5.56 (6H, m), 7.45–7.60 (4H, m), 7.65 (2H, d, J=8.5 Hz), 8.19–8.28 (6H, m).

(2) To a solution of the compound (919 mg), which had been obtained in (1), in tetrahydrofuran (44 ml) and water (31.4 ml), a 10% palladium-carbon catalyst (1.862 g) was added. Hydrogen was allowed to be absorbed into the resulting mixture for 2 hours, while stirring at an external temperature of 30° C. The reaction mixture was treated in a similar manner to that described in Example 40-(2), whereby the title compound (195.2 mg) was obtained as a powder.

(1) By using 4-nitrobenzyl (1R,5R,6S)-6-[(1R)-1-hydroxyethyl]-1-methyl-2-(diphenylphosphoryloxy)-1-carbapen-2-em-3-carboxylate (1.144 g) and (2S,4S)-2-[1-hydroxy-2-[(3R)-3-(N-methyl-N-4-nitrobenzyloxycarbonylaminomethyl)pyrrolidin-1-ylcarbonyl]ethyl]-4-mercapto-1-(4-nitrobenzyloxycarbonyl)pyrrolidine (1.184 g), reaction and isolating operation were carried out in a similar manner to that described in Example 40-(1), whereby 4-nitrobenzyl (1R,5S,6S)-6-[(1R)-1-hydroxyethyl]-2-[(2S,4S)-2-[(2S,4S)-2-[1-hydroxy-2-[(3R)-3-(N-methyl-N-4-nitrobenzyloxycarbonylaminomethyl)pyrrolidin-1-ylcarbonyl]ethyl]-1-(4-nitrobenzyloxycarbonyl)pyrrolidin-4-ylthio]-1-methyl-1-carbapen-2-em-3-carboxylate (1.476 g) was obtained.

Infrared absorption spectrum (KBr) vmax cm$^{-1}$: 3419, 1773, 1705, 1621, 1608, 1522, 1449, 1404, 1375, 1347.

Nuclear magnetic resonance spectrum (400 MHz, CDCl$_3$) δ ppm: 1.28 (3H, d, J=7.2 Hz), 1.37 (3H, d, J=6.2 Hz), 1.92–2.64 (6H, m), 3.00 (3H, d, J=8.2 Hz), 3.05–3.68 (11H, m), 3.93–4.50 (5H, m), 5.17–5.53 (6H, m), 7.52 (4H, d, J=6.8 Hz), 7.66 (2H, d, J=8.5 Hz), 8.22 (6H, d, J=8.7 Hz).

(2) To a solution of the compound (1.476 g), which had been obtained in (1), in tetrahydrofuran (69.8 ml) and water (49.8 ml), a 10% palladium-carbon catalyst (2.99 g) was added. Hydrogen was allowed to be absorbed into the resulting mixture for 2 hours, while stirring at an external temperature of 30° C. The reaction mixture was treated in a similar manner to that described in Example 40-(2), whereby the title compound (235.3 mg) was obtained as a powder.

Infrared absorption spectrum (KBr) vmax cm$^{-1}$: 3365, 1756, 1614, 1455, 1387.

Nuclear magnetic resonance spectrum (400 MHz, D$_2$O) δ ppm: 1.23 (3H, d, J=7.1 Hz), 1.30 (3H, d, J=6.3 Hz), 1.43–1.61 (1H, m), 1.67–1.87 (1H, m), 2.39–2.78 (7H, m), 2.92–3.07 (1H, m), 3.09–3.47 (8H, m), 3.55–3.95 (4H, m), 4.10–4.31 (3H, m).

EXAMPLE 45

(1R,5S,6S)-2-[(2S,4S)-2-[2-[(3R)-3-aminomethylpyrrolidin-1-ylcarbonyl]-1-hydroxyethyl]pyrrolidin-4-ylthio]-6-[(1R)-1-hydroxyethyl]-1methyl-1-carbapen-2-em-3-carboxylic acid (Exemplified Compound 2-2)

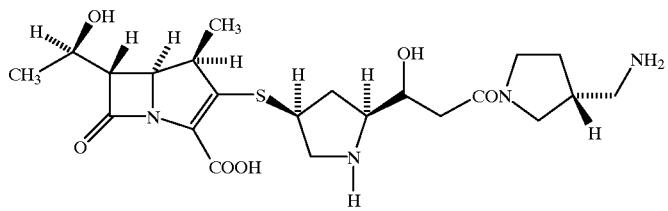

(1) By using 4-nitrobenzyl (1R,5R,6S)-6-[(1R)-1-hydroxyethyl]-1-methyl-2-(diphenylphosphoryloxy)-1-carbapen-2-em-3-carboxylate (199.5 mg) and (2S,4S)-2-[1-hydroxy-2-[(3R)-3-(4-nitrobenzyloxycarbonylaminomethyl)pyrrolidin-1-ylcarbonyl]ethyl]-4-mercapto-1-(4-nitrobenzyloxycarbonyl)pyrrolidine (202.3 mg), reaction and purification were carried out in a similar manner to that described in Example 40-(1), whereby 4-nitrobenzyl (1R,5S,6S)-6-[(1R)-1-hydroxyethyl]-2-[(2S,4S)-2-[1-hydroxy-2-[(3R)-3-(4-nitrobenzyloxycarbonylaminomethyl)pyrrolidin-1-ylcarbonyl]ethyl]-1-(4-nitrobenzyloxycarbonyl)pyrrolidin-4-ylthio]-1-methyl-1-carbapen-2-em-3-carboxylate (237.1 mg) was obtained.

Infrared absorption spectrum (KBr) vmax cm$^{-1}$: 3409, 1773, 1706, 1608, 1522, 1449, 1404, 1375, 1347.

Nuclear magnetic resonance spectrum (400 MHz, CDCl$_3$) δ ppm: 1.23 (3H, d, J=7.2 Hz), 1.38 (3H, d, J=6.2 Hz), 1.58–1.80 (1H, m), 1.93–2.62 (6H, m), 3.12–3.66 (10H, m), 4.04–4.51 (5H, m), 5.10–5.56 (6H, m), 7.46–7.70 (6H, m), 8.22 (6H, d, J=8.5 Hz).

(2) To a solution of the compound (237.1 mg), which had been obtained in (1), in tetrahydrofuran (11.2 ml) and water (8.0 ml), a 10% palladium-carbon catalyst (0.48 g) was added. Hydrogen was allowed to be absorbed into the resulting mixture for 2 hours, while stirring at an external temperature of 30° C. The reaction mixture was treated in a similar manner to that described in Example 40-(2), whereby the title compound (24.1 mg) was obtained as a powder.

Infrared absorption spectrum (KBr) vmax cm$^{-1}$: 3404, 1755, 1610, 1456, 1392.

Nuclear magnetic resonance spectrum (400 MHz, D$_2$O) δ ppm: 1.02 (3H, d, J=7.2 H), 1.10 (3H, d, J=6.4 Hz), 1.26–1.68 (2H, m), 1.94–2.08 (1H, m), 2.21–2.52 (4H, m), 2.76–3.26 (9H, m), 3.35–3.73 (3H, m), 3.91–4.09 (3H, m).

EXAMPLE 46

(1R,5S,6S)-6-[(1R)-1-Hydroxyethyl]-2-[(2S,4S)-2-[-1-hydroxy-2-[(3S)-3-methylaminomethylpyrrolidin-1-ylcarbonyl]ethyl]pyrrolidin-4-ylthio]-1-methyl-1-carbapen-2-em-3-carboxylic acid (Exemplified Compound 2-9)

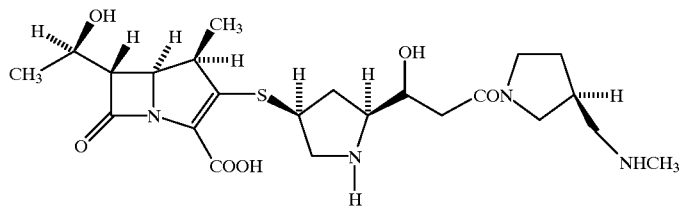

(1) By using 4-nitrobenzyl (1R,5R,6S)-6-[(1R)-1-hydroxyethyl]-1-methyl-2-(diphenylphosphoryloxy)-1-carbapen-2-em-3-carboxylate (660.8 mg) and (2S,4S)-2-[1-hydroxy-2-[(3S)-3-(N-methyl-N-4-nitrobenzyloxycarbonylaminomethyl)pyrrolidin-1-ylcarbonyl)ethyl]-4-mercapto-1-(4-nitrobenzyloxycarbonyl)pyrrolidine (683.5 mg), reaction and purification were carried out in a similar manner to that described in Example 40-(1), whereby 4-nitrobenzyl (1R,5S,6S)-6-[(1R)-1-hydroxyethyl]-2-[(2S,4S)-2-[1-hydroxy-2-[(3S)-3-(N-methyl-N-4-nitrobenzyloxycarbonylaminomethyl)pyrrolidin-1-ylcarbonyl]ethyl]-1-(4-nitrobenzyloxycarbonyl)pyrrolidin-4-ylthio]-1-methyl-1-carbapen-2-em-3-carboxylate (841.4 mg) was obtained.

Infrared absorption spectrum (KBr) vmax cm$^{-1}$: 3429, 1772, 1704, 1621, 1608, 1522, 1449, 1404, 1375, 1347.

Nuclear magnetic resonance spectrum (400 MHz, CDCl$_3$) δ ppm: 1.27 (3H, d, J=7.3 Hz), 1.37 (3H, d, J=6.2 Hz), 1.94–2.07 (1H, m), 2.13–2.64 (5H, m), 2.95–3.04 (3H, m), 3.06–3.69 (11H, m), 3.96–4.50 (6H, m), 5.16–5.54 (6H, m), 7.48–7.69 (6H, m), 8.23 (6H, d, J=8.7 Hz).

(2) To a solution of the compound (841.4 mg), which had been obtained in (1), in tetrahydrofuran (39.8 ml) and water (28.4 ml), a 10% palladium-carbon catalyst (1.704 g) was added. Hydrogen was allowed to be absorbed into the resulting mixture for 2 hours, while stirring at an external temperature of 30° C. The reaction mixture was treated in a similar manner to that described in Example 40-(2), whereby the title compound (96.7 mg) was obtained as a powder.

Infrared absorption spectrum (KBr) νmax cm$^{-1}$: 3374, 1756, 1614, 1455, 1388.

Nuclear magnetic resonance spectrum (400 MHz, D$_2$O) δ ppm: 1.23 (3H, d, J=7.1 Hz), 1.30 (3H, d, J=6.4 Hz), 1.44–1.61 (1H, m), 1.68–1.87 (1H, m), 2.16–2.30 (1H, m), 2.41–2.77 (7H, m), 2.95–3.07 (1H, m), 3.09–3.48 (7H, m), 3.55–3.95 (4H, m), 4.11–4.30 (3H, m).

EXAMPLE 47

(1R,5S,6S)-6-[(1R)-1-Hydroxyethyl]-2-[(2S,4S)-2-[hydroxy-2-(piperazin-1-ylcarbonyl)ethyl]pyrrolidin-4-ylthio]-1-methyl-1-carbapen-2-em-3-carboxylic acid (Exemplified Compound 3-4)

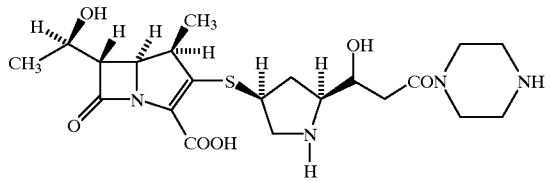

(1) By using 4-nitrobenzyl (1R,5R,6S)-6-[(1R)-1-hydroxyethyl]-1-methyl-2-(diphenylphosphoryloxy)-1-carbapen-2-em-3-carboxylate (1.458 g) and (2S,4S)-2-[1-hydroxy-2-[4-(4-nitrobenzyloxycarbonyl)piperazin-1-ylcarbonyl]ethyl]-4-mercapto-1-(4-nitrobenzyloxycarbonyl)pyrrolidine (1.443 g), reaction and purification were carried out in a similar manner to that described in Example 40-(1), whereby 4-nitrobenzyl (1R,5S,6S)-6-[(1R)-1-hydroxyethyl]-2-[(2S,4S)-2-[1-hydroxy-2-[4-(4-nitrobenzyloxycarbonyl)piperazin-1-ylcarbonyl]ethyl-1-(4-nitrobenzyloxycarbonyl)pyrrolidin-4-ylthio]-1-methyl-1-carbapen-2-em-3-carboxylate (1.558 g) was obtained.

Infrared absorption spectrum (KBr) νmax cm$^{-1}$: 3438, 1773, 1705, 1635, 1608, 1522, 1434, 1407, 1347.

Nuclear magnetic resonance spectrum (400 MHz, CDCl$_3$) δ ppm: 1.28 (3H, d, J=7.2 Hz), 1.38 (3H, d, J=6.3 Hz), 1.93–2.66 (5H, m), 3.24–3.76 (12H, m), 4.01–4.31 (4H, m), 5.18–5.04 (6H, m), 7.53 (4H, d, J=6.5 Hz), 7.66 (2H, d, J=8.6 Hz), 8.23 (6H, d, J=8.3 Hz).

(2) To a solution of the compound (1.558 g), which had been obtained in (1), in tetrahydrofuran (73.7 ml) and water (52.6 ml), a 10% palladium-carbon catalyst (3.16 g) was added. Hydrogen was allowed to be absorbed into the resulting mixture for 2 hours, while stirring at an external temperature of 30° C. The reaction mixture was treated in a similar manner to that described in Example 40-(2), whereby the title compound (231.6 mg) was obtained as a powder.

Infrared absorption spectrum (KBr) νmax cm$^{-1}$: 3390, 1755, 1606, 1449, 1389, 1283.

Nuclear magnetic resonance spectrum (400 MHz, D$_2$O) δ ppm. 1.23 (3H, d, J=7.2 Hz), 1.30 (3H, d, J=6.4 Hz), 1.57–1.74 (1H, m), 2.46–2.81 (4H, m), 3.04–3.25 (5H, m), 3.34–3.99 (8H, m), 4.18–4.30 (3H, m).

EXAMPLE 48

(1R,5S,6S)-6-[(1R)-1-Hydroxyethyl]-2-[(2S,4S)-2-[1-hydroxy-2-(4-methylpiperazin-1-ylcarbonyl)ethyl]pyrrolidin-4-ylthio]-1-carbapen-2-em-3-carboxylic acid (Exemplified Compound 3-5)

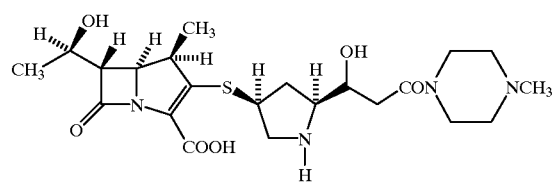

(1) By using 4-nitrobenzyl (1R,5R,6S)-6-[(1R)-1-hydroxyethyl]-1-methyl-2-(diphenylphosphoryloxy)-1-carbapen-2-em-3-carboxylate (3.078 g) and (2S,4S)-2-[1-hydroxy-2-[4-methylpiperazin-1-ylcarbonyl]ethyl]-4-mercapto-1-(4-nitrobenzyloxycarbonyl)pyrrolidine (2.232 g), reaction and purification were carried out in a similar manner to that described Example 40-(1), whereby 4-nitrobenzyl (1R,5S,6S)-6-[(1R)-1-hydroxyethyl]-2-[(2S,4S)-2-[1-hydroxy-2-[4-methylpiperazin-1-ylcarbonyl]ethyl]-1-( 4-nitrobenzyloxycarbonyl)pyrrolidin-4-ylthio]-1-methyl-1-carbapen-2-em-3-carboxylate (3.007 g) was obtained.

Infrared absorption spectrum (KBr) νmax cm$^{-1}$: 3410, 1772, 1704, 1632, 1608, 1522, 1489, 1448, 1404, 1347.

Nuclear magnetic resonance spectrum (400 MHz, CDCl$_3$) δ ppm: 1.27 (3H, d, J=7.3 Hz), 1.37 (3H, d, J=6.7 Hz), 1.91–2.63 (10H, m), 2.93–3.01 (1H, m), 3.06–3.78 (8H, m), 3.97–4.60 (5H, m), 5.16–5.54 (4H, m), 7.52 (2H, d, J=8.3 Hz), 7.67 (2H, d, J=8.7 Hz), 8.22 (2H, d, J=8.7 Hz), 8.24 (2H, d, J=8.3 Hz).

(2) To a solution of the compound (1.127 g), which had been obtained in (1), in tetrahydrofuran (53.3 ml) and water (38.1 ml), a 10% palladium-carbon catalyst (2.28 g) was added. Hydrogen was allowed to be absorbed into the resulting mixture for 2 hours, while stirring at an external temperature of 30° C. The reaction mixture was treated in a similar manner to that described in Example 40-(2), whereby the title compound (365.4 mg) was obtained as a powder.

Infrared absorption spectrum (KBr) νmax cm$^{-1}$: 3355, 1758, 1595, 1488, 1454, 1388, 1251.

Nuclear magnetic resonance spectrum (400 MHz, D$_2$O) δ ppm: 1.23 (3H, d, J=7.2 Hz), 1.30 (3H, d, J=6.4 Hz), 1.71–1.94 (1H, m), 2.54–3.06 (16H, m), 3.29–3.51 (4H, m), 3.62–3.94 (9H, m), 3.95–4.08 (1H, m), 4.21–4.49 (3H, m).

EXAMPLE 49

(1R,5S,6S)-6-[(1R)-1-Hydroxyethyl]-2-[(2S,4S)-2-[1-hydroxy-2-[(3S)-pyrrolidin-3-ylaminocarbonyl]ethyl]pyrrolidin-4-1-methyl-1-carbapen-2-em-3-carboxylic acid (Exemplified Compound 4-1)

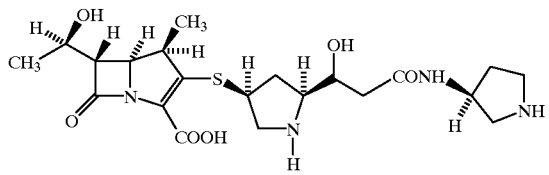

(1) By using 4-nitrobenzyl (1R,5R,6S)-6-[(1R)-1-hydroxyethyl]-1-methyl-2-(diphenylphosphoryloxy)-1-carbapen-2-em-3-carboxylate (367.2 mg) and (2S,4S)-2-[1-hydroxy-2-[(3S)-1-(4-nitrobenzyloxycarbonyl)pyrrolidin-3-ylaminocarbonyl]ethyl]4-mercapto-1-(4-nitrobenzyloxycarbonyl)pyrrolidine (363.3 mg), reaction and purification were carried out in a similar manner to that described in Example 40-(1), whereby 4-nitrobenzyl (1R,5S,6S)-6-[(1R)-1-hydroxyethyl]-2-[(2S,4S)-2-[1-hydroxy-2-[(3S)-1-(4-nitrobenzyloxycarbonyl)pyrrolidin-3-ylaminocarbonyl]ethyl-1-(4-nitrobenzyloxycarbonyl)pyrrolidin-4-ylthio]-1-methyl-1-carbapen-2-em-3-carboxylate (412.8 mg) was obtained.

Infrared absorption spectrum (KBr) vmax cm$^{-1}$: 3401, 1773, 1705, 1607, 1523, 1496, 1406, 1347.

Nuclear magnetic resonance spectrum (400 MHz, CDCl$_3$) δ ppm: 1.27 (3H, d, J=7.1 Hz), 1.38 (3H, d, J=6.1 Hz), 1.72–1.96 (2H, m), 2.12–2.65 (4H, m), 3.21–3.38 (4H, m), 3.49–3.78 (4H, m), 3.96–4.30 (5H, m), 4.44–4.53 (1H, m), 5.16–5.53 (6H, m), 6.56–6.75 (1H, m), 7.51 (4H, d, J=8.1 Hz), 7.65 (2H, d, J=8.5 Hz), 8.19–8.27 (6H, m).

(2) To a solution of the compound (412.8 mg), which had been obtained in (1), in tetrahydrofuran (19.5 ml) and water (13.9 ml), a 10% palladium-carbon catalyst (0.836 g) was added. Hydrogen was allowed to be absorbed into the resulting mixture for 2 hours, while stirring at an external temperature of 30° C. The reaction mixture was treated in a similar manner to that described in Example 40-(2), whereby the title compound (83.5 mg) was obtained as a powder.

Infrared absorption spectrum (KBr) vmax cm$^{-1}$: 3352, 1756, 1649, 1592, 1449, 1390.

Nuclear magnetic resonance spectrum (400 MHz, D$_2$O) δ ppm: 1.23 (3H, d, J=7.2 Hz), 1.30 (3H, d, J=6.3 Hz), 1.48–1.64 (1H, m), 2.01–2.11 (1H, m), 2.31–2.61 (4H, m), 2.99–3.14 (1H, m), 3.20–3.64 (8H, m), 3.80–3.91 (1H, m), 4.09–4.30 (3H, m), 4.44–4.53 (1H, m).

EXAMPLE 50

(1R,5S,6S)-6-[(1R)-1-Hydroxyethyl]-2-[(2S,4S)-2-[1-hydroxy-2-[N-methyl-N-(3S)-pyrrolidin-3-ylaminocarbonyl]ethyl]pyrrolidin-4-ylthio]-1-carbapen-2-em-3-carboxylic acid (Exemplified Compound 4-5)

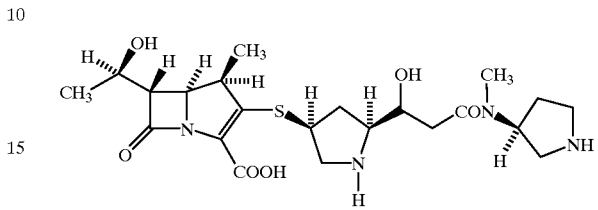

(1) By using 4-nitrobenzyl (1R,5R,6S)-6-[(1R)-1-hydroxyethyl]-1-methyl-2-(diphenylphosphoryloxy)-1-carbapen-2-em-3-carboxylate (339.1 mg) and (2S,4S)-2-[1-hydroxy-2-[N-methyl-N-(3S)-1-(4-nitrobenzyloxycarbonyl)pyrrolidin-3-ylaminocarbonyl]ethyl]-4-mercapto-1-(4-nitrobenzyloxycarbonyl)pyrrolidine (343.1 mg), reaction and purification were carried out in a similar manner to that described in Example 40-(1), whereby 4-nitrobenzyl (1R,5S,6S)-6-[(1R)-1-hydroxyethyl]-2-[(2S,4S)-2-[1-hydroxy-2-[N-methyl-N-(3S)-1-(4-nitrobenzyloxycarbonyl)pyrrolidin-3-ylaminocarbonyl]ethyl]-1-(4-nitrobenzyloxycarbonyl)pyrrolidin-4-ylthio]-1-methyl-1-carbapen-2-em-3-carboxylate (421.1 mg) was obtained.

Infrared absorption spectrum (KBr) vmax cm$^{-1}$: 3438, 1774, 1705, 1632, 1608, 1522, 1495, 1429, 1405, 1347.

Nuclear magnetic resonance spectrum (400 MHz, CDCl$_3$) δ ppm: 1.28 (3H, d, J=7.2 Hz), 1.38 (3H, d, J=6.3 Hz), 1.66–2.65 (7H, m), 2.76–2.91 (3H, m), 3.20–3.76 (8H, m), 3.99–4.47 (5H, m), 5.15–5.54 (6H, m), 7.50 (4H, d, J=8.5 Hz), 7.66 (2H, d, J=8.5 Hz), 8.23 (6H, d, J=8.5 Hz).

(2) To a solution of the compound (421.1 mg), which had been obtained in (1), in tetrahydrofuran (19.9 ml) and water (14.2 ml), a 10% palladium-carbon catalyst (0.853 g) was added. Hydrogen was allowed to be absorbed into the resulting mixture for 2 hours, while stirring at an external temperature of 30° C. The reaction mixture was treated in a similar manner to that described in Example 40-(2), whereby the title compound (73.2 mg) was obtained as a powder.

Infrared absorption spectrum (KBr) vmax cm$^{-1}$: 3394, 1755, 1606, 1489, 1450, 1389.

Nuclear magnetic resonance spectrum (400 MHz, D$_2$O) δ ppm: 1.23 (3H, d, J=6.9 Hz), 1.30 (3H, d, J=6.5 Hz), 1.45–1.64 (1H, m), 2.11–2.21 (1H, m), 2.27–2.92 (4H, m), 2.95–3.11 (4H, m), 3.21–3.67(9H, m), 3.78–3.90 (1H, m), 4.08–4.30 (3H, m).

EXAMPLE 51

(1R,5S,6S)-2-[(2S,4S)-2-[2-(4-Guanylpiperazin-1-ylcarbonyl)-1-hydroxyethyl]-pyrrolidin-4-ylthio]-6-[(1R)-1-hydroxyethyl]-1-methyl-1-carbapen-2-em-3-carboxylic acid (Exemplified Compound 3-1)

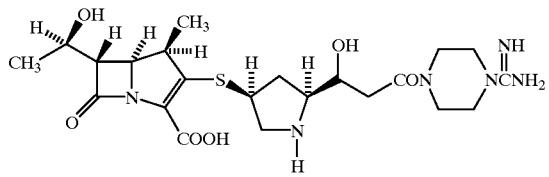

(1) By using 4-nitrobenzyl (1R,5R,6S)-6-[(1R)-1-hydroxyethyl]-1-methyl-2-(diphenylphosphoryloxy)-1-carbapen-2-em-3-carboxylate (1.106 g) and (2S,4S)-2-[1-hydroxy-2-[4-(4-nitrobenzyloxycarbonylguanyl)piperazin-1-ylcarbonyl]ethyl]-4-mercapto-1-(14-nitrobenzyloxycarbonyl)pyrrolidine (1.169 g), reaction and purification were carried out in a similar manner to that described in Example 40-(1), whereby 4-nitrobenzyl (1R,5S,6S)-6-[(1R)-1-hydroxyethyl]-2-[(2S,4S)-2-[1-hydroxy-2-[4-(4-nitrobenzyloxycarbonylguanyl)piperazin-1-ylcarbonyl]ethyl]-1-(4-nitrobenzyloxycarbonyl)pyrrolidin-4-ylthio]-1-methyl-1-carbapen-2-em-3-carboxylate (1.016 g) was obtained.

Infrared absorption spectrum (KBr) vmax cm$^{-1}$: 3415, 1772, 1704, 1643, 1607, 1545, 1522, 1443, 1404, 1375, 1347.

Nuclear magnetic resonance spectrum (400 MHz, CDCl$_3$) δ ppm: 1.27 (3H, d, J=7.3 Hz), 1.37 (3H, d, J=6.3 Hz), 1.84–2.67 (5H, m), 3.16–3.84 (10H, m), 4.01–4.57 (6H, m), 5.16–5.54 (6H, m), 6.96–7.24 (2H, m), 7.49–7.68 (6H, m), 8.16–8.27 (6H, m).

(2) To a solution of the compound (1.016 g), which had been obtained in (1), in tetrahydrofuran (48.0 ml) and water (34.3 ml), a 10% palladium-carbon catalyst (2.057 g) was added. Hydrogen was allowed to be absorbed into the resulting mixture for 2 hours, while stirring at an external temperature of 30° C. The reaction mixture was treated in a similar manner to that described in Example 40-(2), whereby the title compound (195.1 mg) was obtained in the powdery form.

Infrared absorption spectrum (KBr) vmax cm$^{-1}$: 3348, 1754, 1608, 1447, 1390.

Nuclear magnetic resonance spectrum (400 MHz, D$_2$O) δ ppm: 1.23 (3H, d, J=7.2 Hz), 1.30 (3H, d, J=6.3 Hz), 1.42–1.60 (1H, m), 2.40–2.51 (1H, m), 2.59–2.81 (2H, m), 2.94–3.05 (1H, m), 3.17–3.33 (2H, m), 3.36–3.48 (2H, m), 3.53–3.89 (9H, m), 4.10–4.31 (3H, m).

EXAMPLE 52

(1R,5S,6S)-6-[(1R)-1-Hydroxyethyl]-2-[(2S,4S)-2-[1-hydroxy-2-[(3R)-pyrrolidin-3-ylaminocarbonyl]ethyl]pyrrolidin-4-ylthio]-1-methyl-1-carbapen-2-em-3-carboxylic acid (Exemplified Compound 4-1)

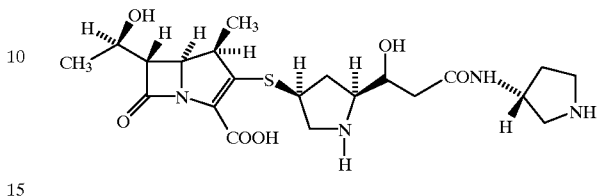

(1) By using 4-nitrobenzyl (1R,5R,6S)-6-[(1R)-1-hydroxyethyl]-1-methyl-2-(diphenylphosphoryloxy)-1-carbapen-2-em-3-carboxylate (433.5 mg) and (2S,4S)-2-[1-hydroxy-2-[(3R)-1-(4-nitrobenzyloxycarbonyl)pyrrolidin-3-ylaminocarbonyl]ethyl]-4-mercapto-1-(4-nitrobenzyloxycarbonyl)pyrrolidine (428.9 mg), reaction and purification were carried out in a similar manner to that described in Example 40-(1), whereby 4-nitrobenzyl (1R,5S,6S)-6-[(1R)-1-hydroxyethyl]-2-[(2R,4S)-2-[1-hydroxy-2 [(3R)-1-(4-nitrobenzyloxycarbonyl)pyrrolidin-3ylaminocarbonyl]ethyl-1-(4-nitrobenzyloxycarbonyl) pyrrolidin-4-ylthio]-1-methyl-1-carbapen-2-em-3-carboxylate (464.8 mg) was obtained.

Infrared absorption spectrum (KBr) vmax cm$^{-1}$: 3393, 1773, 1705, 1607, 1522, 1496, 1431, 1405, 1347.

Nuclear magnetic resonance spectrum (400 MHz, CDCl$_3$) δ ppm: 1.27 (3H, d, J=7.4 Hz), 1.37 (3H, d, J=6.3 Hz), 1.57–2.66 (6H, m), 3.19–3.38 (4H, m), 3.49–3.77 (4H, m), 3.98–4.53 (6H, m), 5.16–5.53 (6H, m), 6.54–6.77 (1H, m), 7.52 (4H, d, J=8.4 Hz), 7.65 (2H, d, J=8.1 Hz), 8.23 (6H, d, J=8.5 Hz).

(2) To a solution of the compound (460.0 mg), which had been obtained in (1), in tetrahydrofuran (21.8 ml) and water (15.5 ml), a 10% palladium-carbon catalyst (0.932 g) was added. Hydrogen was allowed to be absorbed into the resulting mixture for 2 hours, while stirring at an external temperature of 30° C. The reaction mixture was treated in a similar manner to that described in Example 40-(2), whereby the title compound (84.7 mg) was obtained as a powder.

Infrared absorption spectrum (KBr) vmax cm$^{-1}$: 3277, 1755, 1652, 1599, 1554, 1448, 1390.

Nuclear magnetic resonance spectrum (400 MHz, D$_2$O) δ ppm: 1.22 (3H, d, J=7.2 Hz), 1.30 (3H, d, J=6.4 Hz), 1.45–1.61 (1H, m), 2.01–2.10 (1H, m), 2.31–2.63 (4H, m), 2.94–3.09 (1H, m), 3.18–3.60 (7H, m), 3.77–3.89 (1H, m), 4.07–4.31 (4H, m), 4.44–4.52 (1H, m).

EXAMPLE 53

(1R,5S,6S)-2-[(2S,4S)-2-[2-[(3S)-3-Acetimidoylaminopyrrolidin-1-ylcarbonyl]-1-hydroxyethyl]pyrrolidin-4-ylthio]-6-[(1R)-1-hydroxyethyl]-1-methyl-1-carbapen-2-em-3-carboxylic acid (Exemplified Compound 2-5)

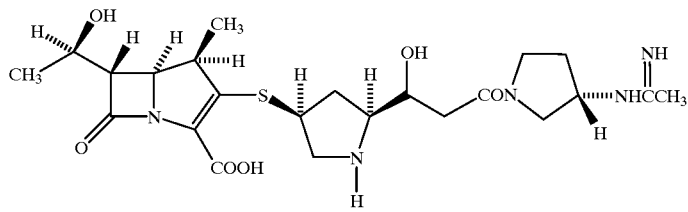

(1) By using 4-nitrobenzyl (1R,5R,6S)-6-[(1R)-1-hydroxyethyl]-1-methyl-2-(diphenylphosphoryloxy)-1-carbapen-2-em-3-carboxylate (563.2 mg) and (2S,4S)-2-[1-hydroxy-2-[(3S)-3-(4-nitrobenzyloxycarbonylacetimidoylamino)pyrrolidin-1-ylcarbonyl]ethyl]-4-mercapto-1-(4-nitrobenzyloxycarbonyl)pyrrolidine (594.3 mg), reaction and purification were carried out in a similar manner to that described in Example 40-(1), whereby 4-nitrobenzyl (1R,5S,6S)-6-[(1R)-1-hydroxyethyl]-2-[(2S,4S)-2-[(3S)-3-(4-nitrobenzyloxycarbonylacetimidoylamino)pyrrolidin-1-ylcarbonyl]ethyl-1-(4-nitrobenzyloxycarbonyl)pyrrolidin-4-ylthio]-1-methyl-1-carbapen-2-em-3-carboxylate (653.2 mg) was obtained as an amorphous substance.

Infrared absorption spectrum (KBr) νmax cm$^{-1}$: 3371, 1773, 1703, 1608, 1551, 1522, 1496, 1446, 1404, 1375, 1347.

Nuclear magnetic resonance spectrum (400 MHz, CDCl$_3$) δ ppm: 1.27 (3H, d, J=7.2 Hz), 1.38 (3H, d, J=6.2 Hz), 1.71–1.81 (1H, m), 1.86–2.66 (9H, m), 3.24–3.87 (8H, m), 3.98–4.68 (6H, m), 5.12–5.55 (6H, m), 7.47–7.70 (6H, m), 8.17–8.29 (6H, m).

(2) To a solution of the compound (653.2 mg), which had been obtained in (1), in tetrahydrofuran (30.9 ml) and water (22.1 ml), a 10% palladium-carbon catalyst (1.323 g) was added. Hydrogen was allowed to be absorbed into the resulting mixture for 2 hours, while stirring at an external temperature of 30° C. The reaction mixture was treated in a similar manner to that described in Example 40-(2), whereby the title compound (139.0 mg) was obtained as a powder.

Infrared absorption spectrum (KBr) νmax cm$^{-1}$: 3278, 1755, 1683, 1618, 1453, 1387.

Nuclear magnetic resonance spectrum (400 MHz, D$_2$O) δ ppm: 1.23 (3H, d, J=7.2 Hz), 1.30 (3H, d, J=6.5 Hz), 1.42–1.59 (1H, m), 2.06–2.74 (8H, m), 2.93–3.04 (1H, m), 3.16–3.31 (2H, m), 3.35–3.46 (2H, m), 3.49–3.98 (5H, m), 4.10–4.38 (4H, m).

EXAMPLE 54

(1R,5S,6S)-2-[(2S,4S)-2-[2-(4-Acetimidoylpiperazin-1-ylcarbonyl)-1-hydroxyethyl]pyrrolidin-4-ylthio]-6-[(1R)-1-hydroxyethyl]-1-methyl-1-carbapen-2-em-3-carboxylic acid
(Exemplified Compound 3-3)

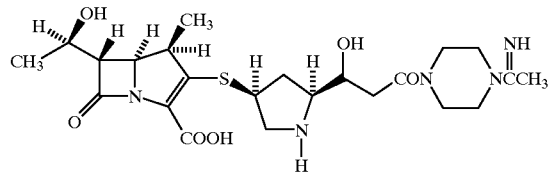

In a similar manner to that described in Example 51-(1) and (2), the title compound was obtained.

Nuclear magnetic resonance spectrum (270 MHz, D$_2$O) δ ppm: 1.23 (3H, d, J=7.6 Hz), 1.30 (3H, d, J=6.3 Hz), 1.40–1.60 (1H, m), 2.10–4.31 (20H, m), 2.35 (3H, s).

EXAMPLE 55

(1R,5S,6S)-6-[(1R)-1-Hydroxyethyl]-2-[(2S,4S)-2-[1-hydroxy-2-[(3S)-1-amidinopyrrolidin-3-ylaminocarbonyl]ethyl]pyrrolidin-4-ylthio]-1-methyl-1-carbapen-2-em-3-carboxylic acid
(Exemplified Compound 4-4)

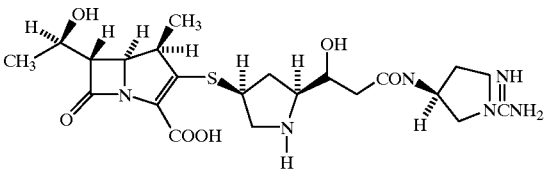

In a similar manner to that described in Example 40-(1) and (2), the title compound was obtained.

Infrared absorption spectrum (KBr) νmax cm$^{-1}$: 3351, 1752, 1674, 1616, 1457, 1390, 1344.

Nuclear magnetic resonance spectrum (400 MHz, D$_2$O) δ ppm: 1.23 (3H, d, J=7.2 Hz), 1.30 (3H, d, J=6.5 Hz), 1.44–1.51 (1H, m), 2.09–2.16 (1H, m), 2.26–2.71 (4H, m), 2.96–3.00 (1H, m), 3.19–3.83 (8H, m), 4.13–4.28 (8H, m).

EXAMPLE 56

(1R,5S,6)-2-[(2S,4S)-2-[1-hydroxy-2-[(3S)-1-Acetimidoylpyrrolidin-3-ylaminocarbonyl]ethyl]pyrrolidin-4-ylthio]-6-[(1R)-1-hydroxyethyl]-1-methyl-1-carbapen-2-em-3-carboxylic acid (Exemplified Compound 4-3)

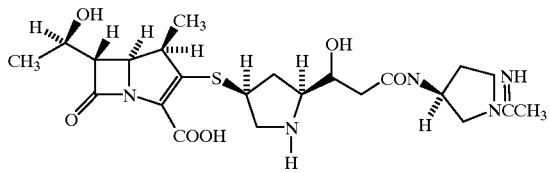

In a similar manner to that described in Example 40-(1) and (2), the title compound can be obtained.

EXAMPLE 57

(1R,5S,6S)-2-[(2S,4)-2-[2-(4-Aminomethylpiperidin-1-ylcarbonyl)-1-hydroxyethyl]pyrrolidin-4-ylthio]-6-[(1R)-1-hydroxyethyl]-1-methyl-1-carbapen-2-em-3-carboxylic acid (Exemplified Compound 2-47)

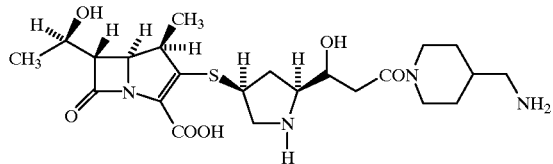

In a similar manner to that described in Example 40-(1) and (2), the title compound can be obtained.

EXAMPLE 58

(1R,5S,6S)-2-[(2S,4S)-2-[2-(3-Aminopiperidin-1-ylcarbonyl)-1-hydroxyethyl]pyrrolidin-4-ylthio]-6-[(1R)-1-hydroxyethyl]-1-methyl-1-carbapen-2-em-3-carboxylic acid (Exemplified Compound 2-37)

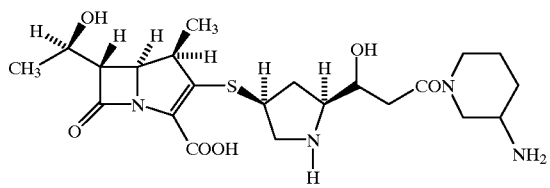

In a similar manner to that described in Example 40-(1) and (2), the title compound can be obtained.

EXAMPLE 59

(1R,5S,6S)-2-[(2S,4S)-2-[2-[(3S)-3-Aminopyrrolidin-1-ylcarbonyl]-(1R)-1-hydroxyethyl]pyrrolidin-4-ylthio]-6-[(1R)-1-hydroxyethyl]-1-methyl-1-carbapen-2-em-3-carboxylic acid (Exemplified Compound 2-1)

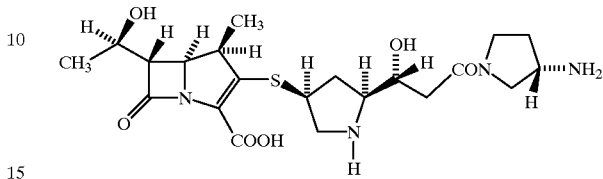

(1) By using 4-nitrobenzyl (1R,5R,6S)-6-[(1R)-1-hydroxyethyl]-1-methyl-2-(diphenylphosphoryloxy)-1-carbapen-2-em-3-carboxylate (1.180 g) and (2S,4S)-2-[(1R)-1-hydroxy-2-[(3S)-3-[3-(4-nitrobenzyloxycarbonylamino)pyrrolidin-1-ylcarbonyl]ethyl]-4-mercapto-1-(4-nitrobenzyloxycarbonyl)pyrrolidine (1.168 g), reaction and purification were carried out in a similar manner to that described in Example 40-(1), whereby 4-nitrobenzyl (1R,5S,6S)-6-[(1R)-1-hydroxyethyl]-2-[(2S,4S)-2-[(1R)-1-hydroxyethyl-2-[(3S)-3-(4-nitrobenzyloxycarbonylamino)pyrrolidin-1-ylcarbonyl]ethyl]-1-(4-nitrobenzyloxycarbonyl)pyrrolidin-4-ylthio]-1-methyl-1-carbapen-2-em-3-carboxylate (1.012 g) was obtained.

Infrared absorption spectrum (KBr) νmax cm$^{-1}$: 3391, 1772, 1707, 1625, 1608, 1522, 1448, 1404, 1375, 1347.

Nuclear magnetic resonance spectrum (400 MHz, CDCl$_3$) δ ppm: 1.27 (3H, d, J=7.0 Hz), 1.37 (3H, d, J=6.3 Hz), 1.81–2.55 (6H, m), 3.18–3.76 (9H, m), 3.95–4.57 (5H, m), 5.06–5.31 (5H, m), 5.50 (1H, d, J=13.7 Hz), 7.39–7.68 (6H, m), 8.22 (6H, d, J=9.5 Hz).

(2) To a solution of the compound (1.012 g), which had been obtained in (1), in tetrahydrofuran (47.8 ml) and water (34.2 ml), a 10% palladium-carbon catalyst (2.05 g) was added. Hydrogen was allowed to be absorbed into the resulting mixture for 2 hours, while stirring at an external temperature of 30° C. The reaction mixture was treated in a similar to that described in Example 40-(2), whereby the title compound (207.2 mg) was obtained as a powder.

Infrared absorption spectrum (KBr) νmax cm$^{-1}$: 3405, 1755, 1610, 1456, 1391.

Nuclear magnetic resonance spectrum (400 MHz, D$_2$O) δ ppm: 1.23 (3H, d, J=7.2 Hz), 1.30 (3H, d, J=6.2 Hz), 1.66–1.78 (1H, m), 1.96–2.17 (1H, m), 2.26–2.46 (1H, m), 2.48–2.72 (2H, m), 3.11–3.19 (1H, m), 3.35–3.68 (9H, m), 3.71–3.80 (1H, m), 3.86–3.99 (2H, m), 4.18–4.36 (3H, m).

(3) The compound (197.3 mg) obtained in (2) was dissolved in water (1 ml). To the resulting solution, 1N hydrochloric acid (0.421 ml) was added, followed by lyophilization, whereby a hydrochloride of the title compound (217.6 mg) was obtained as a powder.

Infrared absorption spectrum (KBr) νmax cm$^{-1}$: 3365, 1759, 1622, 1455, 1393.

Nuclear magnetic resonance spectrum (400 MHz, D$_2$O) δ ppm: 1.23 (3H, d, J=7.2 Hz), 1.28 (3H, d, J=6.4 Hz), 1.87–1.98 (1H, m), 2.07–2.24 (1H, m), 2.33–2.76 (4H, m), 3.34–3.49 (3H, m), 3.56–4.12 (8H, m), 4.20–4.29 (2H, m), 4.45–4.54 (1H, m).

EXAMPLE 60

(1R,5S,6S)-2-[(2S,4S)-2-[2-[(3S)-3-Aminopyrrolidin-1-ylcarbonyl]-(1S)-1-hydroxyethyl]pyrrolidin-4-ylthio]-6-[(1R)-1-hydroxyethyl]-1-methyl-1-carbapen-2-em-3-carboxylic acid (Exemplified Compound 2-1)

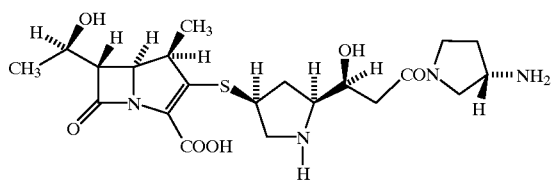

(1) By using 4-nitrobenzyl (1R,5R,6S)-6-[(1R)-1-hydroxyethyl]-1-methyl-2-(diphenylphosphoryloxy)-1-carbapen-2-em-3-carboxylate (2.111 g) and (2S,4S)-2-[(1S)-1-hydroxy-2-[(3S)-3-(4-nitrobenzyloxycarbonylamino)pyrrolidin-1-ylcarbonyl]ethyl]-4-mercapto-1-(4-nitrobenzyloxycarbonyl)pyrrolidine (2.089 g), reaction and purification were carried out in a similar manner to that described in Example 40-(1), whereby 4-nitrobenzyl (1R,5S,6S)-6-[(1R)-1-hydroxyethyl]-2-[(2S,4S)-2-[(1S)-1-hydroxyethyl-2-[(3S)-3-(4-nitrobenzyloxycarbonylamino)pyrrolidin-1-ylcarbonyl]ethyl-1-(4-nitrobenzyloxycarbonyl)pyrrolidin-4-ylthio]-1-methyl-1-carbapen-2-em-3-carboxylate (2.388 g) was obtained.

Infrared absorption spectrum (KBr) νmax cm$^{-1}$: 3374, 1773, 1705, 1623, 1608, 1522, 1448, 1404, 1375, 1347.

Nuclear magnetic resonance spectrum (400 MHz, CDCl$_3$) δ ppm: 1.27 (3H, d, J=7.3 Hz), 1.37 (3H, d, J=6.3 Hz), 1.80–2.67 (7H, m), 3.11–3.71 (8H, m), 4.09–4.34 (5H, m), 5.12–5.30 (5H, m), 5.50 (1H, d, J=13.7 Hz), 7.51 (4H, d, J=8.4 Hz), 7.65 (2H, d, J=8.6 Hz), 8.18–8.50 (6H, m).

(2) To a solution of the compound (1.684 g), which had been obtained in (1), in tetrahydrofuran (70.0 ml) and water (50.0 ml), a 10% palladium-carbon catalyst (3.413 g) was added. Hydrogen was allowed to be absorbed into the resulting mixture for 2 hours, while stirring at an external temperature of 30° C. The reaction mixture was treated in a similar manner to that described in Example 40-(2), whereby the title compound (405.4 mg) was obtained as a powder.

Infrared absorption spectrum (KBr) νmax cm$^{-1}$: 3403, 1755, 1610, 1456, 1390.

Nuclear magnetic resonance spectrum (400 MHz, D$_2$O) δ ppm: 1.23 (3H, d, J=7.2 Hz), 1.30 (3H, d, J=6.3 Hz), 1.56–1.66 (1H, m), 1.92–2.11 (1H, m), 2.21–2.42 (1H, m), 2.50–2.74 (3H, m), 3.18 (1H, dd, J=12.2,4.1 Hz), 3.35–3.98 (10H, m), 4.19–4.31 (3H, m).

(3) The compound (391.1 mg) obtained in (2) was dissolved in water (1 ml). To the resulting solution, 1N hydrochloric acid (0.835 ml) was added, followed by lyophilization, whereby a hydrochloride of the title compound (427.2 mg) was obtained as a powder.

Infrared absorption spectrum (KBr) νmax cm$^{-1}$: 3379, 1758, 1621, 1454, 1391.

Nuclear magnetic resonance spectrum (400 MHz, D$_2$O) δ ppm: 1.22 (3H, d, J=7.2 Hz), 1.28 (3H, d, J=6.4 Hz), 1.73–1.83 (1H, m), 2.07–2.25 (1H, m), 2.34–2.52 (3H, m), 3.32–3.50 (3H, m), 3.59–3.88 (6H, m), 3.96–4.13 (3H, m), 4.20–4.37 (3H, m).

EXAMPLE 61

(1R,5S,6S)-6-[(1R)-1-Hydroxyethyl]-2-[(2S,4S)-2-[(1R)-1-hydroxy-2-(piperazin-1-ylcarbonyl)ethyl]pyrrolidin-4-ylthio]-1-methyl-1-carbapen-2-em-3-carboxylic acid (Exemplified Compound 3-4)

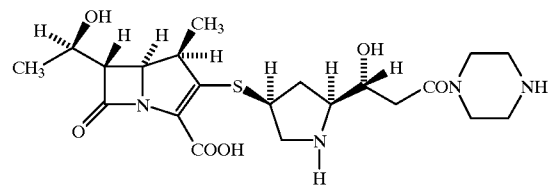

(1) By using 4-nitrobenzyl (1R,5R,6S)-6-[(1R)-1-hydroxyethyl]-1-methyl-2-(diphenylphosphoryloxy)-1-carbapen-2-em-3-carboxylate (434.5 mg) and (2S,4S)-2-[(1R)-1-hydroxy-2-[4-(4-nitrobenzyloxycarbonyl)piperazin-1-ylcarbonyl]ethyl]-4-mercapto-1-(4-nitrobenzyloxycarbonyl)pyrrolidine (429.9 mg), reaction and purification were carried out in a similar manner to that described in Example 40-(1), whereby 4-nitrobenzyl (1R,5S,6S)-6-[(1R)-1-hydroxyethyl]-2-[(2S,4S)-2-[(1R)-1-hydroxy-2-[4-(4-nitrobenzyloxycarbonyl)piperazin-1-ylcarbonyl]ethyl-1-(4-nitrobenzyloxycarbonyl)pyrrolidin-4-ylthio]-1-methyl-1-carbapen-2-em-3-carboxylate (511.4 mg) was obtained.

Infrared absorption spectrum (KBr) νmax cm$^{-1}$: 3453, 1773, 1705, 1636, 1608, 1522, 1496, 1434, 1407, 1374, 1347.

Nuclear magnetic resonance spectrum (400 MHz, CDCl$_3$) δ ppm: 1.27 (3H, d, J=7.2 Hz), 1.38 (3H, d, J=6.2 Hz), 1.66–1.78 (1H, m), 2.16–2.54 (4H, m), 3.18–3.76 (12H, m), 4.00–4.52 (6H, m), 5.16–5.54 (6H, m), 7.53 (4H, d, J=8.7 Hz), 7.66 (2H, d, J=8.7 Hz).

(2) To a solution of the compound (511.4 mg), which had been obtained in (1), in tetrahydrofuran (24.2 ml) and water (17.3 ml), a 10% palladium-carbon catalyst (1.036 g) was added. Hydrogen was allowed to be absorbed into the resulting mixture for 2 hours, while stirring at an external temperature of 30° C. The reaction mixture was treated in a similar manner to that described in Example 40-(2), whereby the title compound (123.7 mg) was obtained as a powder.

Infrared absorption spectrum (KBr) νmax cm$^{-1}$: 3386, 1755, 1606, 1448, 1388.

Nuclear magnetic resonance spectrum (400 MHz, D$_2$O) δ ppm: 1.23 (3H, d, J=7.3 Hz), 1.30 (3H, d, J=6.2 Hz), 1.64–1.74 (1H, m), 2.47–2.56 (1H, m), 2.64–2.79 (2H, m), 3.04–3.19 (5H, m), 3.35–3.50 (4H, m), 3.66–3.93 (5H, m), 4.20–4.30 (3H, m).

EXAMPLE 62

(1R,5S,6S)-6-[(1R)-1-Hydroxyethyl]-2-[(2S,4S)-2-[(1S)-1-hydroxy-2-(piperazin-1-ylcarbonyl)ethyl]pyrrolidin-4-ylthio]-1-methyl-1-carbapen-2-em-3-carboxylic acid (Exemplified Compound 3-4)

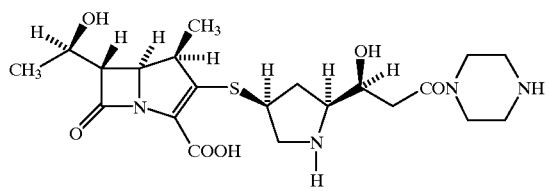

(1) By using 4-nitrobenzyl (1R,5R,6S)-6-[(1R)-1-hydroxyethyl]-1-methyl-2-(diphenylphosphoryloxy)-1-carbapen-2-em-3-carboxylate (461.1 mg) and (2S,4S)-2-[(1S)-1-hydroxy-2-[4-(4-nitrobenzyloxycarbonyl)piperazin-1-ylcarbonyl]ethyl]-4-mercapto-1-(4-nitrobenzyloxycarbonyl)pyrrolidine (456.2 mg), reaction and purification were carried out in a similar manner to that described in Example 40-(1), whereby 4-nitrobenzyl (1R,5S,6S)-6-[(1R)-1-hydroxyethyl]-2-[(2S,4S)-2-[(1S)-1-hydroxy-2-[4-(4-nitrobenzyloxycarbonyl)piperazin-1-ylcarbonyl]ethyl]-1-(4-nitrobenzyloxycarbonyl)pyrrolidin-4-ylthio]-1-methyl-1-carbapen-2-em-3-carboxylate (536.7 mg) was obtained.

Infrared absorption spectrum (KBr) νmax cm$^{-1}$: 3437, 1773, 1705, 1633, 1608, 1522, 1433, 1407, 1375, 1347.

Nuclear magnetic resonance spectrum (400 MHz, CDCl$_3$) δ ppm: 1.28 (3H, d, J=7.3 Hz), 1.38 (3H, d, J=6.1 Hz), 1.71–1.77 (1H, m), 1.92–2.08 (1H, m), 2.30–2.67 (3H, m), 3.16–3.75 (12H, m), 4.09–4.31 (5H, m), 4.40–4.54 (1H, m), 5.17–5.54 (6H, m), 7.53 (4H, d, J=8.6 Hz), 7.66 (2H, d, J=8.3 Hz), 8.20–8.27 (6H, m).

(2) To a solution of the compound (536.7 mg), which had been obtained in (1), in tetrahydrofuran (25.4 ml) and water (18.1 ml), a 10% palladium-carbon catalyst (1.086 g) was added. Hydrogen was allowed to be absorbed into the resulting mixture for 2 hours, while stirring at an external temperature of 30° C. The reaction mixture was treated in a similar manner to that described in Example 40-(2), whereby the title compound (132.2 mg) was obtained as a powder.

Infrared absorption spectrum (KBr) νmax cm$^{-1}$: 3397, 1755, 1607, 1448, 1388, 1281.

Nuclear magnetic resonance spectrum (400 MHz, D$_2$O) δ ppm: 1.23 (3H, d, J=7.2 Hz), 1.30 (3H, d, J=6.5 Hz), 1.55–1.66 (1H, m), 2.52–2.83 (3H, m), 2.99–3.21 (5H, m), 3.34–3.54 (4H, m), 3.62–3.81 (4H, m), 3.89–3.96 (1H, m), 4.16–4.30 (3H, m).

EXAMPLE 63

(1R,5S,6S)-6-[(1R)-1-Hydroxyethyl]-2-[(2S,4S)-2-[(1R)-1-hydroxy-2-[(3R)-3-methylaminomethylpyrrolidin-1-ylcarbonyl]ethyl]pyrrolidin-4-ylthio]-1-methyl-1-carbapen-2-em-3-carboxylic acid (Exemplified Compound 2-9)

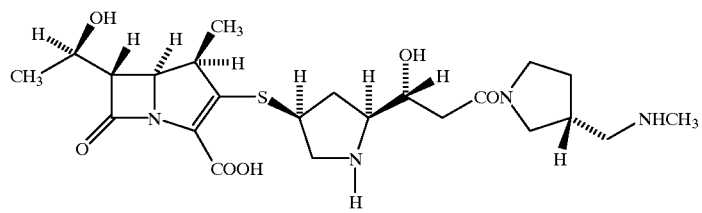

In a similar manner to that described in Example 59-(1) and (2), the title compound can be obtained.

EXAMPLE 64

(1R,5S,6S)-6-[(1R)-1-Hydroxyethyl]-2-[(2S,4S)-2-[(1S)-1-hydroxy-2-[(3R)-3-methylaminomethylpyrrolidin-1-ylcarbonyl]ethyl]pyrrolidin-4-ylthio]-1-methyl-1-carbapen-2-em-3-carboxylic acid (Exemplified Compound 2-9)

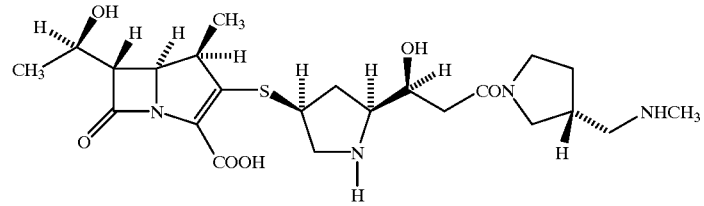

In a similar manner to that described in Example 60-(1) and (2), the title compound can be obtained.

EXAMPLE 65

(1R,5S,6S)-2-[(2S,4S)-2-[(1R)-1-Hydroxy-2-[(3S)-3-methylaminopyrrolidin-1-ylcarbonyl]ethyl]pyrrolidin-4-ylthio]-6-[(1R)-1-hydroxyethyl]-1-methyl-1-carbapen-2-em-3-carboxylic acid
(Exemplified Compound 2-7)

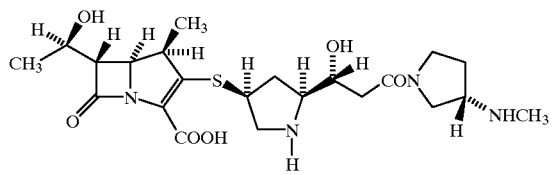

In a similar manner to that described in Example 59-(1) and (2), the title compound can be obtained.

EXAMPLE 66

(1R,5S,6S)-2-[(2S,4S)-2-[(1S)-1-Hydroxy-2-[(3S)-3-methylaminopyrrolidin-1-ylcarbonyl]ethyl]pyrrolidin-4-ylthio]-6-[(1R)-1-hydroxyethyl]-1-methyl-1-carbapen-2-em-3-carboxylic acid
(Exemplified Compound 2-7)

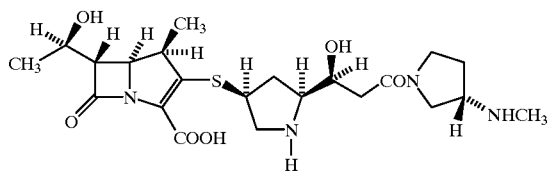

In a similar manner to that described in Example 60-(1) and (2), the title compound can be obtained.

EXAMPLE 67

(1R,5S,6S)-2-[(2S,4S)-2-[(1R)-2-(4-guanylpiperazin-1-ylcarbonyl)-1-hydroxyethyl]pyrrolidin-4-ylthio]-6-[(1R)-1-hydroxyethyl]-1-methyl-1-carbapen-2-em-3-carboxylic acid
(Exemplified Compound 3-1)

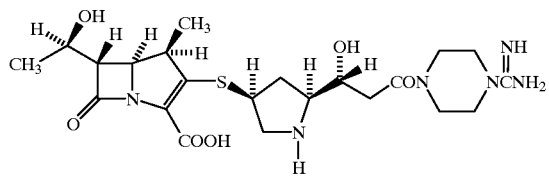

In a similar manner to that described in Example 59-(1) and (2), the title compound was obtained.

Infrared absorption spectrum (KBr) νmax cm$^{-1}$: 3351, 1754, 1608, 1447, 1388.

Nuclear magnetic resonance spectrum (400 MHz, D$_2$O) δ ppm: 1.23 (3H, d, J=7.3 Hz), 1.31 (3H, d, J=6.4 Hz), 1.53–1.60 (1H, m), 2.41–2.49 (1H, m), 2.69–2.71 (2H, m), 2.97 (1H, dd, J=12.0,3.6 Hz), 3.20–3.26 (2H, m), 3.38–3.45 (2H, m), 3.56–3.83 (9H, m), 4.12–4.27 (3H, m).

EXAMPLE 68

(1R,5S,6S)-2-[(2S,4S)-2-[(1S)-2-(4-Guanylpiperazin-1-ylcarbonyl)-1-hydroxyethyl]pyrrolidin-4-ylthio]-6-[(1R)-1-hydroxyethyl]-1-methyl-1-carbapen-2-em-3-carboxylic acid
(Exemplified Compound 3-1)

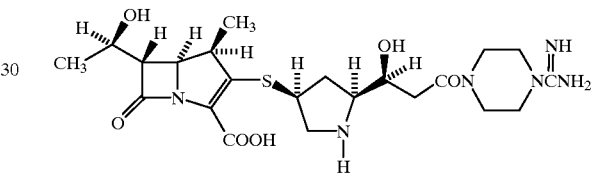

In a similar manner to that described in Example 60-(1) and (2), the title compound was obtained.

Infrared absorption spectrum (KBr) νmax cm$^{-1}$: 3351, 1754, 1609, 1447, 1389.

Nuclear magnetic resonance spectrum (400 MHz, D$_2$O) δ ppm: 1.23 (3H, d, J=7.2 Hz), 1.31 (3H, d, J=6.2 Hz), 1.44–1.51 (1H, m), 2.42–2.50 (1H, m), 2.63 (1H, dd, J=15.3, 3.1 Hz), 2.77 (1H, dd, J=15.3,9.5 Hz), 3.01 (1H, dd, J=12.0, 3.7 Hz), 3.24–3.31 (2H, m), 3.36–3.45 (2H, m), 3.57–3.86 (9H, m), 4.10–4.29 (3H, m).

EXAMPLE 69

(1R,5S,6S)-6-[(1R)-1-Hydroxyethyl]-2-[(2S,4S)-2-[(1R)-2-[(3R)-3-guanidinomethylpyrrolidin-1-ylcarbonyl]-1-hydroxyethyl]pyrrolidin-4-ylthio]-1-methyl-1-carbapen-2-em-3-carboxylic acid
(Exemplified Compound 2-11)

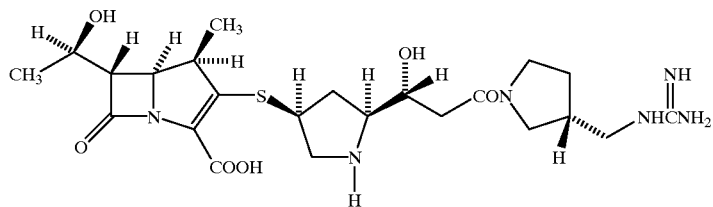

In a similar manner to that described in Example 59-(1) and (2), the title compound can be obtained.

EXAMPLE 70

(1R,5S,6S)-6-[(1R)-1-Hydroxyethyl]-2-[(2S,4S)-2-[(1S)-2-[(3R)-3-guanidinomethylpyrrolidin-1-ylcarbonyl]-1-hydroxyethyl]pyrrolidin-4-ylthio]-1-methyl-1-carbapen-2-em-3-carboxylic acid (Exemplified Compound 2-11)

Infrared absorption spectrum (KBr) νmax cm$^{-1}$: 3325, 1754, 1648, 1602, 1452, 1388, 1284, 1259.

Nuclear magnetic resonance spectrum (400 MHz, D$_2$O) δ ppm: 1.22 (3H, dd, J=7.2, 3.2 Hz), 1.30 (3H, d, J=6.3 Hz), 1.52–1.72 (1H, m), 1.98–2.15 (1H, m), 2.21–2.42 (2H, m), 2.68–2.88 (2H, m), 3.02–3.11 (1H, m), 3.13–3.23 (1H, m), 3.36–3.90 (7H, m), 3.93–4.05 (1H, m), 4.08–4.30 (4H, m), 4.43–4.55 (1H, m), 4.95–5.05 (1H, m).

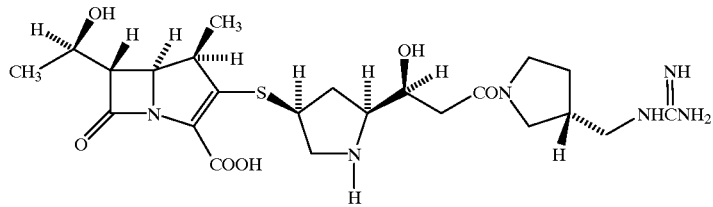

In a similar manner to that described in Example 60-(1) and (2), the title compound can be obtained.

EXAMPLE 71

(1R,5S,6S)-2-[(2S,4)-2-[(3S)-3-[(2S)-1-Amidinoazetidin-2-yl]carbonylamino]pyrrolidin-1-ylcarbonyl]pyrrolidin-4-ylthio]-6-[(1R)-1-hydroxyethyl]-1-methyl-1-carbapen-2-em-3-carboxylic acid (Exemplified Compound 1-129)

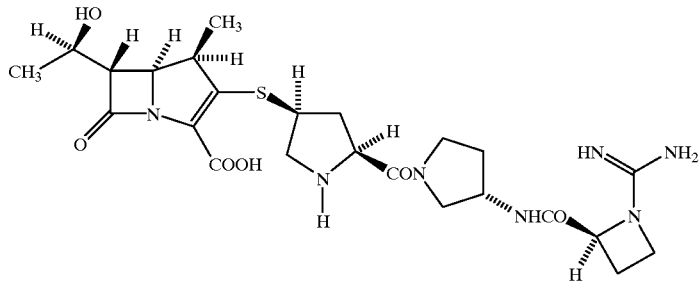

In a similar manner to that described to Example 40-(1) and (2), the title compound was obtained.

EXAMPLE 72

(1R,5S,6S)-2-[(2S,4S)-2-[(3S)-3-(2-guanidinoacetylamino)pyrrolidin-1-ylcarbonyl]-1-methylpyrrolidin-4-ylthio]-6-[(1R)-1-hydroxyethyl]-1-methyl-1-carbapen-2-em-3-carboxylic acid
(Exemplified Compound 1-84)

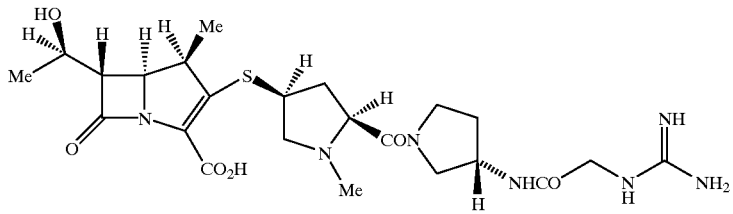

(1) 1.09 g of (2S,4S)-4-(4-methoxybenzylthio)-1-methylpyrrolidine-2-carboxylic acid were suspended in 30 ml of dry acetonitrile, and 691 mg of N,N'-carbonyldiimidazole were added to this suspension, after which the mixture was stirred at 40° C. for 1 hour. At the end of the time, the reaction mixture was cooled with ice, and 2.98 g of (3S)-3-[2-[2,3-bis(4-nitrobenzyloxycarbonyl) guanidino]acetylamino]pyrrolidine trifluoroacetate in 30 ml of dry acetonitrile and 1.7 ml of diisopropylethylamine were added to the mixture, which was then stirred at room temperature overnight. At the end of this time, the reaction mixture was diluted with ethyl acetate and washed with water and brine. The ethyl acetate solution was dried over anhydrous sodium sulfate and then concentrated by evaporation under reduced pressure. The resulting residue was subjected to silica gel column chromatography, eluted with 10% and 20% methanol-ethyl acetate. The fraction containing the desired compound was concentrated by evaporation under reduced pressure to obtain 2.99 g of (2S,4S)-2-[(3S)-3-[2-[2,3-bis(4-nitrobenzyloxycarbonyl)guanidino]acetylamino]pyrrolidin-1-ylcarbonyl]-4-(4-methoxybenzylthio)-1-methylpyrrolidine, as a powder.

Nuclear Magnetic Resonance Spectrum (270 MHz, CDCl$_3$) δ ppm: 1.50–2.62 (7H, m), 2.92–3.18 (2H, m), 3.39–3.83 (10H, m), 4.04–4.18 (3H, m), 4.37–4.54 (1H, m), 5.18–5.33 (4H, m), 6.78–7.87 (2H, m), 7.10–7.24 (2H, m), 7.47–7.60 (4H, m), 8.17–8.28 (2H, m), 8.80–8.95 (1H, b), 11.65–11.75 (1H, b).

(2) 2.99 g of (2S,4S)-2-[(3S)-3-[2-[2,3-bis(4-nitrobenzyloxycarbonyl)guanidino]acetylanino]pyrrolidin-1-ylcarbonyl]-4-(4-methoxybenzylthio)-1-methylpyrrolidine [prepared as described in step (1) above] were dissolved in a mixture of 21 ml of trifluoroacetic acid and 4.1 ml of anisole, and then 1.15 ml of trifluoromethanesulfonic acid were added dropwise, whilst stirring and ice-cooling, to the resulting solution. The reaction mixture was stirred for 20 minutes at room temperature, after which the mixture was poured into ether. The resulting precipitate was collected by filtration and the precipitate was dissolved in ethyl acetate. The ethyl acetate solution was washed with saturated sodium hydrogencarbonate, with water and with brine and dried over anhydrous sodium sulfate. The ethyl acetate solution was concentrated by evaporation under reduced pressure to obtain 1.62 g of (2S,4S)-2-[(3S)-3-[2-[2,3-bis(4-nitrobenzyloxycarbonyl)guanidino]acetylamino] pyrrolidin-1-ylcarbonyl]-4-mercapto-1-methylpyrrolidine, in the form of an amorphous powder.

Nuclear Magnetic Resonance Spectrum (270 MHz, CDCl$_3$) δ ppm: 1.68–2.40 (5H, m), 2.54–2.88 (2H, m), 3.02–3.84 (7H, m), 4.00–4.20 (3H, m), 4.38–4.55 (1H, m), 5.15–5.35 (4H, m), 6.68–6.93 (1H, m), 7.55 (4H, d, J=8.7 Hz), 8.17–8.30 (4H, m), 8.80–9.00 (1H, m), 11.60–11.70 (1H, m).

(3) 1.40 g of 4-nitrobenzyl (1R,5R,6S)-2-(diphenylphosphoryloxy)-6-[(1R)-1-hydroxyethyl]-1-methyl-1-carbapen-2-em-3-carboxylate were dissolved in 20 ml of dry acetonitrile, and a solution of 1.62 g of (2S,4S)-2-[(3S)-3-[2-[2,3-bis(4-nitrobenzyloxycarbonyl) guanidino]acetylamino]pyrrolidin-1-ylcarbonyl]-4-mercapto-1-methylpyrrolidine in 15 ml of dry acetonitrile and 0.42 ml of diisopropylethylamine were added dropwise to the resulting solution, whilst ice-cooling. The resulting mixture was stirred at the same temperature overnight, after which it was concentrated by evaporation under reduced pressure. The resulting residue was diluted with ethyl acetate, and the mixture was washed with water, with an aqueous solution of sodium hydrogencarbonate and brine. The ethyl acetate solution was dried over anhydrous magnesium sulfate and then concentrated by evaporation under reduced pressure. The resulting residue was subjected to silica gel column chromatography, eluted with 10% methanol-ethyl acetate and 10% methanol-dichlorometane. The fraction containing the desired compound was concentrated by evaporation under reduced pressure to obtain 1.2 g of 4-nitrobenzyl (1R,5S,6S)-2-[(3S)-3-[2,3-bis(4-nitrobenzyloxycarbonyl)guanidino]acetylamino]pyrrolidin-1-ylcarbonyl]-1-methylpyrrolidin-4-ylthio]-6-[(1R)-1-hydroxyethyl]-1-methyl-1-carbapen-2-em-3-carboxylate, in the form of an amorphous powder.

Infrared Spectrum (KBr), $v_{max}$ cm$^{-1}$: 3336, 1772, 1741, 1688, 1643, 1610, 1522, 1447, 1378, 1347.

Nuclear Magnetic Resonance Spectrum (270 MHz, CDCl$_3$) δ ppm: 1.17–1.40 (6H, m), 1.64–2.40 (4H, m), 2.33 (3H, s), 2.47–2.80 (2H, m), 3.00–3.38 (3H, m), 3.46–3.83 (5H, m), 3.93–4.60 (5H, m), 5.12–5.54 (6H, m), 7.21 (1H, d, J=6.5 Hz), 7.46–7.70 (6H, m), 8.10–8.28 (6H, m), 8.80–9.10 (1H, b), 11.60 (1H, bs).

(4) 1.20 g of 4-nitrobenzyl (1R,5S,6S)-2-[(2S,4S)-2-[(3S)-3-[2,3-bis(4-nitrobenzyloxycarbonyl)guanidino] acetylamino]pyrrolidin-1-ylcarbonyl]-1-methylpyrrolidin-4-ylthio]-6-[(1R)-1-hydroxyethyl]-1-methyl-1-carbapen-2-em-3-carboxylate were dissolved in 20 ml of tetrahydrofuran and 15 ml of water, and 1.8 g of a 105 w/w palladium-on-carbon catalyst were added to the resulting solution. The mixture was then hydrogenated in an atmosphere of hydrogen at room temperature for 2 hours. At the end of this time, the catalyst was removed by filtration, and the filtrate was washed with diethyl ether. The filtrate was then concentrated to 20 ml by evaporation under reduced pressure The solution was then subjected to reverse phase column chromatography (Cosmosil 75C18-prep, manufactured by Nacalai Tesque), eluted with aqueous acetonitrile. The fraction containing the desired compound was concentrated by evaporation under reduced pressure and then lyophilized to obtain 312 mg of the title compound.

Ultraviolet Spectrum λmax(H$_2$O) nm: 300.

Infrared Spectrum (KBr), ν$_{max}$ cm$^{-1}$: 3344, 1755, 1667, 1633, 1454, 1386, 1339.

Nuclear Magnetic Resonance Spectrum (270 MHz, CDCl$_3$) δ ppm: 1.21 (3H, dd, J=7.1, 2.3 Hz), 1.30 (3H, d, J=6.3 Hz), 1.58–1.73 (1H, m), 1.92–2.37 (5H, m), 2.67–2.93 (2H, m), 3.07–3.16 (1H, m), 3.30–3.93 (8H, m), 4.00 (2H, s), 4.17–4.32 (2H, m), 4.38–4.50 (1H, m).

Referential Example 1

(2S,4S)-4-Mercapto-1-(4-nitrobenzyloxycarbonyl)-2-[(3S)-3-[1-(4-nitrobenzyloxycarbonyl)-L-prolylamino]pyrrolidin-1-ylcarbonyl]pyrrolidine (1) To a solution of 1-(4-nitrobenzyloxycarbonyl)-L-proline (3.67 g) in anhydrous acetonitrile (50 ml), N,N-carbonyldiimidazole (1.86 g) was added at room temperature. After stirring for one hour, a solution of (3S)-3-amino-1(tert-butoxycarbonyl)pyrrolidine (1.86 g) in anhydrous acetonitrile (20 ml) was added to the reaction mixture under ice cooling, followed by stirring at room temperature for 2 hours. The reaction mixture was then concentrated by evaporation under reduced pressure. To the residue, ethyl acetate was added. The resulting mixture was washed with water and saturated saline, dried over anhydrous magnesium sulfate and then concentrated by evaporation under reduced pressure. The residue was purified by chromatography through a silica gel column (ethyl acetate:dichloromethane=1:1), whereby 3.31 g of (3S)-1-(tert-butoxycarbonyl)-3-[1-(4-nitrobenzyloxycarbonyl)-L-prolylamino]pyrrolidine were obtained as a colorless amorphous substance.

Infrared absorption spectrum (KBr) vmax cm$^{-1}$: 3315, 1698, 1608, 1524, 1479, 1405, 1366, 1346, 1244.

Nuclear magnetic resonance spectrum (400 MHz, CDCl$_3$) δ ppm: 1.46 (9H, s), 1.64–2.45 (6H, m), 2.90–3.69 (6H, m), 4.27 (1H, bs), 4.40 (1H, bs), 5.22, 5.27 (each 1H, d, J=14.0 Hz), 7.52 (2H, d, J=8.3 Hz), 8.23 (2H, d, J=8.3 Hz).

(2) To the compound (763 mg) obtained in (1), trifluoroacetic acid (3 ml) was added under ice cooling. The resulting mixture was stirred for 10 minutes, followed by the addition of 1,2-dichloroethane and hexane to give a precipitate. The precipitate was separated by decantation, washed with ether and the solvent was distilled off, whereby (3S)-3-[1-(4-nitrobenzyloxycarbonyl)-L-prolylamino]pyrrolidine trifluoroacetate was obtained. The product was provided for the subsequent step without purification.

Infrared absorption spectrum (KBr) vmax cm$^{-1}$: 1782, 1676, 1551, 1526, 1437, 1408, 1347, 1209, 1171.

Nuclear magnetic resonance spectrum (400 MHz, CDCl$_3$) δ ppm: 1.84–2.50 (6H, m), 3.20–3.75 (6H, m), 4.27 (1H, b), 4.55 (1H, bs), 5.17, 2.26 (each 1H, d, J=13.5 Hz), 7.51 (2H, d, J=8.3 Hz), 8.22 (2H, d, J=8.3 Hz).

(3) To a solution of (2S,4S)-4-(4-methoxybenzyl)thio-1-(4-nitrobenzyloxycarbonyl)-L-proline (772 mg) in anhydrous acetonitrile (12 ml), N,N-carbonyldiimidazole (293 mg) was added, followed by stirring at room temperature for 30 minutes. To the reaction mixture, N,N-diisopropylethylamine (301 μl) and a solution of the compound, which had been obtained in (2), in anhydrous acetonitrile (10 ml) were added and the mixture was stirred overnight at room temperature. The reaction mixture was concentrated by evaporation under reduced pressure. To the residue, ethyl acetate was added. The resulting mixture was washed with water and saturated saline and then concentrated by evaporation under reduced pressure. The residue was purified by chromatography thorough a silica gel column (ethyl acetate:dichloromethane=1:1, methanol:ethyl acetate:dichloromethane=5:47.5:47.5), whereby 1.17 g of (2S,4S)-4-(4-methoxybenzyl)thio-1-(4-nitrobenzyloxycarbonyl)-2-[(3S)-3-[1-(4-nitrobenzyloxycarbonyl)-L-propylamino]pyrrolidin-1-ylcarbonyl]pyrrolidine were obtained as an amorphous substance.

Infrared absorption spectrum (KBr) vmax cm$^{-1}$: 3319, 1709, 1657, 1608, 1521, 1439, 1404, 1346, 1300, 1248.

Nuclear magnetic resonance spectrum (400 MHz, CDCl$_3$) δ ppm: 1.60–2.60 (8H, m), 2.98–4.60 (17H, m), 5.00–5.40 (4H, m), 6.75–6.95 (2H, m), 7.18–7.33 (2H, m), 7.38–7.60 (4H, m), 8.13–8.30 (4H, m).

(4) To a mixture of the compound (1.16 g), which had been obtained in (3), and anisole (1.6 ml), trifluoroacetic acid (5.6 ml) and trifluoromethanesulfonic acid (260 μl) were added under ice cooling, followed by stirring at room temperature for 2 hours. The reaction mixture was concentrated by evaporation under reduced pressure. The residue was dissolved in ethyl acetate. The resulting solution was washed with a saturated aqueous solution of sodium bicarbonate, water and saturated saline, dried over anhydrous magnesium sulfate and then concentrated by evaporation under reduced pressure, whereby 958 mg of the title compound were obtained.

Infrared absorption spectrum (KBr) vmax cm$^{-1}$: 3320, 1709, 1656, 1607, 1522, 1438, 1404, 1346.

Nuclear magnetic resonance spectrum (400 MHz, CDCl$_3$) δ ppm: 1.55–2.80 (8H, m), 3.15–4.58 (12H, m), 5.03–5.43 (4H, m), 7.40–7.60 (4H, m), 8.10–8.30 (4H, m).

Referential Example 2

(2S,4S)-4-Mercapto-2-[(3S)-3-[(2S,4R)-1-(4-nitrobenzyloxycarbonyl)-4-(4-nitrobenzyloxycarbonyloxy)-L-prolylamino]pyrrolidin-1-ylcarbonyl]pyrrolidine (1) To a solution of 4-hydroxy-1-(4-nitrobenzyloxycarbonyl)-L-proline (1.79 g) in anhydrous acetonitrile (30 ml), N,N,-carbonyldiimidazole (981 mg) was added at room temperature, followed by stirring at room temperature for one hour. To the reaction mixture, a solution of (3S)-3-amino-1-(tert-butoxycarbonyl)pyrrolidine (1.02 g) in anhydrous acetonitrile (20 ml) was added under ice cooling. The resulting mixture was stirred at room temperature for 6 hours. The reaction mixture was purified in a similar manner to that described in Referential Example 1-(1), whereby 1.22 g of (3S)-1-(tert-butoxycarbonyl)-3-[1-(4-nitrobenzyloxycarbonyl)-4-hydroxy-L-prolylamino]pyrrolidine were obtained as an amorphous substance.

Infrared absorption spectrum (KBr) vmax cm$^{-1}$: 3401, 3311, 1695, 1674, 1608, 1525, 1407, 1367, 1346.

Nuclear magnetic resonance spectrum (270 MHz, CDCl$_3$) δ ppm: 1.46 (9H, s), 1.55–3.70 (10H, m), 4.30–4.65 (3H, m), 5.24 (2H, s), 7.50 (2H, d, J=8.5 Hz), 8.22 (2H, d, J=8.5 Hz).

(2) To a solution of the compound (1.21 g) obtained in (1) and 4-dimethylaminopyridine (403 mg) in dichloromethane (20 ml), a solution of p-nitrobenzyl chloroformate (708 mg) in dichloromethane (10 ml) was added dropwise while stirring under ice cooling. The reaction mixture was stirred at room temperature for one hour, followed by the addition of ethyl acetate. The resulting mixture was washed with water and saturated saline, dried over anhydrous magnesium sulfate and then concentrated by evaporation under reduced pressure. The residue was purified by chromatography through a silica gel column (ethyl acetate:hexane=8:2), whereby 1.29 g of (3S)-1-(tert-butoxycarbonyl)-3-[(2S,4R)-1-(4-nitrobenzyloxycarbonyl)-4-(4-nitrobenzyloxycarbonyloxy)-L-prolylamino]pyrrolidine were obtained as an amorphous substance.

Infrared absorption spectrum (KBr) νmax cm$^{-1}$: 1752, 1694, 1608, 1524, 1407, 1347, 1264.

Nuclear magnetic resonance spectrum (400 MHz, CDCl$_3$) δ ppm: 1.46 (9H, s), 1.70–4.05 (11H, m), 4.38 (2H, bs), 5.13–5.35 (4H, m), 7.48 (2H, d, J=8.6 Hz), 7.54 (2H, d, J=8.6 Hz), 8.15–8.30 (4H, m).

(3) The compound (1.15 g) obtained in (2) was allowed to react with trifluoroacetic acid (4.5 ml) in a similar manner to that described in Referential Example 1-(2), whereby (3S)-3-[(2S,4R)-1-(4-nitrobenzyloxycarbonyl)-4-(4-nitrobenzyloxycarbonyloxy)-L-prolylamino]pyrrolidine trifluoroacetate was obtained.

Infrared absorption spectrum (CHCl$_3$ Solution) νmax cm$^{-1}$: 1752, 1678, 1609, 1524, 1433, 1407, 1348, 1321, 1267, 1206, 1175.

Nuclear magnetic resonance spectrum (400 MHz, DMSO-d$_6$) δ ppm: 1.60–1.90 (1H, m), 1.96–2.23 (2H, m), 2.30–2.48 (1H, m), 2.85–3.03 (1H, m), 3.11–3.42 (3H, m), 3.62–3.83 (2H, m), 4.18–4.37 (2H, m), 5.10–5.38 (4H, m), 7.50–7.75 (4H, m), 8.18–8.33 (4H, m).

(4) To a solution of (2S,4S)-4-(4-methoxybenzyl)thio-1-(4-nitrobenzyloxycarbonyl)-L-proline (817 mg) in anhydrous acetonitrile (13 ml), N,N'-carbonyldiimidazole (313 mg) was added, followed by stirring at room temperature for 30 minutes. To the reaction mixture, N,N-diisopropylethylamine (305 μl) and a solution of the compound, which had been obtained in (3), in anhydrous acetonitrile (15 ml) were added and the mixture was stirred overnight at room temperature. The reaction mixture was purified in a similar manner to that described in Referential Example 1-(3), whereby 1.53 g of (2S,4S)-4-(4-methoxybenzyl)thio-2-[(3S)-3-[(2S,4R)-1-(4-nitrobenzyloxycarbonyl)4-(4-nitrobenzyloxycarbonyloxy)-L-prolylamino]pyrrolidin-1-ylcarbonyl]pyrrolidine were obtained as an amorphous substance.

Nuclear magnetic resonance spectrum (400 MHz, CDCl$_3$) δ ppm: 1.65–2.78 (6H, m), 3.00–3.55 (4H, m), 3.63–4.55 (14H, m), 5.00–5.40 (8H, m), 6.80–6.92 (2H, m), 7.20–7.32 (2H, m), 7.35–7.60 (6H, m), 8.08–8.30 (6H, m).

(5) To a mixture of the compound (1.50 g), which had been obtained in (4), and anisole (1.7 ml), trifluoroacetic acid (5.9 ml) and trifluoromethanesulfonic acid (270 μl) were added under ice cooling. The resulting mixture was stirred at room temperature for 2 hours. The reaction mixture was purified in a similar manner to that described in Referential Example 1-(4), whereby 1.30 g of the title compound were obtained.

Nuclear magnetic resonance spectrum (400 MHz, CDCl$_3$) δ ppm: 1.87–2.78 (6H, m), 3.17–4.55 (13H, m), 5.00–5.35 (6H, m), 7.37–7.60 (6H, m), 8.08–8.30 (6H, m).

Referential Example 3

(2S,4S)-4-Mercapto-2[(3S)-3-(1-methyl-L-prolylamino)pyrrolidin-1-ylcarbonyl]-1-(4-nitrobenzyloxycarbonyl)pyrrolidine (1) To a suspension of 1-methyl-L-proline (600 mg) and (3S)-3-amino-1-(tert-butoxycarbonyl)pyrrolidine (758 mg) in anhydrous DMF (10 ml), 1-(3-dimethylaminopropyl)-3-ethylcarbodiimide hydrochloride (856 mg) and 1-hydroxybenzotriazole (550 mg) were added. The mixture was stirred overnight at room temperature. To the reaction mixture, ethyl acetate was added. The resulting mixture was washed with an aqueous solution of sodium carbonate, 15% saline and saturated saline, dried over anhydrous magnesium sulfate and then concentrated by evaporation under reduced pressure. The residue was purified by chromatography through a silica gel column (ethyl acetate, 5% methanol/ethyl acetate, 10% methanol/ethyl acetate), whereby 1.11 g of (3S)-1-(tert-butoxycarbonyl)-3-(1-methyl-L-prolylamino)pyrrolidine were obtained.

Infrared absorption spectrum (CHCl$_3$ Solution) νmax cm$^{-1}$: 3337, 1672, 1514, 1478, 1455, 1412, 1368.

Nuclear magnetic resonance spectrum (270 MHz, CDCl$_3$) δ ppm: 1.46 (9H, s), 1.60–1.90 (4H, m), 2.06–2.40 (3H, m), 2.33 (3H, s), 2.80–2.90 (1H, m), 3.00–3.27 (2H, m), 3.32–3.50 (2H, m), 3.60–3.70 (1H, m), 4.35–4.52 (1H, m).

(2) To a solution of the compound (980 mg), which had been obtained in (1), in anhydrous dichloromethane (8 ml), trifluoroacetic acid (4 ml) was added under ice cooling. The resulting mixture was stirred for 10 minutes, followed by concentration under reduced pressure. The residue was washed with hexane and ether, whereby 1.84 g of (3S)-3-(1-methyl-L-prolylamino)pyrrolidine were obtained.

Infrared absorption spectrum (KBr) νmax cm$^{-1}$: 1674, 1570, 1461, 1429, 1398, 1327, 1203, 1142.

Nuclear magnetic resonance spectrum (400 MHz, D$_2$O) δ ppm: 2.00–2.30 (4H, m), 2.32–2.50 (1H, m), 2.52–2.66 (1H, m), 2.95 (3H, s), 3.17–3.33 (2H, m), 3.37–3.68 (3H, m), 3.72–3.84 (3H, m), 4.11–4.21 (1H, m), 4.48–4.60 (1H, m).

(3) To a solution of (2S,4S)-4-(4-methoxybenzyl)thio-1-(4-nitrobenzyloxycarbonyl)-L-proline (1.47 g) in anhydrous acetonitrile (15 ml), N,N-carbonyldiimidazole (562 mg) was added, followed by stirring at room temperature for 30 minutes. To the reaction mixture, N,N-diisopropylethylamine (1.2 ml) and a solution of the compound (1.84 g) obtained in (2) in anhydrous acetonitrile (10 ml) were added and the mixture was stirred overnight at room temperature. The reaction mixture was purified in a similar manner to that described in Referential Example 1-(3), whereby 1.23 g of (2S,4S)-4-(4-methoxybenzyl)thio-2-[(3S)-3-(1-methyl-L-prolylamino)pyrrolidin-1-ylcarbonyl]pyrrolidine were obtained.

Infrared absorption spectrum (KBr) νmax cm$^{-1}$: 3320, 1710, 1656, 1609, 1584, 1512, 1439, 1404, 1346.

Nuclear magnetic resonance spectrum (270 MHz, CDCl$_3$) δ ppm: 1.56–2.55 (10H, m), 2.31 (3H, s), 2.80–2.90 (1H, m), 2.95–3.20 (2H, m), 3.27–4.10 (7H, m), 3.79 (3H, s), 4.30–4.55 (2H, m), 4.98–5.37 (2H, m), 6.85 (2H, d, J=8.6 Hz), 7.18–7.30 (2H, m), 7.37–7.50 (2H, m), 8.18–8.28 (2H, m).

(4) To a mixture of the compound (1.21 g), which had been obtained in (3), with anisole (2.1 ml), trifluoroacetic acid (7.4 ml) and trifluoromethanesulfonic acid (340 μl) were added, followed by stirring at room temperature for 2 hours. The reaction mixture was purified in a similar manner to that described in Referential Example 1-(4), 1.03 g of the title compound were obtained.

Infrared absorption spectrum (KBr) νmax cm$^{-1}$: 3306, 1709, 1655, 1607, 1522, 1441, 1405, 1346, 1283, 1261.

Nuclear magnetic resonance spectrum (400 MHz, DMSO-d$_6$) δ ppm: 1.55–4.70 (23H, m), 5.03–5.30 (2H, m), 7.50–7.68 (2H, m), 8.18–8.28 (2H, m).

Referential Example 4

(2S,4S)-4-Mercapto-1-(4-nitrobenzyloxycarbonyl)-2-[(3S)-3-[1-(4-nitrobenzyloxycarbonyl)piperidin-2-ylcarbonylamino]pyrrolidin-1-ylcarbonyl]pyrrolidine (1) To a solution of 1-(4-nitrobenzyloxycarbonyl)-2-piperidinecarboxylic acid (1.54 g) in anhydrous acetonitrile (30 ml), N,N-carbonyldiimidazole (851 mg) was added at the room temperature, followed by stirring for one hour. The reaction mixture was allowed to react with a solution of (3S)-3-amino-1-(tert-butoxycarbonyl)pyrrolidine (931 mg) in anhydrous acetonitrile (15 ml) under ice cooling in a similar manner to that described in Referential Example 1-(1), whereby 1.81 g of (3S)-1-(tert-butoxycarbonyl)-3-[1-(4-nitrobenzyloxycarbonyl)piperidin-2-ylcarbonylamino] pyrrolidine were obtained as a colorless amorphous substance.

Infrared absorption spectrum (KBr) νmax cm$^{-1}$: 3326, 1699, 1608, 1525, 1408, 1366, 1346, 1255, 1169, 1128.

Nuclear magnetic resonance spectrum (270 MHz, CDCl$_3$) δ ppm: 1.32–1.85 (6H, m), 1.46 (9H, s), 2.07–2.35 (2H, m), 2.78–3.05 (1H, b), 3.07–3.20 (1H, b), 3.28–3.50 (2H, b), 3.57–3.68 (1H, m), 4.00–4.20 (1H, m), 4.37–4.51 (1H, m), 4.75 (1H, bs), 5.17–5.37 (2H, m), 5.93–6.18 (1H, b), 7.52 (2H, d, J=8.6 Hz), 8.24 (2H, d, J=8.6 Hz).

(2) To a solution of the compound (858 mg), which had been obtained in (1), in anhydrous dichloromethane (8 ml), trifluoroacetic acid (4 ml) was added under ice cooling. The mixture was treated in a similar manner to that described in Referential Example 3-(2), whereby (3S)-3-[1-(4-nitrobenzyloxycarbonyl)piperidin-2-ylcarbonylamino] pyrrolidine trifluoroacetate was obtained.

Infrared absorption spectrum (Liquid Film) νmax cm$^{-1}$: 1782, 1675, 1609, 1525, 1434, 1348, 1262, 1172.

Nuclear magnetic resonance spectrum (270 MHz, CDCl$_3$) δ ppm: 1.18–1.80 (5H, m), 1.98–2.25 (2H, m), 2.30–2.50 (1H, m), 2.87–3.68 (6H, m), 3.95–4.18 (1H, m), 4.60 (1H, bs), 4.73 (1H, bs), 5.10–5.50 (2H, m), 7.50 (2H, d, J=8.4 Hz), 8.21 (2H, d, J=8.4 Hz), 8.90–9.13 (1H, b), 9.13–9.47 (1H, b).

(3) To a solution of (2S,4S)-4-(4-methoxybenzyl)thio-1-(4-nitrobenzyloxycarbonyl)-L-proline (843 mg) in anhydrous acetonitrile (13 ml), N,N-carbonyldiimidazole (321 mg) was added, followed by stirring at room temperature for 30 minutes. To the reaction mixture, N,N-diisopropylethylamine (314 μl) and a solution of the compound, which had been obtained in (2), in anhydrous acetonitrile (12 ml) were added and the mixture was stirred overnight at room temperature. The reaction mixture was purified in a similar manner to that described in Referential Example 1-(3), whereby 1.23 g of (2S,4S)-4-(4-methoxybenzyl)thio-1-(4-nitrobenzyloxycarbonyl)-2-[(3S)-3-[1-(4-nitrobenzyloxycarbonyl)piperidin-2-ylcarbonylamino]pyrolidin-1-ylcarbonyl]pyrrolidine were obtained as a colorless amorphous substance.

Infrared absorption spectrum (KBr) νmax cm$^{-1}$: 3327, 1706, 1656, 1608, 1522, 1437, 1405, 1346, 1251, 1170.

Nuclear magnetic resonance spectrum (400 MHz, CDCl$_3$) δ ppm: 1.30–1.80 (8H, m), 1.90–2.30 (2H, m), 2.32–2.50 (1H, m), 2.80–3.85 (9H, m), 3.79 (3H, s), 3.90–4.20 (1H, bm), 4.28–4.42 (1H, m), 4.44–4.62 (1H, b), 4.71 (1H, bs), 5.00–5.37 (4H, m), 6.80–6.90 (2H, m), 7.18–7.30 (2H, m), 7.38–7.58 (4H, m), 8.15–8.30 (4H, m).

(4) To a mixture of the compound (1.20 g), which had been obtained in (3), and anisole (1.6 ml), trifluoroacetic acid (5.7 ml) and trifluoromethanesulfonic acid (262 μl) were added under ice cooling, followed by stirring at room temperature for 2 hours. The reaction mixture was purified in a similar manner to that described in Referential Example 1-(4), whereby 1.03 g of the title compound was obtained as a colorless amorphous substance.

Infrared absorption spectrum (KBr) νmax cm$^{-1}$: 3326, 1706, 1656, 1607, 1522, 1437, 1405, 1346.

Nuclear magnetic resonance spectrum (270 MHz, CDCl$_3$) δ ppm: 1.30–1.78 (8H, m), 1.86–2.33 (4H, m), 2.58–2.72 (1H, m), 3.13–3.90 (5H, m), 3.95–4.18 (2H, m), 4.30–4.60 (2H, m), 4.67–4.78 (1H, m), 5.00–5.36 (4H, m), 7.40–7.57 (4H, m), 8.13–8.28 (4H, m).

Referential Example 5

(2S,4S)-4-Mercapto-1-(4-nitrobenzyloxycarbonyl)-2-[(3S)-3-[(2S)-1-(4-nitrobenzyloxycarbonyl) azetidin-2-ylcarbonylamino]pyrrolidin-1-ylcarbonyl] pyrrolidine (1) To a solution of (2S)-1-(4-nitrobenzyloxycarbonyl)-2-azetidinecarboxylic acid (981 mg) in anhydrous acetonitrile (15 ml), N,N'-carbonyldiimidazole (597 mg) was added at room temperature, followed by stirring for one hour. The reaction mixture was reacted with a solution of (3S)-3-amino-1-(tert-butoxycarbonyl)pyrrolidine (652 mg) in anhydrous acetonitrile (10 ml) under ice cooling in a similar manner to that described in Referential Example 1-(1), whereby 1.33 g of (3S)-1-(tert-butoxycarbonyl)-3-[(2S)-1-(4-nitrobenzyloxycarboyl)azetidin-2-ylcarbonylamino] pyrrolidine were obtained as an amorphous substance.

Infrared absorption spectrum (KBr) νmax cm$^{-1}$: 3308, 1695, 1608, 1524, 1478, 1405, 1366, 1345.

Nuclear magnetic resonance spectrum (270 MHz, CDCl$_3$) δ ppm: 1.46 (9H, s), 1.72–1.88 (1H, m), 2.07–2.22 (1H, m), 2.35–2.70 (2H, b), 3.08–3.25 (1H, b), 3.32–3.50 (2H, b), 3.60–3.70 (1H, m), 3.90–4.10 (2H, m), 4.38–4.51 (1H, m), 4.72 (1H, t, J=7.9 Hz), 5.18, 5.26 (each 1H, d, J=13.2 Hz), 7.51 (2H, d, J=8.6 Hz), 8.24 (2H, d, J=8.6 Hz).

(2) To a solution of the compound (852 mg), which had been obtained in (1), in anhydrous dichloromethane (8 ml), trifluoroacetic acid (4 ml) was added under ice cooling and the mixture was treated in a similar manner to that described in Referential Example 3-(2), whereby (3S)-3-[(2S)-1-(4-nitrobenzyloxycarbonyl)azetidin-2-ylcarbonylamino] pyrrolidine trifluoroacetate was obtained.

Infrared absorption spectrum (Liquid Film) νmax cm$^{-1}$: 1781, 1674, 1610, 1525, 1432, 1406, 1306, 1346, 1299, 1171.

Nuclear magnetic resonance spectrum (270 MHz, CDCl$_3$) δ ppm: 2.00–2.20 (1H, b), 2.30–2.60 (3H, b), 3.25–3.68 (4H, bm), 3.90–4.12 (2H, m), 4.43–4.60 (1H, m), 4.73 (1H, t, J=7.8 Hz), 5.15, 5.24 (each 1H, d, J=13.4 Hz), 7.50 (2H, d, J=8.6 Hz), 8.04 (1H, d, J=6.4 Hz), 8.22 (2H, d, J=8.6 Hz), 9.00–9.40 (1H, b).

(3) To a solution of (2S,4S)-1-(4-methoxybenzyl)thio-1-(4-nitrobenzyloxycarbonyl)-L-proline (890 mg) in anhydrous acetonitrile (13 ml), N,N'-carbonyldiimidazole (339 mg) was added, followed by stirring at room temperature for 30 minutes. To the reaction mixture, N,N-diisopropylethylamine (348 μl) and a solution of the compound, which had been obtained in (2), in anhydrous acetonitrile (10 ml) were added and the mixture was stirred overnight at room temperature. The reaction mixture was purified in a similar manner to that described in Referential Example 1-(3), whereby 1.29 g of (2S,4S)-4-(4-methoxybenzyl)thio-2-[(3S)-3-[(2S)-1-(4-nitrobenzyloxycarbonyl)azetidin-2-ylcarbonylamino] pyrolidin-1-ylcarbonyl]pyrrolidine were obtained.

Infrared absorption spectrum (KBr) νmax cm$^{-1}$: 1712, 1658, 1607, 1521, 1438, 1403, 1345, 1299, 1248.

Nuclear magnetic resonance spectrum (270 MHz, CDCl$_3$) δ ppm: 1.48–2.68 (3H, m), 2.94–3.20 (1H, m), 3.25–4.16

(13H, m), 4.26–4.80 (3H, m), 4.97–5.35 (4H, m), 6.80–6.90 (2H, m), 7.15–7.30 (2H, m), 7.37–7.57 (4H, m), 8.15–8.28 (4H, m).

(4) To a mixture of the compound (1.26 g), which had been obtained in (3), and anisole (1.8 ml), trifluoroacetic acid (6.2 ml) and trifluoromethanesulfonic acid (284 μl) were added, followed by stirring at room temperature for 2 hours. The reaction mixture was purified in a similar manner to that described in Referential Example 1-(4), whereby 1.07 g of the title compound were obtained.

Infrared absorption spectrum (KBr) νmax cm$^{-1}$: 1711, 1655, 1607, 1522, 1438, 1404, 1345, 1295, 1247, 1209, 1168.

Nuclear magnetic resonance spectrum (400 MHz, CDCl$_3$) δ ppm: 1.75–2.80 (6H, m), 3.17–4.30 (9H, m), 4.35–4.80 (3H, m), 5.00–5.40 (4H, m), 7.40–7.65 (4H, m), 8.15–8.30 (4H, m).

Referential Example 6

(2S,4S)-4-Mercapto-1-(4-nitrobenzyloxycarbonyl)-2-[3-[1-(4-nitrobenzyloxycarbonyl)-L-prolylamino]azetidin-1-ylcarbonyl]pyrrolidine (1) To a solution of 1-(4-nitrobenzyloxycarbonyl)-L-proline (2.81 g) in anhydrous acetonitrile (40 ml), N,N-carbonyldiimidazole (1.42 g) was added at room temperature, followed by stirring for one hour. The reaction mixture was allowed to react under ice cooling with a solution of 3-amino-1-(tert-butoxycarbonyl)azetidine (1.31 g) in anhydrous acetonitrile (10 ml) in a similar manner to that described in Referential Example 1-(1), whereby 2.74 g of 1-(tert-butoxycarbonyl)-3-[1-(4-nitrobenzyloxycarbonyl)-L-prolylamino]azetidine were obtained.

Infrared absorption spectrum (KBr) νmax cm$^{-1}$: 3312, 1705, 1608, 1524, 1479, 1405, 1367, 1346, 1298, 1247.

Nuclear magnetic resonance spectrum (400 MHz, CDCl$_3$) δ ppm: 1.85–2.45 (4H, m), 3.40–3.80 (4H, m), 4.10–4.40 (3H, m), 4.52–4.65 (1H, m), 5.23, 5.30 (each 1H, d, J=13.5 Hz), 7.45 (2H, d, J=8.1 Hz), 8.24 (2H, d, J=8.1 Hz).

(2) The compound (762 mg) obtained in (1) and trifluoroacetic acid (3 ml) were treated in a similar manner to that described in Referential Example 1-(2), whereby 3-[1-(4-nitrobenzyloxycarbonyl)-L-prolylamino]azetidine trifluoroacetate was obtained.

Infrared absorption spectrum (Liquid Film) νmax cm$^{-1}$: 1782, 1678, 1526, 1437, 1408, 1347, 1171.

Nuclear magnetic resonance spectrum (400 MHz, CDCl$_3$) δ ppm: 1.90–2.70 (4H, m), 3.45–3.70 (2H, m), 3.90–4.90 (6H, m), 5.20, 5.28 (each 1H, d, J=13.5 Hz), 7.53 (2H, d, J=8.4 Hz), 8.22 (2H, d, J=8.4 Hz).

(3) To a solution of (2S,4S)-4-(4-methoxybenzyl)thio-1-(4-nitrobenzyloxycarbonyl)-L-proline (797 mg) in anhydrous acetonitrile (15 ml), N,N-carbonyldiimidazole (303 mg) was added, followed by stirring at room temperature for 30 minutes. To the reaction mixture, N,N-diisopropylethylamine (311 μl) and a solution of the compound, which had been obtained in (2), in anhydrous acetonitrile (10 ml) were added and the mixture was stirred overnight at room temperature. The reaction mixture was purified in a similar manner to that described in Referential Example 1-(3), whereby 1.06 g of (2S,4S)-4-(4-methoxybenzyl)thio 1-(4-nitrobenzyloxycarbonyl)-2-[3-[1-(4-nitrobenzyloxycarbonyl)-L-prolylamino]azetidine-1-ylcarbonyl]pyrrolidine were obtained.

Infrared absorption spectrum (KBr) νmax cm$^{-1}$: 1709, 1668, 1608, 1522, 1440, 1429, 1404, 1346, 1300, 1248.

Nuclear magnetic resonance spectrum (270 MHz, DMSO-d$_6$) δ ppm: 1.50–1.70 (1H, b), 1.70–1.95 (3H, b), 2.00–2.30 (1H, b), 2.40–2.70 (1H, b), 2.90–4.55 (17H, m), 5.00–5.30 (4H, m), 6.88 (2H, d, J=8.6 Hz), 7.27 (2H, d, J=8.6 Hz), 7.40–7.70 (4H, m), 8.10–8.30 (4H, m), 8.50–8.75 (1H, b).

(4) To a mixture of the compound (1.03 g), which had been obtained in (3), and anisole (1.4 ml), trifluoroacetic acid (5.1 ml) and trifluoromethanesulfonic acid (232 μl) were added under ice cooling, followed by stirring at room temperature for 2 hours. The reaction mixture was purified in a similar manner to that described in Referential Example 1-(4), whereby 774 mg of the title compound were obtained.

Infrared absorption spectrum (KBr) νmax cm$^{-1}$: 3314, 1706, 1658, 1609, 1523, 1460, 1430, 1407, 1346.

Nuclear magnetic resonance spectrum (270 MHz, DMSO-d$_6$) δ ppm: 1.60–1.93 (4H, m), 2.00–2.30 (1H, m), 2.40–2.80 (1H, m), 3.00–4.57 (12H, m), 5.03–5.30 (4H, m), 7.40–7.70 (4H, m), 8.10–8.30 (4H, m), 8.55–8.78 (1H, b).

Referential Example 7

(2S,4S)-4-Mercapto-1-(4-nitrobenzyloxycarbonyl)-2-[(3S)-3-[(1-(4-nitrobenzyloxycarbonyl)-D-prolylamino]pyrrolidin-1-ylcarbonyl]pyrrolidine The title compound can be obtained in a similar manner to that described in Referential Example 1-(1), (2), (3) and (4) by using 1-(4-nitrobenzyloxycarbonyl)-D-proline.

Referential Example 8

(2S,4S)-4-Mercapto-1-(4-nitrobenzyloxycarbonyl)-2-[(3S)-3-[(4-nitrobenzyloxycarbonyl)guanidinoacetylamino]pyrrolidin-1-ylcarbonyl]pyrrolidine (1) To a solution of (3S)-1-(tert-butoxycarbonyl)-3-(aminoacetylamino)pyrrolidine (2.50 g) in water (35 ml), sodium carbonate (1.31 g) and formamidinesulfonic acid (1.53 g) were added under ice cooling and the mixture was stirred overnight at room temperature. To the reaction mixture, tetrahydrofuran (30 ml) was added. To the resulting mixture, a solution of p-nitrobenzyl chloroformate (4.43 g) in tetrahydrofuran (20 ml) and a 1N aqueous sodium hydroxide solution (21 ml) were simultaneously added dropwise, followed by stirring at the same temperature for one hour. To the reaction mixture, ethyl acetate was added. The resulting mixture was washed with water and saturated saline, dried over anhydrous magnesium sulfate and then concentrated by evaporation under reduced pressure, whereby (3S)-1-(tert-butoxycarbonyl)-3-[di(4-nitrobenzyloxycarbonyl)guanidinoacetylamino]pyrrolidine was obtained. The product was provided for the subsequent step.

(2) To a solution of the compound, which had been obtained in (1), in methanol (50 ml), a 1N aqueous sodium hydroxide solution (3 ml) was added, followed by stirring at room temperature for 1 hour. The reaction mixture was concentrated by evaporation under reduced pressure. Ethyl acetate was added to the residue. The resulting mixture was washed with water and saturated saline and then concentrated by evaporation under reduced pressure. The residue was purified by chromatography through a silica gel column (ethyl acetate, 5% methanol/ethyl acetate), whereby 991 mg of (3S)-1-(tert-butoxycarbonyl)-3-[(4- nitrobenzyloxycarbonyl)guanidinoacetylamino]pyrrolidine were obtained as a pale yellow amorphous substance.

Infrared absorption spectrum (KBr) vmax cm$^{-1}$: 1664, 1608, 1524, 1479, 1414, 1368, 1347, 1291.

Nuclear magnetic resonance spectrum (270 MHz, CDCl$_3$) δ ppm: 1.57–1.93 (1H, m), 2.05–2.20 (1H, m), 3.10–3.28 (1H, b), 3.32–3.50 (2H, b), 3.58 (1H, dd, J=11.4, 6.1 Hz), 3.92 (2H, bs), 4.28–4.48 (1H, b), 5.19 (2H, s), 7.54 (2H, d, J=8.6 Hz), 8.20 (2H, d, J=8.6 Hz).

(3) To a solution of the compound (951 mg), which had been obtained in (2), in anhydrous dichloromethane (10 ml), trifluoroacetic acid (4 ml) was added under ice cooling. The mixture was treated in a similar manner to that described in Referential Example 3-(2), whereby (3S)-3-[(4-nitrobenzyloxycarbonyl)guanidinoacetylamino]pyrrolidine-2-trifluoroacetate was obtained.

Infrared absorption spectrum (Liquid Film) vmax cm$^{-1}$: 1752, 1674, 1525, 1436, 1351, 1319, 1246, 1202, 1139.

Nuclear magnetic resonance spectrum (270 MHz, DMSO-d$_6$–D$_2$O) δ ppm: 1.75–2.25 (2H, m), 2.92–3.08 (1H, m), 3.15–3.47 (3H, m), 4.00 (2H, s), 4.25–4.40 (1H, m), 5.42 (2H, s), 7.71 (2H, d, J=8.6 Hz), 8.28 (2H, d, J=8.6 Hz), 8.57 (1H, d, J=6.3 Hz).

(4) To a solution of (2S,4S)-4-(methoxybenzyl)thio-1-(4-nitrobenzyloxycarbonyl)-L-proline (960 mg) in anhydrous acetonitrile (15 ml), N,N-carbonyldiimidazole (365 mg) was added, followed by stirring at room temperature for 30 minutes. To the reaction mixture, N,N-diisopropylethylamine (535 μl) and a solution of the compound, which had been obtained in (3), in anhydrous acetonitrile (15 ml) were added and the mixture was stirred overnight at room temperature. The reaction mixture was purified in a similar manner to that described in Referential Example 1-(3), whereby 986 mg of (2S,4S)-4-(4-methoxybenzyl)thio-1-(4-nitrobenzyloxycarbonyl)-2-[(3S)-3-[(4-nitrobenzyloxycarbonyl)guanidinoacetylamino] pyrrolidin-1-ylcarbonyl]pyrrolidine were obtained as a colorless amorphous substance.

Infrared absorption spectrum (KBr) vmax cm$^{-1}$: 1705, 1655, 1609, 1521, 1441, 1405, 1346, 1290.

Nuclear magnetic resonance spectrum (270 MHz, CDCl$_3$–D$_2$O) δ ppm: 1.70–2.20 (3H, m), 2.36–2.53 (1H, m), 2.95–3.45 (4H, m), 3.65–3.90 (7H, m), 3.79 (3H, s), 4.25–4.47 (2H, m), 5.05–5.20 (4H, m), 6.86 (2H, d, J=8.5 Hz), 7.25 (2H, d, J=8.5 Hz), 7.40–7.58 (4H, m), 8.10–8.27 (4H, m).

(5) To a mixture of the compound (961 mg), which had been obtained in (4), and anisole (1.3 ml), trifluoroacetic acid (4.6 ml) and trifluoromethanesulfonic acid (213 μl) were added under ice cooling, followed by stirring at room temperature for 2 hours. The reaction mixture was purified in a similar manner to that described in Referential Example 1-(4), whereby 773 mg of the title compound were obtained.

Infrared absorption spectrum (KBr) vmax cm$^{-1}$: 3323, 1703, 1652, 1608, 1521, 1441, 1405, 1379, 1346, 1290.

Nuclear magnetic resonance spectrum (400 MHz, CDCl$_3$–D$_2$O) δ ppm: 1.80–2.25 (3H, m), 2.59–2.78 (1H, m), 3.17–3.68 (3H, m), 3.72–3.99 (4H, m), 4.01–4.15 (1H, m), 4.35–4.50 (2H, m), 5.10–5.25 (4H, m), 7.38–7.58 (4H, m), 8.10–8.27 (4H, m).

Referential Example 9

(2S,4S)-4-Mercapto-1-(4-nitrobenzyloxycarbonyl)-2-[(3S)-3-[α,ω-di(4-nitrobenzyloxycarbonyl)-L-arginylamino]pyrrolidin-1-ylcarbonyl]pyrrolidine (1) To a suspension of α,ω-di(4-nitrobenzyloxycarbonyl)-L-arginine (4.68 g) and (3S)-3-amino-1-(tert-butoxycarbonyl)pyrrolidine (1.49 g) in anhydrous DMF (50 ml), 1-(3-dimethylaminopropyl)-3-ethylcarbodiimide hydrochloride (1.68 g) and 4-dimethylaminopyridine (15 mg) were added, followed by stirring at room temperature for 2.5 hours. To the reaction mixture, ethyl acetate was added. The resulting mixture was washed with an aqueous solution of sodium carbonate, 15% saline and saturated saline, dried over anhydrous magnesium sulfate and then concentrated by evaporation under reduced pressure. The residue was purified by chromatography through a silica gel column (ethyl acetate:dichloromethane=1:1, methanol:ethyl acetate:dichloromethane=5:47.5:47.5, methanol:ethyl acetate:dichloromethane=8:46:46), whereby 1.47 g of (3S)-1-(tert-butoxycarbonyl)-3-[(α,ω-di(4-nitrobenzyloxycarbonyl)-L-arginyl]pyrrolidine were obtained as an amorphous substance.

Infrared absorption spectrum (KBr) vmax cm$^{-1}$: 3311, 1723, 1660, 1607, 1523, 1479, 1410, 1367, 1347, 1282.

Nuclear magnetic resonance spectrum (400 MHz, CDCl$_3$) δ ppm: 1.44 (9H, s), 1.52–2.20 (6H, m), 3.10–3.32 (3H, b), 3.32–3.47 (2H, b), 3.50–3.62 (1H, m), 4.13–4.25 (1H, m), 4.30–4.43 (1H, m), 5.16 (4H, s), 7.47 (2H, d, J=8.6 Hz), 7.53 (2H, d, J=8.6 Hz), 8.11–8.25 (4H, m).

(2) The compound (1.42 g) obtained in (1) and trifluoroacetic acid (5 ml) were treated in a similar manner to that described in Referential Example 1-(2), whereby (3S)-3-[α,ω-di(4-nitrobenzyloxycarbonyl)-L-arginyl]pyrrolidine 2-trifluoroacetate was obtained.

Infrared absorption spectrum (KBr) vmax cm$^{-1}$: 1749, 1675, 1609, 1524, 1454, 1439, 1350, 1251, 1204.

Nuclear magnetic resonance spectrum (400 MHz, D$_2$O) δ ppm: 1.60–1.95 (4H, m), 1.95–2.10 (1H, m), 2.29–2.42 (1H, m), 3.17–3.65 (6H, m), 4.02–4.18 (1H, m), 4.41–4.53 (1H, m), 5.14, 5.22 (each 1H, d, J=14.1 Hz), 5.36 (2H, s), 7.50 (2H, d, J=8.6 Hz), 7.58 (2H, d, J=8.6 Hz), 8.15 (2H, d, J=8.6 Hz), 8.19 (2H, d, J=8.6 Hz).

(3) To a solution of (2S,4S)-4-(4-methoxybenzyl)thio-1-(4-nitrobenzyloxycarbonyl)-L-proline (991 mg) in anhydrous acetonitrile (15 ml), N,N-carbonyldiimidazole (376 mg) was added, followed by stirring at room temperature for 30 minutes. To the reaction mixture, N,N-diisopropylethylamine (703 μl) and a solution of the compound obtained in (2) in anhydrous acetonitrile (15 ml) were added and the mixture was stirred overnight at room temperature. The reaction mixture was purified in a similar manner to that described in Referential Example 1-(3), whereby 1.19 g of (2,4S)-4-(4-methoxybenzyloxycarbonyl)thio-1-(4-nitrobenzyloxycarbohyl)-2-[(3S)-3-[α,ω-di(4-nitrobenzyloxycarbonyl)-L-arginylamino]pyrrolidin-1-ylcarbonyl]pyrrolidine were obtained as a colorless amorphous substance.

Infrared absorption spectrum (KBr) vmax cm$^{-1}$: 1709, 1652, 1608, 1521, 1440, 1404, 1346, 1284, 1249.

Nuclear magnetic resonance spectrum (400 MHz, CDCl$_3$) δ ppm: 1.45–2.30 (8H, m), 2.37–2.50 (1H, m), 3.00–3.37 (5H, m), 3.45–3.58 (1H, m), 3.70–3.87 (1H, m), 3.74 (2H, s), 3.79 (3H, s), 3.95–4.09 (2H, m), 4.20–4.31 (1H, m), 4.39 (1H, dd, J=9.1, 7.1 Hz), 4.50–4.70 (1H, b), 5.00–5.29 (6H, m), 5.87 (1H, d, J=7.6 Hz), 6.86 (2H, d, J=8.5 Hz), 7.24 (2H, d, J=8.5 Hz), 7.43 (2H, d, J=8.6 Hz), 7.49 (2H, d, J=8.6 Hz), 7.55 (2H, d, J=8.6 Hz), 8.18 (2H, d, J=8.6 Hz), 8.21 (4H, d, J=8.6 Hz).

(4) To a mixture of the compound (1.16 g), which had been obtained in (3), and anisole (1.2 ml), trifluoroacetic acid (4.3 ml) and trifluoromethanesulfonic acid (197 μl) were added under ice cooling, followed by stirring at room temperature for 2 hours. The reaction mixture was purified in a similar manner to that described in Referential Example 1-(4), whereby 965 mg of the title compound were obtained.

Infrared absorption spectrum (KBr) vmax cm$^{-1}$: 3392, 3319, 1708, 1647, 1608, 1520, 1440, 1405, 1347, 1320, 1284.

Nuclear magnetic resonance spectrum (400 MHz, CDCl$_3$) δ ppm: 1.20–2.30 (8H, m), 2.60–2.70 (1H, m), 3.00–3.60 (6H, m), 3.90–4.33 (4H, m), 4.49 (1H, dd, J=8.7, 7.3 Hz), 4.53–4.70 (1H, b), 5.05–5.35 (6H, m), 5.88 (1H, d, J=7.6 Hz), 7.39–7.60 (6H, m), 8.10–8.30 (6H, m).

Referential Example 10

(2S,4S)-4-Mercapto-1-(4-nitrobenzyloxycarbonyl)-2-[(3R)-3-[1-nitrobenzyloxycarbonyl)-L-prolylamino]pyrrolidin-1-ylcarbonyl]pyrrolidine The title compound was obtained in a similar manner to that described in Referential Example 1-(1), (2), (3) and (4) by using (3R)-3-amino-1-(tert-butoxycarbonyl)pyrrolidine.

Referential Example 11

(2R,4S)-4-Mercapto-1-(4-nitrobenzyloxycarbonyl)-2-[(3S)-3-(4-nitrobenzyloxycarbonyl)pyrrolidin-1-ylcarbonylmethyl]pyrrolidine (1) (2S,4S)-4-(4-Methoxybenzylthio)-1-(4-nitrobenzyloxycarbonyl)-2-pyrrolidinecarboxylic acid (10 g) and triethylamine (3.59 ml) were dissolved in tetrahydrofuran (25 ml), followed by stirring at –15 to –10° C. To the mixture, ethyl chlorocarbonate (2.46 ml) was added at the same temperature, followed by stirring at the same temperature for 15 minutes and then at 0–5° C. for one hour. The reaction mixture was filtered through Celite and the residue was washed with tetrahydrofuran (15 ml). The tetrahydrofuran solution was cooled to 0–5° C., followed by the addition of a solution, which had been obtained by dissolving sodium borohydride (1.9 g) in water (20 ml), in three portions below 25° C. The resulting mixture was stirred at room temperature for one hour. Ethyl acetate (100 ml) was added to the reaction mixture. The resulting mixture was washed successively with water, 1N hydrochloric acid, a saturated aqueous solution of sodium bicarbonate and saline; and then dried over anhydrous sodium sulfate. The solvent was distilled off and the residue was subjected to chromatography through a silica gel column. From the fractions eluted with a 1:1 solvent mixture of ethyl acetate and cyclohexane, (2S,4S)-2-hydroxymethyl-4-(4-methoxybenzylthio)-1-(4-nitrobenzyloxycarbonyl) pyrrolidine (4.3 g) was obtained.

Infrared absorption spectrum (Liquid film) vmax cm$^{-1}$: 3431, 1701, 1608, 1584, 1521, 1513, 1463, 1430, 1405, 1346, 1321, 1301.

Nuclear magnetic resonance spectrum (270 MHz, CDCl$_3$) δ ppm: 1.23–1.61 (1H, m), 2.28–2.40 (1H, m), 2.98–3.20 (2H, m), 3.68–3.83 (3H, m), 3.73 (2H, m), 3.79 (3H, m), 3.92–4.14 (1H, m), 4.26 (1H, t, J=5.6 Hz), 5.21 (2H, s), 6.85 (2H, d, J=8.6 Hz), 7.23 (2H, d, J=8.6 Hz), 7.48 (2H, d, J=8.6 Hz), 8.24 (2H, d, J=8.6 Hz).

(2) The compound (4.8 g) obtained in (1) was dissolved in anhydrous pyridine (34 ml). To the resulting solution, methanesulfonyl chloride (1.29 ml) was added at 0–5° C. The resulting mixture was stirred at room temperature for 30 minutes. The reaction mixture was poured into water, followed by extraction with ethyl acetate. The ethyl acetate layer was washed successively with 1N hydrochloric acid, water, an aqueous sodium bicarbonate solution and saline, and then dried over anhydrous sodium sulfate. The solvent was distilled off and the residue was subjected to chromatography through a silica gel column. From fractions eluted with a 2:3 mixture of ethyl acetate and cyclohexane, (2S, 4S)-2-methanesulfonyloxymethyl)-4-(4-methoxybenzylthio)-1-(4-nitrobenzyloxycarbonyl) pyrrolidine (5.8 g) was obtained.

Infrared absorption spectrum (Liquid film) vmax cm$^{-1}$: 1705, 1608, 1584, 1520, 1513, 1463, 1427, 1404, 1347, 1302.

Nuclear magnetic resonance spectrum (270 MHz, CDCl$_3$) δ ppm: 1.91–2.02 (1H, m), 2.34–2.44 (1H, m), 3.00 (3H, s), 3.07–3.23 (2H, m), 3.74 (2H, s), 3.80 (3H, s), 3.82–4.20 (2H, m), 4.36–4.60 (2H, m), 5.20, 5.23 (2H,sx2), 6.85 (2H, d, J=8.6 Hz), 7.23 (2H, d, J=8.6 Hz), 7.48, 7.54 (2H,dx2, J=8.5 Hz), 8.24 (2H, d, J=8.5 Hz).

(3) The compound (5.37 g) obtained in (2) was dissolved in anhydrous dimethylformamide (34 ml). To the resulting solution, 18-crown-6 (0.28 g) and potassium cyanide (4.1 g) were added, followed by stirring at 50° C. for 24 hours. At the end of this time, the solvent was distilled off and the residue was subjected to chromatography through a silica gel column. From fractions eluted with a 2:1 mixture of cyclohexane and ethyl acetate, (2R,4S)-2-cyanomethyl)-4-(4-methoxybenzylthio)-1-(4-nitrobenzyloxycarbonyl) pyrrolidine (3.3 g) was obtained.

Infrared absorption spectrum (Liquid film) vmax cm$^{-1}$: 2249, 1705, 1608, 1584, 1521, 1513, 1463, 1425, 1402, 1346, 1302.

Nuclear magnetic resonance spectrum (270 MHz, CDCl$_3$) δ ppm: 1.88–2.05 (1H, m), 2.43–2.55 (1H, m), 2.77–2.88 (1H, m), 3.01–3.16 (2H, m), 3.21–3.38 (1H, m), 3.75 (2H, s), 3.80 (3H, s), 3.89–4.14 (2H, m), 5.19, 5.24 (2H,sx2), 6.86 (2H, d, J=8.6 Hz), 7.23 (2H, d, J=8.6 Hz), 7.47 (2H, d, J=8.5 Hz), 8.24 (2H, d, J=8.5 Hz).

(4) In ethanol (15 ml), the compound (1.55 g) obtained in (3) was dissolved. To the resulting solution, 2N sodium hydroxide (15 ml) was added, followed by heating under reflux for 6 hours. The reaction mixture was concentrated. The concentrate was neutralized with 2N hydrochloric acid. After insoluble matter was filtered off, the filtrate was concentrated to dryness. The residue was dissolved in acetonitrile-water (5:1, 40 ml), followed by the addition of triethylamine (0.49 ml). The resulting mixture was cooled to 0 to 5° C., followed by the addition of 4,6-dimethyl-2-(4-nitrobenzyloxycarbonylthio)pyrimidine (1.12 g) and triethylamine (0.71 ml). The resulting mixture was stirred at room temperature for 2 hours. After the reaction, the solvent was distilled off. To the residue, 1N hydrochloric acid was added to make acidic the resulting solution, followed by extraction with ethyl acetate. The extract was washed successively with water and saline and dried over sodium sulfate. The solvent was distilled off and the residue was subjected to chromatography through a silica gel column. From the fractions eluted with a 5:1 mixture of ethyl acetate and cyclohexane→ethyl acetate→a 20:1 mixture of ethyl acetate and methanol, (2R,4S)-2-carboxymethyl-4-(4-methoxybenzylthio)-1-(4-nitrobenzyloxycarbonyl) pyrrolidine (0.52 g) was obtained.

Infrared absorption spectrum (Liquid film) vmax cm$^{-1}$: 1732, 1705, 1608, 1584, 1522, 1513, 1436, 1430, 1404, 1346, 1320, 1301.

Nuclear magnetic resonance spectrum (400 MHz, CDCl$_3$) δ ppm: 1.72–1.82 (1H, m), 2.51–2.58 (1H, m), 2.94–3.31 (3H, m), 3.73 (2H, s), 3.79 (3H, s), 3.81–3.97 (1H, m), 4.09–4.18 (1H, m), 5.19,5.22 (2H,sx2), 6.85 (2H, d, J=8.6 Hz), 7.22 (2H, d, J=8.6 Hz), 7.47 (2H, d, J=8.4 Hz), 8.23 (2H, d, J=8.4 Hz).

(5) The compound (0.52 g) obtained in (4) was dissolved in anhydrous tetrahydrofuran (10.5 ml). To the resulting solution, triethylamine (0.17 ml) and pivaloyl chloride (0.14 ml) were added under ice cooling, followed by stirring at 0–5° C. for 5 minutes. To the reaction mixture, a solution of (3S)-3-(4-nitrobenzyloxycarbonylamino)pyrrolidine hydrochloride (343 mg) in acetonitrile (2.5 ml) was added at the same temperature, followed by the addition of diisopropylethylamine (0.40 ml). The mixture was stirred for one hour. The solvent was then distilled off. Water was added to the residue and the resulting mixture was extracted with ethyl acetate. The ethyl acetate layer was washed with water and saline and then dried over anhydrous sodium sulfate. The solvent was distilled off and the residue was subjected to chromatography on a silica gel column. From the fractions eluted with a 3:2→5:1 mixture of ethyl acetate and cyclohexane, (2R,4S)-4-(4-methoxybenzylthio)-1-(4-nitrobenzyloxycarbonyl)-2-[(3S)-3-(4-nitrobenzyloxycarbonylamino)pyrrolidin-1-ylcarbonylmethyl]pyrrolidine (555 mg) was obtained.

Infrared absorption spectrum (Liquid film) vmax cm$^{-1}$: 1703, 1636, 1609, 1585, 1521, 1441, 1428, 1402, 1347, 1301.

Nuclear magnetic resonance spectrum (400 MHz, CDCl$_3$) δ ppm: 1.75–2.23 (3H, m), 2.44–2.68 (2H, m), 3.09–3.90 (9H, m), 3.73 (2H, s), 3.79 (3H, s), 4.22–4.35 (2H, m), 5.16, 5.19 (4H,sx2), 6.85 (2H, d, J=8.6 Hz), 7.22 (2H, d, J=8.6 Hz), 7.42–7.51 (4H, m), 8.21 (4H, d, J=8.4 Hz).

(6) The compound (542 mg) obtained in (5) was dissolved in the mixture of trifluoroacetic acid (2.71 ml) and anisole (0.54 ml). To the resulting solution, trifluoromethanesulfonic acid (0.17 ml) was added at 0 to 5° C. under ice cooling, followed by stirring at room temperature for 40 minutes. The solvent was distilled off and the residue was washed twice with hexane, followed by evaporation of the solvent. To the residue, an aqueous sodium bicarbonate solution was added to make alkaline the resulting mixture, followed by extraction with ethyl acetate. The ethyl acetate layer was washed with saline and then dried over anhydrous sodium sulfate. The solvent was distilled off, whereby the title compound (450 mg) was obtained.

Infrared absorption spectrum (Liquid film) vmax cm$^{-1}$: 1704, 1632, 1608, 1586, 1522, 1441, 1403, 1347, 1301.

Referential Example 12

(2S,4S)-2-[1-Hydroxy-2-[(3S)-3-(4-nitrobenzyloxycarbonylamino)pyrrolidin-1-ylcarbonyl]ethyl]-4-mercapto-1-(4-nitrobenzyloxycarbonyl)pyrrolidine (1) In anhydrous acetonitrile (100 ml), (2S,4S)-4-(4-methoxybenzylthio)-1-(4-nitrobenzyloxycarbonyl)-2-pyrrolidinecarboxylic acid (10 g) was dissolved. To the resulting solution, N,N'-carbonyldiimidazole (4.0 g) was added, followed by stirring at room temperature for 1.5 hours. To the resulting solution, magnesium t-butylmalonate (19.2 g) was added and the mixture was stirred at 25° C. for 3 days. The reaction mixture was then filtered and the filtrate was concentrated by evaporation under reduced pressure. Water was added to the residue, followed by extraction with ethyl acetate. The extract was washed with water and saline and dried over anhydrous sodium sulfate. The solvent was distilled off and the residue was subjected to chromatography through a silica gel column. From the fractions eluted with ethyl acetate/cyclohexanone=1/2, (2S,4S)-2-(t-butylmalonyl)-4-(4-methoxybenzylthio)-1-(4-nitrobenzyloxycarbonyl)pyrrolidine (7.56 g) was obtained as a powder.

Infrared absorption spectrum (KBr) vmax cm$^{-1}$: 1741, 1717, 1689, 1611, 1585, 1526, 1515, 1476, 1457, 1426, 1402.

Nuclear magnetic resonance spectrum (270 MHz, CDCl$_3$) δ ppm: 1.44, 1.46 (9H,sx2), 1.92–2.10 (1H, m), 2.44–2.57 (1H, m), 3.05–3.20 (1H, m), 3.21–3.53 (3H, m), 3.70 (2H, s), 3.80 (3H, s), 3.72–4.00 (1H, m), 4.38–4.97 (1H, m), 5.11–5.24 (2H, m), 6.85 (2H, d, J=8.6 Hz), 7.22 (2H, d, J=8.6 Hz), 7.46, 7.48 (2H,dx2,J=8.6 Hz), 8.21, 8.24 (2H, dx2,J=8.6 Hz).

(2) The compound (0.91 g) obtained in (1) was dissolved in tetrahydrofuran (10 ml). To the resulting solution, sodium borohydride (0.126 g) was added at 0 to 5° C., followed by stirring at the same temperature for one hour. To the reaction mixture, 1N hydrochloric acid was added and the resulting mixture was extracted with ethyl acetate. The ethyl acetate layer was washed successively with water, an aqueous sodium bicarbonate solution and saline and dried over anhydrous sodium hydroxide. The solvent was distilled off and the residue was subjected to chromatography through a silica gel column. From the fractions eluted with ethyl acetate/methylene chloride=1/10, (2S,4S)-2-(2-t-butoxycarbonyl-1-hydroxyethyl)-4-(4-methoxybenzylthio)-1-(4-nitrobenzyloxycarbonyl)pyrrolidine (0.862 g) was obtained.

Infrared absorption spectrum (Liquid film) vmax cm$^{-1}$: 3447, 1704, 1609, 1585, 1522, 1513, 1428, 1404, 1368, 1346, 1320, 1301.

Nuclear magnetic resonance spectrum (270 MHz, CDCl$_3$) δ ppm: 1.45 (9H, s), 1.78–2.03 (1H, m), 2.17–2.45 (3H, m), 2.90–3.13 (2H, m), 3.73 (2H, s), 3.79 (3H, s), 3.81–3.96 (1H, m), 4.00–4.16 (1H, m), 4.30–4.39 (1H, m), 5.19 (2H, s), 6.84 (2H, d, J=8.5 Hz), 7.22, 7.23 (2H, dx2, J=8.5 Hz), 7.48 (2H, d, J=8.4 Hz), 8.24 (2H, d, J=8.4 Hz).

(3) The compound (0.862 g) obtained in (2) was dissolved in methylene chloride (17 ml). To the resulting solution, trifluoroacetic acid (8.6 ml) was added at 0 to 5° C., followed by stirring at the same temperature for one hour and at room temperature for 10 minutes. The reaction mixture was concentrated by evaporation under reduced pressure, followed by the addition of methylene chloride and then concentration by evaporation under reduced pressure. This procedure was repeated three times. The solvent of the residue was distilled off, whereby (2S,4S)-2-(2-carboxy-1-hydroxyethyl)-4-(4-methoxybenzylthio)-1-(4-nitrobenzyloxycarbonyl)pyrrolidine (0.773 g) was obtained.

Nuclear magnetic resonance spectrum (270 MHz, CDCl$_3$) δ ppm: 1.53–1.78 (1H, m), 2.28–2.66 (3H, m), 2.96–3.16 (2H, m), 3.74 (2H, m), 3.80 (3H, m), 3.83–4.40 (3H, m), 5.21 (2H, s), 6.85 (2H, d, J=8.5 Hz), 7.22 (2H, d, J=8.5 Hz), 7.48 (2H, d, J=8.5 Hz), 8.25 (2H, d, J=8.5 Hz).

(4) The compound (0.773 g) obtained in (3) was dissolved in anhydrous tetrahydrofuran (15 ml). The resulting solution was cooled to −10 to −15° C., followed by the addition of triethylamine (0.242 ml) and pivaloyl chloride (0.194 ml). The resulting mixture was stirred at the same temperature for 5 minutes. To the reaction mixture, a solution of (3S)-3-(4-nitrobenzyloxycarbonylamino)pyrrolidine hydrochloride (0.476 g) in anhydrous acetonitrile (3.9 ml) and diisopropylethylamine (0.687 ml) were added and the mixture was stirred at room temperature for 1 hour and 40 minutes.

The solvent was distilled off and water was added to the residue. The resulting mixture was extracted with ethyl acetate. The ethyl acetate layer was washed with an aqueous sodium bicarbonate solution and saline and then dried over anhydrous sodium sulfate. The solvent was then distilled off. The residue was subjected to chromatography through a silica gel column. From the fractions eluted with ethyl acetate/cyclohexane=10/1, (2S,4S)-2-[1-hydroxy-2-[(3S)-3-(4-nitrobenzyloxycarbonylamino)pyrrolidin-1-ylcarbonyl]ethyl]-4-(4-methoxybenzylthio)-1-(4-nitrobenzyloxycarbonyl)pyrrolidine (0.665 g) was obtained as a powder.

Nuclear magnetic resonance spectrum (270 MHz, CDCl$_3$) δ ppm: 1.71–2.53 (6H, m), 2.92–3.15 (2H, m), 3.30–4.51 (9H, m), 3.73 (2H, s), 3.79 (3H, s), 4.95–5.43 (4H, m), 6.84 (2H, d, J=8.5 Hz), 7.23 (2H, d, J=8.5 Hz), 7.36–7.52 (2H, m), 8.16–8.28 (2H, m).

(5) The compound (0.664 g) obtained in (4) was dissolved in the mixture of anisole (0.664 ml) and trifluoroacetic acid (3.32 ml). To the resulting solution, trifluoromethanesulfonic acid (0.20 ml) was added at 0 to 5° C. under ice cooling, followed by stirring at room temperature for 40 minutes. The solvent was then distilled off. To the residue, sodium bicarbonate was added to make alkaline the resulting mixture, followed by extraction with ethyl acetate. The ethyl acetate layer was washed with saline and then dried over anhydrous sodium sulfate. The solvent was distilled off whereby the title compound (556 mg) was obtained.

Nuclear magnetic resonance spectrum (270 MHz, CDCl$_3$) δ ppm: 1.71–2.71 (6H, m), 3.02–3.31 (2H, m), 3.34–4.51 (9H, m), 5.18 (4H, s), 7.47–7.50 (2H, m), 8.15–8.34 (2H, m).

Referential Example 13

(2S,4S)-4-Mercapto-1-(4-nitrobenzyloxycarbonyl)-2-[(3S)-3-(4-nitrobenzyloxycarbonylamino)pyrrolidin-1-ylcarbonyl-(E)-ethenyl]pyrrolidine (1) In methylene chloride (24 ml), oxalyl chloride (0.40 ml) was dissolved. To the resulting solution, a solution of dimethyl sulfoxide (0.44 ml) in methylene chloride (1.6 ml) was added at −78° C., followed by stirring for 10 minutes. To the resulting solution, a solution of (2S,4S)-2-hydroxymethyl-4-(4-methoxybenzylthio)-1-(4-nitrobenzyloxycarbonyl)pyrrolidine (1 g) in methylene chloride (8 ml) was added dropwise at the same temperature, followed by stirring at −78° C. for 15 minutes and −50 to −60° C. for one hour. To the reaction mixture, triethylamine (2.4 ml) was added, followed by stirring at −14 to −15° C. for 20 minutes. To the reaction mixture, 1N hydrochloric acid was added to make the resulting solution acidic, followed by extraction with methylene chloride. The methylene chloride layer was washed with water and saline and then dried over anhydrous sodium sulfate. The solvent was distilled off, whereby (2S,4S)-2-formyl-4-(4-methoxybenzylthio)-1-(4-nitrobenzyloxycarbonyl)pyrrolidine (1 g) was obtained.

Nuclear magnetic resonance spectrum (270 MHz, CDCl$_3$) δ ppm: 2.16–2.29 (1H, m), 2.31–2.50 (1H, m), 3.18–3.29 (1H, m), 3.37–3.56 (1H, m), 3.61 (2H, s), 3.67–3.77 (1H, m), 3.80 (3H, s), 4.15–4.26 (1H, m), 5.23, 5.25 (2H,sx2), 6.85 (2H, d, J=8.6 Hz), 7.20 (2H, d, J=8.6 Hz), 7.47, 7.51 (2H, dx2, J=8.7 Hz), 8.22, 8.24 (2H, dx2, J=8.7 Hz), 9.67 (1H, d, J=8.7 Hz).

(2) In anhydrous tetrahydrofuran (30 ml), t-butyl diethylphosphonoacetate (0.65 ml) was dissolved. To the resulting solution, 60% sodium hydride (0.11 g) was added under ice cooling, followed by stirring at room temperature for 30 minutes. To the resulting solution, the compound obtained in (1) (1 g) was added and the mixture was stirred at room temperature for 30 minutes. An aqueous ammonium acetate solution was added to the reaction mixture, followed by extraction with ethyl acetate. The ethyl acetate layer was washed with water and saline and then dried over anhydrous sodium sulfate. The solvent was distilled off and the residue was subjected to chromatography through a silica gel column. From the fractions eluted with a 9:1→3:1 mixture of ethyl acetate and cyclohexane, (2S,4S)-2-t-butoxycarbonyl-(E)-ethenyl-4-(4-methoxybenzylthio)-1-(4-nitrobenzyloxycarbonyl)pyrrolidine (0.688 g) was obtained.

Infrared absorption spectrum (Liquid film) νmax cm$^{-1}$: 1709, 1655, 1609, 1585, 1522, 1512, 1456, 1425, 1401, 1367, 1345, 1302.

Nuclear magnetic resonance spectrum (270 MHz, CDCl$_3$) δ ppm: 1.48 (9H, s), 1.68–1.79 (1H, m), 2.41–2.51 (1H, m), 3.03–3.14 (1H, m), 3.16–3.31 (1H, m), 3.72 (2H, s), 3.80 (3H, s), 3.88–4.01 (1H, m), 4.34–4.42 (1H, m), 5.04–5.31 (2H, m), 5.75, 5.81 (1H, dx2, J=15.9 Hz), 6.74–6.82 (1H, m), 6.85 (2H, d, J=8.6 Hz), 7.22 (2H, d, J=8.6 Hz), 7.43–7.49 (2H, m), 8.17–8.29 (2H, m).

(3) In methylene chloride (25 ml), the compound (1.24 g) obtained in (2) was dissolved. To the resulting solution, trifluoroacetic acid (12.4 ml) was added at 0 to 5° C. and the mixture was stirred at 0 to 5° C. for one hour and at room temperature for 10 minutes. The reaction mixture was concentrated by evaporation under reduced pressure; methylene chloride was added to the residue; and the resulting mixture was concentrated by evaporation under reduced pressure. This procedure was repeated three times. The solvent of the residue was distilled off, whereby (2S,4S)-2-carboxy-(E)-ethenyl-4-(4-methoxybenzylthio)-1-(4-nitrobenzyloxycarbonyl)pyrrolidine (1.1 g) was obtained as an amorphous substance.

Nuclear magnetic resonance spectrum (400 MHz, CDCl$_3$+D$_2$O) δ ppm: 1.71–7.81 (1H, m), 2.45–2.52 (1H, m), 3.09–3.17 (1H, m), 3.23–3.35 (1H, m), 3.24 (2H, s), 3.80 (3H, s), 3.90–3.98 (1H, m), 4.40–4.48 (1H, m), 5.06–5.30 (2H, m), 5.82, 5.91 (1H, dx2, J=15.6 Hz), 6.85 (2H, d, J=8.5 Hz), 6.99 (1H, dd, J=15.6, 6.9 Hz), 7.44, 7.48 (2H, dx2, J=8.3 Hz), 8.17, 8.24 (2H ,dx2, J=8.3 Hz).

(4) The compound (1 g) obtained in (3) was dissolved in anhydrous tetrahydrofuran (20 ml). To the resulting solution, triethylamine (0.32 ml) and pivaloyl chloride (0.26 ml) were added at 0 to 5° C., followed by stirring for 5 minutes at the same temperature. To the reaction mixture, a solution of (3S)-3-(4-nitrobenzyloxycarbonylamino)pyrrolidine hydrochloride (637 mg) in anhydrous acetonitrile (4.8 ml) and diisopropylethylamine (0.74 ml) were added, followed by stirring at room temperature for 2 hours. The solvent of the reaction mixture was then distilled off. To the residue, water was added and the resulting mixture was extracted with ethyl acetate. The ethyl acetate layer was washed with an aqueous solution of sodium bicarbonate and saline and then dried over anhydrous sodium sulfate. The solvent was distilled off and the residue was subjected to chromatography through a silica gel column. From the fractions eluted with a 3:1 mixture of ethyl acetate and cyclohexane→ethyl acetate→a 10:1 mixture of ethyl acetate and methanol, (2S,4S)-4-(methoxybenzylthio)-1-(4-nitrobenzyloxycarbonyl)-2-[(3S)-3-(4-nitrobenzyloxycarbonylamino)pyrrolidin-1-ylcarbonyl-(E)-ethenyl]pyrrolidine (1.04 g) was obtained as a powder.

Infrared absorption spectrum (KBr) νmax cm⁻¹: 1708, 1665, 1609, 1521, 1437, 1402, 1346, 1300.

Nuclear magnetic resonance spectrum (270 MHz, CDCl₃) δ ppm: 1.63–2.03 (2H, m), 2.08–2.25 (1H, m), 2.40–2.50 (1H, m), 3.07–4.02 (7H, m), 3.72 (2H, s), 3.80 (3H, s), 4.20–4.34 (1H, m), 4.37–4.45 (1H, m), 4.98–5.30 (4H, m), 5.92–6.23 (1H, m), 6.85 (2H, d, J=8.6 Hz), 7.22 (2H, d, J=8.6 Hz), 7.46 (2H, d, J=8.7 Hz), 7.51 (2H, d, J=7.9 Hz), 8.13–8.24 (2H, m).

(5) The compound (1.0 g) obtained in (4) was dissolved in the mixture of trifluoroacetic acid (5.21 ml) and anisole (1.0 ml). To the resulting solution, trifluoromethanesulfonic acid (0.32 ml) was added at 0 to 5° C. under ice cooling, followed by stirring at room temperature for 40 minutes. The solvent of the reaction mixture was then distilled off. The residue was washed twice with hexane and then the solvent was distilled off. To the residue, an aqueous solution of sodium bicarbonate was added to make alkaline the resulting solution, followed by extraction with ethyl acetate. The ethyl acetate layer was washed with saline and dried over anhydrous sodium sulfate. The solvent was distilled off, whereby the title compound (868 mg) was obtained.

Nuclear magnetic resonance spectrum (270 MHz, CDCl₃) δ ppm: 1.73–2.08 (3H, m), 2.14–2.22 (1H, m), 2.62–2.68 (1H, m), 3.23–3.86 (6H, m), 4.04–4.16 (1H, m), 4.21–4.32 (1H, m), 4.46–4.50 (1H, m), 4.96–5.26 (4H, m), 5.93–6.30 (1H, m), 6.78–6.98 (1H, m), 7.46–7.53 (4H, m), 8.18–8.24 (4H, m).

Referential Example 14

(2S,4S)-4-Mercapto-1-(4-nitrobenzyloxycarbonyl)-2-[(3R)-3-[1-[1-(4-nitrobenzyloxycarbonylamino)pyrrolidin-1-ylcarbonyl-(E)-ethenyl]pyrrolidine The title compound can be obtained in a similar manner to that described in Referential Example 13-(4) and (5) by using the compound obtained in Referential Example 13-(3) and (3R)-3-(4-nitrobenzyloxycarbonylamino)pyrrolidine hydrochloride.

Referential Example 15

(2S,4S)-4-Mercapto-1-(4-nitrobenzyloxycarbonyl)-2-[(3S)-3-[3-(4-nitrobenzyloxycarbonyl)guanidinopropanoylamino]pyrrolidin-1-ylcarbonyl]pyrrolidine (1) tert-Butyl (3S)-3-[3-(4-nitrobenzyloxycarbonyl)guanidinopropanoylamino]-1-pyrrolidinecarboxylate Under ice cooling, N,N-diisopropylethylamine (961 μl) and 3,5-dimethylpyrazole-1-carboxamidine nitrate (1.11 g) were added to a solution of tert-butyl (3S)-3-(3-aminopropanoylamino)-1-pyrrolidinecarboxylate (1.42 g) in anhydrous N,N'-dimethylformamide (10 ml) and the mixture was stirred overnight at room temperature. The reaction mixture was poured into ether (150 ml) to give an oily precipitate. The precipitate was dissolved in anhydrous dichloromethane:anhydrous tetrahydrofuran=5:2 (70 ml). To the resulting solution, a solution of N-(4-nitrobenzyloxycarbonyl)oxy-5-norbornene-2,3-dicarboxyimide (4.35 g) in anhydrous dichloromethane (35 ml) was added dropwise under ice cooling, followed by the addition of N,N-diisopropylamine (1.90 ml). The resulting mixture was stirred overnight. To the reaction mixture, ethyl acetate was added. The resulting mixture was washed with water and saturated saline, dried over anhydrous magnesium sulfate and concentrated by evaporation under reduced pressure. The residue was suspended in methanol (50 ml). To the suspension, a 1N aqueous sodium hydroxide solution (6 ml) was added under ice cooling, followed by stirring overnight. The reaction mixture was concentrated by evaporation under reduced pressure and the residue was dissolved in ethyl acetate. The resulting solution was washed with water and saturated saline, dried over anhydrous magnesium sulfate and concentrated by evaporation under reduced pressure. The residue was separated by chromatography through a silica gel column (ethyl acetate, ethyl acetate-methanol), whereby 955 mg of the title target compound were obtained.

Infrared absorption spectrum (KBr) νmax cm⁻¹: 3315, 1737, 1658, 1606, 1543, 1523, 1494, 1479, 1415.

Nuclear magnetic resonance spectrum (270 MHz, CDCl₃) δ ppm: 1.66–1.90 (1H, m), 2.00–2.20 (1H, b), 2.32–2.50 (2H, b), 3.08–3.25 (1H, b), 3.30–3.45 (2H, b), 3.50–3.63 (3H, m), 4.30–4.46 (1H, m), 5.16 (2H, s), 7.54 (2H, d, J=8.6 Hz), 8.20 (2H, d, J=8.6 Hz).

(2) (3S)-3-[3-(4-Nitrobenzyloxycarbonyl)guanidinopropanoylamino]pyrrolidine ditrifluoroacetate To a solution of the compound (1.34 g), which had been obtained in (1), in anhydrous dichloromethane (10 ml), trifluoroacetic acid (4 ml) was added under ice cooling. The resulting mixture was stirred for one hour and concentrated by evaporation under reduced pressure. The residue was washed with hexane-ether, whereby the title compound was obtained. The product was provided for the subsequent step without purification.

Infrared absorption spectrum (KBr) νmax cm⁻¹: 3305, 1754, 1673, 1612, 1555, 1527, 1435, 1351, 1319.

Nuclear magnetic resonance spectrum (270 MHz, DMSO-d₆) δ ppm: 1.72–1.90 (1H, m), 2.02–2.20 (1H, m), 2.40–2.57 (2H, m), 2.90–3.07 (1H, m), 3.13–3.44 (3H, m), 3.44–3.60 (2H, m), 4.20–4.37 (1H, m), 5.39 (2H, s), 7.69 (2H, d, J=8.7 Hz), 8.27 (2H, d, J=8.7 Hz).

(3) (2S,4S)-4-(4-Methoxybenzyl)thio-1-(4-nitrobenzyloxycarbonyl)-2-[(3S)-3-[3-(4-nitrobenzyloxycarbonyl)guanidinopropanoylamino]pyrrolidin-1-ylcarbonyl]pyrrolidine To a solution of (2S,4S)-4-(4-methoxybenzyl)thio-1-(4-nitrobenzyloxycarbonyl)-L-proline (1.31 g) in anhydrous acetonitrile (20 ml), N,N-carbonyldiimidazole (499 mg) was added. The resulting mixture was stirred at room temperature for 30 minutes, followed by the addition of N,N-diisopropylethylamine (975 μl) and a solution of the compound obtained in (2) in anhydrous acetonitrile (25 ml). The mixture was stirred overnight at room temperature. Ethyl acetate was added to the reaction mixture. The resulting mixture was washed with water and saturated saline, dried over anhydrous magnesium sulfate and concentrated by evaporation under reduced pressure. The residue was purified by chromatography through a silica gel column (ethyl acetate-methanol), whereby 1.41 g of the title compound were obtained as a colorless amorphous substance.

Infrared absorption spectrum (KBr) νmax cm⁻¹: 3316, 1707, 1651, 1608, 1521, 1440, 1405, 1346, 1319, 1286.

Nuclear magnetic resonance spectrum (270 MHz, DMSO-d₆) δ ppm: 1.68–2.52 (5H, m), 3.00–4.18 (13H, m), 3.79 (3H, s), 4.28–4.52 (2H, m), 4.96–5.24 (4H, m), 6.70–6.80 (1H, b), 6.86 (2H, d, J=8.5 Hz), 6.92–7.17 (1H, b), 7.24 (2H, d, J=8.5 Hz), 7.41 (2H, d, J=8.6 Hz), 7.52 (2H, d, J=8.6 Hz), 8.17 (2H, d, J=8.7 Hz), 8.22 (2H, d, J=8.7 Hz).

(4) (2S,4S)-4-Mercapto-1-(4-nitrobenzyloxycarbonyl)-2-[(3S)-3-[3-(4-nitrobenzyloxycarbonyl)guanidinopropanoylamino]pyrrolidin-1-ylcarbonyl]pyrrolidine Under ice cooling, trifluoroacetic acid (6.63 ml) and trifluoromethanesulfonic acid (302 μl) were added to a mixture of the compound (1.39 g), which had been obtained in (3), and anisole (1.87 ml), followed by stirring at room temperature for 2 hours. The reaction mixture was concentrated by evaporation under reduced pressure. After the residue was washed with ether-hexane, it was dissolved in ethyl acetate. The ethyl acetate solution was washed with a saturated aqueous solution of sodium bicarbonate, water and saturated saline, dried over anhydrous magnesium sulfate and concentrated under reduced pressure, whereby 1.21 g of the title compound were obtained as a colorless amorphous substance.

Infrared absorption spectrum (KBr) vmax cm$^{-1}$: 3316, 1708, 1649, 1607, 1521, 1439, 1405, 1373, 1346, 1285.

Nuclear magnetic resonance spectrum (400 MHz, DMSO-d$_6$) δ ppm: 1.60–2.40 (4H, m), 2.60–2.80 (1H, m), 3.05–4.62 (12H, m), 5.02–5.28 (4H, m), 7.47–7.68 (4H, m), 8.15–8.28 (4H, m).

Referential Example 16

(2S,4S)-4-Mercapto-1-(4-nitrobenzyloxycarbonyl)-2-[3-[[2,3-di(4-nitrobenzyloxycarbonyl)guanidino]acetylamino]azetidin-1-ylcarbonyl]pyrrolidine (1) tert-Butyl 3-[[2,3-di(4-nitrobenzyloxycarbonyl)guanidino]acetylamino]-1-azetidinecarboxylate Under ice cooling, a solution of 4-nitrobenzyl [(4-nitrobenzyloxy)carbonyliminopyrazol-1-ylmethyl]carbamate (1.42 g) in tetrahydrofuran (12 ml) was added to a solution of tert-butyl 3-(aminoacetylamino)-1-azetidinecarboxylate (785 mg) in tetrahydrofuran (13 ml) and the mixture was stirred at room temperature for 3 hours. Ethyl acetate was added to the reaction mixture. The resulting mixture was washed with water, an aqueous solution of potassium hydrogensulfate and saturated saline, dried over anhydrous magnesium sulfate and concentrated by evaporation under reduced pressure. The residue was crystallized from diisopropyl ether, followed by washing, whereby 1.94 g of the title compound were obtained as a colorless crystals.

Melting point: 99 to 101° C.

Infrared absorption spectrum (KBr) vmax cm$^{-1}$: 3316, 1744, 1683, 1643, 1626, 1610, 1549, 1524, 1496.

Nuclear magnetic resonance spectrum (270 MHz, CDCl$_3$) δ ppm: 1.43 (9H, s), 3.73 (2H, dd, J=9.5, 5.1 Hz), 4.09 (2H, d, J=5.2 Hz), 4.23 (2H, dd, J=9.5, 7.8 Hz), 4.53–4.67 (1H, m), 5.22 (2H, s), 5.31 (2H, s), 6.69 (1H, d, J=6.9 Hz), 7.54 (4H, d, J=8.2 Hz), 8.22 (2H, d, J=6.6 Hz), 8.25 (2H, d, J=6.6 Hz), 8.90 (1H, t, J=5.2 Hz), 11.65 (1H, s).

(2) 3-[[2,3-di(4-nitrobenzyloxycarbonyl)guanidino]acetylamino]azetidine trifluoroacetate To a solution of the compound (1.92 g), which had been obtained in (1), in anhydrous dichloromethane (10 ml), trifluoroacetic acid (5 ml) was added under ice cooling. The resulting mixture was stirred for one hour, followed by concentration under reduced pressure. The residue was washed with hexane-ether, followed by evaporation of the solvent, whereby 2.78 g of the title target compound were obtained. The product was provided for the subsequent step without purification.

Infrared absorption spectrum (KBr) vmax cm$^{-1}$: 3316, 1756, 1679, 1609, 1599, 1526, 1441, 1393, 1350.

Nuclear magnetic resonance spectrum (270 MHz, DMSO-d$_6$) δ ppm: 3.82–4.20 (6H, m), 4.50–4.70 (1H, m), 5.20 (2H, s), 5.39 (2H, s), 7.61 (2H, d, J=8.6 Hz), 7.71 (2H, d, J=8.6 Hz), 8.24 (2H, d, J=8.3 Hz), 8.27 (2H, d, J=8.3 Hz).

(3) (2S,4S)-4-(4-methoxybenzyl)thio-1-(4-nitrobenzyloxycarbonyl)-2-[3-[[2,3-di(4-nitrobenzyloxycarbonyl)guanidino]acetylamino]azetidin-1-ylcarbonyl]pyrrolidine To a solution of (2S,4S)-4-(4-methoxybenzyl)thio-1-(4-nitrobenzyloxycarbonyl)-L-proline (1.43 g) in anhydrous acetonitrile (22 ml), N,N-carbonyldiimidazole (545 mg) was added. The resulting mixture was stirred at room temperature for 30 minutes. To the reaction mixture, N,N-diisopropylethylamine (581 μl) and a solution of the compound (2.78 g), which had been obtained in (2), in anhydrous acetonitrile (23 ml) were added and the mixture was stirred overnight at room temperature. To the reaction mixture, dichloromethane was added. The resulting mixture was washed with water and saturated saline, dried over anhydrous magnesium sulfate and then concentrated by evaporation under reduced pressure, whereby 2.57 g of the title compound were obtained as a colorless amorphous substance.

Infrared absorption spectrum (KBr) vmax cm$^{-1}$: 3313, 1738, 1706, 1645, 1626, 1609, 1555, 1522, 1438, 1405, 1378, 1347, 1320, 1291, 1250.

Nuclear magnetic resonance spectrum (270 MHz, CDCl$_3$) δ ppm: 1.89–2.07 (1H, m), 2.29–2.42 (1H, m), 3.00–3.17 (1H, m), 3.23–3.38 (1H, m), 3.68–4.47 (13H, m), 4.67–4.80 (1H, m), 5.04–5.33 (6H, m), 6.85 (2H, d, J=8.6 Hz), 7.18–7.30 (2H, m), 7.39–7.58 (6H, m), 8.14–8.28 (6H, m), 8.91 (1H, t, J=5.0 Hz), 11.66 (1H, s).

(4) (2S,4S)-4-Mercapto-1-(4-nitrobenzyloxycarbonyl)-2-[3-[[2,3-di(4-nitrobenzyloxycarbonyl)guanidino]acetylamino]azetidin-1-ylcarbonyl]pyrrolidine Under ice cooling, trifluoroacetic acid (10.17 ml) and trifluoromethanesulfonic acid (463 μl) were added to a mixture of the compound (2.53 g), which had been obtained in (3), and anisole (2.87 ml), followed by stirring at room temperature for 2 hours. The reaction mixture was concentrated by evaporation under reduced pressure. The residue was washed with ether-hexane and then dissolved in ethyl acetate. The ethyl acetate solution was washed with a saturated aqueous solution of sodium bicarbonate, water and saturated saline, dried over anhydrous magnesium sulfate and concentrated by evaporation under reduced pressure, whereby 2.16 g of the title compound were obtained as a colorless amorphous substance.

Infrared absorption spectrum (KBr) vmax cm$^{-1}$: 3315, 1737, 1707, 1645, 1626, 1609, 1554, 1522, 1496, 1434, 1405, 1377, 1347, 1321, 1291.

Nuclear magnetic resonance spectrum (400 MHz, CDCl$_3$) δ ppm: 1.90–2.08 (2H, m), 2.53–2.65 (1H, m), 3.20–3.48 (2H, m), 3.75–4.82 (9H, m), 5.03–5.37 (6H, m), 7.43–7.58 (6H, m), 8.15–8.29 (6H, m), 8.91 (1H, t, J=5.0 Hz), 11.66 (1H, s).

Referential Example 17

(2S,4S)-4-Mercapto-1-(4-nitrobenzyloxycarbonyl)-2-[3-[3-[2,3-di(4-nitrobenzyloxycarbonyl)guanidino]propanoylamino]azetidin-1-ylcarbonyl]pyrrolidine (1) tert-Butyl 3-[[3-[2,3-di(4-nitrobenzyloxycarbonyl)guanidino]propanoylamino]-1-azetidinecarboxylate Under ice cooling, a solution of 4-nitrobenzyl[(4-nitrobenzyloxy)carbonyliminopyrazol-1-ylmethyl]carbamate in tetrahydrofuran (15 ml) was added to a solution of tert-butyl 3-(3-aminopropionylamino)-1-azetidinecarboxylate (545 mg) in tetrahydrofuran (15 ml), followed by stirring at room temperature for 2 hours. Ethyl acetate was added to the reaction mixture. The resulting mixture was washed with water, an aqueous solution of potassium hydrogensulfate and saturated saline, dried over anhydrous magnesium sulfate and concentrated by evaporation under reduced pressure. The residue was purified by chromatography through a silica gel column (ethyl acetate), whereby 1.28 g of the title target compound were obtained as a colorless amorphous substance.

Infrared absorption spectrum (KBr) vmax cm$^{-1}$: 3333, 1739, 1701, 1645, 1609, 1567, 1523, 1496, 1478, 1414, 1379, 1368, 1347.

Nuclear magnetic resonance spectrum (270 MHz, CDCl$_3$) δ ppm: 1.42 (9H, s), 2.52 (2H, t, J=6.0 Hz), 3.68–3.81 (4H, m), 4.23 (2H, dd, J=9.3, 7.8 Hz), 4.57–4.73 (1H, m), 5.22 (2H, s), 5.29 (2H, s), 6.58 (1H, d, J=6.6 Hz), 7.48–7.58 (4H, m), 8.17–8.27 (4H, m), 8.92 (1H, t, J=5.9 Hz), 11.72 (1H, s).

(2) 3-[3-[2,3-Di(4-nitrobenzyloxycarbonyl)guanidino]propanoylamino]azetidine trifluoroacetate (1) To a solution of the compound (1.25 g), which had been obtained in (1), in anhydrous dichloromethane (6 ml), trifluoroacetic acid (3 ml) was added under ice cooling, followed by stirring for one hour. The reaction mixture was then concentrated by evaporation under reduced pressure. The residue was washed with hexane-ether and then the solvent was distilled off, whereby 1.86 g of the title compound were obtained. The product was provided for use in the subsequent step without purification.

Infrared absorption spectrum (KBr) vmax cm$^{-1}$: 3216, 1755, 1678, 1609, 1525, 1456, 1412, 1381, 1350, 1322, 1205, 1145.

Nuclear magnetic resonance spectrum (270 MHz, DMSO-d$_6$+D$_2$O) δ ppm: 2.42 (2H, t, J=6.4 Hz), 3.56 (2H, t, J=6.4 Hz), 3.93 (2H, dd, J=11.2, 7.8 Hz), 4.08 (2H, dd, J=11.2, 8.3 Hz), 4.50–4.67 (1H, m), 5.20 (2H, s), 5.35 (2H, s), 7.63 (2H, d, J=8.5 Hz), 7.68 (2H, d, J=8.5 Hz), 8.24 (2H, d, J=6.8 Hz), 8.27 (2H, d, J=6.8 Hz).

(3) (2S,4)-4-(4-Methoxybenzyl)thio-1-(4-nitrobenzyloxycarbonyl)-2-[[3-[3-[2,3-di(4-nitrobenzyloxycarbonyl)guanidino]propanoylamino]azetidin-1-yl]carbonyl]pyrrolidine To a solution of (2S,4S)-4-(4-methoxybenzyl)thio-1-(4-nitrobenzyloxycarbonyl)-L-proline (909 mg) in anhydrous acetonitrile (13 ml), N,N-carbonyldiimidazole (346 mg) was added, followed by stirring at room temperature for 30 minutes. To the reaction mixture, N,N-diisopropylethylamine (338 μl) and a solution of the compound (1.68 g), which had been obtained in (2), in anhydrous acetonitrile (15 ml) were added and the mixture was stirred overnight at room temperature. Dichloromethane was added to the reaction mixture. The resulting mixture was washed with water and saturated saline, dried over anhydrous magnesium sulfate and concentrated by evaporation under reduced pressure. The residue was purified by chromatography through a silica gel column (ethyl acetate-methanol), whereby 1.88 g of the title target compound were obtained as a colorless amorphous substance.

Infrared absorption spectrum (KBr) vmax cm$^{-1}$: 3330, 1737, 1709, 1644, 1609, 1567, 1522, 1432, 1406, 1379, 1346, 1320, 1252.

Nuclear magnetic resonance spectrum (270 MHz, CDCl$_3$) δ ppm: 1.85–2.08 (1H, m), 2.28–2.58 (3H, m), 3.00–3.17 (1H, m), 3.23–3.37 (1H, m), 3.62–4.01 (10H, m), 4.07–4.28 (2H, m), 4.32–4.46 (1H, m), 4.60–4.83 (1H, m), 5.06–5.32 (6H, m), 6.85 (2H, d, J=8.6 Hz), 7.18–7.32 (2H, m), 7.38–7.60 (6H, m), 8.16–8.28 (6H, m), 8.80–8.92 (1H, m), 11.72 (1H, s).

(4) (2S,4S)-4-Mercapto-1-(4-nitrobenzyloxycarbonyl)-2-[[3-[3-[2,3-di(4-nitrobenzyloxycarbonyl)guanidino]propanoylamino]azetidin-1-yl]carbonyl]pyrrolidine Under ice cooling, trifluoroacetic acid (7.45 ml) and trifluoromethanesulfonic acid (339 μl) were added to a mixture of the compound (1.88 g), which had been obtained in (3), and anisole (2.1 ml), followed by stirring at room temperature for 2 hours. The reaction mixture was concentrated by evaporation under reduced pressure. After washing with ether-hexane, the residue was dissolved in ethyl acetate. The ethyl acetate solution was washed with a saturated aqueous solution of sodium bicarbonate, water and saturated saline, dried over anhydrous magnesium sulfate and concentrated by evaporation under reduced pressure, whereby 1.50 g of the title compound were obtained as a colorless amorphous substance.

Infrared absorption spectrum (KBr) vmax cm$^{-1}$: 3331, 1736, 1709, 1644, 1608, 1567, 1522, 1496, 1432, 1406, 1378, 1347.

Nuclear magnetic resonance spectrum (400 MHz, CDCl$_3$) δ ppm: 1.90–2.10 (2H, m), 2.45–2.74 (3H, m), 3.20–3.47 (2H, m), 3.67–4.85 (9H, m), 5.05–5.42 (6H, m), 7.43–7.62 (6H, m), 8.15–8.30 (6H, m), 8.80–9.00 (1H, m), 11.73 (1H, s).

Referential Example 18

(2S,4S)-2-[(3S)-3-[3-Hydroxy-4-(4-nitrobenzyloxycarbonyl)aminobutanoylamino]pyrrolidin-1-ylcarbonyl]-4-mercapto-1-(4-nitrobenzyloxycarbonyl)pyrrolidine (1) (2S,4S)-2-[(3S)-3-[3-Hydroxy-4-(4-nitrobenzyloxycarbonyl)aminobutanoylamino]pyrrolidin-1-ylcarbonyl]-4-(4-methoxybenzyl)thio-1-(4-nitrobenzyloxycarbonyl)pyrrolidine To a solution of (2S,4S)-4-(4-methoxybenzyl)thio-1-(4-nitrobenzyloxycarbonyl)-L-proline (2.87 g) in anhydrous tetrahydrofuran (30 ml), N,N'-carbonyldiimidazole (1.25 g) was added, followed by stirring at 30° C. for one hour. To the reaction mixture, N,N-diisopropylethylamine (1.68 ml) and a solution of (3S)-3-[3-hydroxy-4-(4-nitrobenzyloxycarbonyl)aminobutanoylamino]pyrrolidine trifluoroacetate (3.19 g) in anhydrous tetrahydrofuran (30 ml) was added. The resulting mixture was allowed to stand overnight at room temperature. The reaction mixture was concentrated by evaporation under reduced pressure and ethyl acetate was added to the residue. The resulting mixture was washed successively with water and saturated saline, dried over anhydrous magnesium sulfate and concentrated by evaporation under reduced pressure. The residue was purified by chromatography (dichloromethane-ethyl acetate-methanol) through a silica gel column, whereby 3.81 g of the title compound were obtained as an amorphous substance.

Infrared absorption spectrum (KBr) vmax cm$^{-1}$: 3316, 1709, 1647, 1609, 1520, 1440, 1346.

Nuclear magnetic resonance spectrum (270 MHz, CDCl$_3$) δ ppm: 1.47–2.72 (8H, m), 2.95–3.58 (6H, m), 3.60–4.18 (4H, m), 3.76 (2H, s), 3.80 (3H, s), 4.20–4.62 (2H, m), 4.97–5.28 (4H, m), 5.35–5.60 (1H, m), 6.80–7.02 (2H, m), 7.17–7.35 (2H, m), 7.41–7.60 (4H, m), 8.13–8.33 (4H, m).

(2) (2S,4S)-2-[(3S)-3-[3-Hydroxy-4-(4-nitrobenzyloxycarbonyl)aminobutanoylamino]pyrrolidin-1-ylcarbonyl]-4-mercapto-1-(4-nitrobenzyloxycarbonyl)pyrrolidine To a mixture of the compound (2.38 g), which had been obtained in (1), and anisole (3.30 ml), trifluoroacetic acid (11.60 ml) and trifluoromethanesulfonic acid (0.53 ml) were added dropwise under ice cooling, followed by stirring at room temperature for one hour. The reaction mixture was diluted with 1,2-dichloroethane and concentrated by evaporation under reduced pressure. The residue was washed successively with hexane and diethyl ether by decantation. To the residue, ethyl acetate and a saturated aqueous solution of sodium bicarbonate were added, followed by stirring. After the organic layer was separated, it was washed successively with water and saturated saline, dried over anhydrous magnesium sulfate and concentrated by evaporation under reduced pressure, whereby 2.01 g of the title target compound were obtained as an amorphous substance.

Infrared absorption spectrum (KBr) vmax cm$^{-1}$: 3319, 1710, 1647, 1608, 1521, 1440, 1346.

Nuclear magnetic resonance spectrum (400 MHz, CDCl$_3$) δ ppm: 1.84–2.36 (7H, m), 2.54–2.77 (1H, m), 3.12–3.59 (6H, m), 3.62–4.15 (4H, m), 4.24–4.50 (3H, m), 5.00–5.38 (4H, m), 5.46–5.60 (1H, m), 7.45–7.52 (4H, m), 8.16–8.23 (4H, m).

Referential Example 19

(2S,4S)-2-[(3S)-3-[4-[2,3-Di(4-nitrobenzyloxycarbonyl)guanidino]-3-hydroxybutanoylamino]pyrrolidin-1-ylcarbonyl]-4-mercapto-1-(4-nitrobenzyloxycarbonyl)pyrrolidine (1) (2S,4S)-2-[(3S)-3-[4-[2,3-Di(4-nitrobenzyloxycarbonyl) guanidino]-2-hydroxybutanoylamino]pyrrolidin-1-ylcarbonyl]-4-(4-methoxybenzyl)thio-1-(4-nitrobenzyloxycarbonyl)pyrrolidine To a solution of (2S,4S)-4-(4-methoxybenzyl)thio-1-(4-nitrobenzyloxycarbonyl)-L-proline (1.62 g) in anhydrous tetrahydrofuran (30 ml), N,N'-carbonyldiimidazole (0.71 g) was added, followed by stirring at room temperature for one hour. To the reaction mixture, N,N-diisopropylethylamine (0.95 ml) and a solution of (3S)-3-[[3-di(4-nitrobenzyloxycarbonyl)guanidino-2-hydroxypropyl]carbonylamino]pyrrolidine trifluoroacetate (1.62 g) in anhydrous tetrahydrofuran (20 ml) were added. The resulting mixture was allowed to stand overnight at room temperature. After concentration of the reaction mixture by evaporation under reduced pressure, ethyl acetate was added to the residue. The resulting mixture was washed successively with water and saturated saline, dried over anhydrous magnesium sulfate and concentrated by evaporation under reduced pressure. The residue was purified by chromatography through a silica gel column (ethyl acetate-methanol), whereby 2.70 g of the title target compound were obtained as an amorphous substance.

Infrared absorption spectrum (KBr) vmax cm$^{-1}$: 3338, 1709, 1645, 1609, 1570, 1522, 1440, 1347.

Nuclear magnetic resonance spectrum (270 MHz, CDCl$_3$) δ ppm: 1.52–2.55 (8H, m), 2.98–3.21 (1H, m), 3.23–4.05 (9H, m), 3.76 (2H, s), 3.80 (3H, s), 4.19–4.62 (2H, m), 4.98–5.36 (6H, m), 6.80–6.97 (2H, m), 7.17–7.38 (2H, m), 7.40–7.59 (6H, m), 8.13–8.28 (6H, m), 8.66–8.78 (1H, m), 11.72 (1H, s).

(2) (2S,4S)-2-[(3S)-3-[4-[2,3-Di(4-nitrobenzyloxycarbonyl) guanidino]-2-hydroxybutanoylamino]pyrrolidin-1-ylcarbonyl]-4-mercapto-1-(4-nitrobenzyloxycarbonyl)pyrrolidine To a mixture of the compound (2.65 g), which had been obtained in (1), and anisole (2.83 ml), trifluoroacetic acid (10 ml) and trifluoromethanesulfonic acid (0.46 ml) were added dropwise under ice cooling, followed by stirring at room temperature for one hour. The reaction mixture was diluted with 1,2-dichloroethane and concentrated by evaporation under reduced pressure. The residue was washed successively with hexane and diethyl ether by decantation. To the residue, ethyl acetate and a saturated aqueous solution of sodium bicarbonate were added, followed by stirring. After the organic layer was separated, it was washed successively with water and saturated saline, dried over anhydrous magnesium sulfate and concentrated by evaporation under reduced pressure, whereby 2.34 g of the title compound were obtained as an amorphous substance.

Infrared absorption spectrum (KBr) vmax cm$^{-1}$: 3337, 1735, 1709, 1645, 1609, 1522, 1440, 1347.

Nuclear magnetic resonance spectrum (400 MHz, CDCl$_3$) δ ppm: 1.63–2.22 (7H, m), 2.32–2.39 (2H, m), 2.63–2.70 (1H, m), 3.19–3.71 (7H, m), 3.73–4.15 (2H, m), 4.38–4.51 (2H, m), 4.98–5.35 (6H, m), 7.43–7.55 (6H, m), 8.17–8.26 (6H, m), 8.70–8.72 (1H, m), 11.73 (1H, s).

Referential Example 20

(2S,4S)-2-[(3S)-3-[(3S,4S)-3-Hydroxy-6-methyl-4-(4-nitrobenzyloxycarbonyl)aminoheptanoylamino]pyrrolidin-1-ylcarbonyl]-4-mercapto-1-(4-nitrobenzyloxycarbonyl)pyrrolidine (1) (2S,4S)-2-[(3S)-3-[(3S,4S)-3-Hydroxy-6-methyl-4-(4-nitrobenzyloxycarbonylaminoheptanoylamino]pyrrolidin-1-ylcarbonyl]-4-(4-methoxybenzyl)thio-1-(4-nitrobenzyloxycarbonyl)pyrrolidine To a solution of (2S,4S)-4-(4-methoxybenzyl)thio-1-(4-nitrobenzyloxycarbonyl)-L-proline (2.82 g) in anhydrous tetrahydrofuran (50 ml), N,N'-carbonyldiimidazole (1.23 g) was added, followed by stirring at room temperature for 30 minutes. To the reaction mixture, a solution of (3S)-3-[3S,4S)-3-hydroxy-6-methyl-4-(4-nitrobenzyloxycarbonyl) aminoheptanoylamino]pyrrolidine (2.67 g) in anhydrous tetrahydrofuran (50 ml) was added. The reaction mixture was treated in a similar manner to that described in Referential Example 18-(1), whereby 3.12 g of the title target compound were obtained as a powder.

Infrared absorption spectrum (KBr) vmax cm$^{-1}$: 3317, 1710, 1645, 1609, 1522, 1440, 1346.

Nuclear magnetic resonance spectrum (270 MHz, CDCl$_3$) δ ppm: 0.81–1.08 (6H, m), 1.18–1.50 (1H, m), 1.51–2.60 (10H, m), 2.98–4.10 (10H, m), 3.78 (2H, s), 3.81 (3H, s), 4.27–4.62 (2H, m), 4.80–5.36 (4H, m), 6.77–7.03 (2H, m), 7.11–7.33 (2H, m), 7.36–7.57 (4H, m), 8.08–8.30 (4H, m).

(2) (2S,4S)-2-[(3S)-3-[(3S,4S)-3-hydroxy-6-methyl-4-(4-nitrobenzyloxycarbonyl)aminoheptanoylamino]pyrolidin-1-ylcarbonyl]-4-mercapto-1-(4-nitrobenzyloxycarbonyl) pyrrolidine To a mixture of the compound (3.10 g), which had been obtained in (1), and anisole (3.90 ml), trifluoroacetic acid (13.90 ml) and trifluoromethanesulfonic acid (0.64 ml) were added dropwise under ice cooling. The reaction mixture was treated in a similar manner to that described in Referential Example 18-(2), whereby 2.66 g of the title compound were obtained as an amorphous substance.

Infrared absorption spectrum (KBr) vmax cm$^{-1}$: 3311, 1710, 1645, 1607, 1522, 1440, 1346.

Nuclear magnetic resonance spectrum (400 MHz, CDCl$_3$) δ ppm: 0.84–0.95 (6H, m), 1.24–1.38 (1H, m), 1.57–1.68 (2H, m), 1.83–2.72 (8H, m), 3.21–3.72 (5H, m), 3.78–4.15 (6H, m), 4.41–4.52 (2H, m), 4.88–5.30 (4H, m), 7.41–7.52 (4H, m), 8.14–8.23 (4H, m).

Referential Example 21

(2S,4S)-2-[(3S)-3-[(3S,4S)-5-Cyclohexyl-3-hydroxy-4-(4-nitrobenzyloxycarbonyl) aminopentanoylamino]pyrrolidin-1-ylcarbonyl]-4-mercapto-1-(4-nitrobenzyloxycarbonyl)pyrrolidine (1) (2S,4S)-2-[(3S)-3-[(3S,4S)-5-Cyclohexyl-3-hydroxy-4-(4-nitrobenzyloxycarbonyl)aminopentanoylamino] pyrrolidin-1-ylcarbonyl]-4-(4-methoxybenzyl)thio-1-(4-nitrobenzyloxycarbonyl)pyrrolidine To a solution of (2S,4S)-4-(4-methoxybenzyl)thio-1-(4-nitrobenzyloxycarbonyl)-L-proline (1.47 g) in anhydrous tetrahydrofuran (30 ml), N,N'-carbonyldiimidazole (0.59 g)

was added, followed by stirring at 30° C. for one hour. To the reaction mixture, a solution of (3S)-3-[(3S,4S)-5-cyclohexyl-3-hydroxy-4-(4-nitrobenzyloxycarbonyl) aminopentanoylamino]pyrrolidine (1.38 g) in anhydrous tetrahydrofuran (30 ml) was added. The reaction mixture was treated in a similar manner to that described in Referential Example 18-(1), whereby 2.43 g of the title target compound were obtained as an amorphous substance.

Infrared absorption spectrum (KBr) vmax cm$^{-1}$: 3310, 1710, 1644, 1609, 1522, 1444, 1346.

Nuclear magnetic resonance spectrum (270 MHz, CDCl$_3$) δ ppm: 0.77–0.99 (2H, m), 1.07–1.43 (6H, m), 1.50–1.90 (7H, m), 2.04–2.50 (6H, m), 3.02–4.02 (8H, m), 3.77 (2H, s), 3.79 (3H, s), 4.32–4.51 (2H, m), 4.85–5.36 (5H, m), 6.85–7.30 (5H, m), 7.40–7.52 (4H, m), 8.13–8.24 (4H, m).

(2) (2S,4S)-2-[(3S)-3-[(3S,4S)-5-Cyclohexyl-3-hydroxy-4-(4-nitrobenzyloxycarbonyl)aminopentanoylamino] pyrrolidin-1-ylcarbonyl]-4-mercapto-1-(4-nitrobenzyloxycarbonyl)pyrrolidine To a mixture of the compound (2.30 g), which had been obtained in (1), and anisole (2.80 ml), trifluoroacetic acid (9.90 ml) and trifluoromethanesulfonic acid (0.47 ml) were added dropwise under ice cooling. The reaction mixture was then treated in a similar manner to that described in Referential Example 18-(2), whereby 2.02 g of the title target compound were obtained as an amorphous substance.

Infrared absorption spectrum (KBr) vmax cm$^{-1}$: 3312, 1710, 1644, 1608, 1522, 1445, 1346.

Nuclear magnetic resonance spectrum (400 MHz, CDCl$_3$) δ ppm: 0.77–1.00 (2H, m), 1.07–1.43 (6H, m), 1.51–1.97 (8H, m), 2.11–2.72 (5H, m), 3.20–4.23 (10H, m), 4.39–4.52 (2H, m), 4.87–5.39 (5H, m), 7.42–7.52 (4H, m), 8.14–8.24 (4H, m).

Referential Example 22

(2S,4S)-2-[(3S)-3-[(3R,4S)-3-Hydroxy-4-(4-nitrobenzyloxycarbonyl)amino-5-phenylpentanoylamino]pyrrolidin-1-ylcarbonyl]-4-mercapto-1-(4-nitrobenzyloxycarbonyl)pyrrolidine (1) (2S,4S)-2-[(3S)-3-[(3R,4S)-3-Hydroxy-4-(4-nitrobenzyloxycarbonyl)amino-5-phenylpentanoylamino] pyrrolidin-1-ylcarbonyl]-4-(4-methoxybenzyl)thio-1-(4-nitrobenzyloxycarbonyl)pyrrolidine To a solution of (2S,4S)-4-(4-methoxybenzyl)thio-1-(4-nitrobenzyloxycarbonyl)-L-proline (2.23 g) in anhydrous tetrahydrofuran (50 ml), N,N'-carbonyldiimidazole (0.97 g) was added, followed by stirring at 30° C. for 30 minutes. To the reaction mixture, a solution of (3S)-3-[(3R,4S)-3-hydroxy-4-(4-nitrobenzyloxycarbonyl)amino-5-phenylpentanoylamino]pyrrolidine (2.28 g) in anhydrous tetrahydrofuran (50 ml) was added. The resulting mixture was treated in a similar manner to that described in Referential Example 18-(1), whereby 2.14 g of the title compound were obtained as a powder.

Infrared absorption spectrum (KBr) vmax cm$^{-1}$: 3314, 1700, 1645, 1609, 1522, 1441, 1346.

Nuclear magnetic resonance spectrum (270 MHz, CDCl$_3$) δ ppm: 1.55–2.58 (7H, m), 2.79–3.57 (7H, m), 3.60–4.10 (4H, m), 3.75 (2H, s), 3.79 (3H, s), 4.22–4.63 (3H, m), 4.88–5.37 (5H, m), 6.80–6.95 (2H, m), 7.08–7.65 (11H, m), 8.10–8.36 (4H, m).

(2) (2S,4S)-2-[(3S)-3-[(3R,4S)-3-Hydroxy-4-(4-nitrobenzyloxycarbonyl)amino-5-phenylpentanoylamino] pyrrolidin-1-ylcarbonyl]-4-mercapto-1-(4-nitrobenzyloxycarbonyl)pyrrolidine To a mixture of the compound (2.10 g), which had been obtained in (1), and anisole (2.57 ml), trifluoroacetic acid (9.10 ml) and trifluoromethanesulfonic acid (0.42 ml) were added dropwise under ice cooling. The reaction mixture was then treated in a similar manner to that described in Referential Example 18-(2), whereby 1.95 g of the title target compound were obtained as a powder.

Infrared absorption spectrum (KBr) vmax cm$^{-1}$: 3312, 1699, 1655, 1644, 1607, 1522, 1441, 1346.

Nuclear magnetic resonance spectrum (400 MHz, DMSO-d$_6$) δ ppm: 1.62–1.86 (2H, m), 1.90–2.38 (3H, m), 2.45–2.86 (2H, m), 2.98–3.98 (14H, m), 4.16–4.60 (2H, m), 4.87–5.25 (4H, m), 7.09–7.65 (9H, m), 8.07–8.25 (4H, m).

Referential Example 23

(2S,4S)-4-Mercapto-1-(4-nitrobenzyloxycarbonyl)-2-[(3S)-3-[[4-di(4-nitrobenzyloxycarbonyl) guanidinomethylcyclohexyl]carbonylamino] pyrrolidin-1-ylcarbonyl]pyrrolidine (1) (2S,4S)-4-(4-Methoxybenzyl)thio-1-(4-nitrobenzyloxycarbonyl)-2-[(3S)-3-[[4-di(4-nitrobenzyloxycarbonyl)guanidinomethylcyclohexyl] carbonylamino]pyrrolidine-1-ylcarbonyl]pyrrolidine To a solution of (2S,4S)-4-(4-methoxybenzyl)thio-1-(4-nitrobenzyloxycarbonyl)-L-proline (0.98 g) in anhydrous acetonitrile (10 ml), N,N'-carbonyldiimidazole (0.39 g) was added, followed by stirring at room temperature for 30 minutes. To the reaction mixture, N,N-diisopropylethylamine (0.96 ml) and a solution of (3S)-3-[[4-di(4-nitrobenzyloxycarbonyl) guanidinomethylcyclohexyl]carbonylamino]pyrrolidine 2-trifluoroacetate (1.90 g) in anhydrous acetonitrile (15 ml) were added. The resulting mixture was treated in a similar manner to that described in Referential Example 18-(1), whereby 2.10 g of the title target compound were obtained as an amorphous substance.

Infrared absorption spectrum (KBr) vmax cm$^{-1}$: 3389, 2933, 1717, 1656, 1608, 1522, 1440, 1346.

Nuclear magnetic resonance spectrum (270 MHz, CDCl$_3$) δ ppm: 0.70–1.06 (2H, m), 1.08–2.25 (12H, m), 2.36–2.57 (1H, m), 3.82–4.07 (9H, m), 3.77 (2H, s), 3.80 (3H, s), 4.30–4.58 (2H, m), 4.88–5.43 (6H, m), 6.81–6.95 (2H, m), 7.20–7.32 (2H, m), 7.38–7.66 (6H, m), 8.12–8.39 (6H, m), 9.22–9.60 (2H, m).

(2) (2S,4S)-4-Mercapto-1-(4-nitrobenzyloxycarbonyl)-2-[(3S)-3-[[4-di(4-nitrobenzyloxycarbonyl) guanidinomethylcyclohexyl]carbonylamino]pyrrolidin-1-ylcarbonyl]pyrrolidine To a mixture of the compound (2.09 g), which had been obtained in (1), and anisole (2.07 ml), trifluoroacetic acid (7.34 ml) and trifluoromethanesulfonic acid (0.34 ml) were added dropwise under ice cooling. The reaction mixture was then treated in a similar manner to that described in Referential Example 18-(2), whereby 1.78 g of the title compound were obtained as an amorphous substance.

Infrared absorption spectrum (KBr) vmax cm$^{-1}$: 3392, 2933, 1717, 1647, 1608, 1522, 1441, 1346.

Nuclear magnetic resonance spectrum (400 MHz, CDCl$_3$) δ ppm: 0.87–0.99 (2H, m), 1.34–1.44 (2H, m), 1.62–2.23 (9H, m), 2.63–2.73 (1H, m), 3.15–3.64 (4H, m), 3.68–4.20 (7H, m), 4.41–4.55 (2H, m), 4.95–5.51 (6H, m), 7.43–7.57 (6H, m), 8.15–8.29 (6H, m), 9.29–9.50 (2H, m).

Referential Example 24

(2S,4S)-4-Mercapto-1-(4-nitrobenzyloxycarbonyl)-2-[(3S)-3-[[4-di(4-nitrobenzyloxycarbonyl) guanidinobenzoyl]amino]pyrrolidin-1-ylcarbonyl] pyrrolidine (1) (2S,4S)-4-(4-Methoxybenzyl)thio-1-(4-nitrobenzyloxycarbonyl)-2-[(3S)-3-[[4-di(4- nitrobenzyloxycarbonyl)guanidinobenzoyl]amino] pyrrolidin-1-yl-carbonyl]pyrrolidine To a solution of (2S,4S)-4-(4-methoxybenzyl)thio-1-(4-nitrobenzyloxycarbonyl)-L-proline (0.62 g), 4-dimethylaminopyridine (0.42 g) and (3S)-3-[[4-di(4-nitrobenzyloxycarbonyl)guanidinobenzoyl]amino] pyrrolidine hydrochloride (0.75 g) in anhydrous N,N-dimethylformamide (35 ml), 1-ethyl-3-(3-dimethylaminopropyl)carbodiimide hydrochloride (0.32 g) and 1-hydroxybenzotriazole (0.22 g) were added and the resulting mixture was allowed to stand overnight at 0° C. To the reaction mixture, ethyl acetate was added. The resulting mixture was washed successively with water and saturated saline, dried over anhydrous magnesium sulfate and then concentrated by evaporation under reduced pressure. The residue was purified by chromatography through a silica gel column (ethyl acetate-methanol), whereby 0.77 g of the title compound was obtained as an amorphous substance.

Infared absorption spectrum (KBr) νmax cm$^{-1}$: 3396, 1729, 1713, 1655, 1609, 1522, 1439, 1346.

Nuclear magnetic resonance spectrum (270 MHz, CDCl$_3$) δ ppm: 1.53–2.62 (7H, m), 3.00–4.25 (11H, m), 4.36–4.52 (1H, m), 4.62–5.43 (6H, m), 6.75–7.00 (2H, m), 7.08–7.60 (10H, m), 7.62–8.36 (8H, m), 9.12–9.70 (2H, m).

(2) (2S,4S)-4-Mercapto-1-(4-nitrobenzyloxycarbonyl)-2-[(3S)-3-[[4-di(4-nitrobenzyloxycarbonyl)guanidinobenzoyl]amino]pyrrolidin-1-yl-carbonyl]-pyrrolidine To a mixture of the compound (1.05 g), which had been obtained in (1), and anisole (1.11 ml), trifluoroacetic acid (3.90 ml) and trfluoromethanesulfonic acid (0.18 ml) were added dropwise under ice cooling. The reaction mixture was then treated in a similar manner to that described in Referential Example 18-(2), whereby 0.91 g of the title compound was obtained as a yellow powder.

Infrared absorption spectrum (KBr) νmax cm$^{-1}$: 3330, 1762, 1703, 1667, 1609, 1586, 1524.

Nuclear magnetic resonance spectrum (400 MHz, CDCl$_3$) δ ppm: 1.89–2.81 (4H, m), 3.27–4.11 (7H, m), 4.40–4.70 (2H, m), 5.05–5.40 (6H, m), 7.27–7.66 (10H, m), 7.92–8.29 (8H, m), 9.65–10.00 (2H, m).

Referential Example 25

(2S,4S)-2-[(3S)-3-[(2S)-2-[2,3-Di(4-nitrobenzyloxycarbonyl)guanidino]-2-methyl-acetylamino]pyrrolidin-1-ylcarbonyl]-4-mercapto-1-(4-nitrobenzyloxycarbonyl)-pyrrolidine (1) (3S)-3-[(2S)-2-[2,3-Di(4-nitrobenzyloxycarbonyl)guanidino]-2-methylacetylamino]-1-pyrrolidinecarboxylate To a solution of tert-butyl (3S)-3-[(2S)-2-amino-2-methylacetylamino]-1-pyrrolidinecarboxylate (713 mg) in anhydrous tetrahydrofuran (15 ml), a solution of 4-nitrobenzyl [(4-nitrobenzyloxy)carbonylimino-pyrazol-1-ylmethyl]carbamate (1.18 g) in tetrahydrofuran (15 ml) was added. The resulting mixture was then treated in a similar manner to that described in Referential Example 16-(1), whereby 1.62 g of the title compound were obtained as an amorphous substance.

Nuclear magnetic resonance spectrum (270 MHz, CDCl$_3$) δ ppm: 1.38–1.50 (12H, m), 1.60–1.87 (1H, m), 2.02–2.20 (1H, m), 3.12–3.30 (1H, b), 3.30–3.50 (2H, b), 3.53–3.65 (1H, m), 4.33–4.46 (1H, m), 4.48–4.63 (1H, m), 5.21 (2H, s), 5.30 (2H, s), 6.50–6.75 (1H, b), 7.48–7.61 (4H, m), 8.18–8.29 (4H, m), 8.73 (1H, d, J=6.6 Hz), 11.67 (1H, s).

(2) (3S)-3-[(2S)-2-[2,3-Di(4-nitrobenzyloxycarbonyl)guanidino]-2-methylacetylamino]pyrrolidine trifluoroacetate To a solution of the compound (1.59 g), which had been obtained in (1), in anhydrous dichloromethane (6 ml), trifluoroacetic acid (3 ml) was added dropwise under ice cooling. The reaction mixture was then treated in a similar manner to that described in Referential Example 16-(2), whereby the title compound was obtained. The product was provided for use in the subsequent reaction without isolation.

Infrared absorption spectrum (KBr) νmax cm$^{-1}$: 1750, 1673, 1623, 1611, 1557, 1525, 1433, 1416, 1381.

Nuclear magnetic resonance spectrum (270 MHz, CDCl$_3$) δ ppm: 1.47 (3H, d, J=6.9 Hz), 2.03–2.43 (2H, m), 3.18–3.60 (4H, m), 4.52–4.72 (2H, nm), 5.25 (2H, s), 5.33 (2H, s), 7.53 (2H, d, J=7.3 Hz), 7.56 (2H, d, J=7.3 Hz), 8.16–8.34 (5H, m), 8.93–9.10 (1H, b), 9.40–9.58 (1H, b).

(3) (2S,4S)-2-[(3S)-3-[(2S)-2-[2,3-Di(4-nitrobenzyloxycarbonyl)guanidino]-2-methylacetylamino] pyrrolidin-1-yl-carbonyl]-4-(4-methoxybenzyl)thio-1-(4-nitrobenzyloxycarbonyl)pyrrolidine To a solution of (2S,4S)-4-(4-methoxybenzyl)thio-1-(4-nitrobenzyloxycarbonyl)-L-proline (1.13 g) in anhydrous acetonitrile (10 ml), N,N'-carbonyldiimidazole (430 mg) was added, followed by stirring at room temperature for one hour. To the reaction mixture, N,N-diisopropylethylamine (0.42 ml) and the compound (2.26 g), which had been obtained in (2), in anhydrous tetraydrofuran (15 ml) were added. The reaction mixture was then treated in a similar manner to that described in Referential Example 16-(3), whereby the title compound (2.06 g) was obtained as an amorphous substance.

Infrared absorption spectrum (KBr) νmax cm$^{-1}$: 3324, 1737, 1709, 1645, 1623, 1610, 1547, 1522, 1436.

Nuclear magnetic resonance spectrum (400 MHz, CDCl$_3$) δ ppm: 1.36 (3H, d, J=7.0 Hz), 1.65–2.18 (2H, m), 2.32–2.50 (1H, m), 3.00–3.21 (1H, m), 3.26–3.55 (3H, m), 3.65–4.04 (3H, m), 4.04–4.25 (3H, m), 4.98–5.34 (8H, m), 6.82–6.90 (2H, m), 7.00–7.10 (1H, m), 7.17–7.30 (2H, m), 7.37–7.58 (6H, m), 8.08–8.28 (6H, m), 9.00 (1H, d, J=6.8 Hz), 11.64 (1H, s).

(4) (2S,4S)-2-[(3S)-3-[(2S)-2-[2,3-Di(4-nitrobenzyloxycarbonyl)guanidino]-2-methylacetylamino] pyrrolidin-1-yl-carbonyl]-4-mercapto-1-(4-nitrobezyloxycarbonyl)pyrrolidine To a mixture of the compound (2.01 g), which had been obtained in (3) and anisole (2.21 ml), trifluoroacetic acid (7.85 ml) and trifluoromethanesulfonic acid (358 μl) were added dropwise under ice cooling. The reaction mixture was then treated in a similar manner to that described in Referential Example 16-(4), whereby 1.71 g of the title compound were obtained as an amorphous substance.

Infrared absorption spectrum (KBr) νmax cm$^{-1}$: 3320, 1737, 1710, 1644, 1624, 1609, 1547, 1522.

Nuclear magnetic resonance spectrum (400 MHz, CDCl$_3$) δ ppm: 1.37 (3H, d, J=6.8 Hz), 1.65–1.98 (2H, m), 2.00–2.20 (2H, m), 2.56–2.75 (2H, m), 3.17–3.59 (4H, m), 3.65–4.20 (3H, m), 4.35–4.65 (3H, m), 5.00–5.37 (6H, m), 7.00–7.13 (1H, m), 7.37–7.60 (6H, m), 8.10–8.30 (6H, m), 8.99 (1H, d, J=6.7 Hz), 11.64 (1H, s).

Referential Example 26

(2S,4S)-2-[3-[(2S)-2-[2,3-Di(4-nitrobenzyloxycarbonyl)guanidino]-2-methylacetylamino]azetidin-1-ylcarbonyl]-4-mercapto-1-(4-nitrobenzyloxycarbonyl)pyrrolidine (1) tert-Butyl 3-[(2S)-2-[2,3-Di(4-nitrobenzyloxycarbonyl)guanidino]-2-methylacetylamino]-1-azetidinecarboxylate To a solution of tert-butyl 3-[(2S)-2-amino-2-methylacetylamino]-1-azetidinecarboxylate (557 mg) in anhydrous tetrahydrofuran (10 ml), a solution of 4-nitrobenzyl [(4-nitrobenzyloxy)carbonylimino-pyrazol-1-ylmethyl]carbamate (974 mg) in tetrahydrofuran (20 ml) was added. The reaction mixture was then treated in a similar manner to that described in Referential Example 16-(1), whereby 1.32 g of the title compound were obtained as an amorphous substance.

Nuclear magnetic resonance spectrum (270 MHz, $CDCl_3$) δ ppm: 1.43 (9H, s), 1.45 (3H, d, J=7.0 Hz), 3.65–3.78 (2H, m), 4.12–4.30 (2H, m), 4.50–4.66 (2H, m), 5.19, 5.24 (each 1H, d, J=13.5 Hz), 5.29 (2H, s), 7.10 (1H, d, J=7.1 Hz), 7.54 (4H, d, J=8.4 Hz), 8.19–8.28 (4H, m), 8.69 (1H, d, J=6.6 Hz), 11.64 (1H, s).

(2) 3-[(2S)-2-[2,3-di(4-nitrobenzyloxycarbonyl)guanidino]-2-methylacetylamino]azetidine trifluoroacetate To a solution of the compound (1.27 g), which had been obtained in (1), in anhydrous dichloromethane (6 ml), trifluoroacetic acid (3 ml) was added dropwise under ice cooling. The reaction mixture was then treated in a similar manner to that described in Referential Example 16-(2), whereby the title compound was obtained. The product was provided for use in the subsequent reaction without isolation.

Infrared absorption spectrum (KBr) vmax $cm^{-1}$: 3212, 1752, 1674, 1622, 1611, 1559, 1525, 1434.

Nuclear magnetic resonance spectrum (270 MHz, DMSO-$d_6$) δ ppm: 1.34 (3H, d, J=6.9 Hz), 3.84–4.22 (4H, m), 4.48–4.68 (2H, m), 5.18, 5.24 (each 1H, d, J=13.9 Hz), 5.38 (2H, s), 7.62 (2H, d, J=8.7 Hz), 7.70 (2H, d, J=8.7 Hz), 8.24 (2H, d, J=5.5 Hz), 8.27 (2H, d, J=5.5 Hz), 8.65–8.87 (2H, b), 8.93 (1H, d, J=6.7 Hz).

(3) (2S,4S)-2-[3-(2S)-2-[2,3-Di(4-nitrobenzyloxycarbonyl) guanidino]-2-methylacetylamino]azetidin-1-ylcarbonyl]-4-(4-methoxybenzyl)thio-1-(4-nitrobenzyloxycarbonyl) pyrrolidine To a solution of (2S,4S)-4-(4-methoxybenzyl)thio-1-(4-nitrobenzyloxycarbonyl)-L-proline (924 mg) in anhydrous acetonitrile (15 ml), N,N'-carbonyldiimidazole (352 mg) was added and the mixture was stirred at room temperature for one hour. To the reaction mixture, N,N-diisopropylethylamine (343 μl) and a solution of the compound (1.76 g), which had been obtained in (2), in anhydrous tetrahydrofuran (15 ml) were added. The resulting mixture was treated in a similar maimer to that described in Referential Example 16-(3), whereby the title compound (1.64 g) was obtained as an amorphous substance.

Infrared absorption spectrum (KBr) vmax $cm^{-1}$: 3319, 1737, 1708, 1644, 1623, 1610, 1522, 1434.

Nuclear magnetic resonance spectrum (400 MHz, $CDCl_3$) δ ppm: 1.44 (3H, d, J=6.9 Hz), 1.85–2.03 (1H, m), 2.30–2.50 (1H, m), 3.00–3.15 (1H, m), 3.23–3.37 (1H, m), 3.66–4.75 (13H, m), 4.98–5.36 (6H, m), 6.85 (2H, d, J=8.6 Hz), 7.28–7.58 (9H, m), 8.63–8.80 (6H, m), 8.77 (1H, d, J=6.7 Hz), 11.66 (1H, s).

(4) (2S,4S)-2-[3-[(2S)-2-[2,3-Di(4-nitrobenzyloxycabonyl) guanidino]-2-methylacetylamino]azetidin-1-ylcarbonyl]-4-mercapto-1-(4-nitrobenzyloxycarbonyl)pyrrolidine To a mixture of the compound (1.62 g), which had been obtained in (3), and anisole (1.81 ml), trifluoroacetic acid (6.42 ml) and trifluoromethanesulfonic acid (292 μl) were added dropwise under ice cooling. The reaction mixture was then treated in a similar manner to that described in Referential Example 16-(4), whereby 1.35 g of the title compound were obtained as an amorphous substance.

Infrared absorption spectrum (KBr) vmax $cm^{-1}$: 3321, 1737, 1708, 1645, 1623, 1548, 1522.

Nuclear magnetic resonance spectrum (400 MHz, $CDCl_3$) δ ppm: 1.45 (3H, d, J=7.0 Hz), 1.88–2.10 (2H, m), 2.46–2.73 (1H, m), 3.18–3.50 (2H, m), 3.75–4.81 (8H, m), 5.02–5.40 (6H, m), 7.39 (1H, d, J=7.6 Hz), 7.43–7.60 (6H, m), 8.10–8.30 (6H, m), 8.77 (1H, d, J=6.8 Hz), 11.66 (1H, s).

Referential Example 27

(2S,4S)-2-[(3S)-3-[(2R)-2-[2,3-Di(4-nitrobenzyloxycarbonyl)guanidino]-2-methylacetylamino]pyrrolidin-1-ylcarbonyl]-4-mercapto-1-(4-nitrobenzyloxycarbonyl)-pyrrolidine (1) tert-Butyl (3S)-3-[(2R)-2-[2,3-di(4-nitrobenzyloxycarbonyl)guanidino]-2-methylacetylamino]-1-pyrrolidinecarboxylate To a solution of tert-butyl (3S)-3-[(2R)-2-amino-2-methylacetylamino]-1-pyrrolidinecarboxylate (448 mg) in anhydrous tetrahydrofuran (20 ml), 4-nitrobenzyl [(4-nitrobenzyloxy)carbonylimino-pyrazol-1-ylmethyl] carbamate (776 mg) was added under ice cooling. The resulting mixture was treated in a similar manner to that described in Referential Example 16-(1), whereby the title compound (1.096 g) was obtained as an amorphous substance.

Infrared absorption spectrum (KBr) vmax $cm^{-1}$: 3316, 1739, 1693, 1645, 1623, 1548, 1524.

Nuclear magnetic resonance spectrum (270 MHz, $CDCl_3$) δ ppm: 1.45 (12H, s), 1.73–1.88 (1H, m), 2.07–2.21 (1H, m), 3.05–3.25 (1H, b), 3.32–3.50 (2H, b), 3.55–3.66 (1H, m), 4.36–4.47 (1H, m), 4.52–4.64 (1H, m), 6.70 (1H, d, J=7.2 Hz), 7.55 (4H, d, J=8.8 Hz), 8.22 (2H, d, J=7.3 Hz), 8.25 (2H, d, J=7.3 Hz), 8.72 (1H, d, J=5.6 Hz), 11.65 (1H, s).

(2) (3S)-3-[(2R)-2-[2,3-Di(4-nitrobenzyloxycarbonyl) guanidino]-2-methylacetylamino]pyrrolidine trifluoroacetate To a solution of the compound (1.087 g), which had been obtained in (1), in anhydrous dichloromethane (5 ml), trifluoroacetic acid (2 ml) was added dropwise under ice cooling. The resulting mixture was treated in a similar manner to that described in Referential Example 16-(2), whereby the title compound was obtained. The product was provided for use in the subsequent reaction without isolation, Infrared absorption spectrum (KBr) vmax $cm^{-1}$: 3290, 1739, 1674, 1645, 1625, 1555, 1524.

Nuclear magnetic resonance spectrum (270 MHz, $CDCl_3+D_2O$) δ ppm: 1.44 (3H, d, J=6.8 Hz), 1.88–2.39 (2H, m), 3.20–3.55 (4H, m), 4.47–4.68 (2H, m), 5.13–5.33 (4H, m), 7.25 (2H, d, J=5.2 Hz), 7.55 (2H, d, J=5.2 Hz), 8.18 (2H, d, J=8.8 Hz), 8.23 (2H, d, J=8.8 Hz).

(3) (2S,4S)-2-[(3S)-3-[(2R)-2-[2,3-Di(4-nitrobenzyloxycarbonyl)guanidino]-2-methylacetylamino] pyrrolidin-1-ylcarbonyl]-4-(4-methoxybenzyl)thio-1-(4-nitrobenzyloxycarbonyl)pyrrolidine To a solution of (2S,4S)-4-(4-methoxybenzyl)thio-1-(4-nitrobenzyloxycarbonyl)-L-proline (737 mg) in anhydrous acetonitrile (20 ml), N,N'-carbonyldiimidazole (281 mg) was added, followed by stirring at room temperature for one hour. To the reaction mixture, N,N-diisopropylethylamine (0.75 ml) and a solution of the compound (1.157 g), which had been obtained in (2), in anhydrous tetrahydrofuran (10 ml) were added. The resulting mixture was treated in a similar manner to that described in Referential Example 16-(3), whereby the title compound (1.394 g) was obtained as an amorphous substance.

Infrared absorption spectrum (KBr) vmax $cm^{-1}$: 3326, 1737, 1709, 1645, 1623, 1610, 1522.

Nuclear magnetic resonance spectrum (270 MHz, $CDCl_3$) δ ppm: 1.40 (3H, d, J=6.9 Hz), 1.93–2.20 (2H, m), 2.30–2.46 (1H, m), 2.94–3.55 (5H, m), 3.60–3.90 (8H, m), 4.20–4.60 (3H, m), 4.92–5.33 (6H, m), 6.77–6.90 (2H, m), 7.15–7.60 (8H, m), 8.07–8.28 (6H, m).

(4) (2S,4S)-4-Mercapto-1-(4-nitrobenzyloxycarbonyl)-2-[(3S)-3-[(2R)-2-[2,3-di(4-nitrobenzyloxycarbonyl)guanidino]-2-methylacetylamino]pyrrolidin-1-ylcarbonyl]pyrrolidine To a mixture of the compound (1.381 g), which had been obtained in (3), and anisole (1.5 ml), trifluoroacetic acid (4.9 ml) and trifluoromethanesulfonic acid (0.27 ml) were added dropwise under ice cooling. The reaction mixture was then treated in a similar manner to that described in Referential Example 16-(4), whereby the title compound (1.216 g) were obtained as an amorphous substance.

Infrared absorption spectrum (KBr) vmax cm$^{-1}$: 3321, 1736, 1710, 1645, 1624, 1609, 1547, 1522.

Nuclear magnetic resonance spectrum (270 MHz, CDCl$_3$) δ ppm: 1.36–1.48 (3H, m), 1.83–2.27 (2H, m), 2.57–2.72 (1H, m), 3.10–3.57 (5H, m), 3.77–3.96 (2H, m), 4.00–4.17 (1H, m), 4.30–4.62 (3H, m), 4.98–5.33 (6H, m), 7.38–7.60 (6H, m), 8.10–8.28 (6H, m).

Referential Example 28

(2S,4S)-2-[3-[(2R)-2-[2,3-Di(4-nitrobenzyloxycarbonyl)guanidino]-2-methylacetylamino]azetidin-1-ylcarbonyl]-4-mercapto-1-(4-nitrobenzyloxycarbonyl)pyrrolidine (1) tert-Butyl 3-[(2R)-2-[2,3-di(4-nitrobenzyloxycarbonyl)guanidino]-2-methylacetylamino]-1-azetidinecarboxylate To a solution of tert-butyl 3-[(2R)-2-amino-2-methylacetylamino]-1-azetidinecarboxylate (443 mg) in anhydrous tetrahydrofuran (20 ml), 4-nitrobenzyl [(4-nitrobenzyloxy)carbonylimino-pyrazol-1-ylmethyl]carbamate (820 mg) was added under ice cooling. The resulting mixture was then treated in a similar manner to that described in Referential Example 16-(1), whereby the title compound (0.860 g) was obtained as an amorphous substance.

Nuclear magnetic resonance spectrum (270 MHz, CDCl$_3$) δ ppm: 1.30–1.50 (12H, m), 3.67–3.78 (2H, m), 4.18–4.30 (2H, m), 4.50–4.67 (2H, m), 5.19, 5.25 (each 1H, d, J=13.5 Hz), 5.29 (2H, s), 7.08 (1H, d, J=7.3 Hz), 7.54 (4H, d, J=8.6 Hz), 8.23 (2H, d, J=5.4 Hz), 8.26 (2H, d, J=5.4 Hz), 8.69 (1H, d, J=7.1 Hz), 11.64 (1H, s).

(2) 3-[(2S)-2-[2,3-Di(4-nitrobenzyloxycarbonyl)guanidino]-2-methylacetylamino]azetidine trifluoroacetate To a solution of the compound (846 mg), which had been obtained in (1), in anhydrous dichloromethane (10 ml), trifluoroacetic acid (3 ml) was added dropwise under ice cooling. The reaction mixture was then treated in a similar manner to that described in Referential Example 16-(2), whereby the title compound was obtained. The product was provided for use in the subsequent reaction without isolation. Infrared absorption spectrum (Liquid film) vmax cm$^{-1}$: 3213, 1758, 1677, 1610, 1600, 1560, 1526.

Nuclear magnetic resonance spectrum (270 MHz, DMSO-d$_6$) δ ppm: 1.33 (3H, d, J=6.9 Hz), 3.70–4.80 (6H, m), 5.20 (2H, s), 5.38 (2H, s), 7.62 (2H, d, J=8.7 Hz), 7.70 (2H, d, J=8.7 Hz), 8.20–8.31 (4H, m), 8.60–8.85 (2H, b), 8.92 (1H, d, J=6.6 Hz).

(3) (2S,4S)-2-[3-[(2S)-2-[2,3-Di(4-nitrobenzyloxycarbonyl)guanidino]-2-methylacetylamino]azetidin-1-ylcarbonyl]-4-(4-methoxybenzyl)thio-1-(4-nitrobenzyloxycarbonyl)pyrrolidine To a solution of (2S,4S)-4-(4-methoxybenzyl)thio-1-(4-nitrobenzyloxycarbonyl)-L-proline (585 mg) in anhydrous acetonitrile (10 ml), N,N'-carbonyldiimidazole (223 mg) was added, followed by stirring at room temperature for one hour. To the reaction mixture, N,N-diisopropylethylamine (0.57 ml) and a solution of the compound (1.26 g), which had been obtained in (2), in anhydrous tetrahydrofuran (10 ml) were added. The resulting mixture was treated in a similar manner to that described in Referential Example 16-(3), whereby the title compound (1.047 g) was obtained as an amorphous substance.

Infrared absorption spectrum (KBr) vmax cm$^{-1}$: 3322, 1736, 1708, 1645, 1623, 1610, 1522, 1436, 1406.

Nuclear magnetic resonance spectrum (270 MHz, CDCl$_3$) δ ppm: 1.44 (3H, d, J=6.9 Hz), 1.90–2.10 (1H, m), 2.26–2.42 (1H, m), 2.95–3.17 (1H, m), 3.22–3.40 (1H, m), 3.63–4.80 (1H, m), 4.95–5.38 (8H, m), 6.86 (2H, d, J=8.7 Hz), 7.15–7.63 (8H, m), 7.55 (1H, d, J=7.8 Hz), 8.10–8.35 (6H, m), 8.72 (1H, d, J=6.8 Hz), 11.65 (1H, s).

(4) (2S,4S)-2-[3-[(2S)-2-[2,3-Di(4-nitrobenzyloxycarbonyl)guanidino]-2-methylacetylamino]azetidin-1-ylcarbonyl]-4-mercapto-1-(4-nitrobenzyloxycarbonyl)pyrrolidine To a mixture of the compound (1.032 g), which had been obtained in (3), and anisole (1.2 ml), trifluoroacetic acid (3.7 ml) and trifluoromethanesulfonic acid (0.2 ml) were added dropwise under ice cooling. The reaction mixture was then treated in a similar manner to that described in Referential Example 16-(4), whereby the title compound (902 mg) was obtained as an amorphous substance.

Infared absorption spectrum (KBr) vmax cm$^{-1}$: 3323, 1736, 1709, 1645, 1623, 1522, 1496, 1434.

Nuclear magnetic resonance spectrum (270 MHz, CDCl$_3$) δ ppm: 1.45 (3H, d, J=7.1 Hz), 1.88–2.17 (1H, m), 2.46–2.68 (1H, m), 3.10–3.60 (2H, m), 3.70–4.85 (8H, m), 5.00–5.47 (6H, m), 7.34–7.63 (6H, m), 7.76 (1H, d, J=8.8 Hz), 8.10–8.40 (6H, m), 8.72 (1H, d, J=6.4 Hz), 11.65 (1H, s).

Referential Example 29

(2S,4S)-2-[(3S)-3-[2-[1-Methyl-2,3-di(4-nitrobenzyloxycarbonyl)guanidino]acetylamino]pyrrolidin-1-ylcarbonyl]-4-mercapto-1-(4-nitrobenzyloxycarbonyl)pyrrolidine (1) tert-Butyl (3S)-3-[2-[1-methyl-2,3-di(4-nitrobenzyloxycarbonyl)guanidino]-acetylamino]-1-pyrrolidinecarboxylate To a solution of tert-butyl (3S)-3-[2-methylaminoacetylamino-1-pyrrolidinecarboxylate (669 mg) in anhydrous tetrahydrofuran (15 ml), 4-nitrobenzyl [(4-nitrobenzyloxy)carbonylimio-imidazol-1-ylmethyl)carbamate (1.11 g) was added under ice cooling. The resulting mixture was treated in a similar manner to that described in Referential Example 16-(1), whereby the title target compound (1.50 g) was obtained as an amorphous substance.

Infrared absorption spectrum (KBr) vmax cm$^{-1}$: 3305, 1759, 1691, 1609, 1523, 1453, 1406, 1367.

Nuclear magnetic resonance spectrum (270 MHz, CDCl$_3$) δ ppm: 1.45 (9H, s), 1.70–1.88 (1H, m), 2.02–2.33 (1H, m), 3.09 (3H, s), 3.15–3.28 (1H, m), 3.32–3.50 (2H, m), 3.53–3.70 (1H, m), 4.28 (2H, s), 4.37–4.50 (1H, m), 5.27 (4H, s), 7.30–7.47 (1H, b), 7.56 (4H, d, J=8.6 Hz), 8.24 (4H, d, J=8.6 Hz).

(2) (3S)-3-[2-[1-Methyl-2,3-di(4-nitrobenzyloxycarbonyl)guanidino]acetylamino]pyrrolidine trifluoroacetate To a solution of the compound (1.48 g), which had been obtained in (1), in anhydrous dichloromethane (8 ml), trifluoroacetic acid (4 ml) was added dropwise under ice cooling. The reaction mixture was then treated in a similar manner to that described in Referential Example 16-(2), whereby the title compound was obtained. The product was provided for use in the subsequent reaction without isolation.

Infrared absorption spectrum (KBr) vmax cm⁻¹: 3212, 1777, 1672, 1609, 1524, 1454, 1436.

Nuclear magnetic resonance spectrum (270 MHz, DMSO-d₆) δ ppm: 1.77–1.95 (1H, m), 2.05–2.23 (1H, m), 2.93–3.50 (7H, m), 4.05, 4.12 (each 1H, d, J=16.5 Hz), 4.23–4.40 (1H, m), 5.16 (4H, s), 7.59 (4H, d, J=9.2 Hz), 8.17 (4H, d, J=9.2 Hz), 8.38 (1H, d, J=6.6 Hz), 8.70–9.00 (2H, b).

(3) (2S,4S)-4-(4-methoxybenzyl)thio-2-[(3S)-3-[2-[1-methyl-2,3-di(4-nitrobenzyloxycarbonyl)guanidino]acetylamino]pyrrolidin-1-ylcarbonyl]-1-(4-nitrobenzyloxycarbonyl)pyrrolidine To a solution of (2S,4S)-4-(4-methoxybenzyl)thio-1-(4-nitrobenzyloxycarbonyl)-L-proline (1.05 g) in anhydrous acetonitrile (10 ml), N,N'-carbonyldiimidazole (401 mg) was added, followed by stirring at room temperature. To the reaction mixture, N,N-diisopropylethylamine (392 μl) and a solution of the compound (2.02 g), which had been obtained in (2), in anhydrous tetrahydrofuran (15 ml) were added. The resulting mixture was treated in a similar manner to that described in Referential Example 16-(3), whereby the title compound (1.69 g) was obtained as an amorphous substance.

Inked absorption spectrum (KBr) vmax cm⁻¹: 3393, 3339, 1756, 1705, 1687, 1656, 1609, 1521, 1441.

Nuclear magnetic resonance spectrum (400 MHz, CDCl₃) δ ppm: 1.60–2.00 (2H, m), 2.03–2.25 (1H, m), 2.40–2.52 (1H, m), 2.97–4.08 (15H, m), 4.23–4.57 (4H, m), 4.90–5.38 (6H, m), 6.80–6.92 (2H, m), 7.10–7.70 (9H, m), 8.08–8.31 (6H, m), 10.85 (1H, b).

(4) (2S,4S)-4-Mercapto-2-[(3S)-3-[2-[1-methyl-2,3-di(4-nitrobenzyloxycarbonyl)guanidino]acetylamino]pyrrolidin-1-ylcarbonyl]-1-(4-nitrobenzylcarbonyl)pyrrolidine To a mixture of the compound (1.66 g), which had been obtained in (3) and anisole (1.83 ml), trifluoroacetic acid (6.49 ml) and trfluoromethanesulfonic acid (296 μl) were added dropwise under ice cooling. The reaction mixture was treated in a similar manner to that described in Referential Example 16-(4), whereby the title compound (1.34 g) were obtained as an amorphous substance.

Infrared absorption spectrum (YBr) vmax cm⁻¹: 3327, 1756, 1705, 1687, 1653, 1608, 1521, 1441.

Nuclear magnetic resonance spectrum (400 MHz, CDCl₃) δ ppm: 1.75–2.27 (3H, m), 2.58–2.75 (1H, m), 3.05–4.55 (15H, m), 4.94–5.38 (6H, m), 7.37–7.62 (7H, m), 8.10–8.33 (6H, m), 10.34 (1H, d, J=27.18 Hz).

Referential Example 30

(2S,4S)-2-[3-[2-[2,3-Di(4-nitrobezyloxycarbonyl)-1-methylguanindino]acetylamino]-azetidin-1-ylcarbonyl]-4-mercapto-1-(4-nitrobenzyloxycarbonyl)pyrrolidine (1) tert-Butyl [3-[2-[2,3-di(4-nitrobenzyloxycarbonyl)-1-methylguanidino]acetylamino-]-1-azetidinecarboxylate To a solution of tert-butyl 3-[2-methylaminoacetylamino]-1-azetidinecarboxylate (670 mg) in anhydrous tetrahydrofuran (15 ml), 4-nitrobenzyl [(4-nitrobenzyloxy)carbonylimino-pyrazol-1-ylmethyl]carbamate (1.07 g) was added under ice cooling. The resulting mixture was treated in a similar manner to that described in Referential Example 16-(1), whereby the title compound (1.22 g) was obtained as an amorphous substance.

Infrared absorption spectrum (KBr) vmax cm⁻¹: 3212, 1758, 1702, 1661, 1609, 1563, 1524.

Nuclear magnetic resonance spectrum (270 MHz, CDCl₃) δ ppm: 1.44 (9H, s), 3.11 (3H, s), 3.70–3.80 (2H, m), 4.20–4.34 (4H, m), 4.50–4.66 (1H, m), 5.27 (2H, s), 7.56 (4H, d, J=8.6 Hz), 7.77 (1H, d, J=6.5 Hz), 8.25 (4H, d, J=8.6 Hz), 10.32–10.47 (1H, b).

(2) 3-[2-[2,3-di(4-nitrobenzyloxycarbonyl)-1-methylguanidino]acetylamino]azetidine trifluoroacetate To a solution of the compound (1.22 g), which had been obtained in (1), in anhydrous dichloromethane (12 ml), trifluoroacetic acid (6 ml) was added dropwise under ice cooling. The reaction mixture was then treated in a similar manner to that described in Referential Example 16-(2), whereby the title compound was obtained. The product was provided for use in the subsequent reaction without isolation.

Infrared absorption spectrum (KBr) vmax cm⁻¹: 3215, 1777, 1676, 1609, 1524, 1454, 1435, 1377, 1351.

Nuclear magnetic resonance spectrum (270 MHz, DMSO-d₆) δ ppm: 3.03 (3H, s), 3.83–4.01 (2H, m), 4.03–4.18 (4H, m), 4.52–4.70 (1H, m), 5.14 (4H, s), 7.56 (4H, d, J=8.7 Hz), 8.15 (4H, d, J=8.7 Hz), 8.56–8.82 (3H, m).

(3) (2S,4S)-4-(4-methoxyubenzyl)thio-1-(4-nitrobenzyloxycarbonyl)-2-[3-[2-[2,3-di(4-nitrobenzyloxycarbonyl)-1-methylguanidino]acetylamino]azetidin-1-ylcarbonyl]pyrrolidine To a solution of (2S,4S) (4-methoxybenzyl)thio-1-(4-nitrobenzyloxycarbonyl)-L-proline (888 mg) in anhydrous acetonitrile (15 ml), N,N'-carbonyldiimidazole (337 mg) was added, followed by stirring at room temperature for one hour. To the reaction mixture, N,N-diisopropylethylamine (330 μl) and a solution of the compound (1.69 g), which had been obtained in (2), in anhydrous tetrahydrofuran (16 ml) were added. The resulting mixture was treated in a similar manner to that described in Referential Example 16-(3), whereby the title compound (1.59 g) was obtained as an amorphous substance.

Infrared absorption spectrum (KBr) vmax cm⁻¹: 3306, 1758, 1705, 1667, 1609, 1521, 1443, 1404.

Nuclear magnetic resonance spectrum (400 MHz, CDCl₃) δ ppm: 1.86–2.03 (1H, m), 2.32–2.53 (1H, m), 3.00–3.17 (4H, m), 3.22–3.37 (1H, m), 3.67–4.47 (13H, m), 4.55–4.76 (1H, m), 4.95–5.38 (6H, m), 6.80–6.90 (2H, m), 7.10–7.60 (8H, m), 8.12–8.31 (6H, m).

(4) (2S,4S)-2-[3-[2-[2,3-Di(4-nitrobenzyloxycarbonyl)-1-methylguanidino]acetylamino]azetidin-1-ylcarbonyl]-4-mercapto-1 -(4-nitrobenzyloxycarbonyl)pyrrolidine To a mixture of the compound (1.58 g), which had been obtained in (3), and anisole (1.77 ml), trifluoroacetic acid (6.26 ml) and trifluoromethanesulfonic acid (285 μl) were added dropwise under ice cooling. The reaction mixture was treated in a similar manner to that described in Referential Example 16-(4), whereby the title compound (1.30 g) was obtained as an amorphous substance.

Infrared absorption spectrum (KBr) vmax cm⁻¹: 3309, 1757, 1705, 1665, 1608, 1522, 1445, 1404.

Nuclear magnetic resonance spectrum (400 MHz, CDCl₃) δ ppm: 1.87–2.08 (2H, m), 2.53–2.70 (1H, m), 3.05–3.15 (3H, m), 3.21–3.50 (2H, m), 3.75–4.82 (9H, m), 5.00–5.40 (6H, m), 7.38–7.60 (6H, m), 8.12–8.33 (6H, m).

Referential Example 31

(2S,4S)-2-[(3S)-3-[L-[N-[2,3-Di(4-nitrobenzyloxycarbonyl)amidino]prolyl]amino]pyrrolidin-1-ylcarbonyl]-4-mercapto-1-(4-nitrobenzyloxycarbonyl)pyrrolidine (1) tert-Butyl (3S)-3-[L-[N-[2,3-di(4-nitrobenzyloxycarbonyl)amidino]prolyl]amino]-1-pyrrolidinecarboxylate To a solution of tert-butyl (3S)-3-(L-prolylamino)-1-pyrrolidinecarboxylate (963 mg) in anhydrous tetrahydrofuran (20 ml), a solution of 4-nitrobenzyl [(4- nitrobenzyloxy)carbonylimino-pyrazol-1-ylmethyl] carbamate (1.44 g) in tetrahydrofuran (15 ml) was added under ice cooling. The resulting mixture was treated in a similar manner to that described in Referential Example 16-(1), whereby the title compound (1.88 g) was obtained as an amorphous substance.

Infared absorption spectrum (KBr) vmax cm$^{-1}$: 3306, 3208, 1754, 1692, 1658, 1606, 1524.

Nuclear magnetic resonance spectrum (270 MHz, CDCl$_3$) δ ppm: 1.43 (9H, s), 1.72–2.34 (6H, m), 3.04–3.80 (6H, m), 4.31–4.50 (1H, b), 4.72–4.90 (1H, b), 5.10–5.42 (4H, b), 6.98–7.22 (1H, b), 7.55 (4H, d, J=8.6 Hz), 8.24 (4H, d, J=8.6 Hz), 10.28–10.60 (1H, b).

(2) (3S)-3-[L-[N-[2,3-Di(4-nitrobenzyloxycarbonyl)amidino]prolyl]amino]pyrrolidine trifluoroacetate To a solution of the compound (1.87 g), which had been obtained in (1), in anhydrous dichloromethane (10 ml), trifluoroacetic acid (5 ml) was added dropwise under ice cooling. The resulting mixture was treated in a similar manner to that described in Referential Example 16-(2), whereby the title compound was obtained. The product was provided for use in the subsequent reaction without isolation.

Infared absorption spectrum (KBr) vmax cm$^{-1}$: 3185, 1777, 1671, 1610, 1525, 1455, 1434, 1378.

Nuclear magnetic resonance spectrum (270 MHz, CDCl$_3$+DMSO-d$_6$) δ ppm: 1.80 (6H, m), 3.03–3.48 (4H, m), 3.56–3.71 (1H, m), 3.77–3.96 (1H, m), 4.56–4.70 (2H, m), 5.00–5.36 (4H, b), 7.53 (4H, d, J=8.7 Hz), 8.17 (4H, d, J=8.7 Hz), 8.41 (1H, d, J=7.5 Hz), 9.06–9.30 (1H, b), 10.30–10.56 (1H, b).

(3) (2S,4S)-2-[(3S)-3-[L-[N-[2,3-di(4-nitrobenzyloxycarbonyl)amidino]prolyl]amino]pyrrolidin-1-ylcarbonyl]-4-(4-methoxybenzyl)thio-1-(4-nitrobenzyloxycarbonyl)pyrrolidine To a solution of (2S,4S)-4-(4-methoxybenzyl)thio-1-(4-nitrobenzyloxycarbonyl)-L-proline (1.28 g) in anhydrous acetonitrile (19 ml), N,N'-carbonyldiimidazole (489 mg) was added, followed by stirring at room temperature for one hour. To the reaction mixture, N,N-diisopropylethylamine (478 μl) and a solution of the compound (2.60 g), which had been obtained in (1), in anhydrous tetrahydrofuran (15 ml) were added. The resulting mixture was treated in a similar manner to that described in Referential Example 16-(3), whereby the title compound (2.09 g) was obtained as an amorphous substance.

Infrared absorption spectrum (KBr) vmax cm$^{-1}$: 3339, 1756, 1706, 1687, 1657, 1608, 1522, 1440.

Nuclear magnetic resonance spectrum (400 MHz, CDCl$_3$) δ ppm: 1.60–2.32 (7H, m), 2.34–2.50 (1H, m), 2.93–5.40 (23H, m), 6.78–6.90 (2H, m), 7.14–7.61 (9H, m), 8.10–8.32 (6H, m).

(4) (2S,4S)-2-[(3S)-3-[L-[N-[2,3-Di(4-nitrobenzyloxycarbonyl)amidino]prolyl]amino]pyrrolidin-1-ylcarbonyl]-4-mercapto-1-(4-nitrobenzyloxycarbonyl)pyrrolidine To a mixture of the compound (2.03 g), which had been obtained in (3), and anisole (2.17 ml), trifluoroacetic acid (7.70 ml) and trifluoromethanesulfonic acid (351 μl) were added dropwise under ice cooling. The reaction mixture was then treated in a similar manner to that described in Referential Example 16-(4), whereby the title compound (1.71 g) were obtained as an amorphous substance.

Infared absorption spectrum (KBr) vmax cm$^{-1}$: 3410, 1755, 1705, 1687, 1655, 1607, 1522, 1496,-1442.

Nuclear magnetic resonance spectrum (400 MHz, CDCl$_3$) δ ppm: 1.74–2.32 (8H, m), 2.52–2.73 (1H, m), 3.08–4.54 (11H, m), 4.65–5.40 (7H, m), 7.13–7.28 (1H, m), 7.40–7.60 (6H, m), 8.12–8.33 (6H, m).

Referential Example 32

(2S,4S)-2-[(3S)-3-[4-[2,3-Di(4-nitrobenzyloxycarbonyl)guanidino]butanoylamino]pyrrolidin-1-ylcarbonyl]-4-mercapto-1-(4-nitrobenzloxycarbonyl)pyrrolidine (1) tert-Butyl (3S)-3-[4-[2,3-di(4-nitrobenzyloxycarbonyl)guanidino]butanoylamino]-1-pyrrolidinecarboxylate To a solution of tert-butyl (3S)-3-(4-aminobutanoylamino)-1-pyrrolidinecarboxylate (1.36 g) in anhydrous tetrahydrofuran (30 ml), 4-nitrobenzyl [(4-nitrobenzyloxy)carbonylimino-pyrazol-1-ylmethyl] carbamate (1.60 g) was added under ice cooling. The resulting (mixture was then treated in a similar manner to that described in Referential Example 16-(1), whereby the title compound (2.50 g) was obtained as an amorphous substance.

Infrared absorption spectrum (KBr) vmax cm$^{-1}$: 3335, 1737, 1693, 1645, 1609, 1573, 1524, 1412, 1347.

Nuclear magnetic resonance spectrum (400 MHz, CDCl$_3$) δ ppm: 1.45 (9H, s), 1.70–2.21 (4H, m), 2.25 (2H, t, J=7.0 Hz), 3.15–3.53 (5H, m), 3.62 (1H, dd, J=11.3, 6.5 Hz), 4.34–4.51 (1H, m), 5.19–5.29 (4H, m), 6.32–6.35 (1H, m), 7.54 (4H, d, J=8.6 Hz), 8.20–8.27 (4H, m), 8.47 (1H, t, J=5.7 Hz), 11.80 (1H, s).

(2) (2S,4S)-2-[(3S)-3-[4-[2,3-di(4-nitrobenzyloxycarbonyl)guanidino]butanoylamino]pyrrolidin-1-ylcarbonyl]-4-(4-methoxybenzyl)thio-1-(4-nitrobenzyloxycarbonyl)pyrrolidine To a solution of the compound (2.50 g), which had been obtained in (1), in anhydrous dichloromethane (25 ml), trifluoroacetic acid (15 ml) was added dropwise under ice cooling, followed by stirring at the same temperature for 15 minutes and at room temperature for 15 minutes. The reaction mixture was diluted with 1,2-dichioroethane and concentrated by evaporation under reduced pressure. The residue was washed successively with hexane and diethyl ether by decantation and then the solvent was distilled off, whereby crude (3S)-3-[4-[2,3,-di(4-nitrobenzyloxycarbonyl)guanidino]butanoylamino]pyrrolidine trifluoroacetate (2.55 g) was obtained. The product was provided for use in the subsequent reaction without isolation.

On the other hand, to a solution of (2S,4S)-4-(4-methoxybenzyl)thio-1-(4-nitrobenzyloxycarbonyl)-L-proline (1.66 g) in anhydrous tetraydrofuran (30 ml), N,N'-carbonyldiimidazole (0.72 g) was added, followed by stirring at room temperature for one hour. To the reaction mixture, N,N-diisopropylethylamine (1.30 mg) and a solution of (3S)-3-[4-[2,3-di(4-nitrobenzyloxycarbonyl)guanidino]butanoylamino]pyrrolidine trifluoroacetate (2.55 g), which had been obtained above, in anhydrous tetrahydrofuran (20 ml) were added and the mixture was allowed to stand overnight at room temperature. After concentration of the reaction mixture by evaporation under reduced pressure, ethyl acetate was added to the residue. The resulting mixture was washed successively with water and saturated saline, dried over anhydrous magnesium sulfate and concentrated by evaporation under reduced pressure. The residue was purified by chromatography through a silica gel column (ethyl acetate-methanol), whereby the title compound (2.56 g) was obtained as an amorphous substance.

Infrared absorption spectrum (KBr) vmax cm$^{-1}$: 3335, 1709, 1644, 1609, 1572, 1522, 1437, 1346.

Nuclear magnetic resonance spectrum (400 MHz, CDCl$_3$) δ ppm: 1.73–2.27 (7H, m), 2.39–2.52 (1H, m), 2.98–3.18

(1H, m), 3.28–4.10 (11H, m), 3.35 (2H, s), 4.20–4.56 (2H, m), 4.95–5.36 (6H, m), 6.31–6.87 (3H, m), 7.21–7.68 (8H, m), 8.14–8.25 (6H, m), 8.41–8.50 (1H, m), 11.79 (1H, d, J=14.8 Hz).

(3) (2S,4S)-2-[(3S)-3-[4-[2,3-di(4-nitrobenzloxycarbonyl) guanidino]butanoylamino]pyrrolidin-1-ylcarbonyl]-4-mercapto-1-(4-nitrobenzyloxycarbonyl)pyrrolidine To a mixture of the compound (2.50 g), which had been obtained in (2), and anisole (2.70 ml), trifluoroacetic acid (9.60 ml) and trifluoromethanesulfonic acid (0.66 ml) were added dropwise under ice cooling. The reaction mixture was treated in a similar manner to that described in Referential Example 16-(4), whereby the title compound (2.15 g) was obtained as an amorphous substance.

Infrared absorption spectrum (KBr) νmax cm$^{-1}$: 3337, 1734, 1709, 1645, 1608, 1522, 1440, 1347.

Nuclear magnetic resonance spectrum (400 MHz, CDCl$_3$) δ ppm: 1.75–2.28 (7H, m), 2.62–2.70 (1H, m), 3.21–3.91 (9H, m), 3.98–4.15 (1H, m), 4.38–4.56 (2H, m), 5.03–5.35 (6H, m), 6.34–7.10 (1H, m), 7.27–7.56 (6H, m), 8.16–8.26 (6H, m), 8.42–8.48 (1H, m), 11.80 (1H, d, J=12.2 Hz).

Referential Example 33

(2S,4S)-2-[3-[4-[2,3-Di(4-nitrobenzyloxycarbonyl) guanidino]butanoylamino]azetidin-1-ylcarbonyl]-4-mercapto-1-(4-nitrobenzyloxycarbonyl)pyrrolidine (1) tert-Butyl [3-[4-[2,3-di(4-nitrobenzyloxycarbonyl) guanidino]butanoylamino]-1-azetidinecarboxylate To a solution of tert-butyl 3-(4-aminobutanoylamino)-1-azetidinecarboxylate (0.89 g) in anhydrous tetrahydrofuran (30 ml), 4-nitrobenzyl [(4-nitrobenzyloxy)carbonylimino-pyrazol-1-ylmethyl]carbamate (1.45 g) was added under ice cooling. The resulting mixture was then treated in a similar manner to that described in Referential Example 16-(1), whereby the title compound (1.95 g) was obtained as an amorphous substance.

Infrared absorption spectrum (KBr) νmax cm$^{-1}$: 3336, 1737, 1699, 1645, 1609, 1572, 1524, 1414, 1380, 1347.

Nuclear magnetic resonance spectrum (400 MHz, CDCl$_3$) δ ppm: 1.39 (9H, s), 1.88–1.95 (2H, m), 2.25–2.29 (2H, m), 3.53 (2H, dd, J=12.5,6.1 Hz), 3.81 (2H, dd, J=9.2, 5.3 Hz), 4.20–4.24 (2H, m), 4.66–4.75 (1H, m), 5.23–5.30 (4H, m), 7.40 (1H, d, J=7.7 Hz), 7.53–7.57 (4H, m), 8.20–8.27 (4H, m), 8.51 (1H, t, J=6.1 Hz), 11.81 (1H, s).

(2) (2S,4S)-2-[3-[4-[2,3-Di(4-nitrobenzyloxycarbonyl) guanidino]butanoylamino]azetidin-1-ylcarbonyl]-4-(4-methoxybenzyl)thio-1-(4-nitrobenzyloxycarbonyl) pyrrolidine To a solution of the compound (1.90 g), which had been obtained in (1), in anhydrous dichloromethane (20 ml), trifluoroacetic acid (10 ml) was added dropwise under ice cooling, followed by stirring at the same temperature for 10 minutes and then at room temperature for 10 minutes. The reaction mixture was diluted with 1,2-dichloroethane and concentrated by evaporation under reduced pressure. The residue was washed successively with hexane and diethyl ether by decantation and the solvent was distilled off, whereby a crude 3-[4-[2,3-di(4-nitrobenzyloxycarbonyl) guanidino]-butanoylamino]azetidine trifluoroacetate (1.93 g) was obtained. The product was provided for use in the subsequent reaction without isolation.

On the other hand, to a solution of (2S,4S)-4-(4-methoxybenzyl)thio-1-(4-nitrobenzyloxycarbonyl)-L-proline (1.30 g) in anhydrous tetrahydrofuran (25 ml), N,N'-carbonyldiimidazole (0.56 g) was added, followed by stirring at room temperature for 30 minutes. To the reaction mixture, N,N-diisopropylethylamine (1.01 ml) and a solution of 3-[4-[2,3-di(4-nitrobenzyloxycarbonyl)guanidino] butanoylamino]azetidine trifluoroacetate (1 93 g), which had been obtained above, in anhydrous tetrahydrofuran (25 ml) were added. The resulting mixture was treated in a similar manner to that described in Referential Example 32-(2), whereby the title compound (2.20 g) was obtained as an amorphous substance.

Infared absorption spectrum (KBr) νmax cm$^{-1}$: 3338, 1709, 1644, 1609, 1574, 1522, 1433,1346.

Nuclear magnetic resonance spectrum (400 MHz, CDCl$_3$) δ ppm: 1.70–2.00 (3H, m), 2.18–2.42 (3H, m), 3.04–3.13 (1H, m), 3.24–3.33 (1H, m), 3.44–3.52 (2H, m), 3.71–4.00 (3H, m), 3.72 (2H, s), 3.79 (3H, m), 4.10–4.41 (3H, m), 4.65–4.78 (1H, m), 5.04–5.34 (6H, m), 6.80 (2H, d, J=8.6 Hz), 7.10–7.27 (3H, m), 7.35–7.55 (6H, m), 8.17–8.26 (6H, m), 8.45–8.53 (1H, m), 11.81 (1H, s).

(3) (2S,4S)-2-[3-[4-[2,3-di(4-nitrobenrzyloxycarbonyl) guanidino]butanoylamino]azetidin-1-ylcarbonyl]-4-mercapto-1-(4-nitrobenzyloxycarbonyl)pyrrolidine To a mixture of the compound (2.10 g), which had been obtained in (2), and anisole (2.38 ml), trifluoroacetic acid (8.50 ml) and trifluoromethanesulfonic acid (0.58 ml) were added dropwise under ice cooling. The reaction mixture was then treated in a similar manner to that described in Referential Example 16-(4), whereby the title compound (1.90 g) was obtained as an amorphous substance.

Infrared absorption spectrum (KBr) νmax cm$^{-1}$: 3337, 1733, 1709, 1645, 1608, 1522, 1433, 1347.

Nuclear magnetic resonance spectrum (400 MHz, CDCl$_3$) δ ppm: 1.87–2.07 (5H, m), 2.17–2.34 (2H, m), 2.50–2.72 (1H, m), 3.20–3.55 (4H, m), 3.91–4.27 (4H, m), 4.29–4.53 (1H, m), 4.63–4.83 (1H, m), 5.05–5.36 (6H, m), 7.27–7.56 (7H, m), 8.18–8.26 (6H, m), 8.46–8.54 (1H, m), 11.81 (1H, s).

Referential Example 34

(2S,4S)-2-[3-[4-[2,3-Di(4-nitrobenzyloxycarbonyl) guanidino]-3-hydroxybutanoylamino]azetidin-1-ylcarbonyl]-4-mercapto-1-(4-nitrobenzyloxycarbonyl)pyrrolidine (1) tert-Buty 3-[4-[2,3-di(4-nitrobenzyloxycarbonyl) guanidino]-3-hydroxybutanoylamino]-1-azetidinecarboxylate To a solution of tert-butyl 3-(4-amino-hydroxybutanoylamino)-1-azetidinecarboxylate (1.01 g) in anhydrous tetaydrofuran (30 ml), 4-nitrobenzyl [(4-nitrobenzyloxy)carbonylimino-pyrazol-1-ylmethyl] carbamate (1.55 g) was added under ice cooling. The resulting mixture was treated in a similar manner to that described in Referential Example 16-(1), whereby the title compound (2.10 g) was obtained as an amorphous substance.

Infrared absorption spectrum (KBr) νmax cm$^{-1}$: 3336, 1737, 1699, 1647, 1609, 1570, 1524, 1414, 1380, 1367, 1348.

Nuclear magnetic resonance spectrum (400 MHz, CDCl$_3$) δ ppm: 1.42 (9H, s), 2.40 (2H, d, J=6.0 Hz), 3.45–3.52 (1H, m), 3.62–3.68 (1H, m), 3.73–3.77 (2H, m), 4.10–4.25 (3H, m), 4.58–4.66 (1H, m), 4.94 (1H, d, J=3.1 Hz), 5.22 (2H, s), 5.30 (2H, s), 6.94 (1H, d, J=7.4 Hz), 7.54–7.56 (4H, m), 8.20–8.26 (4H, m), 8.73 (1H, t, J=5.5 Hz), 11.74 (1H, s).

(2) (2S,4S)-2-[3-[4-[2,3-Di(4-nitrobenzyloxycarbonyl) guanidino]-3-hydroxybutanoylamino]azetidin-1-ylcarbonyl]-4-(4-methoxybenzyl)thio-1-(4-nitrobenzyloxycarbonyl)pyrrolidine To a solution of the compound (2.00 g), which had been obtained in (1), in anhydrous dichloromethane (20 ml), trifluoroacetic acid (10 ml) was added dropwise under ice cooling, followed by stirring at the same temperature for 10 minutes and at room temperature for 20 minutes. The reaction mixture was diluted with 1,2-dichloroethane and concentrated by evaporation under reduced pressure. The residue was washed successively with hexane and diethyl ether by decantation, followed by evaporation of the solvent whereby crude [3-[4-[2,3-di(4-nitrobenzyloxycarbonyl) guanidino]-3-hydroxybutanoylamino]azetidine trifluoroacetate (2.04 g) was obtained. The product was provided for use in the subsequent step without isolation.

On the other hand, to a solution of (2S,4S)-4-(4-methoxybenzyl)thio-1-(4-nitrobenzyloxycarbonyl)-L-proline (1.30 g) in anhydrous tetrahydrofuran (20 ml), N,N'-carbonyldiimidazole (0.60 g) was added, followed by stirring at room temperature for 30 minutes. To the reaction mixture, N,N-isopropylethylamine (0.78 ml) and a solution of [3-[4-[2,3-di(4-nitrobenzyloxycarbonyl)guanidino]-3-hydroxybutanoylamino]azetidine trifluoroacetate (2.04 g), which had been obtained above, in anhydrous tetrahydrofuran (20 ml) were added. The resulting mixture was treated in a similar manner to that described in Referential Example 32-(2), whereby the title compound (2.02 g) was obtained as an amorphous substance.

Infrared absorption spectrum (KBr) vmax cm$^{-1}$: 3335, 1708, 1644, 1609, 1570, 1522, 1440, 1347.

Nuclear magnetic resonance spectrum (400 MHz, CDCl$_3$) δ ppm: 1.86–2.05 (1H, m), 2.32–2.49 (4H, m), 3.04–3.13 (1H, m), 3.25–3.32 (1H, m), 3.40–3.51 (1H, m), 3.59–3.98 (4H, m), 3.72 (2H, s), 3.79 (3H, s), 4.09–4.25 (3H, m), 4.34–4.51 (1H, m), 4.61–4.75 (1H, m), 5.03–5.34 (6H, m), 6.85 (2H, d, J=8.5 Hz), 7.00–7.28 (3H, m), 7.42–7.55 (6H, m), 8.17–8.25 (6H, m), 8.71–8.72 (1H, m), 11.73 (1H, s).

(3) (2S,4S)-4-Mercapto-1-(4-nitrobenzyloxycarbonyl)-2-[[3-[4-[2,3-di(4-nitrobenzyloxycarbonyl)guanidino]-3-hydroxybutanoylamino]azetidin-1-ylcarbonyl]pyrrolidine To a mixture of the compound (2.00 g), which had been obtained in (2), and anisole (2.20 ml), trifluoroacetic acid (7.70 ml) and trifluoromethanesulfonic acid (0.35 ml) were added dropwise under ice cooling. The reaction mixture was treated in a similar manner to that described in Referential Example 16-(4), whereby the title compound (1.75 g) was obtained as an amorphous substance.

Infrared a absorption spectrum (KBr) vmax cm$^{-1}$: 3339, 1735, 1709, 1645, 1609, 1522, 1440, 1347.

Nuclear magnetic resonance spectrum (400 MHz, CDCl$_3$) δ ppm: 1.93–2.05 (2H, m), 2.34–2.42 (2H, m), 2.58–2.64 (1H, m), 3.24–3.50 (3H, m), 3.63–3.68 (1H, m), 3.81–4.47 (7H, m), 4.65–4.91 (2H, m), 5.05–5.30 (6H, m), 7.00–7.31 (1H, m), 7.47–7.55 (6H, m), 8.18–8.26 (6H, m), 8.71–8.73 (1H, m), 11.73 (1H, s).

Referential Example 35

(2S,4S)-2-[(3S)-3-[2-[2,3-Di(4-nitrobenzylcarbonyl) guanidino]acetylamino]-pyrrolidin-1-ylcarbonyl]-4-mercapto-1-(4-nitrobenzyloxycarbonyl)pyrrolidine (1) tert-Butyl (3S)-3-[2-[2,3-di(4-nitrobenzyloxycarbonyl) guanidino]acetylamino]-1-pyrrolidinecarboxylate To a solution of tert-butyl (3S)-3-(2-aminoacetylamino)-1-pyrrolidinecarboxylate (3.07 g) in anhydrous tetrahydrofuran (45 ml), a solution of 4-nitrobenzyl [(4-nitrobenzyloxy)carbonylimino-pyrazol-1-ylmethyl] carbamate (5.38 g) in tetrahydrofuran (35 ml) was added under ice cooling, followed by stirring at room temperature for 30 minutes. Ethyl acetate was added to the reaction mixture. The resulting mixture was washed with water, an aqueous solution of potassium hydrogensulfate and saturated saline, dried over anhydrous magnesium sulfate and then concentrated by evaporation under reduced pressure. The residue was purified by chromatography through a silica gel column (ethyl acetate-dichloromethane), whereby the title compound (7.82 g) was obtained as an amorphous substance.

Infrared absorption spectrum (KBr) vmax cm$^{-1}$: 3308, 1740, 1691, 1646, 1626, 1554, 1524.

Nuclear magnetic resonance spectrum (270 MHz, CDCl$_3$) δ ppm: 1.45 (9H, s), 1.68–1.92 (1H, m), 2.03–2.22 (1H, m), 3.10–3.30 (1H, b), 3.30–3.50 (2H, b), 3.56–3.67 (1H, m), 4.08 (2H, d, J=5.1 Hz), 4.37–4.51 (1H, m), 5.22 (2H, s), 5.31 (2H, s), 6.30–6.40 (1H, m), 7.48–7.60 (4H, m), 8.17–8.30 (4H, m), 8.88–8.98 (1H, m), 11.65 (1H, s).

(2) (3S)-3-[2-[2,3-Di(4-nitrobenzyloxycarbonyl)guanidino] acetylamino]pyrrolidine trifluoroacetate To a solution of the compound (7.82 g), which had been obtained in (1), in anhydrous dichloromethane (10 ml), trifluoroacetic acid (5 ml) was added dropwise under ice cooling, followed by stirring for 4 hours. The reaction mixture was concentrated by evaporation under reduced pressure. The residue was washed with hexane-ether and the solvent was distilled off, whereby 1.00 g of the title compound was obtained. The product was provided for use in the subsequent reaction without purification.

Infrared absorption spectrum (Liquid film) vmax cm$^{-1}$: 1757, 1676, 1610, 1598, 1526, 1440.

Nuclear magnetic resonance spectrum (270 MHz, DMSO-d$_6$) δ ppm: 1.72–1.90 (1H, m), 2.03–2.21 (1H, m), 2.90–3.07 (1H, m), 3.12–3.46 (3H, m), 3.99 (2H, s), 4.20–4.38 (1H, m), 5.20 (2H, s), 5.39 (2H, s), 7.61 (2H, d, J=8.6 Hz), 7.71 (2H, d, J=8.6 Hz), 8.24 (2H, d, J=7.3 Hz), 8.27 (2H, d, J=7.3 Hz), 8.40 (1H, d, J=6.3 Hz).

(3) (2S,4S)-2-[(3S)-3-[2-[2,3-Di(4-nitrobenzyloxycarbonyl) guanidino]acetylamino]pyrrolidin-1-ylcarbonyl]-4-(4-methoxybenzyl)thio-1-(4-nitrobenzyloxycarbonyl) pyrrolidine To a solution of (2S,4S)-4-(4-methoxybenzyl)thio-1-(4-nitrobenzyloxycarbonyl)-L-proline (5.38 g) in anhydrous acetonitrile (70 ml), N,N'-carbonyldiimidazole (2.04 g) was added, followed by stirring at room temperature for one hour. To the reaction mixture, N,N-diisopropylethylamine (2.0 ml) and a solution of the compound (11.00 g), which had been obtained in (2), in anhydrous acetonitrile (35 ml) were added and the mixture was reacted overnight at room temperature. The reaction mixture was concentrated by evaporation under reduced pressure. Ethyl acetate was added to the residue. The resulting mixture was washed with water and saturated saline, dried over anhydrous magnesium sulfate and then concentrated by evaporation under reduced pressure. The residue was purified by chromatography (ethyl acetate-methanol) through a silica gel column, whereby the title target compound (10.09 g) was obtained as an amorphous substance.

Infrared absorption spectrum (KBr) vmax cm$^{-1}$: 3319, 1737, 1708, 1645, 1609, 1552, 1522.

Nuclear magnetic resonance spectrum (270 MHz, CDCl$_3$) δ ppm: 1.60–1.88 (1H, m), 1.98–2.20 (1H, m), 2.30–2.50 (1H, m), 2.94–3.56 (5H, m), 3.66–4.60 (12H, m), 5.00–5.36 (6H, m), 6.80–7.60 (10H, m), 8.06–8.28 (6H, m).

(4) (2S,4S)-2-[(3S)-3-[2-[2,3-Di(4-nitrobenzyloxycarbonyl) guanidino]acetylamino]pyrrolidin-1-ylcarbonyl]-4-mercapto-1-(4-nitrobenzyloxycarbonyl)pyrrolidine To a mixture of the compound (9.90 g), which had been obtained in (3), and anisole (11.1 ml), trifluoroacetic acid (39.2 ml) and trifluoromethanesulfonic acid (1.79 μl) were added dropwise under ice cooling and the mixture was stirred at room temperature for one hour. To the reaction mixture, 1,2-dichloroethane was added, followed by concentration by evaporation under reduced pressure. The residue was dissolved in ethyl acetate. The ethyl acetate solution was washed with a saturated aqueous solution of sodium bicarbonate, water and saturated saline, dried over anhydrous magnesium sulfate and then the solvent was distilled off under reduced pressure, whereby the title compound (8.75 g) was obtained as an amorphous substance.

Infrared absorption spectrum (KBr) νmax cm$^{-1}$: 3326, 1737, 1708, 1645, 1609, 1552, 1522.

Nuclear magnetic resonance spectrum (400 MHz, CDCl$_3$) δ ppm: 1.78–2.22 (3H, m), 2.57–2.68 (1H, m), 3.17–4.60 (12H, m), 5.03–5.38 (6H, m), 7.40–7.60 (6H, m), 8.10–8.28 (6H, m).

Referential Example 36

(2S,4S)-2-[(3S)-3-[N-2-2,3-Di(4-nitrobenzyloxycarbonyl)guanidino]acetyl]-N-methylamino]pyrrolidin-1-ylcarbonyl]-4-mercapto-1-(4-nitrobenzloxycarbonyl)pyrolidine

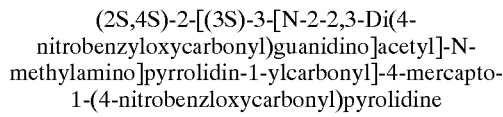

The title compound can be obtained in a similar manner to that described in Referential Example 16-(1), (2), (3) and (4).

Referential Example 37

(2S,4S)-2-[(3S)-3-[N-[2-[2,3-Di(4-nitrobenzyloxycarbonyl)-1-methylguanidino]acetyl] N-methylamino]pyrrolidin-1-ylcarbonyl]-4-mercapto-1-(4-nitrobenzyloxycarbonyl)pyrrolidine

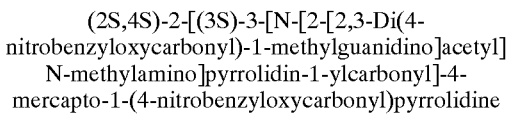

The title compound can be obtained in a similar manner to that described in Referential Example 16-(1), (2), (3) and (4).

Referential Example 38

(2S,4S)-2-[3-[N-[2-[2,3-Di(4-nitrobenzyloxycarbonyl)guanidino]acetyl]-N-methylamino]azetidin-1-ylcarbonyl]-4-mercapto-1-(4-nitrobenzyloxycarbonyl)pyrrolidine

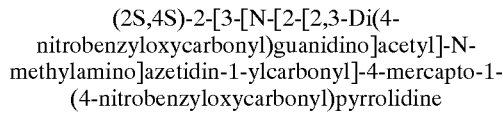

The title compound can be obtained in a similar manner to that described in Referential Example 16-(1), (2), (3) and (4).

Referential Example 39

(2S,4S)-2-[1-Hydroxy-2-[(3S)-3-[N-methyl-N-(4-nitrobenzylcarbonyl)amino]pyrrolidin-1-ylcarbonyl] ethyl]-4-mercapto-1-(4-nitrobenzyloxycarbonyl) pyrrolidine

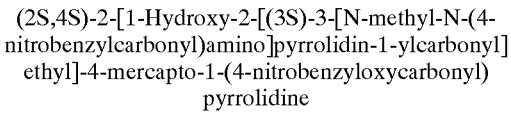

The title compound can be obtained in a similar manner to that described in Referential Example 16-(1), (2), (3) and (4).

Referential Example 40

(2S,4S)-2-[1-Hydroxy-2-[(3S)-3-[N-methyl-N-(4-nitrobenzyloxycarbonyl)amino]pyrolidin-1-ylcarbonyl]ethyl]4-mercapto-1-(4-nitrobenzyloxycarbonyl)pyrrolidine

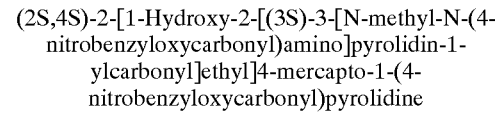

(1) In dimethylformamide (5 ml), (3S)-3-[N-methyl-N-(4-nitrobenzyloxycarbonyl)amino]pyrrolidine trifluoroacetate (400.9 mg) was dissolved. To the solution, N,N-diisopropylethylamine (0.444 ml) and a solution of (2S,4S)-2-(2-carboxy-1-hydroxyethyl)-4-(4-methoxybenzylthio)-1-(4-nitrobenzyloxycarbonyl)pyrrolidine (0.5 g) in dimethylformamide (5 ml), were added at room temperature. To the resulting mixture, 1-hydroxybenzotriazole (151.5 mg), 1-ethyl-3-(3-dimethylaminopropyl)-carbodiimide hydrochloride (273.5 mg) and water (1 ml) were added successively and the mixture was stirred overnight at the same temperature. The reaction mixture was concentrated by evaporation under reduced pressure. Ethyl acetate was then added to the residue. The resulting mixture was washed with water and saturated saline, dried over anhydrous magnesium sulfate and concentrated by evaporation under reduced pressure. The residue was purified by chromatography through a silica gel column (ethyl acetate methanol= 50:1), whereby (2S,4S)-2-[1-hydroxy-2-[(3S)-3-[N-methyl-N-(4-nitrobenzyloxycarbonyl)amino]pyrrolidin-1-ylcarbonyl]ethyl]-4-(4-methoxybenzylthio)-1-(4-nitrobenzyloxycarbonyl)pyrrolidine (523.5 mg) was obtained Infrared absorption spectrum (KBr) νmax cm$^{-1}$: 3400, 2947, 1702, 1634, 1609, 1522, 1494, 1442, 1405, 1345, 1318, 1248.

Nuclear magnetic resonance spectrum (400 MHz, CDCl$_3$) δ ppm: 1.49–2.50 (8H, m), 2.86–3.15 (5H, m), 3.29–4.54 (11H, m), 5.18, 5.21 (4H, s), 6.84 (2H, d, J=6.8 Hz), 7.23 (2H, d, J=6.8 Hz), 7.42–7.61 (4H, m), 8.24 (4H, d, J=8.5 Hz).

(2) The compound (523.5 mg) obtained in (1) was dissolved in anisole (0.524 ml) and trifluoroacetic acid (2.678 ml), followed by the addition of trifluoromethanesulfonic acid (0.154 ml) at 0 to 5° C. under ice cooling. The resulting mixture was stirred at room temperature for 40 minutes. The solvent was then distilled off. Sodium bicarbonate was added to the residue to make it alkaline, followed by extraction with ethyl acetate. The ethyl acetate layer was washed with saline and dried over anhydrous sodium sulfate. The solvent was distilled off, whereby the title compound (440.0 mg) was obtained.

Infrared absorption spectrum (KBr) νmax cm$^{-1}$: 3401, 2952, 1702, 1628, 1609, 1522, 1495, 1443, 1406, 1346, 1319, 1301, 1246.

Referential Example 41

(2S,4S)-2-[1-Hydroxy-2-[(3S)-3-[3-(4-nitrobenzyloxycarbonyl)guanidino]pyrrolidin-1-ylcarbonyl]ethyl]-4-mercapto-1-(4-nitrobenzyloxycarbonyl)pyrrolidine

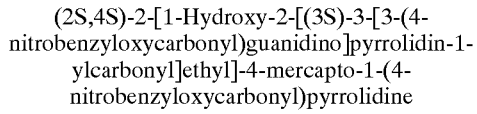

The title compound was obtained in a similar manner to that described in Referential Example 40-(1) and (2).

Infared absorption spectrum (KBr) νmax cm$^{-1}$: 3392, 3326, 1701, 1610, 1584, 1520, 1440, 1404, 1376, 1347, 1321, 1285, 1246.

Nuclear magnetic resonance spectrum (400 MHz, CDCl$_3$) δ ppm: 1.48–2.70 (8H, m), 3.01–3.28 (2H, m), 3.39–3.69 (4H, m), 4.00–4.58 (2H, m), 5.11–5.30 (4H, m), 7.45–7.51 (4H, m), 8.12–8.28 (4H, m).

Referential Example 42

(2S,4S)-2-[1-Hydroxy-2-[(3R)-3-(4-nitrobenzyloxycarbonylamino)pyrrolidin-1-ylcarbonyl]ethyl]-4-mercapto-1-(4-nitrobenzyloxycarbonylpyrrolidine

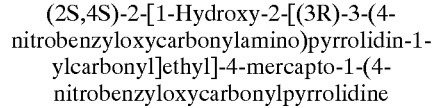

The title compound was obtained in a similar manner to that described in Referential Example 40-(1) and (2).

Infrared absorption spectrum (KBr) νmax cm⁻¹: 3322, 1704, 1625, 1609, 1522, 1444, 1405, 1347, 1321, 1301, 1283, 1247.

Nuclear magnetic resonance spectrum (400 MHz, CDCl$_3$) δ ppm: 1.74–2.69 (7H, m), 3.06–3.26 (2H, m), 3.34–3.74 (4H, m), 3.98–4.34 (4H, m), 5.11–5.30 (4H, m), 7.42–7.58 (4H, m), 8.15–8.27 (4H, m).

Referential Example 43

(2S,4S)-2-[1-Hydroxy-2-[(3R)-3-(N-methyl-N-4-nitrobenzyloxycarbonylamino)pyrrolidin-1-ylcarbonyl]ethyl]-4-mercapto-1-(4-nitrobenzyloxycarbonyl)pyrrolidine The title compound was obtained in a similar manner to that described in Referential Example 40-(1) and (2).

Infrared absorption spectrum (KBr) νmax cm⁻¹: 3402, 1702, 1633, 1608, 1522, 1494, 1444, 1405, 1346, 1320.

Nuclear magnetic resonance spectrum (400 MHz, CDCl$_3$) δ ppm: 1.73–2.70 (9H, m), 2.86–2.94 (3H, m), 3.08–4.29 (8H, m), 5.15–5.30 (4H, m), 7.47–7.59 (4H, m), 8.18–8.30 (4H, m).

Referential Example 44

(2S,4S)-2-[1-Hydroxy-2-[(3R)-3-(N-methyl-N-4-nitrobenzyloxycarbonylaminomethyl)pyrrolidin-1-ylcarbonyl]ethyl]-4-mercapto-1-(4-nitrobenzyloxycarbonyl)pyrrolidine The title compound was obtained in a similar manner to that described in Referential Example 40-(1) and (2).

Nuclear magnetic resonance spectrum (400 MHz, CDCl$_3$) δ ppm: 1.57–2.65 (10H, m), 2.91–3.71 (11H, m), 4.05–4.27 (1H, m), 5.14–5.30 (4H, m), 7.52 (4H, d, J=8.5 Hz), 8.19–8.28 (4H, m).

Referential Example 45

(2S,4S)-2-[1-Hydroxy-2-[(3R)-3-(4-nitrobenzyloxycarbonylaminomethyl)pyrrolidin-1-ylcarbonyl]ethyl]-4-mercapto-1-(4-nitrobenzyloxycarbonyl)pyrrolidine The title compound was obtained in a similar manner to that described in Referential Example 40-(1) and (2).

Infrared absorption spectrum (KBr) νmax cm⁻¹: 3336, 1704, 1622, 1609, 1521, 1448, 1404, 1347, 1322, 1297, 1246.

Nuclear magnetic resonance spectrum (400 MHz, CDCl$_3$) δ ppm: 1.73–1.81 (2H, m), 1.97–2.64 (7H, m), 3.08–3.69 (9H, m), 4.06–4.25 (2H, m), 5.20 (4H, s), 7.52 (4H, d, J=8.1 Hz), 8.23 (4H, d, J=8.4 Hz).

Referential Example 46

(2S,4S)-2-[1-Hydroxy-2-[(3S)-3-(N-methyl-N-4-nitrobenzyloxycarbonylaminomethyl)pyrrolidin-1-ylcarbonyl]ethyl]-4-mercapto-1-(4-nitrobenzyloxycarbonyl)pyrrolidine The title compound was obtained in a similar manner to that described in Referential Example 40-(1) and (2).

Infrared absorption spectrum (KBr) νmax cm⁻¹: 3402, 1791, 1704, 1623, 1609, 1521, 1494, 1446, 1404, 1347, 1297, 1247.

Nuclear magnetic resonance spectrum (400 MHz, CDCl$_3$) δ ppm: 1.56–2.65 (9H, m), 2.94–3.69 (11H, m), 4.05–4.25 (2H, m), 5.22 (4H, s), 7.52 (4H, d, J=8.1 Hz), 8.19–8.27 (4H, m).

Referential Example 47

(2S,4S)-2-[1-Hydroxy-2-[4-(4-nitrobenzyloxycarbonyl)piperazin-1-ylcarbonyl]ethyl]-4-mercapto-1-(4-nitrobenzyloxycarbonyl)pyrrolidine The title compound was obtained in a similar manner to that described in Referential Example 15-(1) and (2).

Infrared absorption spectrum (KBr) νmax cm⁻¹: 3436, 1787, 1702, 1633, 1608, 1521, 1496, 1466, 1435, 1407, 1347, 1321, 1287, 1247.

Nuclear magnetic resonance spectrum (400 MHz, CDCl$_3$) δ ppm: 1.74–1.82 (1H, m), 2.31–2.68 (4H, m), 3.10–3.74 (11H, m), 4.05–4.28 (2H, m), 5.21, 5.25 (4H, s), 7.52 (4H, d, J=8.3 Hz), 8.28 (4H, d, J=8.3 Hz).

Referential Example 48

(2S,4S)-2-[1-Hydroxy-2-[4-methylpiperazin-1ylcarbonyl]ethyl]-4-mercapto-1-(4-nitrobenzyloxycarbonyl)pyrrolidine The title compound was obtained in a similar manner to that described in Referential Example 40-(1) and (2).

Infrared absorption spectrum (KBr) νmax cm⁻¹: 3401, 1699, 1630, 1610, 1522, 1511, 1463, 1440, 1405, 1347, 1320, 1296, 1247.

Nuclear magnetic resonance spectrum (400 MHz, CDCl$_3$) δ ppm: 1.72–1.82 (1H, m), 2.26–2.71 (11H, m), 3.09–3.85 (7H, m), 4.05–4.26 (2H, m), 5.21 (2H, s), 7.52 (2H, d, J=8.3 Hz), 8.23 (2H, d, J=8.3 Hz).

Referential Example 49

(2S,4S)-2-[1-Hydroxy-2-[(3S)-1-(4-nitrobenzyloxycarbonyl)pyrrolidin-3-ylaminocarbonyl]ethyl]-4-mercapto-1-(4-nitrobenzyloxycarbonyl)pyrrolidine The title compound was obtained in a similar manner to that described in Referential Example 40-(1) and (2).

Infrared absorption spectrum (KBr) νmax cm⁻¹: 3325, 1701, 1608, 1522, 1497, 1433, 1406, 1347, 1298, 1246.

Nuclear magnetic resonance spectrum (400 MHz, CDCl$_3$) δ ppm: 1.61–1.96 (3H, m), 2.12–2.65 (4H, m), 3.06–3.36 (3H, m), 3.48–3.58 (2H, m), 3.66–4.20 (4H, m), 4.42–4.54 (1H, m), 5.18–5.28 (4H, m), 7.51 (4H, d, J=8.3 Hz), 8.23 (4H, d, J=8.3 Hz).

Referential Example 50

(2S,4S)-2-[1-Hydroxy-2-[N-methyl-N-(3S)-1-(4-nitrobenzyloxycarbonyl)pyrrolidin-3-ylaminocarbonyl]ethyl]-4-mercapto-1-(4-nitrobenzyloxycarbonyl)pyrrolidine The title compound was obtained in a similar manner to that described in Referential Example 40-(1) and (2).

Infrared absorption spectrum (KBr) νmax cm⁻¹: 3466, 1702, 1632, 1608, 1522, 1494, 1429, 1406, 1347, 1298, 1246.

Nuclear magnetic resonance spectrum (400 MHz, CDCl$_3$) δ ppm: 1.74–2.16 (5H, m), 2.26–2.67 (4H, m), 2.76–2.91 (3H, m), 3.10–3.49 (4H, m), 3.58–3.73 (2H, m), 4.05–4.27 (2H, m), 5.22 (4H, d, J=9.9 Hz), 7.52 (4H, d, J=8.3 Hz), 8.23 (4H, d, J=8.3 Hz).

Referential Example 51

(2S,4S)-2-[1-Hydroxy-2-[4-(4-nitrobenzyloxycarbonylguanyl)piperazin-1-ylcarbonyl]ethyl]-4-mercapto-1-(4-nitrobenzyloxycarbonyl)pyrrolidine The title compound was obtained in a similar manner to that described in Referential Example 40-(1) and (2).

Infrared absorption spectrum (KBr) vmax cm$^{-1}$: 3381, 1699, 1640, 1608, 1544, 1522, 1494, 1440, 1405, 1347.

Nuclear magnetic resonance spectrum (400 MHz, DMSO-d$_6$) δ ppm: 1.69–1.80 (1H, m), 2.17–2.64 (3H, m), 2.81–3.06 (2H, m), 3.13–3.64 (8H, m), 3.96–4.13 (2H, m), 4.24–4.53 (1H, m), 4.96–5.28 (5H, m), 7.60–7.70 (4H, m), 8.18–8.27 (4H, m).

Referential Example 52

(2S,4S)-2-[1-Hydroxy-2-[(3R)-1-(4-nitrobenzyloxycarbonyl)pyrrolidin-3-ylaminocarbonyl]ethyl]-4-mercapto-1-(4-nitrobenzyloxycarbonyl)pyrrolidine The title compound was obtained in a similar manner to that described in Referential Example 40-(1) and (2).

Infrared absorption spectrum (KBr) vmax cm$^{-1}$: 3393, 3339, 1702, 1608, 1522, 1496, 1433, 1406, 1347.

Nuclear magnetic resonance spectrum (400 MHz, CDCl$_3$) δ ppm: 1.56–1.96 (3H, m), 2.14–2.67 (4H, m), 3.07–3.36 (3H, m), 3.51–3.58 (2H, m), 3.65–4.20 (4H, m), 4.45–4.52 (1H, m), 5.18–5.29 (4H, m), 7.52 (4H, d, J=8.3 Hz), 8.23 (4H, d, J=8.3 Hz).

Referential Example 53

(2S,4S)-2-[1-Hydroxy-2-[(3S)-3-(4-nitrobenzyloxycarbonylacetimidoylamino)pyrrolidin-1-ylcarbonyl]ethyl]-4-mercapto-1-(4-nitrobenzyloxycarbonyl pyrrolidine The title compound was obtained in a similar manner to that described in Referential Example 40-(1) and (2).

Infrared absorption spectrum (KBr) vmax cm$^{-1}$: 3306, 1698, 1608, 1553, 1521, 1443, 1404, 1347.

Nuclear magnetic resonance spectrum (400 MHz, CDCl$_3$) δ ppm: 1.71–2.67 (10H, m), 3.09–4.68 (10H, m), 5.16–5.26 (4H, m), 7.49–7.60 (4H, m), 8.19–8.27 (4H, m).

Referential Example 54

(2S,4S)-2-[1-Hydroxy-2-[4(4-nitrobenzyloxycarbonylacetimidoyl)piperazin-1-ylcarbonyl]ethyl]-4-mercapto-1-(4-nitrobenzyloxycarbonyl)pyrrolidine The title compound was obtained in a similar manner to that described in Referential Example 40-(1) and (2).

Infared absorption spectrum (KBr) vmax cm$^{-1}$: 3416, 1781, 1699, 1633, 1608, 1566, 1522, 1496, 1433, 1406, 1347, 1320.

Referential Example 55

(2S,4S)-2-[1Hydroxy-2-[(3S)-1-[N,N'-bis(4-nitrobenzylcarbonyl)guanyl]pyrrolidin-3-ylaminocarbonyl]ethyl]-4-mercapto-1-(4-nitrobenzyloxycarbonyl)pyrrolidine The title compound was obtained in a similar manner to that described in Referential Example 40-(1) and (2).

Infrared absorption spectrum (KBr) vmax cm$^{-1}$: 3408, 3331, 1734, 1702, 1622, 1575, 1522, 1496, 1434, 1379, 1347.

Referential Example 56

(2S,4S)-2-[1-Hydroxy-2-[(3S)-1-(4-nitrobenzyloxycarbonylacetimidoyl)pyrrolidin-3-ylaminocarbonyl]ethyl]-4-mercapto-1-(4-nitrobenzyloxycarbonyl)pyrrolidine The title compound can be obtained in a similar manner to that described in Referential Example 40-(1) and (2).

Referential Example 57

(2S,4S)-2-[1-Hydroxy-2-[4-(4-nitrobenzyloxycarbonylaminomethyl)piperidin-1-ylcarbonyl]ethyl]-4-mercapto-1-(4-nitrobenzyloxycarbonyl)pyrrolidine The title compound can be obtained in a similar manner to that described in Referential Example 40-(1) and (2).

Referential Example 58

(2S,4S)-2-[1-Hydroxy-2-[3-(4-nitrobenzyloxycarbonylamino)pipieridin-1-ylcarbonyl]ethyl]-4-mercapto-1-(4-nitrobenzyloxycarbonyl)pyrrolidine The title compound can be obtained in a similar manner to that described in Referential Example 40-(1) and (2).

Referential Example 59

(2S,4S)-2-[(1R)-1-Hydroxy-2-[(3S)-3-(4-nitrobenzyloxycarbonylamino)pyrrolidin-1-ylcarbonyl]ethyl]-4-mercapto-1-(4-nitrobenzyloxycarbonyl)pyrrolidine (1) In anhydrous dimethylformamide (50 ml), (2S,4S)-2-[-1-hydroxy-2-[t-butoxycarbonyl]ethyl]-4-(methoxybenzylthio)-1-(4-nitrobenzyloxycarbonyl) pyrrolidine (5.05 g) was dissolved. To the solution, imidazole (2.525 g) and t-butyl dimethylsilyl chloride (2.162 g) were added under ice cooling and the mixture was stirred at 60° C. for 2 days. To the reaction mixture, an aqueous solution of sodium bicarbonate was added. The resulting mixture was extracted with ethyl acetate several times. The extract was dried over anhydrous sodium sulfate. The residue was purified by chromatography through a silica gel column (hexane:ethyl acetate=6:1, 3:1), whereby less polar (S)-isomer, that is (2S,4S)-2-[(1S)-1-[t-butoxycarbonyl]ethyl]-4-(4-methoxybenzylthio)-1(4-nitrobenzyloxycarbonyl)pyrrolidine (1.337 g) and polar (R)-isomer, that is (2S,4S)-2-[(1R)-1-[t-butoxycarbonyl]ethyl]-4-(4-methoxybenzylthio)-1-(4-nitrobenzyloxycarbonyl) pyrrolidine (1.147 g) were obtained.

(S)-isomer

Infrared absorption spectrum (KBr) vmax cm$^{-1}$: 2955, 2931, 1709, 1610, 1585, 1525, 1512, 1472, 1463, 1425, 1402, 1367, 1346.

Nuclear magnetic resonance spectrum (400 MHz, CDCl$_3$) δ ppm: −0.15–0.28 (6H, m), 0.76–0.89 (9H, m), 1.43 (9H, d, J=4.4 Hz), 1.68–1.79 (1H, m), 2.19–2.40 (3H, m), 2.87–3.00 (2H, m), 3.72 (2H, s), 3.80 (3H, s), 3.84–4.15 (2H, m), 4.64–4.74 (1H, m), 5.11–5.28 (2H, m), 6.85 (2H, d, J=8.2 Hz), 7.23 (2H, d, J=8.2 Hz), 7.45 (1H, d, J=8.3 Hz), 7.58 (1H, d, J=8.3 Hz), 8.22 (2H, d, J=8.3 Hz).

(R)-isomer

Infrared absorption spectrum (KBr) vmax cm$^{-1}$: 2954, 2931, 1728, 1706, 1610, 1585, 1524, 1512, 1472, 1463, 1426, 1405, 1368, 1347.

Nuclear magnetic resonance spectrum (400 MHz, CDCl$_3$) δ ppm: −0.14–0.05 (6H, m), 0.86 (9H, m), 1.43 (9H, d, J=11.9 Hz), 2.01–2.24 (2H, m), 2.31–2.38 (1H, m), 2.87–3.06 (2H, m), 3.72 (2H, d, J=3.13 Hz), 3.79 (3H, d, J=2.1 Hz), 3.84–3.95 (1H, m), 4.04–4.12 (1H, m), 4.54–4.60 (1H, m), 4.68–4.75 (1H, m), 5.16–5.26 (2H, m), 6.85 (2H, d, J=8.5 Hz), 7.24 (2H, d, J=8.5 Hz), 7.48 (1H, d, J=8.4 Hz), 7.60 (1H, d, J=8.4 Hz), 8.22 (2H, d, J=8.4 Hz).

(2) In dichloromethane (18 ml), the (R)-isomer (1.370 g) obtained in (1) was dissolved. To the solution, trifluoroacetic acid (9 ml) was added under ice cooling and the mixture was stirred for 1 to 2 hours. The reaction mixture was concentrated by evaporation under reduced pressure, and toluene was then added to the residue for azeotropic distillation. This procedure was repeated three times, whereby (2S,4S)-2-[(1R)-2-carboxyl-1-hydroxyethyl]-4-(4-methoxybenzylthio)-1-(4-nitrobenzyloxycarbonyl)pyrrolidine (1.017 g) was obtained.

Infrared absorption spectrum (KBr) νmax cm$^{-1}$: 3417, 2953, 1790, 1705, 1609, 1585, 1522, 1513, 1436, 1407, 1347.

Nuclear magnetic resonance spectrum (400 ml), CDCl$_3$) δ ppm: 1.67–1.70 (1H, m), 2.28–2.54 (3H, m), 2.96–3.13 (2H, m), 3.73 (2H, s), 3.79 (3H, s), 3.80–4.15 (2H, m), 4.28–4.49 (1H, m), 5.18–5.24 (2H, m), 6.85 (4H, d, J=8.6 Hz), 7.23 (2H, d, J=8.6 Hz), 7.47 (2H, d, J=8.4 Hz), 8.25 (2H, d, J=8.4 Hz).

(3) In dimethylformamide (8 ml), (3R)-3-(4-nitrobenzyloxycarbonylamino)pyrrolidine hydrochloride (775 mg) was dissolved, followed by the addition of N,N-diisopropylethylamine (1.119 ml) and a solution of the compound (1.0167 g), which had been obtained in (2), in dimethylformamide (10 ml), under stirring at room temperature. To the mixture, 1-hydroxybenzotriazole (381.7 mg), 1-ethyl-3-(3-dimethylaminopropyl)carbodiimide hydrochloride (689.3 mg) and water (1 ml) were added successively and the mixture was stirred overnight at the same temperature. The reaction mixture was concentrated by evaporation under reduced pressure. Ethyl acetate was then added to the residue. The resulting mixture was washed with water and saturated saline and dried over anhydrous magnesium sulfate. The solvent was distilled off and the residue was purified by chromatography through a silica gel column (hexane:ethyl acetate 1:10), whereby (2S,4S)-2-[(1R)-1-hydroxy-2-[(3S)-3-(4-nitrobenzyloxycarbonylamino)pyrrolidin-1-ylcarbonyl]ethyl]-4-(4-methoxybenzyl))-1-(4-nitrobenzyloxycarbonyl)pyrrolidine (1.088 g) was obtained.

Infrared absorption spectrum (KBr) νmax cm$^{-1}$: 3306, 2950, 1703, 1672, 1625, 1609, 1586, 1521, 1441, 1406, 1347.

Nuclear magnetic resonance spectrum (400 MHz, CDCl$_3$) δ ppm: 1.94–2.47 (7H, m), 3.34–4.31 (14H, m), 5.09 (4H, m), 6.86 (2H, d, J=8.6 Hz), 7.23 (2H, d, J=8.6 Hz), 7.36–7.56 (4H, m), 8.15–8.28 (4H, m).

(4) To the compound (1.088 g) obtained in (3), anisole (1.1 ml) was added under ice cooling. To the resulting mixture, trifluoroacetic acid (5.44 ml) was added. To the resulting solution, trifluoromethanesulfonic acid (0.326 ml) was added and the mixture was stirred at room temperature for 30 minutes. The reaction mixture was concentrated by evaporation under reduced pressure. The residue was washed thrice with hexane, followed by the addition of an aqueous sodium bicarbonate solution. The resulting mixture was extracted with ethyl acetate. The extract was then dried over anhydrous magnesium sulfate. The solvent was then distilled off, whereby the title compound (911 mg) was obtained.

Infrared absorption spectrum (KBr) νmax cm$^{-1}$: 3321, 1792, 1704, 1626, 1609, 1521, 1442, 1405, 1347.

Nuclear magnetic resonance spectrum (400 MHz, CDCl$_3$) δ ppm: 1.76 (1H, d, J=7.0 Hz), 1.96–2.55 (6H, m), 3.07–3.26 (2H, m), 3.44–3.74 (4H, m), 3.90–4.33 (4H, m), 5.13–5.40 (4H, m), 7.41–7.56 (4H, m), 8.15–8.26 (4H, m).

Referential Example 60

(2S,4S)-2-[(1S)-1-Hydroxy-2-[(3S)-3-(4-nitrobenzyloxycarbonylamino)pyrrolidin-1-ylcarbonyl]ethyl]-4-mercapto-1-(4-nitrobenzyloxycarbonyl)pyrrolidine (1) The (S)-isomer (914.1 mg) obtained in Referential Example 59-(1) was treated in a similar manner to that described in Referential Example 59-(2), whereby (2S,4S)-2-[(1S)-2-carboxyl-1-hydroxyethyl]-4-(4-methoxybenzylthio)-1-(4-nitrobenzyloxycarbonyl)pyrrolidine (678.4 mg) was obtained.

Infrared absorption spectrum (KBr) νmax cm$^{-1}$: 3392, 2955, 1787, 1709, 1680, 1610, 1585, 1523, 1512, 1433, 1406, 1347.

Nuclear magnetic resonance spectrum (400 MHz, CDCl$_3$) δ ppm: 1.54–1.65 (1H, m), 2.36–2.65 (3H, m), 2.96–3.15 (2H, m), 3.73 (2H, s), 3.79 (3H, s), 3.82–4.20 (3H, m), 5.21 (2H, s), 6.85 (2H, d, J=8.6 Hz), 7.13–7.30 (2H, m), 7.47 (2H, d, J=8.3 Hz), 8.25 (2H, d, J=8.3 Hz).

(2) The compound (501 mg) obtained in (1) was treated in a similar manner to that described in Referential Example 59-(3), whereby (2S,4S)-2-[(1S)-1-hydroxy-2-[(3S)-3-(4-nitrobenzyloxycarbonylamino)pyrrolidin-1-ylcarbonyl]ethyl]-4-(4-methoxybenzyl)-1-(4-nitrobenzyloxycarbonyl)pyrrolidine (714.6 mg) was obtained.

Infared absorption spectrum (KBr) νmax cm$^{-1}$: 3307, 2952, 1702, 1673, 1626, 1609, 1585, 1522, 1442, 1405, 1390, 1347.

Nuclear magnetic resonance spectrum (400 MHz, CDCl$_3$) δ ppm: 1.74–2.54 (7H, m), 3.48–4.33 (14H, m), 5.12–5.25 (4H, m), 6.84 (2H, d, J=8.3 Hz), 7.23 (2H, d, J=8.3 Hz), 7.41–7.57 (4H, m), 8.16–8.27 (4H, m).

(3) The compound (714 mg) obtained in (2) was treated in a similar manner to that described in Referential Example 59-(4), whereby (2S,4S)-2-[(1S)-1-hydroxy-2-[(3S)-3-(4-nitrobenzyloxycarbonylamino)pyrrolidin-1-ylcarbonyl]ethyl]-4-mercapto-1-(4-nitrobenzyloxycarbonyl)pyrrolidine (598 mg) was obtained.

Infrared absorption spectrum (KBr) νmax cm$^{-1}$: 3320, 1703, 1624, 1609, 1521, 1444, 1404, 1347.

Nuclear magnetic resonance spectrum (400 MHz, CDCl$_3$) δ ppm: 1.75–2.70 (7H, m), 3.09–3.22 (2H, m), 3.36–3.74 (4H, m), 4.05–4.44 (4H, m), 5.19 (4H, s), 7.44–7.57 (4H, m), 8.19–8.26 (4H, m).

Referential Example 61

(2S,4S)-2-[(1R)-1-Hydroxy-2-[4-(4-nitrobenzyloxycarbonyl)piperazin-1-ylcarbonyl]ethyl]-4-mercapto-1-(4-nitrobenzyloxycarbonylpyrrolidine In a similar manner to that described in Referential Example 59-(2), (3) and (4), the title compound was obtained.

Infrared absorption spectrum (KBr) νmax cm$^{-1}$: 3448, 1702, 1636, 1624, 1608, 1520, 1495, 1467, 1433, 1407, 1347.

Nuclear magnetic resonance spectrum (400 MHz, CDCl$_3$) δ ppm: 1.78 (1H, d, J=7.3 Hz), 2.00–2.11 (1H, m), 2.31–2.51 (3H, m), 3.09–3.75 (10H, m), 3.44–4.50 (3H, m), 5.16–5.30 (4H, m), 7.52 (4H, d, J=8.3 Hz), 8.20–8.27 (4H, m).

Referential Example 62

(2S,4S)-2-[(1S)-1-Hydroxy-2-[4-(4-nitrobenzyloxycarbonyl)piperazin-1-ylcarbonyl]ethyl]-4-mercapto-1-(4-nitrobenzyloxycarbonyl)pyrrolidine In a similar manner to that described in Referential Example 60-(1), (2) and (3), the title compound was obtained.

Infrared absorption spectrum (KBr) νmax cm$^{-1}$: 3448, 1702, 1632, 1608, 1521, 1495, 1465, 1435, 1407, 1347.

Nuclear magnetic resonance spectrum (400 MHz, CDCl₃) δ ppm: 1.74–1.94 (2H, m), 2.43–2.69 (3H, m), 3.10–3.21 (2H, m), 3.48–3.72 (8H, m), 4.05–4.29 (3H, m), 5.21, 5.25 (4H, s), 7.52 (4H, d, J=8.3 Hz), 8.24 (4H, d, J=8.3 Hz).

Referential Example 63

(2S,4S)-2-[(1R)-1-Hydroxy-2-[(3R)-3-(N-methyl-N-4-nitrobenzyloxycarbonylaminomethyl)pyrrolidin-1-ylcarbonyl]ethyl]-4-mercapto-1-(4-nitrobenzyloxycarbonyl)pyrolidine In a similar manner to that described in Referential Example 59-(2), (3) and (4), the title compound can be obtained.

Referential Example 64

(2S,4S)-2-[(1S)-1-hydroxy-2-[(3R)-3-(N-methyl-N-4-nitrobenzyloxycarbonylaminomethyl)pyrrolidin-1-ylcarbonyl]ethyl]-4mercapto-1-(4-nitrobenzyloxycarbonyl)pyrrolidine In a similar manner to that described in Referential Example 60-(1), (2) and (3), the title compound can be obtained.

Referential Example 65

(2S,4S-2-[(1R)-1-Hydroxy-2-[(3S)-3-(N-methyl-N-4-nitrobenzyloxycarbonylamino)pyrrolidin-1-ylcarbonyl]ethyl]-4-mercapto-1-(4-nitrobenzyloxycarbonyl)pyrrolidine In a similar manner to that described in Referential Example 59-(2), (3) and (4), the title compound can be obtained.

Referential Example 66

(2S,4S-2-(1S)-1-Hydroxy-2-[(3S)-3-(N-methyl-N-4-nitrobenzyloxycarbonylamino)pyrrolidin-1-ylcarbonyl]ethyl]-4-mercapto-1-(4-nitrobenzyloxycarbonyl)pyrrolidine In a similar manner to that described in Referential Example 60-(1), (2) and (3), the title compound can be obtained.

Referential Example 67

(2S,4S)-2-[(1R)-1-Hydroxy-2-[4-[N,N'-bis(4-nitrobenzyloxycarbonyl)guanyl]piperazin-1-ylcarbonyl]ethyl]-4-mercapto-1-(4-nitrobenzyloxycarbonyl)pyrrolidine In a similar manner to that described in Referential Example 59-(2), (3) and (4), the title compound was obtained.

Infrared absorption spectrum (KBr) vmax cm⁻¹: 3401, 1759, 1705, 1637, 1609, 1522, 1495, 1433, 1348, 1319.

Referential Example 68

(2S,4S)-2-[(1S)-1-Hydroxy-2-[4-[N,N'-bis(4-nitrobenzyloxycarbonyl)guanyl]piperazin-1-ylcarbonyl]ethyl]-4-mercapto-1-(4-nitrobenzyloxycabonyl)pyrrolidine In a similar manner to that described in Referential Example 60-(1), (2) and (3), the title compound was obtained.

Infrared absorption spectrum (KBr) vmax cm⁻¹: 3393, 1759, 1702, 1609, 1522, 1494, 1431, 1347, 1319.

Referential Example 69

(2S,4S)-2-[(1R)-1-Hydroxy-2-[(3S)-3-[2,3-bis(4-nitrobenzyloxycarbonyl)guanidino]pyrrolidin-1-ylcarbonyl]ethyl]-4-mercapto-1-(4-nitrobenzyloxycarbonylpyrrolidine In a similar manner to that described in Referential Example 59-(2), (3) and (4), the title compound can be obtained.

Referential Example 70

(2S,4S)-2-[(1S)-1-Hydroxy-2-[(3S)-3-[2,3-bis(4-nitrobezyloxycarbonyl)guanidino]pyrrolidine-1-ylcarbonyl]ethyl]-4-mercapto-1-(4-nitrobenzylcarbonyl)pyrrolidine In a similar manner to that described in Referential Example 60-(1), (2) and (3), the title compound can be obtained.

Referential Example 71

(2S,4S)-2-[(3S)-3-[(2S)-1-[2,3-Di(4-nitrobenzyloxycarbonyl)amidinoazetidin-2-yl]-carbonyl]amino]pyrrolidin-1-ylcarbonyl]-4-mercapto-1-(4-nitrobenzyloxycarbonyl)pyrrolidine In a similar manner to that described in Referential Example 31-(1), (2), (3), and (4), the title compound was obtained.

Infrared absorption spectrum (KBr) vmax cm⁻¹: 3234, 1799, 1763, 1732, 1712, 1651, 1608, 1521.

Nuclear magnetic resonance spectrum (400 MHz, DMSO-d₆) δ ppm: 1.54–2.83 (6H, m), 3.04–4.57 (13H, m), 4.94–5.38 (6H, m), 7.42–7.72 (6H, m), 8.08–8.30 (6H, m), 8.33–8.50 (1H, b), 10.42–10.60 (1H, b).

(Test)

Antibacterial activity was measured by the agar plate dilution method, whereby the minimal inhibitory concentration (μg/ml) against various pathogenic bacteria was determined. The results are shown in Table 5. In the Table, bacteria A, B and C provided for the test are as follows:

A: *Staphylococcus aureus* 209P
B: *Escherichia coli* NIHJ
C: *Pseudomonas aeruginosa* 1001

TABLE 5

Minimal inhibitory concentration (μg/ml)

| Compound | Microorganism | | |
| --- | --- | --- | --- |
|  | A | B | C |
| Compound of Ex. 1 | ≦0.01 | ≦0.01 | 0.1 |
| Compound of Ex. 8 | ≦0.01 | ≦0.01 | 0.05 |
| Compound of Ex. 12 | ≦0.01 | 0.02 | 0.2 |
| Compound of Ex. 17 | ≦0.01 | ≦0.01 | 0.05 |
| Compound of Ex. 27 | ≦0.01 | ≦0.01 | 0.05 |
| Compound of Ex. 49 | ≦0.01 | 0.02 | 0.4 |
| Compound of Ex. 51 | ≦0.01 | 0.02 | 0.2 |
| Compound of Ex. 59 | ≦0.01 | 0.02 | 0.2 |
| Compound of Ex. 60 | ≦0.01 | 0.02 | 0.4 |
| Imipenem | ≦0.01 | 0.05 | 3.1 |

The above results indicate that the compounds of the present invention possess strong antibacterial activity.

In addition, the compounds of the present invention are stable against dehydropeptidase I and β-lactamase and exhibit a high urinary recovery rate. Furthermore, they exhibit low nephrotoxicity.

Formulation Example 1

| Capsule | |
|---|---|
| Compound of Example 1 | 50 mg |
| Lactose | 128 mg |
| Corn starch | 70 mg |
| Magnesium stearate | 2 mg |
| | 250 mg |

The above ingredients, each in powdery form, were mixed and sifted through a 60-mesh sieve and then filled in No. 3 gelatin capsules, each containing 25 mg, whereby capsules were prepared.

Formulation Example 2

| Tablet | |
|---|---|
| Compound of Example 1 | 50 mg |
| Lactose | 126 mg |
| Corn starch | 23 mg |
| Magnesium stearate | 1 mg |
| | 200 mg |

The above ingredients, each in powdery form, were mixed, subjected to wet granulation with corn starch, dried and then tableted by a tableting machine, whereby tablets, each 200 mg, were prepared. The tablets can be coated with sugar if necessary.

We claim:

1. A 1-methylcarbapenem compound of the formula (I):

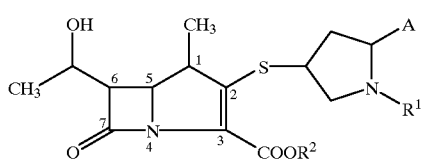

(I)

wherein:

$R^1$ represents a hydrogen atom or a $C_{1-4}$ alkyl group, $R^2$ represents a hydrogen atom or an ester residue which can be hydrolyzed in vivo, and A represents a group of the formula (A1)

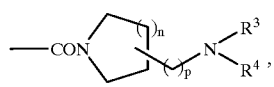

(A1)

wherein, in the formula (A1):

n stands for 0, 1 or 2, p stands for 0, 1 or 2, $R^3$ represents a hydrogen atom or a $C_{1-4}$ alkyl group, and $R^4$ represents a group of the formula (Q2)

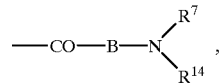

(Q2)

B represents a phenylene, phenylene($C_1$–$C_3$)alkyl, cyclohexylene, cyclohexylene($C_1$–$C_3$)alkyl or a $C_{1-5}$ alkylene group which is unsubstituted or substituted by one to three substituents which are the same or different from each other and each represents an amino, hydroxyl, cyclohexyl($C_1$–$C_3$)alkyl, $C_{1-4}$ alkyl, phenyl or benzyl group, $R^7$ represents a hydrogen atom or a $C_{1-4}$ alkyl group, and $R^{14}$ represents a group of the formula —C(=NH)$R^8$, wherein $R^8$ represents a hydrogen atom, a $C_{1-4}$ alkyl group or a group of the formula —NR$^9$R$^{10}$, in which $R^9$ and $R^{10}$ are the same as or different from each other and each represents a hydrogen atom or a $C_{1-4}$ alkyl group;

or a pharmacologically acceptable salt thereof.

2. A 1-methylcarbapenem compound according to claim 1, wherein $R^1$ represents a hydrogen atom or a methyl group;

or a pharmacologically acceptable salt thereof.

3. A methylcarbapenem compound according to claim 1, wherein:

$R^1$ represents a hydrogen atom or a methyl group, $R^2$ represents a hydrogen atom, n represents 0 or 1, p represents 0, $R^3$ represents a hydrogen atom or a methyl group, $R^7$ represents a hydrogen atom or a methyl group, $R^{14}$ represents an amidino group, and B represents a methylene group, a methylmethylene group of the formula (—CH(CH$_3$)—) or an ethylene group;

or a pharmacologically acceptable salt thereof.

4. A pharmacologically acceptable salt of 2-{2-[3-(2-guanidinoacetylamino)pyrrolidin-1-ylcarbonyl]-1-methylpyrrolidin-4-ylthio}-6-(1-hydroxyethyl)-1-methyl-1-carbapen-2-em-3-carboxylic acid.

5. A 1-methylcarbapenem compound according to claim 1, selected from the group consisting of 2-{2-[3-(2-guanidinoacetylamino)pyrrolidin-1-ylcarbonyl]pyrrolidin-4-ylthio}-6-(1-hydroxyethyl)-1-methyl-1-carbapen-2-em-3-carboxylic acid, 2-{2-{3-[2-(1-methylguanidino)acetylamino]pyrrolidin-1-ylcarbonyl}pyrrolidin-4-ylthio}-6-(1-hydroxyethyl)-1-methyl-1-carbapen-2-em-3-carboxylic acid, 2-{2-{3-[2-guanidino-2-methylacetylamino]pyrrolidin-1-ylcarbonyl}pyrrolidin-4-ylthio}-6-(1-hydroxyethyl)-1-methyl-1-carbapen-2-em-3-carboxylic acid, 2-{2-[3-(3-guanidinopropanoylamino)azetidin-1-ylcarbonyl]pyrrolidin-4-ylthio}-6-(1-hydroxyethyl)-1-methyl-1-carbapen-2-em-3-carboxylic acid, 2-{2-[3-(2-guanidino-2-methylacetylamino)azetidin-1-ylcarbonyl]pyrrolidin-4-ylthio}-6-(1-hydroxyethyl)-1-methyl-1-carbapen-2-em-3-carboxylic acid, 2-{2-{3-[N-(2-guanidinoacetyl)-N-methylamino]pyrrolidin-1-ylcarbonyl}pyrrolidin-4-ylthio}-6(1-hydroxyethyl)-1-methyl-1-carbapen-2-em-3-carboxylic acid, 2-{2-[3-(4-guanidino-3-hydroxybutanoylamino)azetidin-1-ylcarbonyl]pyrrolidin-4-ylthio}-6-(1-hydroxyethyl)-1-methy-1-carbapen-2-em-3-carboxylic acid, and 2-{2-[3-(2-guanidinoacetylamino)pyrrolidin-1-ylcarbonyl]-1-methylpyrrolidin-4-ylthio}-6-(1-hydroxyethyl)-1-methyl-1-carbapen-2-em-3-carboxylic acid;

or a pharmacologically acceptable salt thereof.

6. A 1-methylcarbapenem compound according to claim 1, wherein (1R,5S,6S)-2-[(2S,4S)-2-[3S)-3-(guanidinoacetylamino) pyrrolidin-1-ylcarbonyl]pyrrolidin-4-ylthio]-6-[(1R)-1-hydroxyethyl]-1-methyl-1-carbapen-2-em-3-carboxylic acid.

7. A 1-methylcarbapenem compound according to claim 1, wherein:

$R^1$ represents a hydrogen atom or a methyl group, n stands for 0 or 1, p stands for 0 or 1, $R^3$ represents a hydrogen atom, a methyl or ethyl group, $R^7$ represents a hydrogen atom, a methyl or ethyl group, $R^{14}$ represents a formimidoyl, acetimidoyl or amidino group, and B represents a 1,4-phenylene, 1,4-cyclohexylenemethyl, methylene, methylmethylene (—CH(CH$_3$)—), ethylene, trimethylene or 2-hydroxypropylene group;

or a pharmacologically acceptable salt thereof.

8. A 1-methylcarbapenem compound according to claim 1, wherein:

$R^1$ represents a hydrogen atom or a methyl group, n stands for 0 or 1, p stands for 0, $R^3$ represents a hydrogen atom or a methyl group, $R^7$ represents a hydrogen atom or a methyl group, $R^{14}$ represents an amidino group, and B represents a methylene, methylmethylene (—CH(CH$_3$)—), ethylene, trimethylene or 2-hydroxypropylene group;

or a pharmacologically acceptable salt thereof.

9. A 1-methylcarbapenem compound according to claim 1, wherein:

$R^1$ represents a hydrogen atom or a methyl group, n stands for 0 or 1, p stands for 0, $R^3$ represents a hydrogen atom, $R^7$ represents a hydrogen atom, $R^{14}$ represents an amidino group, and B represents a methylene, methylmethylene (—CH(CH$_3$)—), ethylene group;

or a pharmacologically acceptable salt thereof.

10. 2-{2-[3-(2-Guanidinoacetylamino)pyrrolidin-1-ylcarbonyl]-1-methylpyrrolidin-4-ylthio}-6-(1-hydroxyethyl)-1-methyl-1-carbapen-2-em-3-carboxylic acid.

11. A process for the preparation of a 1-methylcarbapenem compound or a pharmacologically acceptable salt thereof according to claims 2, 7, 8, 9, 10, 1, 5, 6, 3, or 4 which comprises reacting a carbapenem compound of the following formula (II):

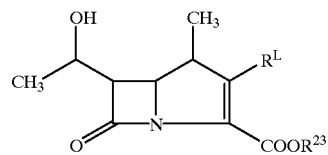

wherein $R^L$ represents a leaving group and $R^{23}$ represents a protecting group of a carboxyl group with a mercaptopyrrolidine compound of the following formula (III):

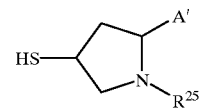

wherein $R^{25}$ represents a protecting group of an amino group or a $C_{1-4}$ alkyl group and A' represents a group of the following formula (A1):

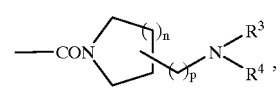

wherein n stands for 0, 1 or 2, p stands for 0, 1 or 2, $R^3$ represents a hydrogen atom or a $C_{1-4}$ alkyl group, and $R^4$ represents a group of formula (Q2):

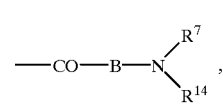

wherein B represents a phenylene, phenylene ($C_1$–$C_3$) alkyl, cyclohexylene, cyclohexylene ($C_1$–$C_3$) alkyl or a $C_{1-5}$ alkylene group which is unsubstituted or substituted by one to three substituents which are the same or different from each other and each represents an amino, hydroxyl, cyclohexyl ($C_1$–$C_3$) alkyl, $C_{1-4}$ alkyl, phenyl or benzyl group, $R^7$ represents a hydrogen atom or a $C_{1-4}$ alkyl group, and $R^{14}$ represents a group of the formula —C(=NH)$R^8$, wherein $R^8$ represents a hydrogen atom, a $C_{1-4}$ alkyl group or a group of the formula —NR$^9$R$^{10}$, in which $R^9$ and $R^{10}$ are the same as or different from each other and each represents a hydrogen atom or a $C_{1-4}$ alkyl group; with the proviso that any one of the amino group, hydroxyl group or imino group included in the group of A' are protected; optionally removing the protecting group; and then optionally converting the product into a pharmacologically acceptable salt or an ester which can be hydrolyzed in vivo.

12. A method for the treatment of infectious bacterial diseases, which comprises administering, to a warm-blooded animal, a pharmacologically effective amount of a 1-methylcarbapenem compound or pharmacologically acceptable salt thereof according to claims 2, 7, 8, 9, 10, 1, 5, 6, 3, or 4.

13. A pharmaceutical composition for the treatment of infectious bacterial diseases, which comprises a pharmacologically effective amount of a 1-methylcarbapenem compound or pharmacologically acceptable salt thereof according to claims 2, 7, 8, 9, 10, 1, 5, 6, 3 or 4 and a pharmacologically acceptable carrier.

14. The method of claim 12, wherein said warm-blooded animal is a human.

* * * * *

UNITED STATES PATENT AND TRADEMARK OFFICE
CERTIFICATE OF CORRECTION

PATENT NO.   : 6,090,802
DATED        : July 18, 2000
INVENTOR(S)  : Kawamoto et al.

It is certified that error appears in the above-identified patent and that said Letters Patent is hereby corrected as shown below:

Column 188,
Line 39, after "isolation" delete "," and insert -- . --.
Line 39, "Infrared absorption" begins a new paragraph.

Column 191,
Line 39, delete "(YBr)" and insert -- (KBr) --.
Line 44, delete "J=27.18" and insert -- J=27.8 --.

Column 192,
Line 22, after "(2S, 4S)" insert -- -4- --.

Column 199,
Lines 49-52, delete in entirety and insert -- (2S, 4S)-2-[4-[2-[2, 3-Di (4-nitrobenzyloxycarbonyl) guanidino]acetylamino]piperidin-1-ylcarbonyl]-4-mercapto-1-(4-nitrobenzyloxycarbonyl)pyrrolidine --.

Signed and Sealed this

Eighteenth Day of December, 2001

Attest:

JAMES E. ROGAN
*Director of the United States Patent and Trademark Office*

*Attesting Officer*

UNITED STATES PATENT AND TRADEMARK OFFICE
CERTIFICATE OF CORRECTION

PATENT NO. : 6,090,802
DATED : July 18, 2000
INVENTOR(S) : Kawamoto et al.

It is certified that error appears in the above-identified patent and that said Letters Patent is hereby corrected as shown below:

<u>Column 104,</u>
Line 59, delete "(0.97 g)" and insert -- (0.977 g) --.

Signed and Sealed this

Twenty-eighth Day of June, 2005

JON W. DUDAS
*Director of the United States Patent and Trademark Office*